United States Patent
Harris et al.

(10) Patent No.: US 8,323,916 B2
(45) Date of Patent: Dec. 4, 2012

(54) METHOD OF DETECTING ENDOMETRIAL CANCER COMPRISING MEASURING LEVELS OF FIBROCYSTIN-L

(75) Inventors: Peter C. Harris, Rochester, MN (US); Marie C. Hogan, Rochester, MN (US); Christopher J. Ward, Rochester, MN (US); Matthew D. Griffin, Galway (IE)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/170,458

(22) Filed: Jun. 28, 2011

(65) Prior Publication Data

US 2011/0256558 A1    Oct. 20, 2011

Related U.S. Application Data

(60) Division of application No. 12/613,753, filed on Nov. 6, 2009, now abandoned, which is a continuation of application No. 11/202,548, filed on Aug. 12, 2005, now abandoned, which is a continuation-in-part of application No. PCT/US2004/004300, filed on Feb. 12, 2004, now abandoned.

(60) Provisional application No. 60/446,860, filed on Feb. 12, 2003.

(51) Int. Cl.
*G01N 33/567* (2006.01)
*G01N 33/574* (2006.01)
*C07K 16/30* (2006.01)

(52) U.S. Cl. ............... 435/7.23; 530/387.7; 530/387.9

(58) Field of Classification Search .................. None
See application file for complete search history.

(56) References Cited

U.S. PATENT DOCUMENTS

| 4,946,778 A | 8/1990 | Ladner et al. |
| 5,451,683 A | 9/1995 | Barrett et al. |
| 5,733,729 A | 3/1998 | Lipshutz et al. |
| 5,770,722 A | 6/1998 | Lockhart et al. |
| 6,342,581 B1 | 1/2002 | Rosen et al. |
| 2004/0023241 A1 | 2/2004 | Alsobrook, II et al. |

FOREIGN PATENT DOCUMENTS

| WO | WO 98/20019 | 5/1998 |
| WO | WO 99/57318 | 11/1999 |

OTHER PUBLICATIONS

Abstract of Lian et al, 2011. Xi Bao Yu Fen Zi Mian Yi Xue Za Zhi. 27(1); 1 page as printed.*
GenBank Accession No. AAL74290 dated Apr. 1, 2002; 3 pages.
GenBank Accession No. AAN05018 dated Sep. 10, 2002; 3 pages.
GenBank Accession No. AV706327 dated Oct. 9, 2000; 2 pages.
GenBank Accession No. AY219181 dated Mar. 13, 2003; 6 pages.
GenBank Accession No. AY219182 dated Mar. 13, 2003; 6 pages.
GenBank Accession No. CAAB01002621 dated Jul. 25, 2002; 11 pages.
GenBank Accession No. NP_032617 dated Sep. 24, 2006; 19 pages.

(Continued)

*Primary Examiner* — Zachary Howard
(74) *Attorney, Agent, or Firm* — Fish & Richardson P.C.

(57) ABSTRACT

Nucleic acids encoding fibrocystin-L polypeptides and fibrocystin-L polypeptides are provided. Antibodies against the polypeptides, vectors and host cells containing the nucleic acids, methods for using the nucleic acids and polypeptides, and compositions and articles of manufacture also are provided.

3 Claims, 27 Drawing Sheets

OTHER PUBLICATIONS

GenBank Accession No. NP_032901 dated Aug. 13, 2006; 5 pages.
GenBank Accession No. NP_037522 dated Sep. 23, 2005; 2 pages.
GenBank Accession No. NP_619615 dated May 7, 2006; 4 pages.
GenBank Accession No. NP_621862 dated Dec. 3, 2005; 3 pages.
GenBank Accession No. NW_000106 dated Apr. 28, 2006; 77 pages.
GenBank Accession No. NP_061159 dated Aug. 20, 2006; 2 pages.
GenBank Accession No. ZP_00018581 dated Nov. 14, 2002; 2 pages.
Ausubel et al. (eds.), "Mutagenesis of Cloned DNA," *Short Protocols in Molecular Biology*, 1992, Chapter 8, Green Publishing Associates John Wiley & Sons.
Calame and Eaton, "Transcriptional Controlling Elements in the Immunoglobulin and T Cell Receptor Loci," *Adv. Immunol.*, 1988, 43:235-275.
Cole et al., "The EBV-Hybridoma Technique and Its Application to Human Lung Cancer," *Monoclonal Antibodies and Cancer Therapy*, 1985, Alan R. Liss, Inc. pp. 77-96.
Cote et al., "Generation of human monoclonal antibodies reactive with cellular antigens," *Proc. Natl. Acad. Sci. USA*, 1983, 80:2026-2030.
De St. Growth, "Production of Monoclonal Antibodies: Strategy and Tactis," *J. Immunol. Meth.*, 1980, 35:1-21.
Flohe and Schwabe, "Kinetics of Purified Catechol *O*-Methyltransferase," *Biochim. Biophys. Acta*, 1970, 220:469-476.
Griffin et al., "Blockade of T Cell Activation Using a Surface-Linked Single-Chain Antibody to CTLA-4 (CD152)," *J. Immunol.*, 2000, 164:4433-4442.
Guatelli et al., "Isothermal, in vitro amplification of nucleic acids by a multienzyme reaction modeled after retroviral replication," *Proc. Natl. Acad. Sci. USA*, 1990, 87:1874-1878.
Hacia et al., "Detection of heterozygous mutations in *BRCA1* using high density oligonucleotide arrays and two-colour fluorescence analysis," *Nat. Genet.*, 1996, 14:441-447.
Huse et al., "Generation of a Large Combinatorial Library of the Immunoglobulin Repertoire in Phage Lambda," *Science*, 1989, 246:1275-1281.
Köhler and Milstein, "Continuous cultures of fused cells secreting antibody of predefined specificity," *Nature*, 1975, 256:495-497.
Kozbor and Roder, "The production of monoclonal antibodies from human lymphocytes," *Immunology Today*, 1983, 4:72-79.
Lewis, "PCR's Competitors Are Alive and Well and Moving Rapidly Towards Commercialization," *Genetic Engineering News*, 1992, 12(9):1, 3 pages.
Martin et al., "Structure and motility of primary cilia in the follicular epithelium of the human thyroid," *Virchows Archiv B Cell Pathol*, 1988, 55:159-166.
Prince et al., "Robust and Accurate Single Nucleotide Polymorphism Genotying by Dynamic Allele-Specific Hybridization (DASH): Design Criteria and Assay Validation," *Genome Res.*, 2001, 11:152-162.
Risinger et al., "Gene Expression Profiling of Microsatellite Unstable and Microsatellite Stable Endometrial Cancers Indicates Distinct Pathways of Aberrant Signaling," *Cancer Res.*, 2005, 65(12):5031-5037.
Schafer and Hawkins, "DNA variation and the future of human genetics," *Nat. Biotechnol.*, 1998, 15:33-39.
Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.
Takayama, "Single cilia formation in cells of the testicular interstitium in infertile men," *Int. J. Androl.*, 1981, 4:246-256.
Tilgmann and Kalkkinen, "Purification and partial characterization of rat liver soluble catechol-*O*-methyltransferase," *FEBS*, 1990, 264:95-99.
Underhill et al., "Detection of Numerous Y Chromosome Biallelic Polymorphisms by Denaturing High-Performance Liquid Chromatography," *Genome Res.*, 1997, 7:996-1005.
Ward et al., "The gene mutated in autosomal recessive polycystic kidney disease encodes a large, receptor-like protein," *Nature Genet.*, 2002, 30:259-269.
Ward et al., "Polycystin, the polycystic kidney disease 1 protein, is expressed by epithelial cells in fetal, adult, and polycystic kidney," *Proc. Natl. Acad. Sci. USA*, 1996, 93:1524-1528.
Weiss, "Hot Prospect for New Gene Amplifier," *Science*, 1991, 254:1292-1293.
Wheatley, "Cilia and centrioles of the rat adrenal cortex," *J. Anat.*, 1967, 101:223-237.
Winoto and Baltimore, "A novel, inducible and T cell-specific enhancer located at the 3' end of the T cell receptor α locus," *EMBO J.*, 1989, 8(3):729-733.
Hogan et al., "Expression analysis of *PKHDL1* and the encoded protein fibrocystin-L," *J. Amer. Soc. Nephrol.*, 2005, 16:P136A.
GenBank Accession No. AC021001 dated May 7, 2001, 60 pages.
GenBank Accession No. T43498 dated Jan. 21, 2000, 5 pages.
GenBank Accession No. NW_000106 dated Apr. 28, 2006, 2 pages.
GenBank Accession No. AB055648 dated Feb. 14, 2001, 6 pages.
Miller et al., "A Novel Polypeptide Secreted by Activated Human T Lymphocytes," *J. Immunol.*, 1989, 143(9):2907-2916.
Hogan et al., "*PKHDL1*, a homolog of the autosomal recessive polycystic kidney disease gene, encodes a receptor with inducible T lymphoycyte expression," *Hum. Mol. Genet.*, 2003, 12(6):685-698.
Wells, *Biochemistry*, 1990, 29(37): 8509-8517.
Ngo et al., "The protein folding problem and tertiary structure prediction, Chapter 14: Computational Complexity Protein Structure Prediction, and the Levinthal Paradox," 1994, pp. 433-440 and 492-495.
Bork, *Genome Research*, 2000, 10: 398.
Skolnick et al., *Trends in Biotech.*, 2000, 18(1): 34.
Doerks et al., *Trends in Genetics*, 1998, 14(6): 248.
Brenner, *Trends in Genetics*, 1999, 15(4): 132.
Phillips, *J. Pharm Pharmacology*, 2001, 53: 1169-1174.

* cited by examiner

ATGGGACACCTGTGGCTCCTGGGTATTTGGGGCCTCTGTGGGCTGCTCCTG
TGTGCCGCGGATCCCAGCACAGATGGCTCTCAAATAATCCCCAAAGTCAC
AGAAATAATACCTAAATATGGCAGTATAAATGGAGCAACAAGGCTGACTA
TAAGAGGGGAAGGTTTTTCTCAAGCAAACCAGTTTAACTATGGAGTTGAT
AACGCTGAGTTGGGAAACAGTGTGCAATTAATTTCTTCTTTCCAGTCAATT
ACTTGTGATGTAGAAAAAGATGCAAGTCATTCAACTCAAATTACATGCTA
TACTAGAGCAATGCCGGAAGATTCCTACACTGTTAGAGTCAGTGTGGACG
GGGTTCCTGTTACGGAAAATAACACCTGCAAAGGTCACATCAACAGCTGG
GAATGTACCTTCAACGCAAAAAGTTTTAGAACCCCAACAATAAGAAGCAT
CACACCTTTATCTGGAACTCCAGGTACACTAATAACAATCCAAGGCAGAA
TCTTCACTGATGTCTATGGAAGTAATATTGCACTAAGCTCAAATGGGAAA
AATGTTAGGATTTTGAGAGTTTACATTGGAGGAATGCCCTGTGAGCTTCTC
ATACCACAATCTGATAATTTATATGGTCTAAAACTGGATCATCCAAATGG
AGATATGGGTTCTATGGTTTGTAAGACGACTGGAACTTTTATTGGTCATCA
CAATGTCAGCTTCATCTTAGATAATGATTATGGAAGGAGTTTTCCACAGAA
AATGGCATATTTTGTTTCTTCTCAATAAAATTGCAATGTTTCAAACATA
TGCAGAGGTCACCATGATTTTCCCTTCACAAGGAAGCATTCGAGGTGGCA
CCACGCTGACAATAAGTGGGCGTTTCTTTGATCAGACAGATTTCCCCGTCA
GAGTTCTAGTTGGAGGTGAACCTTGTGATATTTTGAATGTCACAGAAAAT
AGTATATGTTGCAAGACACCCCCCAAACCTCATATTCTCAAAACTGTATAT
CCAGGAGGGAGAGGCCTGAAGCTTGAGGTGTGGAATAATAGCCGTCCAAT
ACGTTTGGAAGAGATACTGGAATACAATGAAAAAACGCCTGGGTACATGG
GTGCCAGTTGGGTAGATTCAGCTTCCTATATTTGGCTCATGGAACAAGACA
CATTTGTTGCACGCTTTAGTGGATTTTTGGTGGCTCCAGATTCTGATGTTTA
TAGATTCTACATCAAGGGTGATGACCGTTATGCTATTTATTTTAGCCAGAC
TGGACTTCCAGAAGATAAGGTGAGGATTGCATATCATTCTGCTAATGCCA
ACAGTTATTTTTCCAGTCCAACACAAAGATCAGATGATATTCATCTGCAGA
AAGGAAAAGAATACTATATTGAAATCTTGCTGCAGGAGTACAGATTAAGT
GCATTTGTTGATGTTGGACTGTACCAGTATCGAAATGTTTATACTGAACAA
CAAACAGGAGATGCAGTGAATGAAGAACAAGTTATCAAATCCCAGTCGA
CAATCCTCCAGGAAGTACAGGTTATAACATTGGAAAACTGGGAAACAACT
AATGCAATTAATGAGGTTCAGAAGATCAAGGTAACCAGCCCATGTGTGGA
AGCTAATTCATGTTCACTTTACCAATATAGATTAATCTATAATATGGAAAA
AACTGTCTTCCTACCTGCTGATGCTTCTGAATTCATACTGCAATCAGCCTT
GAATGACCTCTGGTCTATAAAACCGGACACAGTTCAAGTAATAAGAACAC
AAAATCCCCAGAGCTATGTCTACATGGTAACATTCATATCAACTAGAGGA
GACTTTGATCTGCTTGGTTATGAAGTAGTTGAAGGGAATAATGTCACACTG
GATATTACAGAACAAACCAAAGGAAAACCCAACTTGGAGACATTCACACT
GAATTGGGATGGGATCGCTTCTAAGCCACTCACTCTATGGTCATCAGAAG
CTGAATTTCAGGGAGCAGTGGAAGAAATGGTTAGCACTAAGTGTCCACCA
CAAATTGCAAATTTTGAAGAAGGATTTGTTGTGAAATATTTCAGAGACTAT
GAAACTGATTTTAATCTGGAACATATTAACAGAGGGCAGAAGACAGCTGA
AACCGATGCTTACTGTGGTCGTTATTCCCTGAAAAACCCAGCTGTTCTTTT
TGACTCAGCAGATGTTAAACCAAACAGACGACCATATGGAGATATTTTAT
TGTTTCCTTATAATCAGTTATGTTTAGCATACAAAGGATTCCTGGCAAATT

Figure 4B

```
ATATTGGTCTAAAATTTCAGTACCAAGACAATAGCAAGATTACTAGAAGC
ACTGATACACAGTTTACATACAACTTTGCTTATGGAAACAACTGGACTTAC
ACTTGCATAGACCTTCTGGATCTCGTAAGAACGAAATACACTGGGACAAA
TGTTTCTCTTCAGAGGATTAGCTTACATAAAGCATCAGAATCACAGTCCTT
CTATGTGGATGTAGTGTACATTGGACACACATCTACAATCTCAACATTGGA
TGAAATGCCCAAGAGAAGACTTCCTGCATTAGCAAATAAAGGAATATTCT
TAGAGCACTTTCAGGTGAATCAGACCAAAACAAATGGGCCAACTATGACA
AACCAATATTCTGTTACCATGACTTCATACAATTGCAGTTACAATATACCC
ATGATGGCTGTGAGCTTTGGGCAGATAATCACACATGAGACAGAGAACGA
GTTTGTCTACAGAGGAAATAATTGGCCAGGCGAGTCAAAAATTCATATTC
AAAGAATTCAAGCTGCATCTCCACCTCTAAGTGGCAGCTTTGACATTCAA
GCTTATGGACATATTCTTAAAGGCCTCCCCGCTGCTGTGTCAGCTGCAGAT
CTGCAGTTTGCACTCCAGAGTCTGGAGGGAATGGGAAGAATCTCAGTTAC
ACGAGAGGGAACCTGTGCTGGCTACGCGTGGAACATCAAATGGAGAAGC
ACCTGCGGAAAGCAGAATCTTCTACAGATTAATGATTCCAACATTATTGG
AGAAAAGGCTAATATGACAGTTACAAGGATAAAGGAAGGTGGCTTATTCA
GACAACATGTACTTGGAGACCTACTTCGTACACCCAGTCAACAGCCACAG
GTTGAAGTCTATGTCAATGGAATTCCAGCTAAATGTTCAGGTGACTGTGG
ATTTACATGGGATTCCAACATTACTCCCCTAGTCTTGGCGATAAGCCCTTC
TCAAGGGTCCTATGAAGAAGGCACAATTCTAACCATAGTGGGTTCTGGAT
TTTCTCCTAGTTCAGCTGTAACAGTCTCAGTTGGACCAGTAGGTTGTTCTC
TTCTTTCTGTGGATGAAAAGAGCTCAAGTGCCAGATTCTGAATGGAAGT
GCTGGACATGCCCCGTTGCTGTGTCCATGGCTGATGTTGGACTAGCACAG
AATGTAGGGGGTGAAGAGTTCTACTTTGTTTATCAGAGTCAGATCTCACAT
ATCTGGCCTGATTCTGGAAGCATAGCAGGTGGTACTCTACTGACTTTATCT
GGATTTGGCTTTAATGAAAATTCAAAGGTATTAGTTGGAAATGAAACCTG
CAATGTGATTGAAGGGGATTTGAATAGGATAACCTGCAGGACACCAAAAA
AAACTGAGGGTACAGTTGATATTTCAGTTACTACCAATGGATTTCAAGCC
ACAGCAAGGGATGCTTTTAGTTATAATTGTTTACAGACACCAATTATAACT
GATTTTAGTCCAAAAGTACGAACAATACTAGGAGAAGTTAATTTAACAAT
TAAGGGCTATAATTTTGGAAATGAACTCACACAAAACATGGCGGTGTATG
TTGGAGGAAAAACCTGCCAGATTCTTCACTGGAACTTCACAGATATTAGA
TGCCTTTTGCCCAAGTTGTCTCCTGGAAAACATGATATCTATGTAGAAGTC
AGAAACTGGGGTTTTGCATCAACAAGAGACAAATTAAATTCTTCAATACA
GTATGTTTTAGAAGTGACCAGCATGTTTCCACAAAGAGGCTCCTTGTTTGG
TGGAACTGAAATCACCATAAGGGGTTTTGGATTCAGCACAATACCAGCTG
AGAATACCGTGCTGTTAGGGTCCATCCCTTGCAATGTTACATCATCATCAG
AAAATGTCATAAAATGTATTCTTCATTCAACTGGGAATATATTCAGGATTA
CCAACAATGGGAAAGATTCAGTACATGGATTAGGTTATGCCTGGTCACCA
CCAGTCCTAAATGTGTCTGTGGGGACACAGTGGCATGGCATTGGCAAAC
ACATCCGTTTCTTAGAGGGATAGGATATAGGATTTTTTCTGTCTCCAGTCC
TGGAAGTGTAATTTATGATGGCAAAGGATTCACAAGTGGAAGACAAAAAT
CTACATCAGGTTCATTTCTTACCAATTTACTTCTCCTGGAATCCATTATTA
TAGCAGCGGGTATGTTGATGAGGCTCACTCCATTTTCTCCAAGGAGTCAT
TAATGTTTTACCAGCTGAAACCAGACACATTCCCTTGCACCTGTTTGTGGG
```

Figure 4C

```
TCGCTCTGAAGCCACATATGCTTATGGAGGACCTGAGAATTTGCACTTGG
GAAGCTCTGTGGCAGGCTGCCTAGCAACAGAACCCCTGTGCAGCCTGAAC
AATACCAGGGTTAAAAATTCAAAAAGATTGCTATTTGAGGTTTCAAGTTG
TTTTTCACCATCTATAAGCAACATTACTCCGTCCACTGGAACAGTAAATGA
ACTAATAACAATTATTGGACATGGCTTTAGTAATCTCCCATGGGCTAATAA
GGTTACAATTGGTAGCTACCCCTGTGTCGTAGAAGAAAGTAGTGAGGATT
CAATTACATGTCATATTGACCCTCAAAACTCAATGGATGTTGGTATCAGGG
AAACTGTCACTTTGACTGTCTACAACCTGGGCACTGCTATCAATACGTTGT
CCAATGAATTTGATAGGCGATTTGTACTTTTGCCAAACATTGACCTGGTGT
TGCCAAATGCAGGATCAACTACAGGAATGACAAGCGTGACCATAAAAGG
CTCTGGATTTGCCGTTTCTTCTGCAGGTGTAAAAGTCCTTATGGGTCATTTC
CCATGTAAAGTTCTATCAGTGAATTATACGGCCATTGAATGTGAAACATCC
CCTGCTGCCCAACAGCTTGTGGATGTAGATCTTCTAATACATGGAGTGCCT
GCCCAGTGCCAGGGAAACTGCACCTTTTCATACTTAGAAAGCATCACTCCT
TACATAACAGGAGTCTTCCCAAACTCTGTCATAGGATCTGTAAAAGTTCTT
ATTGAAGGAGAAGGTTTGGGGACTGTTTTGGAGGACATTGCTGTTTTCATT
GGAAATCAACAGTTCAGAGCAATAGAGGTTAATGAAAACAACATCACTGC
TCTTGTGACTCCTCTCCCAGTTGGACATCATTCTGTTAGTGTTGTGGTGGG
AAGTAAAGGCTTGGCTCTGGGAAACCTGACTGTCAGCAGCCCCCCAGTAG
CATCTCTATCACCAACTTCTGGAAGCATTGGTGGTGGAACTACACTGGTGA
TCACAGGAAATGGCTTCTATCCAGGCAACACTACAGTCACTATTGGGGAT
GAACCTTGTCAAATTATTTCCATCAACCCCAATGAAGTCTACTGCCGCACT
CCCGCTGGGACCACTGGAATGGTCGATGTTAAAATCTTTGTTAATACAATT
GCTTATCCACCTTTGCTTTTTACATATGCCCTGGAGGATACTCCATTTCTCA
GAGGAATTATCCCAAGCAGAGGTCCACCAGGAACTGAAATTGAGATCACT
GGATCCAACTTTGGCTTTGAGATCTTGGAAATCTCCGTGATGATAAATAAC
ATTCAGTGTAATGTAACCATGGCCAATGATAGTGTGTTGCAGTGCATCGTG
GGAGATCATGCTGGGGGCACATTTCCTGTTATGATGCATCATAAGACAAA
AGGCTCAGCCATGTCCACAGTTGTATTTGAGTACCCGCTTAATATTCAAAA
TATTAATCCAAGCCAAGGGAGCTTTGGTGGGGGTCAAACCATGACTGTGA
CAGGCACCGGATTTAATCCACAAAATTCAATTATATTAGTTTGTGGCTCAG
AATGTGCAATTGACAGGCTTAGATCTGATTACACAACACTATTATGTGAA
ATTCCATCTAATAATGGCACGGGAGCTGAGCAAGCCTGTGAAGTGAGTGT
GGTTAATGGGAAAGATTTGTCACAGTCCATGACTCCGTTTACGTACGCAGT
GTCACTGACTCCACTCATCACTGCAGTATCTCCTAAGAGAGGCAGTACAG
CAGGGGGCACCAGACTGACAGTCGTGGGATCAGGATTCAGTGAAAATATG
GAGGATGTTCATATCACCATAGCTGAAGCCAAATGTGATGTTGAGTATTC
CAACAAGACACACATCATCTGCATGACAGATGCCCATACTCTATCAGGGT
GGGCTCCAGTTTGTGTCCACATCAGAGGTGTCGGCATGGCCAAACTGGAT
AATGCTGACTTTCTTTATGTTGATGCCTGGTCCTCCAATTTCTCATGGGGG
GGAAAATCTCCCCCAGAAGAAGGATCTCTTGTTGTTATTACAAAAGGACA
GACCATTCTCCTGGATCAAAGCACCCCTATTTTGAAAATGTTGCTTATTCA
GGGTGGGACTCTAATATTTGATGAAGCTGACATTGAACTCCAGGCAGAAA
ATATTCTAATTACAGATGGAGGTGTTCTTCAGATTGGAACAGAGACATCC
CCATTCCAACACAAGGCTGTCATTACCTTGCATGGTCACCTGCGATCTCCT
```

Figure 4D

GAGCTCCCTGTCTATGGTGCCAAAACACTGGCTGTGCGGGAGGGAATCCT
GGATCTGCACGGTGTGCCTGTTCCTGTGACCTGGACTCGCTTGGCTCATAC
TGCAAAGGCAGGGGAAAGAATTTTAATTTTACAAGAAGCAGTAACATGGA
AACCAGGAGATAACATTGTAATTGCAAGCACAGGACACAGACACAGTCA
AGGAGAGAATGAAAAAATGACCATTGCATCTGTGTCTGCTGATGGCATAA
ACATAACACTAAGTAACCCACTAAATTACACACACTTAGGAATTACGGTC
ACACTCCCTGATGGAACTCTGTTTGAAGCAAGAGCAGAAGTTGGAATTCT
TACAAGAAATATTTTAATAAGAGGATCTGATAATGTTGAGTGGAATAACA
AAATTCCTGCATGTCCTGATGGATTTGACACAGGAGAATTTGCTACACAG
ACCTGTCTCCAAGGAAAGTTTGGAGAAGAAATAGGAAGTGACCAATTTGG
AGGCTGCGTTATGTTTCATGCTCCTGTACCTGGTGCTAACATGGTAACTGG
GAGAATAGAATATGTAGAGGTATTCCATGCTGGCCAGGCTTTCCGGTTGG
GGCGATATCCAATACATTGGCACCTGCTTGGAGACTTACAGTTTAAATCTT
ATGTAAGAGGCTGTGCAATTCACCAGGCCTATAACAGAGCTGTTACTATT
CATAACACACACCATCTTCTGGTTGAGAGGAATATTATATATGATATTAAG
GGAGGAGCATTTTTTATAGAAGATGGTATTGAACATGGCAATATCCTCCA
GTATAACTTGGCAGTATTTGTACAGCAAAGTACCAGTCTTCTGAATGATGA
TGTGACCCCGGCTGCATTTTGGGTCACCAACCCGAACAATACCATACGAC
ACAATGCTGTTGCTGGTGGCACTCACTTTGGCTTTTGGTACCGGATGAACA
ACCACCCTGATGGGCCATCCTATGACAGAAACATTTGTCAAAAAAGAGTT
CCCCTTGGCGAATTTTTTAACAATACTGTCCATTCTCAAGGTTGGTTTGGA
ATGTGGATCTTTGAGGAATATTTCCCCATGCAAACGGGATCTTGTACATCT
ACAGTGCCTGCGCCTGCAATATTTAACTCACTTACTACTTGGAATTGTCAA
AAAGGAGCTGAATGGGTCAATGGAGGTGCCCTTCAGTTCCATAACTTTGT
GATGGTGAATAACTATGAGGCTGGAATTGAGACTAAGAGGATCCTGGCTC
CTTATGTTGGAGGGTGGGGTGAAACCAATGGAGCGGTGATTAAAAATGCC
AAAATAGTCGGCCATCTTGATGAACTGGGAATGGGGTCTGCATTTTGCAC
AGCAAAAGGCCTGGTTCTCCCATTTAGTGAAGGCTTGACTGTCTCTTCTGT
GCACTTTATGAACTTTGACCGTCCCAACTGTGTAGCTTTGGGAGTGACATC
CATCTCTGGAGTTTGTAATGACAGATGTGGGGGTTGGAGTGCAAAGTTTG
TTGACGTCCAGTATTCTCACACACCGAACAAGGCTGGCTTTCGCTGGGAA
CATGAAATGGTAATGATTGATGTTGATGGCTCACTTACAGGGCACAAAGG
ACATACCGTCATTCCACACAGCTCATTGCTAGACCCTTCTCATTGTACTCA
GGAAGCTGAGTGGAGCATTGGGTTCCCTGGATCAGTCTGTGATGCTTCAG
TCAGCTTTCACCGTTTAGCGTTCAACCAGCCTTCTCCAGTATCTCTGCTTGA
AAAGGATGTGGTTCTTTCAGACTCTTTTGGCACAAGCATTATTCCATTTCA
GAAGAAACGACTGACTCATATGTCTGGATGGATGGCTCTGATTCCAAATG
CAAATCACATTAACTGGTATTTTAAAGGTGTGGATCACATAACCAACATTT
CATATACATCGACATTCTATGGATTCAAGGAAGAAGACTATGTAATTATA
TCACATAACTTCACTCAAAATCCTGACATGTTTAATATTATTGATATGAGG
AATGGTTCCTCAAATCCATTGAATTGGAATACTAGCAAGAATGGGGACTG
GCACCTTGAAGCAAACACTAGTACTCTATATTACTTGGTGTCAGGAAGAA
ATGACCTTCATCAGAGTCAGCTCATTTCTGGGAACCTGGATCCTGATGTGA
AAGACGTTGTTATTAATTTCCAAGCTTACTGTTGTATTCTCCAGGATTGCTT
TCCTGTACATCCGCCATCAAGAAAACCAATTCCCAAGAAGCGACCAGCCA

Figure 4E

CATATAATTTATGGTCAAATGATTCTTTTGGCAATCATCACGAGAAAATA
ATTATACTGTACCTCACCCAGGGGCAAATGTGATTATACCTGAAGGAACA
TGGATTGTAGCTGACATAGATATGCCATCAATGGAAAGACTCATTATTTG
GGGGGTTCTAGAACTGGAAGATAAATACAATGTAGGAGCTGCAGAATCTT
CTTACAGAGAAGTTGTTTTGAATGCTACCTACATATCACTGCAGGGAGGT
AGATTAATCGGTGGCTGGGAAGATAACCCTTTTAAAGGAGACTTAAAGAT
TGTTCTTAGAGGAAATCATACTACACAAGACTGGGCTCTTCCAGAAGGAC
CAAATCAAGGGGCAAAGGTCTTAGGGGTGTTTGGTGAGCTGGATCTTCAT
GGAATTCCACATTCAATATATAAAACTAAGCTCTCAGAAACTGCATTTGC
AGGTTCCAAAGTCCTGTCTCTGATGGATGCTGTGGATTGGCAGGAGGGAG
AAGAGATTGTGATAACAACCACAAGCTACGATTTCCACCAGACAGAAACA
AGAAGTATCGTTAAAATCCTGCATGATCATAAAATTCTCATTCTTAATGAT
AGCCTTTCCTATACTCACTTTGCTGAAAAATACCATGTCCCTGGAACTGGT
GAGAGCTACACGTTAGCAGCTGATGTTGGGATACTGAGTAGGAACATCAA
AATAGTTGGTGAAGATTACCCCGGTTGGTCTGAGGACTCTTTTGGAGCAC
GCGTACTGGTTGGCTCATTCACTGAAAATATGATGACATTTAAAGGAAAT
GCAAGAATAAGTAATGTGGAATTTTATCACAGTGGTCAAGAAGGCTTCAG
GGATAGCACAGATCCAAGATATGCTGTAACGTTTCTTAACCTAGGACAGA
TTCAAGAACATGGCTCATCTTATATTCGAGGCTGTGCTTTTCACCATGGCT
TCTCTCCAGCAATTGGTGTATTTGGGACAGATGGATTGGACATAGATGAC
AACATCATTCACTTTACAGTGGGGAAGGCATAAGAATATGGGGAATGC
CAACCGAGTCCGAGGGAATTTGATTGCACTTTCGGTTTGGCCAGGAACCT
ATCAGAACAGAAAAGATTTAAGTTCAACTCTCTGGCATGCAGCAATTGAG
ATAAATAGAGGGACCAATACAGTTTTACAGAATAATGTAGTGGCTGGATT
TGGAAGAGCAGGATACCGCATTGATGGTGAACCTTGCCCAGGCCAGTTTA
ATCCTGTGGAAAAGTGGTTTGACAATGAAGCCCATGGAGGTTTATATGGG
ATCTATATGAACCAAGATGGCCTTCCTGGATGTTCTCTTATACAAGGATTT
ACCATTTGGACATGCTGGGATTATGGAATTTATTTTCAGACCACAGAGAGT
GTGCACATTTATAATGTGACCCTGGTTGACAATGGAATGGCCATTTTTCCA
ATGATTTACATGCCAGCTGCTATATCACACAAAATTTCCAGTAAAAATGTA
CAAATTAAGAGCTCATTAATTGTTGGAAGTAGCCCTGGGTTTAATTGCTCT
GATGTCCTAACTAATGATGATCCTAATATTGAACTCACTGCTGCTCATCGG
AGTCCTAGATCTCCATCAGGTGGGAGAAGTGGGATTTGTTGGCCTACCTTT
GCTTCAGCTCATAACATGGCACCCCGAAAGCCCCATGCAGGAATCATGAG
TTACAATGCCATCAGTGGCCTTTTGGACATCTCAGGTTCAACATTTGTTGG
ATTTAAGAATGTTTGTTCAGGGGAAACTAATGTTATATTCATTACTAACCC
TTTAAATGAGGATTTACAGCATCCAATCCATGTGAAGAATATAAAACTGG
TTGATACCACTGAACAATCAAAAATATTTATACATAGGCCTGATATAAGT
AAGGTCAATCCATCTGATTGTGTAGACATGGTTTGTGATGCCAAGAGGAA
ATCTTTTCTTAGAGACATAGATGGCTCCTTTCTGGGGAATGCTGGTTCTGT
GATACCTCAAGCAGAATATGAATGGGACGGAAACAGCCAAGTAGGAATT
GGAGACTACAGAATTCCTAAGGCGATGCTCACATTCTTGAATGGAAGTAG
AATTCCTGTCACTGAGAAAGCACCTCATAAAGGAATTATTAGAGATTCAA
CCTGTAAGTACCTTCCAGAGTGGCAGAGCTATCAGTGCTTTGGGATGGAA
TATGCAATGATGGTTATTGAAAGTCTGGATCCTGACACAGAAACTCGAAG

Figure 4F

ACTTTCCCCAGTGGCTATAATGGGCAACGGTTATGTTGATCTTATTAATGG
CCCACAGGATCATGGCTGGTGTGCTGGATATACATGCCAGAGAAGGCTGT
CCCTGTTTCACAGCATTGTGGCTCTGAACAAATCTTATGAAGTTTACTTCA
CTGGCACCAGTCCTCAGAATCTTCGACTGATGTTGCTTAATGTTGATCATA
ACAAGGCTGTTCTAGTAGGAATTTTCTTTTCCACACTTCAACGTTTGGATG
TCTATGTGAACAACTTATTGGTCTGTCCAAAAACTACAATATGGAATGCCC
AGCAGAAACACTGTGAACTTAATAACCATCTGTACAAAGACCAATTCCTT
CCTAACCTGGATTCCACTGTCCTTGGTGAAAACTACTTTGATGGAACCTAC
CAGATGCTTTATCTTTGGTTAAAGGAACTATACCTGTTGAAATTCACACT
GCCACAGTGATATTTGTTTCTTTCCAATTATCTGTTGCAACAGAAGATGAC
TTTTATACCTCTCACAATCTGGTTAAAAATCTTGCCTTGTTCCTAAAGATA
CCAAGTGACAAAATCCGTATCAGCAAAATAAGAGGGAAGAGTCTGAGGA
GGAAGAGATCCATGGGATTCATAATTGAAATAGAGATTGGAGACCCTCCT
ATTCAGTTCATAAGCAATGGCACCACAGGTCAGATGCAGTTATCTGAACT
CCAGGAAATTGCTGGTTCTCTTGGACAAGCTGTAATTTTAGGAAACATCA
GTAGTATCCTTGGATTTAACATTTCGTCCATGTCTATTACTAATCCCCTCCC
CAGCCCAAGTGACTCTGGGTGGATTAAGGTGACTGCCCAGCCAGTTGAAA
GGTCTGCATTTCCTGTTCATCACGTGGCCTTCGTGTCCTCACTCTTAGTGAT
CACTCAGCCGGTGGCAGCACAGCCAGGACAGCCATTTCCTCAGCAGCCTT
CGGTAAAGGCAACAGATTCTGACGGTAACTGTGTATCAGTTGGAATTACT
GCACTAACTTTGAGGGCCATACTCAAGGACTCCAATAATAACCAAGTCAA
TGGCCTTAGTGGAAATACAACAATTCCGTTTAGCAGCTGTTGGGCCAACT
ACACAGACCTTACTCCCCTTAGAACAGGAAAAAATTATAAGATTGAATTT
ATACTGGATAATGTTGTTGGGGTAGAATCCAGAACTTTCAGCCTGCTGGC
AGAGTCTGTCTCTAGCAGTGGCAGCAGCAGCAGCAGCAACAGCAAAGCAT
CAACTGTGGGTACATATGCCCAGATAATGACTGTAGTAATTAGCTGTCTG
GTTGGAAGAATGTGGCTCTTGGAAATATTTATGGCTGCAGTTTCAACTTTG
AATATAACTTTAAGAAGCTACTAA (SEQ ID NO:1)

Figure 5A

ATGGGACACCTGTGGCTCTCAGGGACCTGGTTTCTCTTTGGGCTGCTTTGG
TGTGCAGCAGATTCCCACAAAGGTAGCTCTGAGACAATTCCCAAAGTGAC
AGAAGTTATACCTAAATATGGCAGCATAAACGGAGCAACAAGACTGACC
ATCAAGGGAGAAGGTTTTTCTCAAGCAAGTCAGTTCAACTATGGAGCTGA
CAATACTGAATTGGGAAACCATGTGCAATTAGTTTCTTCTTTCCAGTCGAT
TACTTGTGATGTGGAAAAAGATTCAAGTCATTCAACTCAAATTACATGCTA
TACTCGAGCAATGCCAGAAGACACCTACTCTGTTCGAGTCAGTGTGGATG
GAGTGCCAGTTGCAGAAAATAACACTTGTAAAGGGGTTGCCAGCAGCTGG
GCATGTAGTTTCAGTACAAAAAGTTTTAGAACCCCCACAATAAGGAGCAT
CACACCTTTATCTGGAACTCCAGGTACATTAATAACAATTAAAGGCAGGC
TCTTCACTGATGTCTATGGAAGTAATACAGCACTGAGCTCAAATGGAAGA
AATGTTAGGATTCTAAGAATTTATATCGGAGGAATGCCCTGTGAACTCCTC
ATACCACATTCTGATGATTTGTATGGTCTAAAACTCGATCATGCCAATGGA
GATACAGGGTCTGTGACATGTAAGACCACTGGGACTTACATTGGTCACCA
CAATGTCAGCTTCATCTTAGATAGTGATTATGGAAGGAGTTTCCCAGAGA
AAATGACATATTTTGTTTCATCTCTCAATAAAATTTCAATGTTTCAAACAT
ATCCAGAGGTCGTGATGGTCTCACCATCAAAAGGCAGCACTGAAGGTGGC
ACCCTATTGACAATACACGGGCACTTCTTCGATCAGACTGATCTCCCAGTG
AGAGTGCTAGTTGGAGGTCAAGCCTGTGCTATTTTGAATGTCACAGAAAA
TACTATATACTGCAAGACTCCTCCCAAACCACACATCCTCAAAGCTACATA
TCCAGGTGGAAGAGGCCTAAAGGTTGAGGTCTGGAATAATAGCCGGCCAG
CACATCTTGAAGATATACTTGAATACAATGAGCATACCCCAGGGTACATG
GGTGCCACTTGGACGGATTCTGCTTCCTATGTTTGGCCTATAGAACAAGAC
ACATTTGTTGCACGCATCAGTGGATTTTTGGTGCCCCAGATTCTGATGTT
TACAGGTTTTATATCAGAGGTGATGACCGCTATGCTATTTATTTCAGCCAA
ACTGGGCGCACAGAAGACAAGGTGAGGATTGCGTATTACTCTGGAAATGC
CAACACTTATTTTTCAAATTCAACACAAAGATCAGATGAGATTCATCTTCA
GAAAGGAAAAGAGTATTACATTGAAATCTTGCTGCAAGAGTATACATTAA
GTGCTTTTGTTGATGTTGGACTGTACCAGTATAAAAATGTCTTTACTGAAC
AGCAGACAGGAGATGCACTAAATGAAGAACAAGTCATCAAATCTCAGTC
AACAGTTGTCCCCGAAGTACAGATTATAACATTGGAAAACTGGGAGACAG
CTGATGTGACTAATGAAGTCCAGCAGGTCACAGTAACCAGCCCGTGTGTG
GGAGCTAACTCATGTTCCCTTTCCCAATACAGATTCATCTACAACATGGAA
AAGACTGTCTGGCTGCCCGCTGATGCTTCTGACTTCACGTTGAAATCAGCT
TTAAATGACCTTTGGTCTATAAAGCCAGATTCAGTTCAAGTGACCAGCAA
GAGGGATCTCCAGAGCTATATCTACACAATAACCTTTGTATCAACTAGAG
GAGACTTTGATCTGCTTGGTTATGAAGTATTTGAAGGAAGTAATGTCACGC
TGAGTATCACAGAACAAACCAAAGGAAAACCCAATTTGGAGACGTTTACA
TTAAACTGGGATGGGATTGCTTCTAAGCCCCTTACCCCAGAGTCATCGGA
AGCTGAATTTCAGGTAGCAGTGGAAGAGATGGTGAGTGCCAAGTGTCCGC
CGGAAATAGCACATTTGGAAGAAGGATTTCTAGTGAAATACTTCAGAGAC
TACGAAACTGATTTTGAACTGGAGCATATTAATAGAGGGCAGAAGACGGC
CGAAACAGATGCATATTGTGGCCGTTACTCCCTGAAAAACCCAGCTGTAC
TTTTTGACTCGACAGATGTTAAGCCAAACAAATCACCATATGGAGACATTT
TATTATTTCCTTATAATCAGTTGTGTTTAGCATACAAAGGATCTCTGGCCA
ACTTCATTGATCTCAAGTTCAAGTACCAAGACAGTGGCAAGATCATTAGA

Figure 5B

AGTGCTGATGTACAATTTGAATATAACTTTGCTTCTGGAAATAAGTGGACT
TACACTTGCATAGATCTTCTAGATTTCTTACAAACCAAATATGCTGGGACG
AGTTTTCTCTACAAAGGATTACCTTACAAAAATCGTCAGAATTCCAGTCC
ATTTATGTGGATGCAGTGTACATTGGACAGACACCTACAGTCTCTGTCTTG
GATGATATGCCAAAGAGGAGACCTCCAGCACTAGCAAACAAAGGAATAT
TTTTAAAGCATTTTCAGGTTAATCGGACCAAATTAAATGGATCAGCTATGA
CAATTCAGTATTCAGTTACCATAACTTCATATAACTGCAGTCATAATATAC
CTATGATGGCTGTGAGCTTTGGACAGATAATCACAAATGAGACCAAGAAT
GAGTTGGTTTACAGAGGAAATAATTGGCCAGGGGAGTCAAAGATTCGTAT
TCAAAAAATTCAGGAAGCTTCTCCACCTATAAGCGGCAGCTTTGATGTTCA
AGCTTATGGACATACCCTGAAAGGCATCCCTGCTGCTGTGCCAGCTGCAG
ACTTGCAGTTTGCTCTGCAAAGCCTGGAAGAAATAGAACAAGTCTCAGTA
AACAGAGAAGGAACCTGTGCTGGCTATTCATGGAGCATCAGATGGACAAG
CCCCCGTGGAAAGCAACCTCTTCTGCAGATCAATGATTCCAACATTATCGG
AGAAAAGGCTAATGTAACAGTTACCACAATAAAGGAAGGTGGCTTATTTA
GACAACGTATCCCTGGAGACATGCTTCGTACACTGAATCAGCAACCACAG
GTTGAAGTCTATGTCAATGGAATTCCAGCCAAATGTTCAGGTGACTGTGG
GTTTACATGGATGCCATGATTACTCCCTGATCTTGACAACAACACCTTC
CGAAGGATCCTATGCAGAAAGCACGATTCTAACCATAGCAGGCTCTGGAT
TTTCTCCCACCTCAGCTGTATCCGTCTCTGTTGGTTCTACCAGATGCTCTCT
TCTCTCTGTGGAGGAAAATGAGATCAAGTGCCAGATTCTGAATGGAAGTG
CTGGACATGTACCAGTTGCTGTGTCCATTGCTGATGTTGGACTAGCACAGA
ATCTAGAGGGTGAGGGATCCCACTTCATTTATCGGAGTCAGATCTCACAT
GTCTGGCCTGATTCTGGAAGCCTGGCAGGTGGTACTCTGCTGACAATATCT
GGATTTGGTTTTAGTGAAAATTCAACAGTTTTAGTTGGAAATGAAACCTGC
AATGTGATCGAAGGAGATTTGAATAGGATAACCTGCAGAACATCAAAAA
GAATTGAGGGTACAGTTGATATTTCTGTCATTACCAATGGAATTCAAGTCA
CAGCAAAGGACAGTTTTAGTTACAGCTGCTTACAAACACCAGTTGTCACT
GACTTCAGCCCAAAAGAACGGACAGTTCTGGGAAAGGTCAATTTAACAAT
TAAAGGTTATAACTTTGGAAATGAACTCGCACAAAATACGGTGTATGTTG
GAAGAAAGCACTGCCAGGTACTTCACTCAAACTTCACAGACATTACATGC
CTTTTGCCCACGTTACCTCCAGGAAAACATGATATCTATGTGAAAGTCAGA
AACTGGGGTTTGGCGTCAACAAGGAACAAGTTAAATGCTTCCATACTGTA
CATTTTGGAAGTCATCCACATGTTTCCCCAGAGAGGCTCTTTGTATGGTGG
CACTGAAATCACTATAATGGGTTTTGGGTTCAGCACAATACCAACTGAGA
ATTCTGTTCTCTTAGGCTCCTTCCCATGTGACATTACATCATCAGAAA
ATGTCATCAAATGTACTCCATTCAACAGGGACAGTATTCAGAATTACCA
ACAACGGTTCACATTTAGTGCATGGACTAGGTTATGCCTGGTCACCATCAG
TCTTAAATGTGACTGTGGGCGATACCGTGGTGTGGTCCTGGCAAGCACAC
CCCTTTCTTAGGGGTATAGGGTACAGAATTTTCTCAGTCTCCAGTCCCGGA
AGTGTAACTTATGATGACAAAGGATTTACAAATGGGAGACAAAAATCTGC
ATCCGGTTCATTTTCTTACCAGTTTACTTCCCCTGGAATCTATTACTACAGC
AGCGGGTATGTTGATGAGGCTCACTCCATATCTCTCCAAGGAGTCATTAAT
GTTTTTCCAGCTGAAGCCAGGCACATTCCCCTGTACCTGTTTGTGGGAAAC
ATTGAGGCGACATATGTTCCAGCAGGCCCTGCGCATTTACAGTTGGCAAG
TACTGCAGCAGGCTGCCTAGCAACAGAACCCCTGTGTGGTCTGAATGATA

Figure 5C

CAAGGGTTAAACATTCAAATAAATTATTCTTCGAGCTTTCAAATTGCATTT
CACCCTCTATCATCAACATTACTCCCTCTACCGGAACAGCAAATGAACTTA
TAACTATCATTGGACATGGCTTCAGTAGTCTTCCATGTGCTAATAAGGTTA
CAATTGGTAGCTACCCTTGTGTTGTAGAAGAAAGTAGTGAAAATTCTATTA
TATGTCATATTGACCCACAAAACTCAATGAATGTTGGCATTAGAGAAATT
GTTACTTTGATTGTCTACAACCTGGGCACTGCTATCAACACACTGACCAAA
GCATTTGACAGGCGGTTTGTACTTTTGCCAAACATAGATATGGTGATGCCA
AAAGCAGGGTCAACTACAGGAATGACAAGGGTAACCATACAAGGCTCTG
GATTTATGTCTTCTCCTGAAGGTGTAGAAGTCTTTATGGGTGATTTCCCAT
GTAAAGTTCTATCTGTGACCTACACAGCTATTGAATGTGAAACATCTCCGG
CTCCCCAACAGCTTGTTCTTGTAGACATTCTAATACATGGAGTGCCTGCCC
AATGTCAGAGCAACTGCAGCTTTTCATATTTAGAAAACATTGCTCCCTATG
TAACAGGAATCTTCCCAAACTCAATCCAAGGATATGGAAATGTCCTCATC
AAAGGAGAACGTTTTGGGACAGTGTTGGAAGAGATTTCTATATTTATTGG
AAGTCAGCAATTCAGAGTAATAGATGTTAATGAAAATAATATTACTGTCC
TCATGACTCCACTAGAAGCTGGACTTCATTCTCAGTGTTGTTGTTGGGT
CTAAGGGCTTGGCTCTAGGAAATCTAACCATCAGCAGCCCTGCAGTAGCT
TCTGTCTCACCAACCTCTGGAAGCATTGCTGGTGGAACGACTTTGATGATA
ACAGGCAATGGATTTTCTCCTGGAAACACCACAGTTACTGTTGGGGATCA
GCCTTGTCAAATTACGTTCATCAGCTCCAGTGAGGTCTACTGTAGCACCCC
AGCTGGGAGAGCTGGTACAGCCAATCTGAAGATTAGTGTCAATGCGATCA
TCTACCCACCTTTGTCATTTACATATGCCATGGAAGATACTCCATTTCTCA
AAAGAATCATCCCTAATAGAGGTCTACCAGGAACTGAAGTTGAAATAACT
GGGTCTAATCTTGGATTTGCTATCTCCGATGTTTCAGTGATGATAAAAGAG
AGTGTATGTAATGTGACCACTGTCAATGACACTGTGTTACAGTGCACTGTG
GGAGAGCATGCAGGGGGCATTTTCCCTGTGACGATGCTTCATAAGACAAA
AGGCTCTGCTGTCTCCTCTGTTGCATTTGAGTACCCACTTTCTATTCAGAAT
ATTTATCCAACACAAGGGAGCTTTGGTGGTGGGCAAACCTTGACTGTGAC
AGGCATGGGATTTGATCCATGGAATTCAACCATATTGGTCTGTAACTCTGA
ATGTGCAGTTGACAAACTAAGATCTAACTCTACAACACTGTTCTGTGTGAT
TCCTCCTAACAATGGCAAGGGACATGATCAAGTCTGTGGAGTGAGTGTGG
TCAACGGGAAAGACTCATCTCATTCCACGAAGCTATTTACATACACCTTGT
CGCTGACTCCCCTCATCACTGAAATATCTCCCAGGAGAGGCAGCACTGCT
GGGGGCACCAGGCTTACAGTCACAGGATCTGGATTCAGTGAAAACACACA
GGGTGTTCAAGTCTTCGTAGGCAACAGCAAATGTGATATCCAATATTCCA
ACAAGACACATATCGTCTGCATGACAAGTGTTCATGTTCCTTCAGGATGG
GTTCCAGTTCATGTCAACATCAAAAACATCGGCCTGGCCAAATTGGAGAA
TGCTGACTTCTTATATGCCGATGTTTGGTCTGCCAACTCCTCATGGGGAGG
AAGTCCACCACCAGAGGAAGGATCACTTGCCGTTATTACAAAAGGGCAGA
TAATTCTGCTGGACCAAAGTACTCCTATTCTTAAAATGTTACTCATTCAAG
GTGGGACTCTGATATTTGATGAAGCTAATATTGAACTCCAGGCAGAAAAT
ATCCTAATCACAGATGGGGCGTACTTCAGATTGGGACAGAAGCATCCCC
GTTCCAACACCGGGCTGTCATTACTCTTCATGGGCATCTTAGATCTCCTGA
GCTCCCTGTATATGGAGCTAAGACATTGGGAGTACGTGAGGGCACACTGG
ATCTTCACGGTCTGCCTATTCCTGTGGTCTGGACTCGCTTGACCCATACGG
CAAATGCAGGAGAATGGACTTTAACTGTACAAGAAGCAGTGACATGGAA

Figure 5D

GGCAGGAGATAACATTGTGATTGCAAGCACAGGACACAGACACAGCCAA
GCAGAGAATGAGAAGCGGACCATCGCGTCGGTGTCCGCTGATGGAATGCA
CATAACCTTAACTAAGCCACTCAACTACACACACTTGGGAATTACCACCA
CACTTCCCGATGGAACTGTGTTTGAAGCCAGGGCAGAAGTTGGAATTCTT
ACAAGAAATATTTTAATAAGAGGGTCTGATAATGTGGAGTGGAATGACAA
GATTCCATCATGTCCCGATGGATTTGATACAGGAGAATTTGCTACACAGA
CATGCCTTCAAGGAAAGTTTGGAGAAGAAATGGGAAGTGACCAGTTTGGA
GGCTGTATTATGTTGCATGCTCCCTTACCTGGGGCTGACATGGTAACTGGA
AGAATAGAATACGTAGAGGTGTTCCATGCTGGTCAATCTTTCCGTTTGGGA
CGATACCCAATACATTGGCACCTGCTTGGAGATTTACAGTTCAAATCCTAT
GTGAAAGGCTGTGCAATTCATCAATCATACAACAGAGCTATTACAATCCA
CAATACGCATCACCTTCTTGTGGAGAGGAATATTATATATGATATAAAAG
GAGGAGCATTTTTCATAGAAGATGGTATTGAACATGGCAACATTCTGCAA
TATAATCTGGCAGTCTTTGTACAGCAAAGTACCAGTCTACTGAATGATGAT
GTGACCCCAGCTGCATTCTGGGTAACCAATCCTAACAACACCATTCGACA
CAATGCGGCTGCTGGGGGCACTCACTTTGGCTTTTGGTACAGAATGAATG
ACCACCCTGATGGCCCATCTTTTGACCGAAACATTTGCCAAAAACGAATTC
CGCTTGGAGAATTCTTTAACAATACTGTTCATTCTCAGGGGTGGTTTGGAC
TGTGGATTTTTGAAGAGTATTTCCCCATGCAAACAGGATCTTGTACCTCTA
CAGTGCCAGTGCCTGCCATCTTTAACTCACTCACTGTGTGGAACTGTCAAA
AAGGAGCTGAATGGGTGAACGGAGGGGCCCTGCAGTTCCACAACTTTGTG
ATGGTGAACAACAATGAGGCTGGCATTGAGACCAAGAGGATCCTGGCTCC
CTATGTTGGAGGATGGGGGGAAAGCAATGGAGCTGTGATTAAAAATGCCA
AAATCGTTGGTCATCTTGATGAGCTGGGAATGGGACCCACATTTTGCACTT
CAAAAGGCCTGGTTCTCCCATTTAGTCAAGGCCTGACTGTGTCGTCTGTGC
ACTTTATGAATTTTGACCGCCATGCCTGTGTGGCTTTAGGAGTAACATCAA
TCACTGGGGTGTGTAATGACAGATGTGGAGGCTGGAGTGCTAAGTTTGTT
GGCATCCGGTATTTTCATGCACCCAATAAGGGTGGTTTTCGTTGGGAACAC
GAAGCAGTACTGATTGACGTTGACGGCTCACTAACAGGGCACAGAGGGCA
CACTGTCGTTCCACACAGCTCCTTACTGGACCCTTCACACTGTACTCAAGA
GCCTGCATGGAGCATTGGTTTTCCTGGCTCCATCTGTGATGCCTCTGTCAG
CTTCCACCGGCTAGCATTCAACAAGCCTTCCCCAGTATCTTTACTTGAAAA
AGATGTGGTTCTTTCAGACTCTTTTGGCACTAGCATTGTTCCCTTTCAGAA
GAAACGACTGACCCATATGTCAGGGTGGATGGCTCTGATTCCAAATGCAA
ATCACATTAACTGGTATTTTAAAGGTGTGGAGCACTTAACCAACATATCAT
ATACTTCCACATTCTATGGATTTAAGGAAGAAGACTATGTAATTATATCAC
ATAACTTCACTCAAAATCCTGATATGTTTAATGTTGTTGATATGAGGAATG
GCTCCGCAAACCCATTGAATTGGAATTCTAGTAAGAATGGAGACTGGCAT
CTTGAAGCAAACACCAGTACTCTCTATTATTTGGTGTCAGGGAGAAGTGA
CCTACCTCAGAGCCAGCCCATCTCTGGGACCCTAGATCCTGGTGTGAAGG
ATGTGATTATTAATTTCCAAGCTTACTGCTGTGTTCTCCAAGACTGCTTTCC
AGTTCATCCACCATCAAGAAAACCAATTCCCAGGAAACGACCAGCCGCTT
ACAATTTATGGTCCAATGAGTCCTTCTGGCAATCATCCCCAGAGAACAATT
ATACTGTACCTCGCCCAGGAGCAAATGTGATTATTCCTGAAGGAACATGG
ATTGTAGCTGATGTGGATATACCCCAGTGGAAAGACTCATTATTTGGGG
AGTTCTAGAAATGGAAGATAAATCTGAGATAGGAGTAGCAGGCCCCACCT

Figure 5E

ATAGAAGAGTTGTTTTAAATGCCACCTACATATCAGTACAGGGAGGGAGA
TTAATTGGTGGCTGGGAAGATAACCCCTTTAAAGGAGAATTACAGATTGT
TCTTCGAGGAAATCATTCTACCCCAGAATGGGCTTTTCCAGACGGACCGA
ATCAAGGGGCAAAGGTGTTAGGAGTGTTTGGTGAGCTGGACCTGCATGGA
CTTCCACATTCAGTTTATAAAACTAAACTGTTAGAAACTGCGGAAGCAGG
CTCCAAAATCTTATCTCTAGTGGATGCTGTGGATTGGCAGGAGGGAGAAG
ATGTTGTAATAACTACCACAAGCTATGATTTACACCAGACGGAGATCAGA
AGGATTGCTAAAATCCTACATGGGCACAAAATTCTCATCCTCAATGATAG
CCTTTCCTACACTCACCTTGCTGAAAGACAGTGGATCTCTGGAACAGCTCA
GAGCTACACATTATCAGCTGATGTTGGGATACTGAGTAGGAACATCAAAA
TAGTTGGTGACGATTACTCGGTTTTGTCCAAAGACTCTTTTGGTGCACGGA
TCCTAGTTGGCTCATTCACTGGAAACATGATGACATTTAAAGGAAATGCA
AGAATAAGTAATGTGGAATTTCATCACAGTGGTCAAGAAGGCTACAGGGA
TAGCACCGATCCAAGATATGCTGTGACATTTCTTAACCTGGGACAGATTCA
AGATCATGGCTTGTCTTATGTTCGAGGCTGTGCATTTCATCATGTGTTCTCC
CCAGCAATTGGTGTGTTTGGGACTGATGGGGTGGACATAGATGACAACAT
CATCTACTTTACAGTAGGAGAAGGTATAAGAATATGGGGGGATGCCAACA
GAGTACGTGGAAATTTGGTCACCCTTTCAGTTTGGCCAGGAACCTACCAG
AACAGAAAAGACTTGAGTTCGACACTTTGGCATGCAGCAATTGAGATAAA
CAGAGGGACCAATACAGTCTTACAAAATAATGTAGTCGCTGGATTTGGAA
GAGTAGGATACCGCATTGATGGTGAACCATGCTCAAGCCAGGCTAATTCC
ATGGAAAACTGGTTTAACAATGAAGCCCATGGAGGTTTGTATGGCATCTA
CATGAACCAGGATGGCCTTCCTGGTTGTTCTCTTATTCAAGGATTTACTAT
TTGGACATGCTGGGACTATGGAATTTATTTTCAGACCACGGAGAGCGTGC
ATATCTATAACGTGACGCTGGTGAACAACGGGATGAGCATCTTTTCAATG
GTCTACATGCCACCTTCTGTGTCCCACAAAATTTCCAGCAAAACAGTAAA
AATTAAGAACTCATTAATTGTTGGAAGCAGCCCTGAGTTTAACTGTTCTGA
CGTCTTAACTAATGACAGTCCTGATGTAGAACTCACCTCTGCACATCGAAG
TTCTAGGCCCCGTCAGGTGGGAGAAGTGGGATTTGCTGGCCAACATTTG
CTTCAGCTCATAACATGGCACCTCGGAAGCCTCATGCCGGGATCATGAGT
TACAATGCAATCAGTGGCCTTTTGCATGTCTCAGATTCAACATTTGTTGGA
TTTAAGGATGTTTGTTCAGGAGAAACTAATGTGATATTCATTACTAATCCT
TTAAATGAAGACTTACAGCATCCAATCCATGTGAAGAATGTCCAACTCAT
TGACACTATTGAACAATCCAAAGTATTCATACATAGACCTGATATAAGTA
AAGTGAACCCATCTGATTGTGTGGACATGGTTTGTGATGCCAAGAGAAAA
TCTTTTCTTAGAGACCTGGATGGTTCCTTTCTGGGGAATTCTGGGTCAGTG
ATCCCTCAAGCTGAGTATGAGTGGGATGGAAACAGCCAACTGGGAATTGG
AGACTACAGAATTCCAAAGGCGATGCTCACATACTTGAATGGAAGTAGAA
TTCCTGTAACTGAGAAAGCACCTCATAAAGGGATTATTAGAGATGCAACC
TGTAAATACATCCCAGAGTGGCAGAGCTATCAGTGTTCTGGAATGGAATA
TGCAATGATGGTACTGGAAAGCCTGGATTCTGACACAGAGACACGAAGAC
TATCCCCAGTGGCTATCATGAGCAATGGTTATGTTGATCTCATTAATGGCC
CACAGGACCATGGCTGGTGTGCGGGGTATACATGCCAAAGAAGACTGTCT
CTGTTCCATGGCATAGTGGCTCTGAACAAAAAGTATGAGGTTTACTTTACC
GGGACCAGTCCTCAGAATCTTCGGCTGATGTTGCTTAATGTTGAACATAAT
AAGGCAGTTCTAGTAGGAATTTTTTTTCCACACTTCAGCGTCTGGATGTC

Figure 5F

TATGTGAACAATTCCTTGGTCTGTCCCAAAAATACAGCATGGAATGCCCA
AAAGAAACACTGTGAACTTGAAAGGCATCTGAGCACAGAACAATTCCTTC
CTAACTTGGGTTCCACTGTCCCTGGTGAAAACTACTTTGATAGAACCTACC
AGATGCTGTACCTTTTCCTGAAAGGAACTACACCTGTGGAGGTCCACACT
GCTACTGTCATCTTTGTATCTTTCCACCTGCCGGTTATGACAGCAGATGAG
TTTTTAGCTCACACAACCTGGTTAGAAATCTTGCCTTGTTCCTAAAAATA
CCAAGTGACAAAATCCGTGTCAGCAGAATAATAGGAGCAAGTCTGAGAA
AGAAGCGATCCACAGGACACATAATGGAATTTGAGATTGGGGCTGCTCCC
ACTCAGTTCTTGAGCAATTCTACCACAGGTCAAATGCAGTTGTCTGAGCTC
CAGGAAATTACTGACTCTCTTGGACAAGCTGTTGTCCTAGGAAAAATTAG
TACTATTCTTGGATTCAATATTTCTTCCATGTCTATTACCAGTCCCATCCCC
CAACCAACTGATTCTGGCTGGATTAAGGTGACTGCCCAGCCAGTTGAAAG
ATCTGCATTTCCCGTTCACTACCTGGCCCTTGTGTCTTCACTCTCAGTGGTT
GCTCAGCCAGTGGCAGCCCAGCCCGGACAGCCCTTTCCTCAGCAGCCCTC
AGTAAAGGCAGTAGATCCTGAGGGTAACTGTGTATCAGTTGGAATTACAT
CGCTTACTTTGAAGGCTATCCTAAAGGACTCCAATAACAACCAAGTTGGT
GGCCTTAGTGGAAATACAACAATTCCATTTAGCACCTGTTGGGCCAACTAT
ACAGACCTCACTCCTCACAGAACAGGAAAAAATTATAAAATTGAATTTGT
CCTGGATAATACTGTTCGTGTGGATTCACGACCCTTCAGCCTGTCAGCACA
GAGTGTCCCTGGTGGCAGTGGAAGTAGCCCGGGTAGTGGCAGCAGCAGCA
GTGGCCACAGCAAAGCCTCCTCTGTGGGGACACCTGTCCAGACACTGGCT
GTCATAACAGCGTGCCTTGTAGGAAGACTACTGCTCTTGGAAGTATTTATG
GCTGCAGTTTTCATTTTGAACACAACTGTAGGAATCAACTGA (SEQ ID
NO:2)

Figure 6A

MGHLWLLGIWGLCGLLLCAADPSTDGSQIIPKVTEIIPKYGSINGATRLTIRGE
GFSQANQFNYGVDNAELGNSVQLISSFQSITCDVEKDASHSTQITCYTRAMPE
DSYTVRVSVDGVPVTENNTCKGHINSWECTFNAKSFRTPTIRSITPLSGTPGTL
ITIQGRIFTDVYGSNIALSSNGKNVRILRVYIGGMPCELLIPQSDNLYGLKLDHP
NGDMGSMVCKTTGTFIGHHNVSFILDNDYGRSFPQKMAYFVSSLNKIAMFQT
YAEVTMIFPSQGSIRGGTTLTISGRFFDQTDFPVRVLVGGEPCDILNVTENSICC
KTPPKPHILKTVYPGGRGLKLEVWNNSRPIRLEEILEYNEKTPGYMGASWVDS
ASYIWLMEQDTFVARFSGFLVAPDSDVYRFYIKGDDRYAIYFSQTGLPEDKV
RIAYHSANANSYFSSPTQRSDDIHLQKGKEYYIEILLQEYRLSAFVDVGLYQY
RNVYTEQQTGDAVNEEQVIKSQSTILQEVQVITLENWETTNAINEVQKIKVTS
PCVEANSCSLYQYRLIYNMEKTVFLPADASEFILQSALNDLWSIKPDTVQVIRT
QNPQSYVYMVTFISTRGDFDLLGYEVVEGNNVTLDITEQTKGKPNLETFTLN
WDGIASKPLTLWSSEAEFQGAVEEMVSTKCPPQIANFEEGFVVKYFRDYETD
FNLEHINRGQKTAETDAYCGRYSLKNPAVLFDSADVKPNRRPYGDILLFPYN
QLCLAYKGFLANYIGLKFQYQDNSKITRSTDTQFTYNFAYGNNWTYTCIDLL
DLVRTKYTGTNVSLQRISLHKASESQSFYVDVVYIGHTSTISTLDEMPKRRLP
ALANKGIFLEHFQVNQTKTNGPTMTNQYSVTMTSYNCSYNIPMMAVSFGQII
THETENEFVYRGNNWPGESKIHIQRIQAASPPLSGSFDIQAYGHILKGLPAAVS
AADLQFALQSLEGMGRISVTREGTCAGYAWNIKWRSTCGKQNLLQINDSNII
GEKANMTVTRIKEGGLFRQHVLGDLLRTPSQQPQVEVYVNGIPAKCSGDCGF
TWDSNITPLVLAISPSQGSYEEGTILTIVGSGFSPSSAVTVSVGPVGCSLLSVDE
KELKCQILNGSAGHAPVAVSMADVGLAQNVGGEEFYFVYQSQISHIWPDSGS
IAGGTLLTLSGFGFNENSKVLVGNETCNVIEGDLNRITCRTPKKTEGTVDISVT
TNGFQATARDAFSYNCLQTPIITDFSPKVRTILGEVNLTIKGYNFGNELTQNM
AVYVGGKTCQILHWNFTDIRCLLPKLSPGKHDIYVEVRNWGFASTRDKLNSSI
QYVLEVTSMFPQRGSLFGGTEITIRGFGFSTIPAENTVLLGSIPCNVTSSSENVIK
CILHSTGNIFRITNNGKDSVHGLGYAWSPPVLNVSVGDTVAWHWQTHPFLRG
IGYRIFSVSSPGSVIYDKGFTSGRQKSTSGSFSYQFTSPGIHYYSSGYVDEAHS
IFLQGVINVLPAETRHIPLHLFVGRSEATYAYGGPENLHLGSSVAGCLATEPLC
SLNNTRVKNSKRLLFEVSSCFSPSISNITPSTGTVNELITIIGHGFSNLPWANKVT
IGSYPCVVEESSEDSITCHIDPQNSMDVGIRETVTLTVYNLGTAINTLSNEFDRR
FVLLPNIDLVLPNAGSTTGMTSVTIKGSGFAVSSAGVKVLMGHFPCKVLSVN
YTAIECETSPAAQQLVDVDLLIHGVPAQCQGNCTFSYLESITPYITGVFPNSVIG
SVKVLIEGEGLGTVLEDIAVFIGNQQFRAIEVNENNITALVTPLVGHHSVSVV
VGSKGLALGNLTVSSPPVASLSPTSGSIGGGTTLVITGNGFYPGNTTVTIGDEP
CQIISINPNEVYCRTPAGTTGMVDVKIFVNTIAYPPLLFTYALEDTPFLRGIIPSR
GPPGTEIEITGSNFGFEILEISVMINNIQCNVTMANDSVLQCIVGDHAGGTFPV
MMHHKTKGSAMSTVVFEYPLNIQNINPSQGSFGGGQTMTVTGTGFNPQNSIIL
VCGSECAIDRLRSDYTTLLCEIPSNNGTGAEQACEVSVVNGKDLSQSMTPFTY
AVSLTPLITAVSPKRGSTAGGTRLTVVGSGFSENMEDVHITIAEAKCDVEYSN
KTHIICMTDAHTLSGWAPVCVHIRGVGMAKLDNADFLYVDAWSSNFSWGG
KSPPEEGSLVVITKGQTILLDQSTPILKMLLIQGGTLIFDEADIELQAENILITDG
GVLQIGTETSPFQHKAVITLHGHLRSPELPVYGAKTLAVREGILDLHGVPVPV
TWTRLAHTAKAGERILILQEAVTWKPGDNIVIASTGHRHSQGENEKMTIASVS
ADGINITLSNPLNYTHLGITVTLPDGTLFEARAEVGILTRNILIRGSDNVEWNN
KIPACPDGFDTGEFATQTCLQGKFGEEIGSDQFGGCVMFHAPVPGANMVTGR

Figure 6B

IEYVEVFHAGQAFRLGRYPIHWHLLGDLQFKSYVRGCAIHQAYNRAVTIHNT
HHLLVERNIIYDIKGGAFFIEDGIEHGNILQYNLAVFVQQSTSLLNDDVTPAAF
WVTNPNNTIRHNAVAGGTHFGFWYRMNNHPDGPSYDRNICQKRVPLGEFFN
NTVHSQGWFGMWIFEEYFPMQTGSCTSTVPAPAIFNSLTTWNCQKGAEWVN
GGALQFHNFVMVNNYEAGIETKRILAPYVGGWGETNGAVIKNAKIVGHLDE
LGMGSAFCTAKGLVLPFSEGLTVSSVHFMNFDRPNCVALGVTSISGVCNDRC
GGWSAKFVDVQYSHTPNKAGFRWEHEMVMIDVDGSLTGHKGHTVIPHSSLL
DPSHCTQEAEWSIGFPGSVCDASVSFHRLAFNQPSPVSLLEKDVVLSDSFGTSII
PFQKKRLTHMSGWMALIPNANHINWYFKGVDHITNISYTSTFYGFKEEDYVII
SHNFTQNPDMFNIIDMRNGSSNPLNWNTSKNGDWHLEANTSTLYYLVSGRN
DLHQSQLISGNLDPDVKDVVINFQAYCCILQDCFPVHPPSRKPIPKKRPATYNL
WSNDSFWQSSRENNYTVPHPGANVIIPEGTWIVADIDMPSMERLIIWGVLELE
DKYNVGAAESSYREVVLNATYISLQGGRLIGGWEDNPFKGDLKIVLRGNIHTT
QDWALPEGPNQGAKVLGVFGELDLHGIPHSIYKTKLSETAFAGSKVLSLMDA
VDWQEGEEIVITTTSYDFHQTETRSIVKILHDHKILILNDSLSYTHFAEKYHVP
GTGESYTLAADVGILSRNIKIVGEDYPGWSEDSFGARVLVGSFTENMMTFKG
NARISNVEFYHSGQEGFRDSTDPRYAVTFLNLGQIQEHGSSYIRGCAFHHGFSP
AIGVFGTDGLDIDDNIIHFTVGEGIRIWGNANRVRGNLIALSVWPGTYQNRKD
LSSTLWHAAIEINRGTNTVLQNNVVAGFGRAGYRIDGEPCPGQFNPVEKWFD
NEAHGGLYGIYMNQDGLPGCSLIQGFTIWTCWDYGIYFQTTESVHIYNVTLV
DNGMAIFPMIYMPAAISHKISSKNVQIKSSLIVGSSPGFNCSDVLTNDDPNIELT
AAHRSPRSPSGGRSGICWPTFASAHNMAPRKPHAGIMSYNAISGLLDISGSTFV
GFKNVCSGETNVIFITNPLNEDLQHPIHVKNIKLVDTTEQSKIFIHRPDISKVNP
SDCVDMVCDAKRKSFLRDIDGSFLGNAGSVIPQAEYEWDGNSQVGIGDYRIP
KAMLTFLNGSRIPVTEKAPHKGIIRDSTCKYLPEWQSYQCFGMEYAMMVIES
LDPDTETRRLSPVAIMGNGYVDLINGPQDHGWCAGYTCQRRLSLFHSIVALN
KSYEVYFTGTSPQNLRLMLLNVDHNKAVLVGIFFSTLQRLDVYVNNLLVCPK
TTIWNAQQKHCELNNHLYKDQFLPNLDSTVLGENYFDGTYQMLYLLVKGTIP
VEIHTATVIFVSFQLSVATEDDFYTSHNLVKNLALFLKIPSDKIRISKIRGKSLR
RKRSMGFIIEIEIGDPPIQFISNGTTGQMQLSELQEIAGSLGQAVILGNISSILGFN
ISSMSITNPLPSPSDSGWIKVTAQPVERSAFPVHHVAFVSSLLVITQPVAAQPG
QPFPQQPSVKATDSDGNCVSVGITALTLRAILKDSNNNQVNGLSGNTTIPFSSC
WANYTDLTPLRTGKNYKIEFILDNVVGVESRTFSLLAESVSSSGSSSSSNSKAS
TVGTYAQIMTVVISCLVGRMWLLEIFMAAVSTLNITLRSY (SEQ ID NO:3)

Figure 7A

MGHLWLSGTWFLFGLLWCAADSHKGSSETIPKVTEVIPKYGSINGATRLTIKG
EGFSQASQFNYGADNTELGNHVQLVSSFQSITCDVEKDSSHSTQITCYTRAMP
EDTYSVRVSVDGVPVAENNTCKGVASSWACSFSTKSFRTPTIRSITPLSGTPGT
LITIKGRLFTDVYGSNTALSSNGRNVRILRIYIGGMPCELLIPHSDDLYGLKLD
HANGDTGSVTCKTTGTYIGHHNVSFILDSDYGRSFPEKMTYFVSSLNKISMFQ
TYPEVVMVSPSKGSTEGGTLLTIHGHFFDQTDLPVRVLVGGQACAILNVTENT
IYCKTPPKPHILKATYPGGRGLKVEVWNNSRPAHLEDILEYNEHTPGYMGAT
WTDSASYVWPIEQDTFVARISGFLVPPDSDVYRFYIRGDDRYAIYFSQTGRTE
DKVRIAYYSGNANTYFSNSTQRSDEIHLQKGKEYYIEILLQEYTLSAFVDVGL
YQYKNVFTEQQTGDALNEEQVIKSQSTVVPEVQIITLENWETADVTNEVQQV
TVTSPCVGANSCSLSQYRFIYNMEKTVWLPADASDFTLKSALNDLWSIKPDS
VQVTSKRDLQSYIYTITFVSTRGDFDLLGYEVFEGSNVTLSITEQTKGKPNLET
FTLNWDGIASKPLTPESSEAEFQVAVEEMVSAKCPPEIAHLEEGFLVKYFRDY
ETDFELEHINRGQKTAETDAYCGRYSLKNPAVLFDSTDVKPNKSPYGDILLFP
YNQLCLAYKGSLANFIDLKFKYQDSGKIIRSADVQFEYNFASGNKWTYTCIDL
LDFLQTKYAGTSFSLQRITLQKSSEFQSIYVDAVYIGQTPTVSVLDDMPKRRPP
ALANKGIFLKHFQVNRTKLNGSAMTIQYSVTITSYNCSHNIPMMAVSFGQIIT
NETKNELVYRGNNWPGESKIRIQKIQEASPPISGSFDVQAYGHTLKGIPAAVPA
ADLQFALQSLEEIEQVSVNREGTCAGYSWSIRWTSPRGKQPLLQINDSNIIGEK
ANVTVTTIKEGGLFRQRIPGDMLRTLNQQPQVEVYVNGIPAKCSGDCGFTWD
AMITPLILTTTPSEGSYAESTILTIAGSGFSPTSAVSVSVGSTRCSLLSVEENEIK
CQILNGSAGHVPVAVSIADVGLAQNLEGEGSHFIYRSQISHVWPDSGSLAGGT
LLTISGFGFSENSTVLVGNETCNVIEGDLNRITCRTSKRIEGTVDISVITNGIQVT
AKDSFSYSCLQTPVVTDFSPKERTVLGKVNLTIKGYNFGNELAQNTVYVGRK
HCQVLHSNFTDITCLLPTLPPGKHDIYVKVRNWGLASTRNKLNASILYILEVIH
MFPQRGSLYGGTEITIMGFGFSTIPTENSVLLGSFPCDITSSSENVIKCTLHSTGT
VFRITNNGSHLVHGLGYAWSPSVLNVTVGDTVVWSWQAHPFLRGIGYRIFSV
SSPGSVTYDDKGFTNGRQKSASGSFSYQFTSPGIYYYSSGYVDEAHSISLQGVI
NVFPAEARHIPLYLFVGNIEATYVPAGPAHLQLASTAAGCLATEPLCGLNDTR
VKHSNKLFFELSNCISPSIINITPSTGTANELITIIGHGFSSLPCANKVTIGSYPCV
VEESSENSIICHIDPQNSMNVGIREIVTLIVYNLGTAINTLTKAFDRRFVLLPNID
MVMPKAGSTTGMTRVTIQGSGFMSSPEGVEVFMGDFPCKVLSVTYTAIECET
SPAPQQLVLVDILIHGVPAQCQSNCSFSYLENIAPYVTGIFPNSIQGYGNVLIKG
ERFGTVLEEISIFIGSQQFRVIDVNENNITVLMTPLEAGLHSLSVVVGSKGLAL
GNLTISSPAVASVSPTSGSIAGGTTLMITGNGFSPGNTTVTVGDQPCQITFISSSE
VYCSTPAGRAGTANLKISVNAIIYPPLSFTYAMEDTPFLKRIIPNRGLPGTEVEI
TGSNLGFAISDVSVMIKESVCNVTTVNDTVLQCTVGEHAGGIFPVTMLHKTK
GSAVSSVAFEYPLSIQNIYPTQGSFGGGQTLTVTGMGFDPWNSTILVCNSECA
VDKLRSNSTTLFCVIPPNNGKGHDQVCGVSVVNGKDSSHSTKLFTYTLSLTPL
ITEISPRRGSTAGGTRLTVTGSGFSENTQGVQVFVGNSKCDIQYSNKTHIVCMT
SVHVPSGWVPVHVNIKNIGLAKLENADFLYADVWSANSSWGGSPPPEEGSLA
VITKGQIILLDQSTPILKMLLIQGGTLIFDEANIELQAENILITDGGVLQIGTEASP
FQHRAVITLHGHLRSPELPVYGAKTLGVREGTLDLHGLPIPVVWTRLTHTAN
AGEWTLTVQEAVTWKAGDNIVIASTGHRHSQAENEKRTIASVSADGMHITLT
KPLNYTHLGITTTLPDGTVFEARAEVGILTRNILIRGSDNVEWNDKIPSCPDGF
DTGEFATQTCLQGKFGEEMGSDQFGGCIMLHAPLPGADMVTGRIEYVEVFHA

Figure 7B

GQSFRLGRYPIHWHLLGDLQFKSYVKGCAIHQSYNRAITIHNTHHLLVERNIIY
DIKGGAFFIEDGIEHGNILQYNLAVFVQQSTSLLNDDVTPAAFWVTNPNNTIR
HNAAAGGTHFGFWYRMNDHPDGPSFDRNICQKRIPLGEFFNNTVHSQGWFG
LWIFEEYFPMQTGSCTSTVPVPAIFNSLTVWNCQKGAEWVNGGALQFHNFV
MVNNNEAGIETKRILAPYVGGWGESNGAVIKNAKIVGHLDELGMGPTFCTSK
GLVLPFSQGLTVSSVHFMNFDRHACVALGVTSITGVCNDRCGGWSAKFVGIR
YFHAPNKGGFRWEHEAVLIDVDGSLTGHRGHTVVPHSSLLDPSHCTQEPAWS
IGFPGSICDASVSFHRLAFNKPSPVSLLEKDVVLSDSFGTSIVPFQKKRLTHMS
GWMALIPNANHINWYFKGVEHLTNISYTSTFYGFKEEDYVIISHNFTQNPDMF
NVVDMRNGSANPLNWNSSKNGDWIHLEANTSTLYYLVSGRSDLPQSQPISGT
LDPGVKDVIINFQAYCCVLQDCFPVHPPSRKPIPRKRPAAYNLWSNESFWQSS
PENNYTVPRPGANVIIPEGTWIVADVDIPPVERLIIWGVLEMEDKSEIGVAGPT
YRRVVLNATYISVQGGRLIGGWEDNPFKGELQIVLRGNHSTPEWAFPDGPNQ
GAKVLGVFGELDLHGLPHSVYKTKLLETAEAGSKILSLVDAVDWQEGEDVVI
TTTSYDLHQTEIRRIAKILHGHKILILNDSLSYTHLAERQWISGTAQSYTLSAD
VGILSRNIKIVGDDYSVLSKDSFGARILVGSFTGNMMTFKGNARISNVEFHHS
GQEGYRDSTDPRYAVTFLNLGQIQDHGLSYVRGCAFHHVFSPAIGVFGTDGV
DIDDNIIYFTVGEGIRIWGDANRVRGNLVTLSVWPGTYQNRKDLSSTLWHAAI
EINRGTNTVLQNNVVAGFGRVGYRIDGEPCSSQANSMENWFNNEAHGGLYG
IYMNQDGLPGCSLIQGFTIWTCWDYGIYFQTTESVHIYNVTLVNNGMSIFSMV
YMPPSVSHKISSKTVKIKNSLIVGSSPEFNCSDVLTNDSPDVELTSAHRSSRPPS
GGRSGICWPTFASAHNMAPRKPHAGIMSYNAISGLLHVSDSTFVGFKDVCSG
ETNVIFITNPLNEDLQHPIHVKNVQLIDTIEQSKVFIHRPDISKVNPSDCVDMVC
DAKRKSFLRDLDGSFLGNSGSVIPQAEYEWDGNSQLGIGDYRIPKAMLTYLN
GSRIPVTEKAPHKGIIRDATCKYIPEWQSYQCSGMEYAMMVLESLDSDTETRR
LSPVAIMSNGYVDLINGPQDHGWCAGYTCQRRLSLFHGIVALNKKYEVYFTG
TSPQNLRLMLLNVEHNKAVLVGIFFSTLQRLDVYVNNSLVCPKNTAWNAQK
KHCELERHLSTEQFLPNLGSTVPGENYFDRTYQMLYLFLKGTTPVEVHTATVI
FVSFHLPVMTADEFFSSHNLVRNLALFLKIPSDKIRVSRIIGASLRKKRSTGHIM
EFEIGAAPTQFLSNSTTGQMQLSELQEITDSLGQAVVLGKISTILGFNISSMSITS
PIPQPTDSGWIKVTAQPVERSAFPVHYLALVSSLSVVAQPVAAQPGQPFPQQP
SVKAVDPEGNCVSVGITSLTLKAILKDSNNNQVGGLSGNTTIPFSTCWANYTD
LTPHRTGKNYKIEFVLDNTVRVDSRPFSLSAQSVPGGSGSSPGSGSSSSGHSKA
SSVGTPVQTLAVITACLVGRLLLLEVFMAAVFILNTTVGIN (SEQ ID NO:4)

SEQUENCE LISTING

```
<160> NUMBER OF SEQ ID NOS: 206

<210> SEQ ID NO 1
<211> LENGTH: 12732
<212> TYPE: DNA
<213> ORGANISM: Homo sapiens

<400> SEQUENCE: 1
atgggacacc tgtggctcct gggtatttgg ggcctctgtg ggctgctcct gtgtgccgcg      60
gatcccagca cagatggctc tcaaataatc cccaaagtca cagaaataat acctaaatat     120
ggcagtataa atggagcaac aaggctgact ataagagggg aaggttttc tcaagcaaac      180 cagtttaact atggagttga taacgctgag ttgggaaaca gtgtgcaatt aatttcttct     240
ttccagtcaa ttacttgtga tgtagaaaaa gatgcaagtc attcaactca aattacatgc     300
```

```
tatactagag caatgccgga agattcctac actgttagag tcagtgtgga cggggttcct    360
gttacggaaa ataacacctg caaaggtcac atcaacagct gggaatgtac cttcaacgca    420
aaaagtttta gaaccccaac aataagaagc atcacacctt tatctggaac tccaggtaca    480
ctaataacaa tccaaggcag aatcttcact gatgtctatg aagtaatat tgcactaagc     540
tcaaatggga aaaatgttag gattttgaga gtttacattg gaggaatgcc ctgtgagctt    600
ctcataccac aatctgataa tttatatggt ctaaaactgg atcatccaaa tggagatatg    660
ggttctatgg tttgtaagac gactggaact tttattggtc atcacaatgt cagcttcatc    720
ttagataatg attatggaag gagttttcca cagaaaatgg catattttgt ttcttctctc    780
aataaaattg caatgtttca aacatatgca gaggtcacca tgattttccc ttcacaagga    840
agcattcgag gtggcaccac gctgacaata agtgggcgtt tctttgatca gacagatttc    900
cccgtcagag ttctagttgg aggtgaacct tgtgatattt tgaatgtcac agaaaatagt    960
atatgttgca agacaccccc caaacctcat attctcaaaa ctgtatatcc aggagggaga   1020
ggcctgaagc ttgaggtgtg gaataatagc cgtccaatac gtttggaaga gatactggaa   1080
tacaatgaaa aaacgcctgg gtacatgggt gccagttggg tagattcagc ttcctatatt   1140
tggctcatgg aacaagacac atttgttgca cgctttagtg gattttggt ggctccagat    1200
tctgatgttt atagattcta catcaagggt gatgaccgtt atgctattta ttttagccag   1260
actggacttc cagaagataa ggtgaggatt gcatatcatt ctgctaatgc caacagttat   1320
ttttccagtc aacacaaag atcagatgat attcatctgc agaaaggaaa agaatactat    1380
attgaaatct gctgcagga gtacagatta agtgcatttg ttgatgttgg actgtaccag    1440
tatcgaaatg tttatactga acaacaaaca ggagatgcag tgaatgaaga acaagttatc   1500
aaatcccagt cgacaatcct ccaggaagta caggttataa cattggaaaa ctgggaaaca   1560
actaatgcaa ttaatgaggt tcagaagatc aaggtaacca gcccatgtgt ggaagctaat   1620
tcatgttcac tttaccaata tagattaatc tataatatgg aaaaaactgt cttcctacct   1680
gctgatgctt ctgaattcat actgcaatca gccttgaatg acctctggtc tataaaaccg   1740
gacacagttc aagtaataag aacacaaaat ccccagagct atgtctacat ggtaacattc   1800
atatcaacta gaggagactt tgatctgctt ggttatgaag tagttgaagg gaataatgtc   1860
acactggata ttacagaaca aaccaaagga aaacccaact tggagacatt cacactgaat   1920
tgggatggga tcgcttctaa gccactcact ctatggtcat cagaagctga atttcaggga   1980
gcagtggaag aaatggttag cactaagtgt ccaccacaaa ttgcaaattt tgaagaagga   2040
tttgttgtga atatttcag agactatgaa actgatttta atctggaaca tattaacaga   2100
gggcagaaga cagctgaaac cgatgcttac tgtggtcgtt attccctgaa aaacccagct   2160
gttcttttg actcagcaga tgttaaacca aacagacgac catatggaga tattttattg   2220
tttccttata atcagttatg tttagcatac aaaggattcc tggcaaatta tattggtcta   2280
aaatttcagt accaagacaa tagcaagatt actagaagca ctgatacaca gtttacatac   2340
aactttgctt atggaaacaa ctggacttac acttgcatag accttctgga tctcgtaaga   2400
acgaaataca ctgggacaaa tgttttctctt cagaggatta gcttacataa agcatcagaa   2460
tcacagtcct tctatgtgga tgtagtgtac attggacaca atctacaat ctcaacattg    2520
gatgaaatgc ccaagagaag acttcctgca ttagcaaata aaggaatatt cttagagcac   2580
tttcaggtga atcagaccaa aacaaatggg ccaactatga caaaccaata ttctgttacc   2640
atgacttcat acaattgcag ttacaatata cccatgatgg ctgtgagctt tgggcagata   2700
```

```
atcacacatg agacagagaa cgagtttgtc tacagaggaa ataattggcc aggcgagtca   2760
aaaattcata ttcaaagaat tcaagctgca tctccacctc taagtggcag ctttgacatt   2820
caagcttatg gacatattct taaaggcctc cccgctgctg tgtcagctgc agatctgcag   2880
tttgcactcc agagtctgga gggaatggga agaatctcag ttacacgaga gggaacctgt   2940
gctggctacg cgtggaacat caaatggaga agcacctgcg gaaagcagaa tcttctacag   3000
attaatgatt ccaacattat tggagaaaag gctaatatga cagttacaag gataaaggaa   3060
ggtggcttat tcagacaaca tgtacttgga gacctacttc gtacacccag tcaacagcca   3120
caggttgaag tctatgtcaa tggaattcca gctaaatgtt caggtgactg tggatttaca   3180
tgggattcca acattactcc cctagtcttg gcgataagcc cttctcaagg gtcctatgaa   3240
gaaggcacaa ttctaaccat agtgggttct ggattttctc ctagttcagc tgtaacagtc   3300
tcagttggac cagtaggttg ttctcttctt tctgtggatg aaaagagct caagtgccag    3360 attctgaatg gaagtgctgg acatgccccc gttgctgtgt ccatggctga tgttggacta   3420
gcacagaatg tagggggtga agagttctac tttgtttatc agagtcagat ctcacatatc   3480
tggcctgatt ctgaagcat agcaggtggt actctactga ctttatctgg atttggcttt    3540
aatgaaaatt caaaggtatt agttggaaat gaaacctgca atgtgattga aggggatttg   3600
aataggataa cctgcaggac accaaaaaaa actgagggta cagttgatat ttcagttact   3660
accaatggat ttcaagccac agcaagggat gcttttagtt ataattgttt acagacacca   3720
attataactg attttagtcc aaaagtacga acaatactag gagaagttaa tttaacaatt   3780
aagggctata attttggaaa tgaactcaca caaaacatgg cggtgtatgt tggaggaaaa   3840
acctgccaga ttcttcactg gaacttcaca gatattagat gccttttgcc caagttgtct   3900
cctggaaaac atgatatcta tgtagaagtc agaaactggg gttttgcatc aacaagagac   3960
aaattaaatt cttcaataca gtatgtttta gaagtgacca gcatgtttcc acaaagaggc   4020
tccttgtttg gtggaactga aatcaccata aggggttttg gattcagcac aataccagct   4080
gagaataccg tgctgttagg gtccatccct tgcaatgtta catcatcatc agaaaatgtc   4140
ataaaatgta ttcttcattc aactgggaat atattcagga ttaccaacaa tgggaaagat   4200
tcagtacatg gattaggtta tgcctggtca ccaccagtcc taaatgtgtc tgtggggac    4260 acagtggcat ggcattggca acacatccg tttcttagag ggataggata taggattttt    4320
tctgtctcca gtcctggaag tgtaatttat gatggcaaag gattcacaag tggaagacaa   4380
aaatctacat caggttcatt ttcttaccaa tttacttctc ctggaatcca ttattatagc   4440
agcgggtatg ttgatgaggc tcactccatt ttttctccaag gagtcattaa tgttttacca   4500
gctgaaacca gacacattcc cttgcacctg tttgtgggtc gctctgaagc cacatatgct   4560
tatggaggac ctgagaattt gcacttggga agctctgtgg caggctgcct agcaacagaa   4620
cccctgtgca gcctgaacaa taccagggtt aaaaattcaa aaagattgct atttgaggtt   4680
tcaagttgtt tttcaccatc tataagcaac attactccgt ccactggaac agtaaatgaa   4740
ctaataacaa ttattggaca tggctttagt aatctcccat gggctaataa ggttacaatt   4800
ggtagctacc cctgtgtcgt agaagaaagt agtgaggatt caattacatg tcatattgac   4860
cctcaaaact caatggatgt tggtatcagg gaaactgtca ctttgactgt ctacaacctg   4920
ggcactgcta tcaatacgtt gtccaatgaa tttgataggc gatttgtact tttgccaaac   4980
attgacctgg tgttgccaaa tgcaggatca actacaggaa tgacaagcgt gaccataaaa   5040
ggctctggat ttgccgtttc ttctgcaggt gtaaaagtcc ttatgggtca tttcccatgt   5100
```

```
aaagttctat cagtgaatta tacggccatt gaatgtgaaa catcccctgc tgcccaacag     5160
cttgtggatg tagatcttct aatacatgga gtgcctgccc agtgccaggg aaactgcacc     5220
ttttcatact tagaaagcat cactccttac ataacaggag tcttcccaaa ctctgtcata     5280
ggatctgtaa aagttcttat tgaaggagaa ggtttgggga ctgttttgga ggacattgct     5340
gttttcattg gaaatcaaca gttcagagca atagaggtta atgaaaacaa catcactgct     5400
cttgtgactc ctctcccagt tggacatcat tctgttagtg ttgtggtggg aagtaaaggc     5460
ttggctctgg gaaacctgac tgtcagcagc cccccagtag catctctatc accaacttct     5520
ggaagcattg gtggtggaac tacactggtg atcacaggaa atggcttcta tccaggcaac     5580
actacagtca ctattgggga tgaaccttgt caaattattt ccatcaaccc caatgaagtc     5640
tactgccgca ctcccgctgg gaccactgga atggtcgatg ttaaaatctt tgttaataca     5700
attgcttatc cacctttgct ttttacatat gccctggagg atactccatt tctcagagga     5760
attatcccaa gcagaggtcc accaggaact gaaattgaga tcactggatc caactttggc     5820
tttgagatct tggaaatctc cgtgatgata aataacattc agtgtaatgt aaccatggcc     5880
aatgatagtg tgttgcagtg catcgtggga gatcatgctg ggggcacatt tcctgttatg     5940
atgcatcata agacaaaagg ctcagccatg tccacagttg tatttgagta cccgcttaat     6000
attcaaaata ttaatccaag ccaagggagc tttggtgggg gtcaaaccat gactgtgaca     6060
ggcaccggat ttaatccaca aaattcaatt atattagttt gtggctcaga atgtgcaatt     6120
gacaggctta gatctgatta cacaacacta ttatgtgaaa ttccatctaa taatggcacg     6180
ggagctgagc aagcctgtga agtgagtgtg gttaatggga agatttgtc acagtccatg      6240 actccgttta cgtacgcagt gtcactgact ccactcatca ctgcagtatc tcctaagaga     6300
ggcagtacag caggggcac cagactgaca gtcgtgggat caggattcag tgaaaatatg      6360
gaggatgttc atatcaccat agctgaagcc aatgtgatg ttgagtattc caacaagaca      6420
cacatcatct gcatgacaga tgcccatact ctatcagggt gggctccagt tgtgtccac      6480 atcagaggtg tcggcatggc caaactggat aatgctgact tctttatgt tgatgcctgg      6540 tcctccaatt tctcatgggg gggaaaatct cccccagaag aaggatctct tgttgttatt      6600
acaaaaggac agaccattct cctggatcaa agcacccca ttttgaaaat gttgcttatt       6660
cagggtggga ctctaatatt tgatgaagct gacattgaac tccaggcaga aaatattcta      6720
attacagatg gaggtgttct tcagattgga acagagacat ccccattcca acacaaggct     6780
gtcattacct tgcatggtca cctgcgatct cctgagctcc ctgtctatgg tgccaaaaca     6840
ctggctgtgc gggagggaat cctggatctg cacggtgtgc ctgttcctgt gacctggact     6900
cgcttggctc atactgcaaa ggcaggggaa agaattttaa ttttacaaga agcagtaaca    6960
tggaaaccag gagataacat tgtaattgca agcacaggac acagacacag tcaaggagag     7020
aatgaaaaaa tgaccattgc atctgtgtct gctgatggca taaacataac actaagtaac     7080
ccactaaatt acacacactt aggaattacg gtcacactcc ctgatggaac tctgtttgaa     7140
gcaagagcag aagttggaat tcttacaaga aatattttaa taagaggatc tgataatgtt     7200
gagtggaata caaaaattcc tgcatgtcct gatggatttg acacaggaga atttgctaca     7260
cagacctgtc tccaaggaaa gtttggagaa gaaataggag gtgaccaatt tggaggctgc     7320
gttatgtttc atgctcctgt acctggtgct aacatggtaa ctgggagaat agaatatgta     7380
gaggtattcc atgctggcca ggcttttccgg ttggggcgat atccaataca ttggcacctg    7440
cttggagact tacagtttaa atcttatgta agaggctgtg caattcacca ggcctataac      7500
```

```
agagctgtta ctattcataa cacacaccat cttctggttg agaggaatat tatatatgat    7560
attaagggag gagcattttt tatagaagat ggtattgaac atggcaatat cctccagtat    7620
aacttggcag tatttgtaca gcaaagtacc agtcttctga atgatgatgt gaccccggct    7680
gcattttggg tcaccaaccc gaacaatacc atacgacaca atgctgttgc tggtggcact    7740
cactttggct tttggtaccg gatgaacaac caccctgatg ggccatccta tgacagaaac    7800
atttgtcaaa aaagagttcc ccttggcgaa ttttttaaca atactgtcca ttctcaaggt    7860
tggtttggaa tgtggatctt tgaggaatat ttccccatgc aaacgggatc ttgtacatct    7920
acagtgcctg cgcctgcaat atttaactca cttactactt ggaattgtca aaaaggagct    7980
gaatgggtca atggaggtgc ccttcagttc cataactttg tgatggtgaa taactatgag    8040
gctggaattg agactaagag gatcctggct ccttatgttg gagggtgggg tgaaaccaat    8100
ggagcggtga ttaaaaatgc caaaatagtc ggccatcttg atgaactggg aatggggtct    8160
gcattttgca cagcaaaagg cctggttctc ccatttagtg aaggcttgac tgtctcttct    8220
gtgcacttta tgaactttga ccgtcccaac tgtgtagctt gggagtgac atccatctct    8280 ggagtttgta atgacagatg tgggggttgg agtgcaaagt tgttgacgt ccagtattct    8340 cacacaccga acaaggctgg ctttcgctgg gaacatgaaa tggtaatgat tgatgttgat    8400
ggctcactta cagggcacaa aggacatacc gtcattccac acagctcatt gctagaccct    8460
tctcattgta ctcaggaagc tgagtggagc attgggttcc ctggatcagt ctgtgatgct    8520
tcagtcagct ttcaccgttt agcgttcaac cagccttctc cagtatctct gcttgaaaag    8580
gatgtggttc tttcagactc ttttggcaca agcattattc catttcagaa gaaacgactg    8640
actcatatgt ctggatggat ggctctgatt ccaaatgcaa atcacattaa ctggtatttt    8700
aaaggtgtgg atcacataac caacatttca tatacatcga cattctatgg attcaaggaa    8760
gaagactatg taattatatc acataacttc actcaaaatc ctgacatgtt taatattatt    8820
gatatgagga atggttcctc aaatccattg aattggaata ctagcaagaa tggggactgg    8880 cacctttgaag caaacactag tactctatat tacttggtgt caggaagaaa tgaccttcat    8940
cagagtcagc tcatttctgg gaacctggat cctgatgtga agacgttgt tattaatttc    9000 caagcttact gttgtattct ccaggattgc tttcctgtac atccgccatc aagaaaacca    9060
attcccaaga agcgaccagc cacatataat ttatggtcaa atgattcttt ttggcaatca    9120
tcacgagaaa ataattatac tgtacctcac ccagggggcaa atgtgattat acctgaagga    9180
acatggattg tagctgacat agatatgcca tcaatggaaa gactcattat tgggggggtt    9240
ctagaactgg aagataaata caatgtagga gctgcagaat cttcttacag agaagttgtt    9300
ttgaatgcta cctacatatc actgcaggga ggtagattaa tcggtggctg ggaagataac    9360 cctttttaaag gagacttaaa gattgttctt agaggaaatc atactacaca agactgggct    9420
cttccagaag gaccaaatca aggggcaaag gtcttagggg tgtttggtga gctggatctt    9480
catggaattc cacattcaat atataaaact aagctctcag aaactgcatt tgcaggttcc    9540
aaagtcctgt ctctgatgga tgctgtggat tggcaggagg gagaagagat tgtgataaca    9600
accacaagct acgatttcca ccagacagaa acaagaagta tcgttaaaat cctgcatgat    9660
cataaaattc tcattcttaa tgatagcctt tcctatactc actttgctga aaaataccat    9720
gtccctggaa ctggtgagag ctacacgtta gcagctgatg ttgggatact gagtaggaac    9780
atcaaaatag ttgtgaagaa ttaccccggt tggtctgagg actcttttgg agcacgcgta    9840
ctggttggct cattcactga aaatatgatg acatttaaag gaaatgcaag aataagtaat    9900
```

```
gtggaatttt atcacagtgg tcaagaaggc ttcagggata gcacagatcc aagatatgct   9960
gtaacgtttc ttaacctagg acagattcaa gaacatggct catcttatat tcgaggctgt  10020
gcttttcacc atggcttctc tccagcaatt ggtgtatttg ggacagatgg attggacata  10080
gatgacaaca tcattcactt tacagtgggg gaaggcataa gaatatgggg gaatgccaac  10140
cgagtccgag ggaatttgat tgcactttcg gtttggccag gaacctatca gaacagaaaa  10200
gatttaagtt caactctctg gcatgcagca attgagataa atagagggac caatacagtt  10260
ttacagaata atgtagtggc tggatttgga agagcaggat accgcattga tggtgaacct  10320
tgcccaggcc agtttaatcc tgtggaaaag tggtttgaca atgaagccca tggaggttta  10380
tatgggatct atatgaacca agatggcctt cctggatgtt ctcttataca aggatttacc  10440
atttggacat gctgggatta tggaatttat tttcagacca cagagagtgt gcacatttat  10500
aatgtgaccc tggttgacaa tggaatggcc attttttccaa tgatttacat gccagctgct  10560
atatcacaca aaatttccag taaaaatgta caaattaaga gctcattaat tgttggaagt  10620
agccctgggt ttaattgctc tgatgtccta actaatgatg atcctaatat tgaactcact  10680
gctgctcatc ggagtcctag atctccatca ggtgggagaa gtgggatttg ttggcctacc  10740
tttgcttcag ctcataacat ggcaccccga aagccccatg caggaatcat gagttacaat  10800
gccatcagtg gccttttgga catctcaggt tcaacatttg ttggatttaa gaatgtttgt  10860
tcagggaaaa ctaatgttat attcattact aaccctttaa atgaggattt acagcatcca  10920
atccatgtga agaatataaa actggttgat accactgaac aatcaaaaat atttatacat  10980
aggcctgata taagtaaggt caatccatct gattgtgtag acatggtttg tgatgccaag  11040
aggaaatctt ttcttagaga catagatggc tcctttctgg ggaatgctgg ttctgtgata  11100
cctcaagcag aatatgaatg ggacggaaac agccaagtag gaattggaga ctacagaatt  11160
cctaaggcga tgctcacatt cttgaatgga agtagaattc ctgtcactga gaaagcacct  11220
cataaaggaa ttattagaga ttcaacctgt aagtaccttc cagagtggca gagctatcag  11280
tgctttggga tggaatatgc aatgatggtt attgaaagtc tggatcctga cacagaaact  11340
cgaagacttt ccccagtggc tataatgggc aacggttatg ttgatcttat taatggccca  11400
caggatcatg gctggtgtgc tggatataca tgccagagaa ggctgtccct gtttcacagc  11460
attgtggctc tgaacaaatc ttatgaagtt tacttcactg gcaccagtcc tcagaatctt  11520
cgactgatgt tgcttaatgt tgatcataac aaggctgttc tagtaggaat tttcttttcc  11580
acacttcaac gtttggatgt ctatgtgaac aacttattgg tctgtccaaa aactacaata  11640
tggaatgccc agcagaaaca ctgtgaactt aataaccatc tgtacaaaga ccaattcctt  11700
cctaacctgg attccactgt ccttggtgaa aactactttg atggaaccta ccagatgctt  11760
tatctttttgg ttaaaggaac tatacctgtt gaaattcaca ctgccacagt gatatttgtt  11820
tctttccaat tatctgttgc aacagaagat gactttatata cctctcacaa tctggttaaa  11880
aatcttgcct tgttcctaaa gataccaagt gacaaaatcc gtatcagcaa aataagaggg  11940
aagagtctga ggaggaagag atccatggga ttcataattg aaatagagat tggagaccct  12000
cctattcagt tcataagcaa tggcaccaca ggtcagatgc agttatctga actccaggaa  12060
attgctggtt ctcttggaca agctgtaatt ttaggaaaca tcagtagtat ccttggattt  12120
aacatttcgt ccatgtctat tactaatccc ctccccagcc caagtgactc tgggtggatt  12180
aaggtgactc cccagccagt tgaaaggtct gcatttcctg ttcatcacgt ggccttcgtg  12240
tcctcactct tagtgatcac tcagccggtg gcagcacagc caggacagcc atttcctcag  12300
```

| | |
|---|---|
| cagccttcgg taaaggcaac agattctgac ggtaactgtg tatcagttgg aattactgca | 12360 |
| ctaactttga gggccatact caaggactcc aataataacc aagtcaatgg ccttagtgga | 12420 |
| aatacaacaa ttccgtttag cagctgttgg gccaactaca cagaccttac tcccttaga | 12480 |
| acaggaaaaa attataagat tgaatttata ctggataatg ttgttggggt agaatccaga | 12540 |
| actttcagcc tgctggcaga gtctgtctct agcagtggca gcagcagcag cagcaacagc | 12600 |
| aaagcatcaa ctgtgggtac atatgcccag ataatgactg tagtaattag ctgtctggtt | 12660 |
| ggaagaatgt ggctcttgga aatatttatg gctgcagttt caactttgaa tataacttta | 12720 |
| agaagctact aa | 12732 |

<210> SEQ ID NO 2
<211> LENGTH: 12750
<212> TYPE: DNA
<213> ORGANISM: Mus musculus

<400> SEQUENCE: 2

| | |
|---|---|
| atgggacacc tgtggctctc agggacctgg tttctctttg gctgctttg gtgtgcagca | 60 |
| gattcccaca aaggtagctc tgagacaatt cccaaagtga cagaagttat acctaaatat | 120 |
| ggcagcataa acggagcaac aagactgacc atcaagggag aaggttttc tcaagcaagt | 180 |
| cagttcaact atgagctga caatactgaa ttggaaaacc atgtgcaatt agttcttct | 240 |
| ttccagtcga ttacttgtga tgtggaaaaa gattcaagtc attcaactca aattacatgc | 300 |
| tatactcgag caatgccaga agacacctac tctgttcgag tcagtgtgga tggagtgcca | 360 |
| gttgcagaaa ataacacttg taaggggtt gccagcagct gggcatgtag tttcagtaca | 420 |
| aaaagtttta gaaccccac aataaggagc atcacacctt atctggaaac tccaggtaca | 480 |
| ttaataacaa ttaaaggcag gctcttcact gatgtctatg gaagtaatac agcactgagc | 540 |
| tcaaatggaa gaaatgttag gattctaaga atttatatcg gaggaatgcc ctgtgaactc | 600 |
| ctcataccac attctgatga tttgtatggt ctaaaactcg atcatgccaa tggagataca | 660 |
| gggtctgtga catgtaagac cactgggact acatggtc accacaatgt cagcttcatc | 720 |
| ttagatagtg attatggaag gagtttccca gagaaaatga catattttgt ttcatctctc | 780 |
| aataaaatttt caatgttca aacatatcca gaggtcgtga tggtctcacc atcaaaaggc | 840 |
| agcactgaag gtggcaccct attgacaata cacgggcact tcttcgatca gactgatctc | 900 |
| ccagtgagag tgctagttgg aggtcaagcc tgtgctattt tgaatgtcac agaaaatact | 960 |
| atatactgca agactcctcc caaaccacac atcctcaaag ctacatatcc aggtggaaga | 1020 |
| ggcctaaagg ttgaggtctg gaataatagc cggccagcac atcttgaaga tacttgaa | 1080 |
| tacaatgagc atacccagg gtacatgggt gccacttgga cggattctgc ttcctatgtt | 1140 |
| tggcctatag aacaagacac atttgttgca cgcatcagtg atttttggt gccccagat | 1200 |
| tctgatgttt acaggtttta tatcagaggt gatgaccgct atgctattta tttcagccaa | 1260 |
| actgggcgca cagaagacaa ggtgaggatt gcgtattact ctggaaatgc caacacttat | 1320 |
| ttttcaaatt caacacaaag atcagatgag attcatcttc agaaaggaaa agagtattac | 1380 |
| attgaaatct gctgcaaga gtatacatta agtgcttttg ttgatgttgg actgtaccag | 1440 |
| tataaaaatg tctttactga acagcagaca ggagatgcac taaatgaaga caagtcatc | 1500 |
| aaatctcagt caacagttgt ccccgaagta cagattataa cattggaaaa ctgggagaca | 1560 |
| gctgatgtga ctaatgaagt ccagcaggtc acagtaacca gccgtgtgt gggagctaac | 1620 |
| tcatgttccc tttcccaata cagattcatc tacaacatgg aaaagactgt ctggctgccc | 1680 |

```
gctgatgctt ctgacttcac gttgaaatca gctttaaatg acctttggtc tataaagcca  1740
gattcagttc aagtgaccag caagagggat ctccagagct atatctacac aataaccttt  1800
gtatcaacta gaggagactt tgatctgctt ggttatgaag tatttgaagg aagtaatgtc  1860
acgctgagta tcacagaaca aaccaaagga aaacccaatt tggagacgtt tacattaaac  1920
tgggatggga ttgcttctaa gccccttacc ccagagtcat cggaagctga atttcaggta  1980
gcagtggaag agatggtgag tgccaagtgt ccgccggaaa tagcacattt ggaagaagga  2040
tttctagtga atacttcag agactacgaa actgattttg aactggagca tattaataga  2100
gggcagaaga cggccgaaac agatgcatat tgtggccgtt actccctgaa aacccagct  2160
gtacttttg actcgacaga tgttaagcca aacaaatcac catatggaga cattttatta  2220
tttccttata atcagttgtg tttagcatac aaaggatctc tggccaactt cattgatctc  2280
aagttcaagt accaagacag tggcaagatc attagaagtg ctgatgtaca atttgaatat  2340
aactttgctt ctggaaataa gtggacttac acttgcatag atcttctaga tttcttacaa  2400
accaaatatg ctgggacgag ttttttctcta caaaggatta ccttacaaaa atcgtcagaa  2460
ttccagtcca tttatgtgga tgcagtgtac attggacaga cacctacagt ctctgtcttg  2520
gatgatatgc caagaggag acctccagca ctagcaaaca aaggaatatt tttaaagcat  2580
tttcaggtta tcggaccaa attaaatgga tcagctatga caattcagta ttcagttacc  2640
ataacttcat ataactgcag tcataatata cctatgatgg ctgtgagctt tggacagata  2700
atcacaaatg agaccaagaa tgagttggtt tacagaggaa ataattggcc aggggagtca  2760
aagattcgta ttcaaaaaat tcaggaagct tctccaccta taagcggcag ctttgatgtt  2820
caagcttatg gacataccct gaaaggcatc cctgctgctg tgccagctgc agacttgcag  2880
tttgctctgc aaagcctgga agaaatagaa caagtctcag taaacagaga aggaacctgt  2940
gctggctatt catggagcat cagatggaca agcccccgtg gaaagcaacc tcttctgcag  3000
atcaatgatt ccaacattat cggagaaaag gctaatgtaa cagttaccac aataaaggaa  3060
ggtggcttat ttagacaacg tatccctgga gacatgcttc gtacactgaa tcagcaacca  3120
caggttgaag tctatgtcaa tggaattcca gccaaatgtt caggtgactg tgggtttaca  3180
tgggatgcca tgattactcc cctgatcttg acaacaacac cttccgaagg atcctatgca  3240
gaaagcacga ttctaaccat agcaggctct ggattttctc ccacctcagc tgtatccgtc  3300
tctgttggtt ctaccagatg ctctcttctc tctgtggagg aaaatgagat caagtgccag  3360
attctgaatg gaagtgctgg acatgtacca gttgctgtgt ccattgctga tgttggacta  3420
gcacagaatc tagagggtga gggatcccac ttcatttatc ggagtcagat ctcacatgtc  3480
tggcctgatt ctggaagcct ggcaggtggt actctgctga caatatctgg atttggtttt  3540
agtgaaaatt caacagtttt agttggaaat gaaacctgca atgtgatcga aggagatttg  3600
aataggataa cctgcagaac atcaaaaaga attgagggta cagttgatat ttctgtcatt  3660
accaatggaa ttcaagtcac agcaaaggac agttttagtt acagctgctt acaaacacca  3720
gttgtcactg acttcagccc aaaagaacgg acagttctgg aaaggtcaa tttaacaatt  3780
aaaggttata acттттggaaа tgaactcgca caaaatacgg tgtatgttgg aagaaagcac  3840
tgccaggtac ttcactcaaa cttcacagac attacatgcc ttttgcccac gttacctcca  3900
ggaaaacatg atatctatgt gaaagtcaga aactggggtt tggcgtcaac aaggaacaag  3960
ttaaatgctt ccatactgta cатттттggaa gtcatccaca tgtttcccca gagaggctct  4020
ttgtatggtg gcactgaaat cactataatg ggttttgggt tcagcacaat accaactgag  4080
```

```
aattctgttc tcttaggctc cttcccatgt gacattacat catcatcaga aaatgtcatc   4140
aaatgtactc tccattcaac agggacagta ttcagaatta ccaacaacgg ttcacattta   4200
gtgcatggac taggttatgc ctggtcacca tcagtcttaa atgtgactgt ggcgatacc    4260 gtggtgtggt cctggcaagc acaccccttt cttaggggta tagggtacag aattttctca   4320
gtctccagtc ccggaagtgt aacttatgat gacaaaggat ttacaaatgg gagacaaaaa   4380
tctgcatccg gttcattttc ttaccagttt acttcccctg gaatctatta ctacagcagc   4440
gggtatgttg atgaggctca ctccatatct ctccaaggag tcattaatgt ttttccagct   4500
gaagccaggc acattcccct gtacctgttt gtgggaaaca ttgaggcgac atatgttcca   4560
gcaggccctg cgcatttaca gttggcaagt actgcagcag gctgcctagc aacagaaccc   4620
ctgtgtggtc tgaatgatac aagggttaaa cattcaaata aattattctt cgagctttca   4680
aattgcattt caccctctat catcaacatt actccctcta ccggaacagc aaatgaactt   4740
ataactatca ttggacatgg cttcagtagt cttccatgtg ctaataaggt tacaattggt   4800
agctacccct tgtgttgtaga agaaagtagt gaaaattcta ttatatgtca tattgaccca   4860
caaaactcaa tgaatgttgg cattagagaa attgttactt tgattgtcta caacctgggc   4920
actgctatca acacactgac caaagcattt gacaggcggt ttgtacttt gccaaacata    4980 gatatggtga tgccaaaagc agggtcaact acaggaatga caagggtaac catacaaggc   5040 tctggatttta tgtcttctcc tgaaggtgta gaagtcttta tgggtgattt cccatgtaaa   5100
gttctatctg tgacctacac agctattgaa tgtgaaacat ctccggctcc caacagctt    5160 gttcttgtag acattctaat acatggagtg cctgcccaat gtcagagcaa ctgcagcttt   5220
tcatatttag aaaacattgc tccctatgta acaggaatct tcccaaactc aatccaagga   5280
tatggaaatg tcctcatcaa aggagaacgt tttgggacag tgttggaaga gatttctata   5340
tttattggaa gtcagcaatt cagagtaata gatgttaatg aaaataatat tactgtcctc   5400
atgactccac tagaagctgg acttcattct ctcagtgttg ttgttgggtc taagggcttg   5460
gctctaggaa atctaaccat cagcagccct gcagtagctt ctgtctcacc aacctctgga   5520
agcattgctg gtggaacgac tttgatgata acaggcaatg gattttctcc tggaaacacc   5580
acagttactg ttggggatca gccttgtcaa attacgttca tcagctccag tgaggtctac   5640
tgtagcaccc cagctgggag agctggtaca gccaatctga agattagtgt caatgcgatc   5700
atctacccac ctttgtcatt tacatatgcc atggaagata ctccatttct caaaagaatc   5760
atccctaata gaggtctacc aggaactgaa gttgaaataa ctgggtctaa tcttggatttt   5820 gctatctccg atgtttcagt gatgataaaa gagagtgtat gtaatgtgac cactgtcaat   5880
gacactgtgt tacagtgcac tgtgggagag catgcagggg gcattttccc tgtgacgatg   5940
cttcataaga caaaggctc tgctgtctcc tctgttgcat ttgagtaccc actttctatt    6000
cagaatattt atccaacaca agggagcttt ggtggtgggc aaaccttgac tgtgacaggc   6060
atgggatttg atccatggaa ttcaaccata ttggtctgta actctgaatg tgcagttgac   6120
aaactaagat ctaactctac aacactgttc tgtgtgattc ctcctaacaa tggcaaggga   6180
catgatcaag tctgtggagt gagtgtggtc aacgggaaag actcatctca ttccacgaag   6240
ctatttacat acaccttgtc gctgactccc ctcatcactg aaatatctcc caggagaggc   6300
agcactgctg ggggcaccag gcttacagtc acaggatctg gattcagtga aaacacacag   6360
ggtgttcaag tcttcgtagg caacagcaaa tgtgatatcc aatattccaa caagacacat   6420
atcgtctgca tgacaagtgt tcatgttcct tcaggatggg ttccagttca tgtcaacatc   6480
```

```
aaaaacatcg gcctggccaa attggagaat gctgacttct tatatgccga tgtttggtct    6540
gccaactcct catggggagg aagtccacca ccagaggaag gatcacttgc cgttattaca    6600
aaagggcaga taattctgct ggaccaaagt actcctattc ttaaaatgtt actcattcaa    6660
ggtgggactc tgatatttga tgaagctaat attgaactcc aggcagaaaa tatcctaatc    6720
acagatgggg gcgtacttca gattgggaca gaagcatccc cgttccaaca ccgggctgtc    6780
attactcttc atgggcatct tagatctcct gagctccctg tatatggagc taagacattg    6840
ggagtacgtg agggcacact ggatcttcac ggtctgccta ttcctgtggt ctggactcgc    6900
ttgacccata cggcaaatgc aggagaatgg actttaactg tacaagaagc agtgacatgg    6960
aaggcaggag ataacattgt gattgcaagc acaggacaca gacacagcca agcagagaat    7020
gagaagcgga ccatcgcgtc ggtgtccgct gatggaatgc ataaccctt aactaagcca    7080 ctcaactaca cacacttggg aattaccacc acacttcccg atggaactgt gtttgaagcc    7140
agggcagaag ttggaattct tacaagaaat attttaataa gagggtctga taatgtggag    7200
tggaatgaca agattccatc atgtcccgat ggatttgata caggagaatt tgctacacag    7260
acatgccttc aaggaaagtt tggagaagaa atgggaagtg accagtttgg aggctgtatt    7320
atgttgcatg ctcccttacc tggggctgac atggtaactg gaagaataga atacgtagag    7380
gtgttccatg ctggtcaatc tttccgtttg gacgatacc caatacattg gcacctgctt    7440
ggagatttac agttcaaatc ctatgtgaaa ggctgtgcaa ttcatcaatc atacaacaga    7500
gctattacaa tccacaatac gcatcacctt cttgtggaga ggaatattat atatgatata    7560
aaaggaggag catttttcat agaagatggt attgaacatg caacattct gcaatataat    7620 ctggcagtct ttgtacagca aagtaccagt ctactgaatg atgatgtgac cccagctgca    7680
ttctgggtaa ccaatcctaa caacaccatt cgacacaatg cggctgctgg gggcactcac    7740
tttggctttt ggtacagaat gaatgaccac cctgatggcc catctttga ccgaaacatt    7800 tgccaaaaac gaattccgct tggagaattc tttaacaata ctgttcattc tcaggggtgg    7860
tttggactgt ggattttga agagtatttc cccatgcaaa caggatcttg tacctctaca    7920
gtgccagtgc ctgccatctt taactcactc actgtgtgga actgtcaaaa aggagctgaa    7980
tgggtgaacg gaggggccct gcagttccac aactttgtga tggtgaacaa caatgaggct    8040
ggcattgaga ccaagaggat cctggctccc tatgttggag gatgggggga aagcaatgga    8100
gctgtgatta aaaatgccaa aatcgttggt catcttgatg agctgggaat gggacccaca    8160
ttttgcactt caaaaggcct ggttctccca tttagtcaag gcctgactgt gtcgtctgtg    8220
cactttatga attttgaccg ccatgcctgt gtggctttag gagtaacatc aatcactggg    8280
gtgtgtaatg acagatgtgg aggctggagt gctaagtttg ttggcatccg gtattttcat    8340
gcacccaata agggtggttt tcgttgggaa cacgaagcag tactgattga cgttgacggc    8400
tcactaacag ggcacagagg gcacactgtc gttccacaca gctccttact ggacccttca    8460
cactgtactc aagagcctgc atggagcatt ggttttcctg gctccatctg tgatgcctct    8520
gtcagcttcc accggctagc attcaacaag ccttccccag tatctttact tgaaaaagat    8580
gtggttcttt cagactcttt tggcactagc attgttccct tcagaagaa acgactgacc    8640 catatgtcag ggtggatggc tctgattcca aatgcaaatc acattaactg gtattttaaa    8700
ggtgtggagc acttaaccaa catatcatat acttccacat tctatggatt taaggaagaa    8760
gactatgtaa ttatatcaca taacttcact caaaatcctg atatgtttaa tgttgttgat    8820
atgaggaatg gctccgcaaa cccattgaat tggaattcta gtaagaatgg agactggcat    8880
```

```
cttgaagcaa acaccagtac tctctattat ttggtgtcag ggagaagtga cctacctcag    8940
agccagccca tctctgggac cctagatcct ggtgtgaagg atgtgattat taatttccaa    9000
gcttactgct gtgttctcca agactgcttt ccagttcatc caccatcaag aaaaccaatt    9060
cccaggaaac gaccagccgc ttacaattta tggtccaatg agtccttctg gcaatcatcc    9120
ccagagaaca attatactgt acctcgccca ggagcaaatg tgattattcc tgaaggaaca    9180
tggattgtag ctgatgtgga tataccccca gtggaaagac tcattatttg gggagttcta    9240
gaaatggaag ataaatctga gataggagta gcaggcccca cctatagaag agttgtttta    9300
aatgccacct acatatcagt acagggaggg agattaattg gtggctggga agataacccc    9360
tttaaaggag aattacagat tgttcttcga ggaaatcatt ctaccccaga atgggctttt    9420
ccagacggac cgaatcaagg ggcaaaggtg ttaggagtgt ttggtgagct ggacctgcat    9480
ggacttccac attcagttta taaaactaaa ctgttagaaa ctgcggaagc aggctccaaa    9540
atcttatctc tagtggatgc tgtggattgg caggagggag aagatgttgt aataactacc    9600
acaagctatg atttacacca gacggagatc agaaggattg ctaaaatcct acatgggcac    9660
aaaattctca tcctcaatga tagccttcc tacactcacc ttgctgaaag acagtggatc    9720
tctggaacag ctcagagcta cacattatca gctgatgttg ggatactgag taggaacatc    9780
aaaatagttg gtgacgatta ctcggttttg tccaaagact cttttggtgc acggatccta    9840
gttggctcat tcactggaaa catgatgaca tttaaaggaa atgcaagaat aagtaatgtg    9900
gaatttcatc acagtggtca agaaggctac agggatagca ccgatccaag atatgctgtg    9960
acatttctta acctgggaca gattcaagat catggcttgt cttatgttcg aggctgtgca   10020
tttcatcatg tgttctcccc agcaattggt gtgtttggga ctgatggggt ggacatagat   10080
gacaacatca tctactttac agtaggagaa ggtataagaa tatgggggga tgccaacaga   10140
gtacgtggaa atttggtcac cctttcagtt tggccaggaa cctaccagaa cagaaaagac   10200
ttgagttcga cactttggca tgcagcaatt gagataaaca gagggaccaa tacagtctta   10260
caaaataatg tagtcgctgg atttggaaga gtaggatacc gcattgatgg tgaaccatgc   10320
tcaagccagg ctaattccat ggaaaactgg tttaacaatg aagcccatgg aggtttgtat   10380
ggcatctaca tgaaccagga tggccttcct ggttgttctc ttattcaagg atttactatt   10440
tggacatgct gggactatgg aatttatttt cagaccacgg agagcgtgca tatctataac   10500
gtgacgctgg tgaacaacgg gatgagcatc ttttcaatgg tctacatgcc accttctgtg   10560
tcccacaaaa tttccagcaa aacagtaaaa attaagaact cattaattgt tggaagcagc   10620
cctgagttta actgttctga cgtcttaact aatgacagtc ctgatgtaga actcacctct   10680
gcacatcgaa gttctaggcc cccgtcaggt gggagaagtg ggatttgctg gccaacattt   10740
gcttcagctc ataacatggc acctcggaag cctcatgccg ggatcatgag ttacaatgca   10800
atcagtggcc ttttgcatgt ctcagattca acatttgttg gatttaagga tgtttgttca   10860
ggagaaacta atgtgatatt cattactaat cctttaaatg aagacttaca gcatccaatc   10920
catgtgaaga atgtccaact cattgacact attgaacaat ccaaagtatt catacataga   10980
cctgatataa gtaaagtgaa cccatctgat tgtgtggaca tggtttgtga tgccaagaga   11040
aaatcttttc ttagagacct ggatggttcc tttctgggga attctgggtc agtgatccct   11100
caagctgagt atgagtggga tgaaacagca caactgggaa ttggagacta cagaattcca   11160
aaggcgatgc tcacatactt gaatggaagt agaattcctg taactgagaa agcacctcat   11220
aaagggatta ttagagatgc aacctgtaaa tacatcccag agtggcagag ctatcagtgt   11280
```

```
tctggaatgg aatatgcaat gatggtactg gaaagcctgg attctgacac agagacacga   11340
agactatccc cagtggctat catgagcaat ggttatgttg atctcattaa tggcccacag   11400
gaccatggct ggtgtgcggg gtatacatgc caaagaagac tgtctctgtt ccatggcata   11460
gtggctctga acaaaaagta tgaggtttac tttaccggga ccagtcctca gaatcttcgg   11520
ctgatgttgc ttaatgttga acataataag gcagttctag taggaatttt tttttccaca   11580
cttcagcgtc tggatgtcta tgtgaacaat tccttggtct gtcccaaaaa tacagcatgg   11640
aatgcccaaa agaaacactg tgaacttgaa aggcatctga gcacagaaca attccttcct   11700
aacttgggtt ccactgtccc tggtgaaaac tactttgata gaacctacca gatgctgtac   11760
cttttcctga aggaactac acctgtggag gtccacactg ctactgtcat ctttgtatct   11820
ttccacctgc cggttatgac agcagatgag ttttttagct cacacaacct ggttagaaat   11880
cttgccttgt tcctaaaaat accaagtgac aaaatccgtg tcagcagaat aataggagca   11940
agtctgagaa agaagcgatc cacaggacac ataatgaatt tgagattgg ggctgctccc   12000 actcagttct tgagcaattc taccacaggt caaatgcagt tgtctgagct ccaggaaatt   12060
actgactctc ttgacaagc tgttgtccta ggaaaaatta gtactattct tggattcaat   12120
atttcttcca tgtctattac cagtcccatc ccccaaccaa ctgattctgg ctggattaag   12180
gtgactgccc agccagttga agatctgca tttcccgttc actacctggc ccttgtgtct   12240
tcactctcag tggttgctca gccagtggca gcccagcccg gacagcccct tcctcagcag   12300
ccctcagtaa aggcagtaga tcctgagggt aactgtgtat cagttggaat acatcgctt   12360 actttgaagg ctatcctaaa ggactccaat aacaaccaag ttggtggcct tagtggaaat   12420
acaacaattc catttagcac ctgttgggcc aactatacag acctcactcc tcacagaaca   12480
ggaaaaaatt ataaaattga atttgtcctg gataatactg ttcgtgtgga ttcacgaccc   12540
ttcagcctgt cagcacagag tgtccctggt ggcagtggaa gtagcccggg tagtggcagc   12600
agcagcagtg gccacagcaa agcctcctct gtggggacac ctgtccagac actggctgtc   12660
ataacagcgt gccttgtagg aagactactg ctcttggaag tatttatggc tgcagttttc   12720
attttgaaca caactgtagg aatcaactga                                    12750
```

<210> SEQ ID NO 3
<211> LENGTH: 4243
<212> TYPE: PRT
<213> ORGANISM: Homo sapiens
<400> SEQUENCE: 3

```
Met Gly His Leu Trp Leu Leu Gly Ile Trp Gly Leu Cys Gly Leu Leu
1               5                   10                  15

Leu Cys Ala Ala Asp Pro Ser Thr Asp Gly Ser Gln Ile Ile Pro Lys
                20                  25                  30

Val Thr Glu Ile Ile Pro Lys Tyr Gly Ser Ile Asn Gly Ala Thr Arg
            35                  40                  45

Leu Thr Ile Arg Gly Glu Gly Phe Ser Gln Ala Asn Gln Phe Asn Tyr
        50                  55                  60

Gly Val Asp Asn Ala Glu Leu Gly Asn Ser Val Gln Leu Ile Ser Ser
65                  70                  75                  80

Phe Gln Ser Ile Thr Cys Asp Val Glu Lys Asp Ala Ser His Ser Thr
                85                  90                  95

Gln Ile Thr Cys Tyr Thr Arg Ala Met Pro Glu Asp Ser Tyr Thr Val
            100                 105                 110
```

-continued

```
Arg Val Ser Val Asp Gly Val Pro Val Thr Glu Asn Thr Cys Lys
            115                 120                 125

Gly His Ile Asn Ser Trp Glu Cys Thr Phe Asn Ala Lys Ser Phe Arg
    130                 135                 140

Thr Pro Thr Ile Arg Ser Ile Thr Pro Leu Ser Gly Thr Pro Gly Thr
145                 150                 155                 160

Leu Ile Thr Ile Gln Gly Arg Ile Phe Thr Asp Val Tyr Gly Ser Asn
                165                 170                 175

Ile Ala Leu Ser Ser Asn Gly Lys Asn Val Arg Ile Leu Arg Val Tyr
            180                 185                 190

Ile Gly Gly Met Pro Cys Glu Leu Leu Ile Pro Gln Ser Asp Asn Leu
        195                 200                 205

Tyr Gly Leu Lys Leu Asp His Pro Asn Gly Asp Met Gly Ser Met Val
    210                 215                 220

Cys Lys Thr Thr Gly Thr Phe Ile Gly His His Asn Val Ser Phe Ile
225                 230                 235                 240

Leu Asp Asn Asp Tyr Gly Arg Ser Phe Pro Gln Lys Met Ala Tyr Phe
                245                 250                 255

Val Ser Ser Leu Asn Lys Ile Ala Met Phe Gln Thr Tyr Ala Glu Val
            260                 265                 270

Thr Met Ile Phe Pro Ser Gln Gly Ser Ile Arg Gly Gly Thr Thr Leu
        275                 280                 285

Thr Ile Ser Gly Arg Phe Phe Asp Gln Thr Asp Phe Pro Val Arg Val
    290                 295                 300

Leu Val Gly Gly Glu Pro Cys Asp Ile Leu Asn Val Thr Glu Asn Ser
305                 310                 315                 320

Ile Cys Cys Lys Thr Pro Pro Lys Pro His Ile Leu Lys Thr Val Tyr
                325                 330                 335

Pro Gly Gly Arg Gly Leu Lys Leu Glu Val Trp Asn Asn Ser Arg Pro
            340                 345                 350

Ile Arg Leu Glu Glu Ile Leu Glu Tyr Asn Glu Lys Thr Pro Gly Tyr
        355                 360                 365

Met Gly Ala Ser Trp Val Asp Ser Ala Ser Tyr Ile Trp Leu Met Glu
    370                 375                 380

Gln Asp Thr Phe Val Ala Arg Phe Ser Gly Phe Leu Val Ala Pro Asp
385                 390                 395                 400

Ser Asp Val Tyr Arg Phe Tyr Ile Lys Gly Asp Asp Arg Tyr Ala Ile
                405                 410                 415

Tyr Phe Ser Gln Thr Gly Leu Pro Glu Asp Lys Val Arg Ile Ala Tyr
            420                 425                 430

His Ser Ala Asn Ala Asn Ser Tyr Phe Ser Ser Pro Thr Gln Arg Ser
        435                 440                 445

Asp Asp Ile His Leu Gln Lys Gly Lys Glu Tyr Tyr Ile Glu Ile Leu
    450                 455                 460

Leu Gln Glu Tyr Arg Leu Ser Ala Phe Val Asp Val Gly Leu Tyr Gln
465                 470                 475                 480

Tyr Arg Asn Val Tyr Thr Glu Gln Gln Thr Gly Asp Ala Val Asn Glu
                485                 490                 495

Glu Gln Val Ile Lys Ser Gln Ser Thr Ile Leu Gln Glu Val Gln Val
            500                 505                 510

Ile Thr Leu Glu Asn Trp Glu Thr Thr Asn Ala Ile Asn Glu Val Gln
        515                 520                 525

Lys Ile Lys Val Thr Ser Pro Cys Val Glu Ala Asn Ser Cys Ser Leu
    530                 535                 540
```

```
Tyr Gln Tyr Arg Leu Ile Tyr Asn Met Glu Lys Thr Val Phe Leu Pro
545                 550                 555                 560

Ala Asp Ala Ser Glu Phe Ile Leu Gln Ser Ala Leu Asn Asp Leu Trp
            565                 570                 575

Ser Ile Lys Pro Asp Thr Val Gln Val Ile Arg Thr Gln Asn Pro Gln
                580                 585                 590

Ser Tyr Val Tyr Met Val Thr Phe Ile Ser Thr Arg Gly Asp Phe Asp
            595                 600                 605

Leu Leu Gly Tyr Glu Val Val Glu Gly Asn Asn Val Thr Leu Asp Ile
        610                 615                 620

Thr Glu Gln Thr Lys Gly Lys Pro Asn Leu Glu Thr Phe Thr Leu Asn
625                 630                 635                 640

Trp Asp Gly Ile Ala Ser Lys Pro Leu Thr Leu Trp Ser Ser Glu Ala
                645                 650                 655

Glu Phe Gln Gly Ala Val Glu Glu Met Val Ser Thr Lys Cys Pro Pro
            660                 665                 670

Gln Ile Ala Asn Phe Glu Glu Gly Phe Val Val Lys Tyr Phe Arg Asp
        675                 680                 685

Tyr Glu Thr Asp Phe Asn Leu Glu His Ile Asn Arg Gly Gln Lys Thr
690                 695                 700

Ala Glu Thr Asp Ala Tyr Cys Gly Arg Tyr Ser Leu Lys Asn Pro Ala
705                 710                 715                 720

Val Leu Phe Asp Ser Ala Asp Val Lys Pro Asn Arg Arg Pro Tyr Gly
                725                 730                 735

Asp Ile Leu Leu Phe Pro Tyr Asn Gln Leu Cys Leu Ala Tyr Lys Gly
            740                 745                 750

Phe Leu Ala Asn Tyr Ile Gly Leu Lys Phe Gln Tyr Gln Asp Asn Ser
        755                 760                 765

Lys Ile Thr Arg Ser Thr Asp Thr Gln Phe Thr Tyr Asn Phe Ala Tyr
770                 775                 780

Gly Asn Asn Trp Thr Tyr Thr Cys Ile Asp Leu Leu Asp Leu Val Arg
785                 790                 795                 800

Thr Lys Tyr Thr Gly Thr Asn Val Ser Leu Gln Arg Ile Ser Leu His
                805                 810                 815

Lys Ala Ser Glu Ser Gln Ser Phe Tyr Val Asp Val Val Tyr Ile Gly
            820                 825                 830

His Thr Ser Thr Ile Ser Thr Leu Asp Glu Met Pro Lys Arg Arg Leu
        835                 840                 845

Pro Ala Leu Ala Asn Lys Gly Ile Phe Leu Glu His Phe Gln Val Asn
850                 855                 860

Gln Thr Lys Thr Asn Gly Pro Thr Met Thr Asn Gln Tyr Ser Val Thr
865                 870                 875                 880

Met Thr Ser Tyr Asn Cys Ser Tyr Asn Ile Pro Met Met Ala Val Ser
                885                 890                 895

Phe Gly Gln Ile Ile Thr His Glu Thr Glu Asn Glu Phe Val Tyr Arg
            900                 905                 910

Gly Asn Asn Trp Pro Gly Glu Ser Lys Ile His Ile Gln Arg Ile Gln
        915                 920                 925

Ala Ala Ser Pro Pro Leu Ser Gly Ser Phe Asp Ile Gln Ala Tyr Gly
930                 935                 940

His Ile Leu Lys Gly Leu Pro Ala Ala Val Ser Ala Ala Asp Leu Gln
945                 950                 955                 960

Phe Ala Leu Gln Ser Leu Glu Gly Met Gly Arg Ile Ser Val Thr Arg
```

-continued

```
                965                 970                 975
Glu Gly Thr Cys Ala Gly Tyr Ala Trp Asn Ile Lys Trp Arg Ser Thr
            980                 985                 990
Cys Gly Lys Gln Asn Leu Leu Gln Ile Asn Asp Ser Asn Ile Ile Gly
        995                 1000                1005
Glu Lys Ala Asn Met Thr Val Thr Arg Ile Lys Glu Gly Gly Leu Phe
    1010                1015                1020
Arg Gln His Val Leu Gly Asp Leu Leu Arg Thr Pro Ser Gln Gln Pro
1025                1030                1035                1040
Gln Val Glu Val Tyr Val Asn Gly Ile Pro Ala Lys Cys Ser Gly Asp
                1045                1050                1055
Cys Gly Phe Thr Trp Asp Ser Asn Ile Thr Pro Leu Val Leu Ala Ile
            1060                1065                1070
Ser Pro Ser Gln Gly Ser Tyr Glu Glu Gly Thr Ile Leu Thr Ile Val
        1075                1080                1085
Gly Ser Gly Phe Ser Pro Ser Ser Ala Val Thr Val Ser Val Gly Pro
    1090                1095                1100
Val Gly Cys Ser Leu Leu Ser Val Asp Glu Lys Glu Leu Lys Cys Gln
1105                1110                1115                1120
Ile Leu Asn Gly Ser Ala Gly His Ala Pro Val Ala Val Ser Met Ala
                1125                1130                1135
Asp Val Gly Leu Ala Gln Asn Val Gly Gly Glu Glu Phe Tyr Phe Val
            1140                1145                1150
Tyr Gln Ser Gln Ile Ser His Ile Trp Pro Asp Ser Gly Ser Ile Ala
        1155                1160                1165
Gly Gly Thr Leu Leu Thr Leu Ser Gly Phe Gly Phe Asn Glu Asn Ser
    1170                1175                1180
Lys Val Leu Val Gly Asn Glu Thr Cys Asn Val Ile Glu Gly Asp Leu
1185                1190                1195                1200
Asn Arg Ile Thr Cys Arg Thr Pro Lys Lys Thr Glu Gly Thr Val Asp
                1205                1210                1215
Ile Ser Val Thr Thr Asn Gly Phe Gln Ala Thr Ala Arg Asp Ala Phe
            1220                1225                1230
Ser Tyr Asn Cys Leu Gln Thr Pro Ile Ile Thr Asp Phe Ser Pro Lys
        1235                1240                1245
Val Arg Thr Ile Leu Gly Glu Val Asn Leu Thr Ile Lys Gly Tyr Asn
    1250                1255                1260
Phe Gly Asn Glu Leu Thr Gln Asn Met Ala Val Tyr Val Gly Gly Lys
1265                1270                1275                1280
Thr Cys Gln Ile Leu His Trp Asn Phe Thr Asp Ile Arg Cys Leu Leu
                1285                1290                1295
Pro Lys Leu Ser Pro Gly Lys His Asp Ile Tyr Val Glu Val Arg Asn
            1300                1305                1310
Trp Gly Phe Ala Ser Thr Arg Asp Lys Leu Asn Ser Ser Ile Gln Tyr
        1315                1320                1325
Val Leu Glu Val Thr Ser Met Phe Pro Gln Arg Gly Ser Leu Phe Gly
    1330                1335                1340
Gly Thr Glu Ile Thr Ile Arg Gly Phe Gly Phe Ser Thr Ile Pro Ala
1345                1350                1355                1360
Glu Asn Thr Val Leu Leu Gly Ser Ile Pro Cys Asn Val Thr Ser Ser
                1365                1370                1375
Ser Glu Asn Val Ile Lys Cys Ile Leu His Ser Thr Gly Asn Ile Phe
            1380                1385                1390
```

```
Arg Ile Thr Asn Asn Gly Lys Asp Ser Val His Gly Leu Gly Tyr Ala
    1395                1400                1405

Trp Ser Pro Pro Val Leu Asn Val Ser Val Gly Asp Thr Val Ala Trp
    1410                1415                1420

His Trp Gln Thr His Pro Phe Leu Arg Gly Ile Gly Tyr Arg Ile Phe
1425                1430                1435                1440

Ser Val Ser Ser Pro Gly Ser Val Ile Tyr Asp Gly Lys Gly Phe Thr
                1445                1450                1455

Ser Gly Arg Gln Lys Ser Thr Ser Gly Ser Phe Ser Tyr Gln Phe Thr
                1460                1465                1470

Ser Pro Gly Ile His Tyr Tyr Ser Ser Gly Tyr Val Asp Glu Ala His
            1475                1480                1485

Ser Ile Phe Leu Gln Gly Val Ile Asn Val Leu Pro Ala Glu Thr Arg
            1490                1495                1500

His Ile Pro Leu His Leu Phe Val Gly Arg Ser Glu Ala Thr Tyr Ala
1505                1510                1515                1520

Tyr Gly Gly Pro Glu Asn Leu His Leu Gly Ser Ser Val Ala Gly Cys
                1525                1530                1535

Leu Ala Thr Glu Pro Leu Cys Ser Leu Asn Asn Thr Arg Val Lys Asn
            1540                1545                1550

Ser Lys Arg Leu Leu Phe Glu Val Ser Ser Cys Phe Ser Pro Ser Ile
            1555                1560                1565

Ser Asn Ile Thr Pro Ser Thr Gly Thr Val Asn Glu Leu Ile Thr Ile
            1570                1575                1580

Ile Gly His Gly Phe Ser Asn Leu Pro Trp Ala Asn Lys Val Thr Ile
1585                1590                1595                1600

Gly Ser Tyr Pro Cys Val Val Glu Glu Ser Ser Glu Asp Ser Ile Thr
                1605                1610                1615

Cys His Ile Asp Pro Gln Asn Ser Met Asp Val Gly Ile Arg Glu Thr
            1620                1625                1630

Val Thr Leu Thr Val Tyr Asn Leu Gly Thr Ala Ile Asn Thr Leu Ser
            1635                1640                1645

Asn Glu Phe Asp Arg Arg Phe Val Leu Leu Pro Asn Ile Asp Leu Val
            1650                1655                1660

Leu Pro Asn Ala Gly Ser Thr Thr Gly Met Thr Ser Val Thr Ile Lys
1665                1670                1675                1680

Gly Ser Gly Phe Ala Val Ser Ser Ala Gly Val Lys Val Leu Met Gly
                1685                1690                1695

His Phe Pro Cys Lys Val Leu Ser Val Asn Tyr Thr Ala Ile Glu Cys
            1700                1705                1710

Glu Thr Ser Pro Ala Ala Gln Gln Leu Val Asp Val Asp Leu Leu Ile
            1715                1720                1725

His Gly Val Pro Ala Gln Cys Gln Gly Asn Cys Thr Phe Ser Tyr Leu
            1730                1735                1740

Glu Ser Ile Thr Pro Tyr Ile Thr Gly Val Phe Pro Asn Ser Val Ile
1745                1750                1755                1760

Gly Ser Val Lys Val Leu Ile Glu Gly Glu Gly Leu Gly Thr Val Leu
                1765                1770                1775

Glu Asp Ile Ala Val Phe Ile Gly Asn Gln Gln Phe Arg Ala Ile Glu
            1780                1785                1790

Val Asn Glu Asn Asn Ile Thr Ala Leu Val Thr Pro Leu Pro Val Gly
            1795                1800                1805

His His Ser Val Ser Val Val Val Gly Ser Lys Gly Leu Ala Leu Gly
            1810                1815                1820
```

-continued

Asn Leu Thr Val Ser Ser Pro Pro Val Ala Ser Leu Ser Pro Thr Ser
1825                1830                1835                1840

Gly Ser Ile Gly Gly Gly Thr Thr Leu Val Ile Thr Gly Asn Gly Phe
            1845                1850                1855

Tyr Pro Gly Asn Thr Thr Val Thr Ile Gly Asp Glu Pro Cys Gln Ile
        1860                1865                1870

Ile Ser Ile Asn Pro Asn Glu Val Tyr Cys Arg Thr Pro Ala Gly Thr
    1875                1880                1885

Thr Gly Met Val Asp Val Lys Ile Phe Val Asn Thr Ile Ala Tyr Pro
1890                1895                1900

Pro Leu Leu Phe Thr Tyr Ala Leu Glu Asp Thr Pro Phe Leu Arg Gly
1905                1910                1915                1920

Ile Ile Pro Ser Arg Gly Pro Pro Gly Thr Glu Ile Glu Ile Thr Gly
            1925                1930                1935

Ser Asn Phe Gly Phe Glu Ile Leu Glu Ile Ser Val Met Ile Asn Asn
            1940                1945                1950

Ile Gln Cys Asn Val Thr Met Ala Asn Asp Ser Val Leu Gln Cys Ile
    1955                1960                1965

Val Gly Asp His Ala Gly Gly Thr Phe Pro Val Met Met His His Lys
    1970                1975                1980

Thr Lys Gly Ser Ala Met Ser Thr Val Val Phe Glu Tyr Pro Leu Asn
1985                1990                1995                2000

Ile Gln Asn Ile Asn Pro Ser Gln Gly Ser Phe Gly Gly Gly Gln Thr
            2005                2010                2015

Met Thr Val Thr Gly Thr Gly Phe Asn Pro Gln Asn Ser Ile Ile Leu
            2020                2025                2030

Val Cys Gly Ser Glu Cys Ala Ile Asp Arg Leu Arg Ser Asp Tyr Thr
    2035                2040                2045

Thr Leu Leu Cys Glu Ile Pro Ser Asn Gly Thr Gly Ala Glu Gln
    2050                2055                2060

Ala Cys Glu Val Ser Val Val Asn Gly Lys Asp Leu Ser Gln Ser Met
2065                2070                2075                2080

Thr Pro Phe Thr Tyr Ala Val Ser Leu Thr Pro Leu Ile Thr Ala Val
            2085                2090                2095

Ser Pro Lys Arg Gly Ser Thr Ala Gly Gly Thr Arg Leu Thr Val Val
            2100                2105                2110

Gly Ser Gly Phe Ser Glu Asn Met Glu Asp Val His Ile Thr Ile Ala
    2115                2120                2125

Glu Ala Lys Cys Asp Val Glu Tyr Ser Asn Lys Thr His Ile Ile Cys
    2130                2135                2140

Met Thr Asp Ala His Thr Leu Ser Gly Trp Ala Pro Val Cys Val His
2145                2150                2155                2160

Ile Arg Gly Val Gly Met Ala Lys Leu Asp Asn Ala Asp Phe Leu Tyr
            2165                2170                2175

Val Asp Ala Trp Ser Ser Asn Phe Ser Trp Gly Gly Lys Ser Pro Pro
            2180                2185                2190

Glu Glu Gly Ser Leu Val Val Ile Thr Lys Gly Gln Thr Ile Leu Leu
    2195                2200                2205

Asp Gln Ser Thr Pro Ile Leu Lys Met Leu Leu Ile Gln Gly Gly Thr
    2210                2215                2220

Leu Ile Phe Asp Glu Ala Asp Ile Glu Leu Gln Ala Glu Asn Ile Leu
2225                2230                2235                2240

Ile Thr Asp Gly Gly Val Leu Gln Ile Gly Thr Glu Thr Ser Pro Phe

-continued

Gln His Lys Ala Val Ile Thr Leu His Gly His Leu Arg Ser Pro Glu
                2245                2250                2255

Leu Pro Val Tyr Gly Ala Lys Thr Leu Ala Val Arg Glu Gly Ile Leu
    2275                2280                2285

Asp Leu His Gly Val Pro Val Pro Val Thr Trp Thr Arg Leu Ala His
    2290                2295                2300

Thr Ala Lys Ala Gly Glu Arg Ile Leu Ile Leu Gln Glu Ala Val Thr
2305                2310                2315                2320

Trp Lys Pro Gly Asp Asn Ile Val Ile Ala Ser Thr Gly His Arg His
                2325                2330                2335

Ser Gln Gly Glu Asn Glu Lys Met Thr Ile Ala Ser Val Ser Ala Asp
                2340                2345                2350

Gly Ile Asn Ile Thr Leu Ser Asn Pro Leu Asn Tyr Thr His Leu Gly
                2355                2360                2365

Ile Thr Val Thr Leu Pro Asp Gly Thr Leu Phe Glu Ala Arg Ala Glu
    2370                2375                2380

Val Gly Ile Leu Thr Arg Asn Ile Leu Ile Arg Gly Ser Asp Asn Val
2385                2390                2395                2400

Glu Trp Asn Asn Lys Ile Pro Ala Cys Pro Asp Gly Phe Asp Thr Gly
                2405                2410                2415

Glu Phe Ala Thr Gln Thr Cys Leu Gln Gly Lys Phe Gly Glu Glu Ile
                2420                2425                2430

Gly Ser Asp Gln Phe Gly Gly Cys Val Met Phe His Ala Pro Val Pro
                2435                2440                2445

Gly Ala Asn Met Val Thr Gly Arg Ile Glu Tyr Val Glu Val Phe His
                2450                2455                2460

Ala Gly Gln Ala Phe Arg Leu Gly Arg Tyr Pro Ile His Trp His Leu
2465                2470                2475                2480

Leu Gly Asp Leu Gln Phe Lys Ser Tyr Val Arg Gly Cys Ala Ile His
                2485                2490                2495

Gln Ala Tyr Asn Arg Ala Val Thr Ile His Asn Thr His His Leu Leu
                2500                2505                2510

Val Glu Arg Asn Ile Ile Tyr Asp Ile Lys Gly Gly Ala Phe Phe Ile
                2515                2520                2525

Glu Asp Gly Ile Glu His Gly Asn Ile Leu Gln Tyr Asn Leu Ala Val
                2530                2535                2540

Phe Val Gln Gln Ser Thr Ser Leu Leu Asn Asp Asp Val Thr Pro Ala
2545                2550                2555                2560

Ala Phe Trp Val Thr Asn Pro Asn Asn Thr Ile Arg His Asn Ala Val
                2565                2570                2575

Ala Gly Gly Thr His Phe Gly Phe Trp Tyr Arg Met Asn Asn His Pro
                2580                2585                2590

Asp Gly Pro Ser Tyr Asp Arg Asn Ile Cys Gln Lys Arg Val Pro Leu
                2595                2600                2605

Gly Glu Phe Phe Asn Asn Thr Val His Ser Gln Gly Trp Phe Gly Met
    2610                2615                2620

Trp Ile Phe Glu Glu Tyr Phe Pro Met Gln Thr Gly Ser Cys Thr Ser
2625                2630                2635                2640

Thr Val Pro Ala Pro Ala Ile Phe Asn Ser Leu Thr Thr Trp Asn Cys
                2645                2650                2655

Gln Lys Gly Ala Glu Trp Val Asn Gly Gly Ala Leu Gln Phe His Asn
                2660                2665                2670

-continued

```
Phe Val Met Val Asn Asn Tyr Glu Ala Gly Ile Glu Thr Lys Arg Ile
            2675                2680                2685

Leu Ala Pro Tyr Val Gly Gly Trp Gly Glu Thr Asn Gly Ala Val Ile
            2690                2695                2700

Lys Asn Ala Lys Ile Val Gly His Leu Asp Glu Leu Gly Met Gly Ser
2705                2710                2715                2720

Ala Phe Cys Thr Ala Lys Gly Leu Val Leu Pro Phe Ser Glu Gly Leu
            2725                2730                2735

Thr Val Ser Ser Val His Phe Met Asn Phe Asp Arg Pro Asn Cys Val
            2740                2745                2750

Ala Leu Gly Val Thr Ser Ile Ser Gly Val Cys Asn Asp Arg Cys Gly
            2755                2760                2765

Gly Trp Ser Ala Lys Phe Val Asp Val Gln Tyr Ser His Thr Pro Asn
            2770                2775                2780

Lys Ala Gly Phe Arg Trp Glu His Glu Met Val Met Ile Asp Val Asp
2785                2790                2795                2800

Gly Ser Leu Thr Gly His Lys Gly His Thr Val Ile Pro His Ser Ser
            2805                2810                2815

Leu Leu Asp Pro Ser His Cys Thr Gln Glu Ala Glu Trp Ser Ile Gly
            2820                2825                2830

Phe Pro Gly Ser Val Cys Asp Ala Ser Val Ser Phe His Arg Leu Ala
            2835                2840                2845

Phe Asn Gln Pro Ser Pro Val Ser Leu Leu Glu Lys Asp Val Val Leu
            2850                2855                2860

Ser Asp Ser Phe Gly Thr Ser Ile Ile Pro Phe Gln Lys Lys Arg Leu
2865                2870                2875                2880

Thr His Met Ser Gly Trp Met Ala Leu Ile Pro Asn Ala Asn His Ile
            2885                2890                2895

Asn Trp Tyr Phe Lys Gly Val Asp His Ile Thr Asn Ile Ser Tyr Thr
            2900                2905                2910

Ser Thr Phe Tyr Gly Phe Lys Glu Glu Asp Tyr Val Ile Ile Ser His
            2915                2920                2925

Asn Phe Thr Gln Asn Pro Asp Met Phe Asn Ile Ile Asp Met Arg Asn
            2930                2935                2940

Gly Ser Ser Asn Pro Leu Asn Trp Asn Thr Ser Lys Asn Gly Asp Trp
2945                2950                2955                2960

His Leu Glu Ala Asn Thr Ser Thr Leu Tyr Tyr Leu Val Ser Gly Arg
            2965                2970                2975

Asn Asp Leu His Gln Ser Gln Leu Ile Ser Gly Asn Leu Asp Pro Asp
            2980                2985                2990

Val Lys Asp Val Val Ile Asn Phe Gln Ala Tyr Cys Cys Ile Leu Gln
            2995                3000                3005

Asp Cys Phe Pro Val His Pro Pro Ser Arg Lys Pro Ile Pro Lys Lys
            3010                3015                3020

Arg Pro Ala Thr Tyr Asn Leu Trp Ser Asn Asp Ser Phe Trp Gln Ser
3025                3030                3035                3040

Ser Arg Glu Asn Asn Tyr Thr Val Pro His Pro Gly Ala Asn Val Ile
            3045                3050                3055

Ile Pro Glu Gly Thr Trp Ile Val Ala Asp Ile Asp Met Pro Ser Met
            3060                3065                3070

Glu Arg Leu Ile Ile Trp Gly Val Leu Glu Leu Glu Asp Lys Tyr Asn
            3075                3080                3085

Val Gly Ala Ala Glu Ser Ser Tyr Arg Glu Val Val Leu Asn Ala Thr
            3090                3095                3100
```

```
Tyr Ile Ser Leu Gln Gly Gly Arg Leu Ile Gly Gly Trp Glu Asp Asn
3105                3110                3115                3120

Pro Phe Lys Gly Asp Leu Lys Ile Val Leu Arg Gly Asn His Thr Thr
                3125                3130                3135

Gln Asp Trp Ala Leu Pro Glu Gly Pro Asn Gln Gly Ala Lys Val Leu
        3140                3145                3150

Gly Val Phe Gly Glu Leu Asp Leu His Gly Ile Pro His Ser Ile Tyr
            3155                3160                3165

Lys Thr Lys Leu Ser Glu Thr Ala Phe Ala Gly Ser Lys Val Leu Ser
3170                3175                3180

Leu Met Asp Ala Val Asp Trp Gln Glu Gly Glu Glu Ile Val Ile Thr
3185                3190                3195                3200

Thr Thr Ser Tyr Asp Phe His Gln Thr Glu Thr Arg Ser Ile Val Lys
                3205                3210                3215

Ile Leu His Asp His Lys Ile Leu Ile Leu Asn Asp Ser Leu Ser Tyr
                3220                3225                3230

Thr His Phe Ala Glu Lys Tyr His Val Pro Gly Thr Gly Glu Ser Tyr
            3235                3240                3245

Thr Leu Ala Ala Asp Val Gly Ile Leu Ser Arg Asn Ile Lys Ile Val
        3250                3255                3260

Gly Glu Asp Tyr Pro Gly Trp Ser Glu Asp Ser Phe Gly Ala Arg Val
3265                3270                3275                3280

Leu Val Gly Ser Phe Thr Glu Asn Met Met Thr Phe Lys Gly Asn Ala
                3285                3290                3295

Arg Ile Ser Asn Val Glu Phe Tyr His Ser Gly Gln Glu Gly Phe Arg
                3300                3305                3310

Asp Ser Thr Asp Pro Arg Tyr Ala Val Thr Phe Leu Asn Leu Gly Gln
            3315                3320                3325

Ile Gln Glu His Gly Ser Ser Tyr Ile Arg Gly Cys Ala Phe His His
        3330                3335                3340

Gly Phe Ser Pro Ala Ile Gly Val Phe Gly Thr Asp Gly Leu Asp Ile
3345                3350                3355                3360

Asp Asp Asn Ile Ile His Phe Thr Val Gly Glu Gly Ile Arg Ile Trp
                3365                3370                3375

Gly Asn Ala Asn Arg Val Arg Gly Asn Leu Ile Ala Leu Ser Val Trp
            3380                3385                3390

Pro Gly Thr Tyr Gln Asn Arg Lys Asp Leu Ser Ser Thr Leu Trp His
        3395                3400                3405

Ala Ala Ile Glu Ile Asn Arg Gly Thr Asn Thr Val Leu Gln Asn Asn
3410                3415                3420

Val Val Ala Gly Phe Gly Arg Ala Gly Tyr Arg Ile Asp Gly Glu Pro
3425                3430                3435                3440

Cys Pro Gly Gln Phe Asn Pro Val Glu Lys Trp Phe Asp Asn Glu Ala
                3445                3450                3455

His Gly Gly Leu Tyr Gly Ile Tyr Met Asn Gln Asp Gly Leu Pro Gly
            3460                3465                3470

Cys Ser Leu Ile Gln Gly Phe Thr Ile Trp Thr Cys Trp Asp Tyr Gly
        3475                3480                3485

Ile Tyr Phe Gln Thr Thr Glu Ser Val His Ile Tyr Asn Val Thr Leu
        3490                3495                3500

Val Asp Asn Gly Met Ala Ile Phe Pro Met Ile Tyr Met Pro Ala Ala
3505                3510                3515                3520

Ile Ser His Lys Ile Ser Ser Lys Asn Val Gln Ile Lys Ser Ser Leu
```

-continued

```
            3525                3530                3535
Ile Val Gly Ser Ser Pro Gly Phe Asn Cys Ser Asp Val Leu Thr Asn
                3540                3545                3550

Asp Asp Pro Asn Ile Glu Leu Thr Ala Ala His Arg Ser Pro Arg Ser
                3555                3560                3565

Pro Ser Gly Gly Arg Ser Gly Ile Cys Trp Pro Thr Phe Ala Ser Ala
                3570                3575                3580

His Asn Met Ala Pro Arg Lys Pro His Ala Gly Ile Met Ser Tyr Asn
3585                3590                3595                3600

Ala Ile Ser Gly Leu Leu Asp Ile Ser Gly Ser Thr Phe Val Gly Phe
                3605                3610                3615

Lys Asn Val Cys Ser Gly Glu Thr Asn Val Ile Phe Ile Thr Asn Pro
                3620                3625                3630

Leu Asn Glu Asp Leu Gln His Pro Ile His Val Lys Asn Ile Lys Leu
                3635                3640                3645

Val Asp Thr Thr Glu Gln Ser Lys Ile Phe Ile His Arg Pro Asp Ile
                3650                3655                3660

Ser Lys Val Asn Pro Ser Asp Cys Val Asp Met Val Cys Asp Ala Lys
3665                3670                3675                3680

Arg Lys Ser Phe Leu Arg Asp Ile Asp Gly Ser Phe Leu Gly Asn Ala
                3685                3690                3695

Gly Ser Val Ile Pro Gln Ala Glu Tyr Glu Trp Asp Gly Asn Ser Gln
                3700                3705                3710

Val Gly Ile Gly Asp Tyr Arg Ile Pro Lys Ala Met Leu Thr Phe Leu
                3715                3720                3725

Asn Gly Ser Arg Ile Pro Val Thr Glu Lys Ala Pro His Lys Gly Ile
                3730                3735                3740

Ile Arg Asp Ser Thr Cys Lys Tyr Leu Pro Glu Trp Gln Ser Tyr Gln
3745                3750                3755                3760

Cys Phe Gly Met Glu Tyr Ala Met Met Val Ile Glu Ser Leu Asp Pro
                3765                3770                3775

Asp Thr Glu Thr Arg Arg Leu Ser Pro Val Ala Ile Met Gly Asn Gly
                3780                3785                3790

Tyr Val Asp Leu Ile Asn Gly Pro Gln Asp His Gly Trp Cys Ala Gly
                3795                3800                3805

Tyr Thr Cys Gln Arg Arg Leu Ser Leu Phe His Ser Ile Val Ala Leu
                3810                3815                3820

Asn Lys Ser Tyr Glu Val Tyr Phe Thr Gly Thr Ser Pro Gln Asn Leu
3825                3830                3835                3840

Arg Leu Met Leu Leu Asn Val Asp His Asn Lys Ala Val Leu Val Gly
                3845                3850                3855

Ile Phe Phe Ser Thr Leu Gln Arg Leu Asp Val Tyr Val Asn Asn Leu
                3860                3865                3870

Leu Val Cys Pro Lys Thr Thr Ile Trp Asn Ala Gln Gln Lys His Cys
                3875                3880                3885

Glu Leu Asn Asn His Leu Tyr Lys Asp Gln Phe Leu Pro Asn Leu Asp
                3890                3895                3900

Ser Thr Val Leu Gly Glu Asn Tyr Phe Asp Gly Thr Tyr Gln Met Leu
3905                3910                3915                3920

Tyr Leu Leu Val Lys Gly Thr Ile Pro Val Glu Ile His Thr Ala Thr
                3925                3930                3935

Val Ile Phe Val Ser Phe Gln Leu Ser Val Ala Thr Glu Asp Asp Phe
                3940                3945                3950
```

```
Tyr Thr Ser His Asn Leu Val Lys Asn Leu Ala Leu Phe Leu Lys Ile
        3955                3960                3965

Pro Ser Asp Lys Ile Arg Ile Ser Lys Ile Arg Gly Lys Ser Leu Arg
    3970                3975                3980

Arg Lys Arg Ser Met Gly Phe Ile Ile Glu Ile Glu Ile Gly Asp Pro
3985                3990                3995                4000

Pro Ile Gln Phe Ile Ser Asn Gly Thr Thr Gly Gln Met Gln Leu Ser
        4005                4010                4015

Glu Leu Gln Glu Ile Ala Gly Ser Leu Gly Gln Ala Val Ile Leu Gly
        4020                4025                4030

Asn Ile Ser Ser Ile Leu Gly Phe Asn Ile Ser Ser Met Ser Ile Thr
        4035                4040                4045

Asn Pro Leu Pro Ser Pro Ser Asp Ser Gly Trp Ile Lys Val Thr Ala
        4050                4055                4060

Gln Pro Val Glu Arg Ser Ala Phe Pro Val His His Val Ala Phe Val
4065                4070                4075                4080

Ser Ser Leu Leu Val Ile Thr Gln Pro Val Ala Ala Gln Pro Gly Gln
        4085                4090                4095

Pro Phe Pro Gln Gln Pro Ser Val Lys Ala Thr Asp Ser Asp Gly Asn
        4100                4105                4110

Cys Val Ser Val Gly Ile Thr Ala Leu Thr Leu Arg Ala Ile Leu Lys
        4115                4120                4125

Asp Ser Asn Asn Asn Gln Val Asn Gly Leu Ser Gly Asn Thr Thr Ile
        4130                4135                4140

Pro Phe Ser Ser Cys Trp Ala Asn Tyr Thr Asp Leu Thr Pro Leu Arg
4145                4150                4155                4160

Thr Gly Lys Asn Tyr Lys Ile Glu Phe Ile Leu Asp Asn Val Val Gly
        4165                4170                4175

Val Glu Ser Arg Thr Phe Ser Leu Leu Ala Glu Ser Val Ser Ser Ser
        4180                4185                4190

Gly Ser Ser Ser Ser Ser Asn Ser Lys Ala Ser Thr Val Gly Thr Tyr
        4195                4200                4205

Ala Gln Ile Met Thr Val Val Ile Ser Cys Leu Val Gly Arg Met Trp
        4210                4215                4220

Leu Leu Glu Ile Phe Met Ala Ala Val Ser Thr Leu Asn Ile Thr Leu
4225                4230                4235                4240

Arg Ser Tyr

<210> SEQ ID NO 4
<211> LENGTH: 4249
<212> TYPE: PRT
<213> ORGANISM: Mus musculus

<400> SEQUENCE: 4

Met Gly His Leu Trp Leu Ser Gly Thr Trp Phe Leu Phe Gly Leu Leu
1               5                   10                  15

Trp Cys Ala Ala Asp Ser His Lys Gly Ser Ser Glu Thr Ile Pro Lys
            20                  25                  30

Val Thr Glu Val Ile Pro Lys Tyr Gly Ser Ile Asn Gly Ala Thr Arg
        35                  40                  45

Leu Thr Ile Lys Gly Glu Gly Phe Ser Gln Ala Ser Gln Phe Asn Tyr
    50                  55                  60

Gly Ala Asp Asn Thr Glu Leu Gly Asn His Val Gln Leu Val Ser Ser
65                  70                  75                  80

Phe Gln Ser Ile Thr Cys Asp Val Glu Lys Asp Ser Ser His Ser Thr
```

```
                     85                  90                  95
Gln Ile Thr Cys Tyr Thr Arg Ala Met Pro Glu Asp Thr Tyr Ser Val
                100                 105                 110

Arg Val Ser Val Asp Gly Val Pro Val Ala Glu Asn Asn Thr Cys Lys
                115                 120                 125

Gly Val Ala Ser Ser Trp Ala Cys Ser Phe Ser Thr Lys Ser Phe Arg
                130                 135                 140

Thr Pro Thr Ile Arg Ser Ile Thr Pro Leu Ser Gly Thr Pro Gly Thr
145                 150                 155                 160

Leu Ile Thr Ile Lys Gly Arg Leu Phe Thr Asp Val Tyr Gly Ser Asn
                165                 170                 175

Thr Ala Leu Ser Ser Asn Gly Arg Asn Val Arg Ile Leu Arg Ile Tyr
                180                 185                 190

Ile Gly Gly Met Pro Cys Glu Leu Leu Ile Pro His Ser Asp Asp Leu
                195                 200                 205

Tyr Gly Leu Lys Leu Asp His Ala Asn Gly Asp Thr Gly Ser Val Thr
                210                 215                 220

Cys Lys Thr Thr Gly Thr Tyr Ile Gly His His Asn Val Ser Phe Ile
225                 230                 235                 240

Leu Asp Ser Asp Tyr Gly Arg Ser Phe Pro Glu Lys Met Thr Tyr Phe
                245                 250                 255

Val Ser Ser Leu Asn Lys Ile Ser Met Phe Gln Thr Tyr Pro Glu Val
                260                 265                 270

Val Met Val Ser Pro Ser Lys Gly Ser Thr Glu Gly Gly Thr Leu Leu
                275                 280                 285

Thr Ile His Gly His Phe Phe Asp Gln Thr Asp Leu Pro Val Arg Val
                290                 295                 300

Leu Val Gly Gly Gln Ala Cys Ala Ile Leu Asn Val Thr Glu Asn Thr
305                 310                 315                 320

Ile Tyr Cys Lys Thr Pro Pro Lys Pro His Ile Leu Lys Ala Thr Tyr
                325                 330                 335

Pro Gly Gly Arg Gly Leu Lys Val Glu Val Trp Asn Asn Ser Arg Pro
                340                 345                 350

Ala His Leu Glu Asp Ile Leu Glu Tyr Asn Glu His Thr Pro Gly Tyr
                355                 360                 365

Met Gly Ala Thr Trp Thr Asp Ser Ala Ser Tyr Val Trp Pro Ile Glu
                370                 375                 380

Gln Asp Thr Phe Val Ala Arg Ile Ser Gly Phe Leu Val Pro Pro Asp
385                 390                 395                 400

Ser Asp Val Tyr Arg Phe Tyr Ile Arg Gly Asp Asp Arg Tyr Ala Ile
                405                 410                 415

Tyr Phe Ser Gln Thr Gly Arg Thr Glu Asp Lys Val Arg Ile Ala Tyr
                420                 425                 430

Tyr Ser Gly Asn Ala Asn Thr Tyr Phe Ser Asn Ser Thr Gln Arg Ser
                435                 440                 445

Asp Glu Ile His Leu Gln Lys Gly Lys Glu Tyr Tyr Ile Glu Ile Leu
450                 455                 460

Leu Gln Glu Tyr Thr Leu Ser Ala Phe Val Asp Val Gly Leu Tyr Gln
465                 470                 475                 480

Tyr Lys Asn Val Phe Thr Glu Gln Gln Thr Gly Asp Ala Leu Asn Glu
                485                 490                 495

Glu Gln Val Ile Lys Ser Gln Ser Thr Val Val Pro Glu Val Gln Ile
                500                 505                 510
```

```
Ile Thr Leu Glu Asn Trp Glu Thr Ala Asp Val Thr Asn Glu Val Gln
        515                 520                 525

Gln Val Thr Val Thr Ser Pro Cys Val Gly Ala Asn Ser Cys Ser Leu
530                 535                 540

Ser Gln Tyr Arg Phe Ile Tyr Asn Met Glu Lys Thr Val Trp Leu Pro
545                 550                 555                 560

Ala Asp Ala Ser Asp Phe Thr Leu Lys Ser Ala Leu Asn Asp Leu Trp
                565                 570                 575

Ser Ile Lys Pro Asp Ser Val Gln Val Thr Ser Lys Arg Asp Leu Gln
                580                 585                 590

Ser Tyr Ile Tyr Thr Ile Thr Phe Val Ser Thr Arg Gly Asp Phe Asp
        595                 600                 605

Leu Leu Gly Tyr Glu Val Phe Glu Gly Ser Asn Val Thr Leu Ser Ile
        610                 615                 620

Thr Glu Gln Thr Lys Gly Lys Pro Asn Leu Glu Thr Phe Thr Leu Asn
625                 630                 635                 640

Trp Asp Gly Ile Ala Ser Lys Pro Leu Thr Pro Glu Ser Ser Glu Ala
                645                 650                 655

Glu Phe Gln Val Ala Val Glu Glu Met Val Ser Ala Lys Cys Pro Pro
                660                 665                 670

Glu Ile Ala His Leu Glu Glu Gly Phe Leu Val Lys Tyr Phe Arg Asp
                675                 680                 685

Tyr Glu Thr Asp Phe Glu Leu Glu His Ile Asn Arg Gly Gln Lys Thr
        690                 695                 700

Ala Glu Thr Asp Ala Tyr Cys Gly Arg Tyr Ser Leu Lys Asn Pro Ala
705                 710                 715                 720

Val Leu Phe Asp Ser Thr Asp Val Lys Pro Asn Lys Ser Pro Tyr Gly
                725                 730                 735

Asp Ile Leu Leu Phe Pro Tyr Asn Gln Leu Cys Leu Ala Tyr Lys Gly
                740                 745                 750

Ser Leu Ala Asn Phe Ile Asp Leu Lys Phe Lys Tyr Gln Asp Ser Gly
        755                 760                 765

Lys Ile Ile Arg Ser Ala Asp Val Gln Phe Glu Tyr Asn Phe Ala Ser
770                 775                 780

Gly Asn Lys Trp Thr Tyr Thr Cys Ile Asp Leu Leu Asp Phe Leu Gln
785                 790                 795                 800

Thr Lys Tyr Ala Gly Thr Ser Phe Ser Leu Gln Arg Ile Thr Leu Gln
                805                 810                 815

Lys Ser Ser Glu Phe Gln Ser Ile Tyr Val Asp Ala Val Tyr Ile Gly
                820                 825                 830

Gln Thr Pro Thr Val Ser Val Leu Asp Asp Met Pro Lys Arg Arg Pro
        835                 840                 845

Pro Ala Leu Ala Asn Lys Gly Ile Phe Leu Lys His Phe Gln Val Asn
850                 855                 860

Arg Thr Lys Leu Asn Gly Ser Ala Met Thr Ile Gln Tyr Ser Val Thr
865                 870                 875                 880

Ile Thr Ser Tyr Asn Cys Ser His Asn Ile Pro Met Met Ala Val Ser
                885                 890                 895

Phe Gly Gln Ile Ile Thr Asn Glu Thr Lys Asn Glu Leu Val Tyr Arg
                900                 905                 910

Gly Asn Asn Trp Pro Gly Glu Ser Lys Ile Arg Ile Gln Lys Ile Gln
        915                 920                 925

Glu Ala Ser Pro Pro Ile Ser Gly Ser Phe Asp Val Gln Ala Tyr Gly
930                 935                 940
```

```
His Thr Leu Lys Gly Ile Pro Ala Ala Val Pro Ala Ala Asp Leu Gln
945                 950                 955                 960

Phe Ala Leu Gln Ser Leu Glu Glu Ile Glu Gln Val Ser Val Asn Arg
            965                 970                 975

Glu Gly Thr Cys Ala Gly Tyr Ser Trp Ser Ile Arg Trp Thr Ser Pro
            980                 985                 990

Arg Gly Lys Gln Pro Leu Leu Gln Ile Asn Asp Ser Asn Ile Ile Gly
            995                 1000                1005

Glu Lys Ala Asn Val Thr Val Thr Thr Ile Lys Glu Gly Gly Leu Phe
1010                1015                1020

Arg Gln Arg Ile Pro Gly Asp Met Leu Arg Thr Leu Asn Gln Gln Pro
1025                1030                1035                1040

Gln Val Glu Val Tyr Val Asn Gly Ile Pro Ala Lys Cys Ser Gly Asp
            1045                1050                1055

Cys Gly Phe Thr Trp Asp Ala Met Ile Thr Pro Leu Ile Leu Thr Thr
            1060                1065                1070

Thr Pro Ser Glu Gly Ser Tyr Ala Glu Ser Thr Ile Leu Thr Ile Ala
            1075                1080                1085

Gly Ser Gly Phe Ser Pro Thr Ser Ala Val Ser Val Ser Val Gly Ser
            1090                1095                1100

Thr Arg Cys Ser Leu Leu Ser Val Glu Glu Asn Glu Ile Lys Cys Gln
1105                1110                1115                1120

Ile Leu Asn Gly Ser Ala Gly His Val Pro Val Ala Val Ser Ile Ala
            1125                1130                1135

Asp Val Gly Leu Ala Gln Asn Leu Glu Gly Glu Gly Ser His Phe Ile
            1140                1145                1150

Tyr Arg Ser Gln Ile Ser His Val Trp Pro Asp Ser Gly Ser Leu Ala
            1155                1160                1165

Gly Gly Thr Leu Leu Thr Ile Ser Gly Phe Gly Phe Ser Glu Asn Ser
            1170                1175                1180

Thr Val Leu Val Gly Asn Glu Thr Cys Asn Val Ile Glu Gly Asp Leu
1185                1190                1195                1200

Asn Arg Ile Thr Cys Arg Thr Ser Lys Arg Ile Glu Gly Thr Val Asp
            1205                1210                1215

Ile Ser Val Ile Thr Asn Gly Ile Gln Val Thr Ala Lys Asp Ser Phe
            1220                1225                1230

Ser Tyr Ser Cys Leu Gln Thr Pro Val Val Thr Asp Phe Ser Pro Lys
            1235                1240                1245

Glu Arg Thr Val Leu Gly Lys Val Asn Leu Thr Ile Lys Gly Tyr Asn
1250                1255                1260

Phe Gly Asn Glu Leu Ala Gln Asn Thr Val Tyr Val Gly Arg Lys His
1265                1270                1275                1280

Cys Gln Val Leu His Ser Asn Phe Thr Asp Ile Thr Cys Leu Leu Pro
            1285                1290                1295

Thr Leu Pro Pro Gly Lys His Asp Ile Tyr Val Lys Val Arg Asn Trp
            1300                1305                1310

Gly Leu Ala Ser Thr Arg Asn Lys Leu Asn Ala Ser Ile Leu Tyr Ile
            1315                1320                1325

Leu Glu Val Ile His Met Phe Pro Gln Arg Gly Ser Leu Tyr Gly Gly
            1330                1335                1340

Thr Glu Ile Thr Ile Met Gly Phe Gly Phe Ser Thr Ile Pro Thr Glu
1345                1350                1355                1360

Asn Ser Val Leu Leu Gly Ser Phe Pro Cys Asp Ile Thr Ser Ser Ser
```

-continued

```
                1365                1370                1375
Glu Asn Val Ile Lys Cys Thr Leu His Ser Thr Gly Thr Val Phe Arg
        1380                1385                1390
Ile Thr Asn Asn Gly Ser His Leu Val His Gly Leu Gly Tyr Ala Trp
        1395                1400                1405
Ser Pro Ser Val Leu Asn Val Thr Val Gly Asp Thr Val Val Trp Ser
        1410                1415                1420
Trp Gln Ala His Pro Phe Leu Arg Gly Ile Gly Tyr Arg Ile Phe Ser
1425                1430                1435                1440
Val Ser Ser Pro Gly Ser Val Thr Tyr Asp Asp Lys Gly Phe Thr Asn
                1445                1450                1455
Gly Arg Gln Lys Ser Ala Ser Gly Ser Phe Ser Tyr Gln Phe Thr Ser
                1460                1465                1470
Pro Gly Ile Tyr Tyr Tyr Ser Ser Gly Tyr Val Asp Glu Ala His Ser
                1475                1480                1485
Ile Ser Leu Gln Gly Val Ile Asn Val Phe Pro Ala Glu Ala Arg His
        1490                1495                1500
Ile Pro Leu Tyr Leu Phe Val Gly Asn Ile Glu Ala Thr Tyr Val Pro
1505                1510                1515                1520
Ala Gly Pro Ala His Leu Gln Leu Ala Ser Thr Ala Ala Gly Cys Leu
                1525                1530                1535
Ala Thr Glu Pro Leu Cys Gly Leu Asn Asp Thr Arg Val Lys His Ser
                1540                1545                1550
Asn Lys Leu Phe Phe Glu Leu Ser Asn Cys Ile Ser Pro Ser Ile Ile
                1555                1560                1565
Asn Ile Thr Pro Ser Thr Gly Thr Ala Asn Glu Leu Ile Thr Ile Ile
        1570                1575                1580
Gly His Gly Phe Ser Ser Leu Pro Cys Ala Asn Lys Val Thr Ile Gly
1585                1590                1595                1600
Ser Tyr Pro Cys Val Val Glu Glu Ser Ser Asn Ser Ile Ile Cys
                1605                1610                1615
His Ile Asp Pro Gln Asn Ser Met Asn Val Gly Ile Arg Glu Ile Val
                1620                1625                1630
Thr Leu Ile Val Tyr Asn Leu Gly Thr Ala Ile Asn Thr Leu Thr Lys
        1635                1640                1645
Ala Phe Asp Arg Arg Phe Val Leu Leu Pro Asn Ile Asp Met Val Met
        1650                1655                1660
Pro Lys Ala Gly Ser Thr Thr Gly Met Thr Arg Val Thr Ile Gln Gly
1665                1670                1675                1680
Ser Gly Phe Met Ser Ser Pro Glu Gly Val Glu Val Phe Met Gly Asp
                1685                1690                1695
Phe Pro Cys Lys Val Leu Ser Val Thr Tyr Thr Ala Ile Glu Cys Glu
                1700                1705                1710
Thr Ser Pro Ala Pro Gln Gln Leu Val Leu Val Asp Ile Leu Ile His
                1715                1720                1725
Gly Val Pro Ala Gln Cys Gln Ser Asn Cys Ser Phe Ser Tyr Leu Glu
        1730                1735                1740
Asn Ile Ala Pro Tyr Val Thr Gly Ile Phe Pro Asn Ser Ile Gln Gly
1745                1750                1755                1760
Tyr Gly Asn Val Leu Ile Lys Gly Glu Arg Phe Gly Thr Val Leu Glu
                1765                1770                1775
Glu Ile Ser Ile Phe Ile Gly Ser Gln Gln Phe Arg Val Ile Asp Val
                1780                1785                1790
```

```
Asn Glu Asn Asn Ile Thr Val Leu Met Thr Pro Leu Glu Ala Gly Leu
            1795                1800                1805

His Ser Leu Ser Val Val Gly Ser Lys Gly Leu Ala Leu Gly Asn
        1810                1815                1820

Leu Thr Ile Ser Ser Pro Ala Val Ala Ser Val Ser Pro Thr Ser Gly
1825                1830                1835                1840

Ser Ile Ala Gly Gly Thr Thr Leu Met Ile Thr Gly Asn Gly Phe Ser
                1845                1850                1855

Pro Gly Asn Thr Thr Val Thr Val Gly Asp Gln Pro Cys Gln Ile Thr
            1860                1865                1870

Phe Ile Ser Ser Ser Glu Val Tyr Cys Ser Thr Pro Ala Gly Arg Ala
        1875                1880                1885

Gly Thr Ala Asn Leu Lys Ile Ser Val Asn Ala Ile Ile Tyr Pro Pro
    1890                1895                1900

Leu Ser Phe Thr Tyr Ala Met Glu Asp Thr Pro Phe Leu Lys Arg Ile
1905                1910                1915                1920

Ile Pro Asn Arg Gly Leu Pro Gly Thr Glu Val Glu Ile Thr Gly Ser
            1925                1930                1935

Asn Leu Gly Phe Ala Ile Ser Asp Val Ser Val Met Ile Lys Glu Ser
        1940                1945                1950

Val Cys Asn Val Thr Thr Val Asn Asp Thr Val Leu Gln Cys Thr Val
    1955                1960                1965

Gly Glu His Ala Gly Gly Ile Phe Pro Val Thr Met Leu His Lys Thr
1970                1975                1980

Lys Gly Ser Ala Val Ser Ser Val Ala Phe Glu Tyr Pro Leu Ser Ile
1985                1990                1995                2000

Gln Asn Ile Tyr Pro Thr Gln Gly Ser Phe Gly Gly Gln Thr Leu
            2005                2010                2015

Thr Val Thr Gly Met Gly Phe Asp Pro Trp Asn Ser Thr Ile Leu Val
        2020                2025                2030

Cys Asn Ser Glu Cys Ala Val Asp Lys Leu Arg Ser Asn Ser Thr Thr
    2035                2040                2045

Leu Phe Cys Val Ile Pro Pro Asn Asn Gly Lys Gly His Asp Gln Val
    2050                2055                2060

Cys Gly Val Ser Val Val Asn Gly Lys Asp Ser Ser His Ser Thr Lys
2065                2070                2075                2080

Leu Phe Thr Tyr Thr Leu Ser Leu Thr Pro Leu Ile Thr Glu Ile Ser
        2085                2090                2095

Pro Arg Arg Gly Ser Thr Ala Gly Gly Thr Arg Leu Thr Val Thr Gly
            2100                2105                2110

Ser Gly Phe Ser Glu Asn Thr Gln Gly Val Gln Val Phe Val Gly Asn
        2115                2120                2125

Ser Lys Cys Asp Ile Gln Tyr Ser Asn Lys Thr His Ile Val Cys Met
    2130                2135                2140

Thr Ser Val His Val Pro Ser Gly Trp Val Pro Val His Val Asn Ile
2145                2150                2155                2160

Lys Asn Ile Gly Leu Ala Lys Leu Glu Asn Ala Asp Phe Leu Tyr Ala
            2165                2170                2175

Asp Val Trp Ser Ala Asn Ser Trp Gly Gly Ser Pro Pro Glu
        2180                2185                2190

Glu Gly Ser Leu Ala Val Ile Thr Lys Gly Gln Ile Ile Leu Leu Asp
    2195                2200                2205

Gln Ser Thr Pro Ile Leu Lys Met Leu Leu Ile Gln Gly Gly Thr Leu
    2210                2215                2220
```

```
Ile Phe Asp Glu Ala Asn Ile Glu Leu Gln Ala Glu Asn Ile Leu Ile
2225                2230                2235                2240

Thr Asp Gly Gly Val Leu Gln Ile Gly Thr Glu Ala Ser Pro Phe Gln
            2245                2250                2255

His Arg Ala Val Ile Thr Leu His Gly His Leu Arg Ser Pro Glu Leu
        2260                2265                2270

Pro Val Tyr Gly Ala Lys Thr Leu Gly Val Arg Glu Gly Thr Leu Asp
    2275                2280                2285

Leu His Gly Leu Pro Ile Pro Val Val Trp Thr Arg Leu Thr His Thr
2290                2295                2300

Ala Asn Ala Gly Glu Trp Thr Leu Thr Val Gln Glu Ala Val Thr Trp
2305                2310                2315                2320

Lys Ala Gly Asp Asn Ile Val Ile Ala Ser Thr Gly His Arg His Ser
            2325                2330                2335

Gln Ala Glu Asn Glu Lys Arg Thr Ile Ala Ser Val Ser Ala Asp Gly
        2340                2345                2350

Met His Ile Thr Leu Thr Lys Pro Leu Asn Tyr Thr His Leu Gly Ile
    2355                2360                2365

Thr Thr Thr Leu Pro Asp Gly Thr Val Phe Glu Ala Arg Ala Glu Val
2370                2375                2380

Gly Ile Leu Thr Arg Asn Ile Leu Ile Arg Gly Ser Asp Asn Val Glu
2385                2390                2395                2400

Trp Asn Asp Lys Ile Pro Ser Cys Pro Asp Gly Phe Asp Thr Gly Glu
            2405                2410                2415

Phe Ala Thr Gln Thr Cys Leu Gln Gly Lys Phe Gly Glu Glu Met Gly
        2420                2425                2430

Ser Asp Gln Phe Gly Gly Cys Ile Met Leu His Ala Pro Leu Pro Gly
    2435                2440                2445

Ala Asp Met Val Thr Gly Arg Ile Glu Tyr Val Glu Val Phe His Ala
2450                2455                2460

Gly Gln Ser Phe Arg Leu Gly Arg Tyr Pro Ile His Trp His Leu Leu
2465                2470                2475                2480

Gly Asp Leu Gln Phe Lys Ser Tyr Val Lys Gly Cys Ala Ile His Gln
            2485                2490                2495

Ser Tyr Asn Arg Ala Ile Thr Ile His Asn Thr His Leu Leu Val
        2500                2505                2510

Glu Arg Asn Ile Ile Tyr Asp Ile Lys Gly Gly Ala Phe Phe Ile Glu
    2515                2520                2525

Asp Gly Ile Glu His Gly Asn Ile Leu Gln Tyr Asn Leu Ala Val Phe
2530                2535                2540

Val Gln Gln Ser Thr Ser Leu Leu Asn Asp Asp Val Thr Pro Ala Ala
2545                2550                2555                2560

Phe Trp Val Thr Asn Pro Asn Asn Thr Ile Arg His Asn Ala Ala Ala
            2565                2570                2575

Gly Gly Thr His Phe Gly Phe Trp Tyr Arg Met Asn Asp His Pro Asp
        2580                2585                2590

Gly Pro Ser Phe Asp Arg Asn Ile Cys Gln Lys Arg Ile Pro Leu Gly
    2595                2600                2605

Glu Phe Phe Asn Asn Thr Val His Ser Gln Gly Trp Phe Gly Leu Trp
2610                2615                2620

Ile Phe Glu Glu Tyr Phe Pro Met Gln Thr Gly Ser Cys Thr Ser Thr
2625                2630                2635                2640

Val Pro Val Pro Ala Ile Phe Asn Ser Leu Thr Val Trp Asn Cys Gln
```

```
                    2645                2650                2655
Lys Gly Ala Glu Trp Val Asn Gly Gly Ala Leu Gln Phe His Asn Phe
                2660                2665                2670
Val Met Val Asn Asn Glu Ala Gly Ile Glu Thr Lys Arg Ile Leu
            2675                2680                2685
Ala Pro Tyr Val Gly Gly Trp Gly Glu Ser Asn Gly Ala Val Ile Lys
        2690                2695                2700
Asn Ala Lys Ile Val Gly His Leu Asp Glu Leu Gly Met Gly Pro Thr
2705                2710                2715                2720
Phe Cys Thr Ser Lys Gly Leu Val Leu Pro Phe Ser Gln Gly Leu Thr
                2725                2730                2735
Val Ser Ser Val His Phe Met Asn Phe Asp Arg His Ala Cys Val Ala
                2740                2745                2750
Leu Gly Val Thr Ser Ile Thr Gly Val Cys Asn Asp Arg Cys Gly Gly
            2755                2760                2765
Trp Ser Ala Lys Phe Val Gly Ile Arg Tyr Phe His Ala Pro Asn Lys
        2770                2775                2780
Gly Gly Phe Arg Trp Glu His Glu Ala Val Leu Ile Asp Val Asp Gly
2785                2790                2795                2800
Ser Leu Thr Gly His Arg Gly His Thr Val Val Pro His Ser Ser Leu
                2805                2810                2815
Leu Asp Pro Ser His Cys Thr Gln Glu Pro Ala Trp Ser Ile Gly Phe
                2820                2825                2830
Pro Gly Ser Ile Cys Asp Ala Ser Val Ser Phe His Arg Leu Ala Phe
            2835                2840                2845
Asn Lys Pro Ser Pro Val Ser Leu Leu Glu Lys Asp Val Val Leu Ser
        2850                2855                2860
Asp Ser Phe Gly Thr Ser Ile Val Pro Phe Gln Lys Lys Arg Leu Thr
2865                2870                2875                2880
His Met Ser Gly Trp Met Ala Leu Ile Pro Asn Ala Asn His Ile Asn
                2885                2890                2895
Trp Tyr Phe Lys Gly Val Glu His Leu Thr Asn Ile Ser Tyr Thr Ser
                2900                2905                2910
Thr Phe Tyr Gly Phe Lys Glu Glu Asp Tyr Val Ile Ser His Asn
            2915                2920                2925
Phe Thr Gln Asn Pro Asp Met Phe Asn Val Val Asp Met Arg Asn Gly
        2930                2935                2940
Ser Ala Asn Pro Leu Asn Trp Asn Ser Ser Lys Asn Gly Asp Trp His
2945                2950                2955                2960
Leu Glu Ala Asn Thr Ser Thr Leu Tyr Tyr Leu Val Ser Gly Arg Ser
                2965                2970                2975
Asp Leu Pro Gln Ser Gln Pro Ile Ser Gly Thr Leu Asp Pro Gly Val
            2980                2985                2990
Lys Asp Val Ile Ile Asn Phe Gln Ala Tyr Cys Cys Val Leu Gln Asp
        2995                3000                3005
Cys Phe Pro Val His Pro Pro Ser Arg Lys Pro Ile Pro Arg Lys Arg
    3010                3015                3020
Pro Ala Ala Tyr Asn Leu Trp Ser Asn Glu Ser Phe Trp Gln Ser Ser
3025                3030                3035                3040
Pro Glu Asn Asn Tyr Thr Val Pro Arg Pro Gly Ala Asn Val Ile Ile
                3045                3050                3055
Pro Glu Gly Thr Trp Ile Val Ala Asp Val Asp Ile Pro Pro Val Glu
            3060                3065                3070
```

-continued

Arg Leu Ile Ile Trp Gly Val Leu Glu Met Glu Asp Lys Ser Glu Ile
         3075                3080                3085

Gly Val Ala Gly Pro Thr Tyr Arg Arg Val Val Leu Asn Ala Thr Tyr
        3090                3095                3100

Ile Ser Val Gln Gly Gly Arg Leu Ile Gly Gly Trp Glu Asp Asn Pro
3105                3110                3115                3120

Phe Lys Gly Glu Leu Gln Ile Val Leu Arg Gly Asn His Ser Thr Pro
        3125                3130                3135

Glu Trp Ala Phe Pro Asp Gly Pro Asn Gln Gly Ala Lys Val Leu Gly
        3140                3145                3150

Val Phe Gly Glu Leu Asp Leu His Gly Leu Pro His Ser Val Tyr Lys
        3155                3160                3165

Thr Lys Leu Leu Glu Thr Ala Glu Ala Gly Ser Lys Ile Leu Ser Leu
        3170                3175                3180

Val Asp Ala Val Asp Trp Gln Glu Gly Glu Asp Val Val Ile Thr Thr
3185                3190                3195                3200

Thr Ser Tyr Asp Leu His Gln Thr Glu Ile Arg Arg Ile Ala Lys Ile
        3205                3210                3215

Leu His Gly His Lys Ile Leu Ile Leu Asn Asp Ser Leu Ser Tyr Thr
        3220                3225                3230

His Leu Ala Glu Arg Gln Trp Ile Ser Gly Thr Ala Gln Ser Tyr Thr
        3235                3240                3245

Leu Ser Ala Asp Val Gly Ile Leu Ser Arg Asn Ile Lys Ile Val Gly
        3250                3255                3260

Asp Asp Tyr Ser Val Leu Ser Lys Asp Ser Phe Gly Ala Arg Ile Leu
3265                3270                3275                3280

Val Gly Ser Phe Thr Gly Asn Met Met Thr Phe Lys Gly Asn Ala Arg
        3285                3290                3295

Ile Ser Asn Val Glu Phe His His Ser Gly Gln Glu Gly Tyr Arg Asp
        3300                3305                3310

Ser Thr Asp Pro Arg Tyr Ala Val Thr Phe Leu Asn Leu Gly Gln Ile
        3315                3320                3325

Gln Asp His Gly Leu Ser Tyr Val Arg Gly Cys Ala Phe His His Val
        3330                3335                3340

Phe Ser Pro Ala Ile Gly Val Phe Gly Thr Asp Gly Val Asp Ile Asp
3345                3350                3355                3360

Asp Asn Ile Ile Tyr Phe Thr Val Gly Glu Gly Ile Arg Ile Trp Gly
        3365                3370                3375

Asp Ala Asn Arg Val Arg Gly Asn Leu Val Thr Leu Ser Val Trp Pro
        3380                3385                3390

Gly Thr Tyr Gln Asn Arg Lys Asp Leu Ser Ser Thr Leu Trp His Ala
        3395                3400                3405

Ala Ile Glu Ile Asn Arg Gly Thr Asn Thr Val Leu Gln Asn Asn Val
        3410                3415                3420

Val Ala Gly Phe Gly Arg Val Gly Tyr Arg Ile Asp Gly Glu Pro Cys
3425                3430                3435                3440

Ser Ser Gln Ala Asn Ser Met Glu Asn Trp Phe Asn Asn Glu Ala His
        3445                3450                3455

Gly Gly Leu Tyr Gly Ile Tyr Met Asn Gln Asp Gly Leu Pro Gly Cys
        3460                3465                3470

Ser Leu Ile Gln Gly Phe Thr Ile Trp Thr Cys Trp Asp Tyr Gly Ile
        3475                3480                3485

Tyr Phe Gln Thr Thr Glu Ser Val His Ile Tyr Asn Val Thr Leu Val
        3490                3495                3500

```
Asn Asn Gly Met Ser Ile Phe Ser Met Val Tyr Met Pro Pro Ser Val
3505                3510                3515                3520

Ser His Lys Ile Ser Ser Lys Thr Val Lys Ile Lys Asn Ser Leu Ile
            3525                3530                3535

Val Gly Ser Ser Pro Glu Phe Asn Cys Ser Asp Val Leu Thr Asn Asp
        3540                3545                3550

Ser Pro Asp Val Glu Leu Thr Ser Ala His Arg Ser Ser Arg Pro Pro
        3555                3560                3565

Ser Gly Gly Arg Ser Gly Ile Cys Trp Pro Thr Phe Ala Ser Ala His
    3570                3575                3580

Asn Met Ala Pro Arg Lys Pro His Ala Gly Ile Met Ser Tyr Asn Ala
3585                3590                3595                3600

Ile Ser Gly Leu Leu His Val Ser Asp Ser Thr Phe Val Gly Phe Lys
                3605                3610                3615

Asp Val Cys Ser Gly Glu Thr Asn Val Ile Phe Ile Thr Asn Pro Leu
            3620                3625                3630

Asn Glu Asp Leu Gln His Pro Ile His Val Lys Asn Val Gln Leu Ile
            3635                3640                3645

Asp Thr Ile Glu Gln Ser Lys Val Phe Ile His Arg Pro Asp Ile Ser
3650                3655                3660

Lys Val Asn Pro Ser Asp Cys Val Asp Met Val Cys Asp Ala Lys Arg
3665                3670                3675                3680

Lys Ser Phe Leu Arg Asp Leu Asp Gly Ser Phe Leu Gly Asn Ser Gly
            3685                3690                3695

Ser Val Ile Pro Gln Ala Glu Tyr Glu Trp Asp Gly Asn Ser Gln Leu
        3700                3705                3710

Gly Ile Gly Asp Tyr Arg Ile Pro Lys Ala Met Leu Thr Tyr Leu Asn
        3715                3720                3725

Gly Ser Arg Ile Pro Val Thr Glu Lys Ala Pro His Lys Gly Ile Ile
    3730                3735                3740

Arg Asp Ala Thr Cys Lys Tyr Ile Pro Glu Trp Gln Ser Tyr Gln Cys
3745                3750                3755                3760

Ser Gly Met Glu Tyr Ala Met Met Val Leu Glu Ser Leu Asp Ser Asp
            3765                3770                3775

Thr Glu Thr Arg Arg Leu Ser Pro Val Ala Ile Met Ser Asn Gly Tyr
        3780                3785                3790

Val Asp Leu Ile Asn Gly Pro Gln Asp His Gly Trp Cys Ala Gly Tyr
        3795                3800                3805

Thr Cys Gln Arg Arg Leu Ser Leu Phe His Gly Ile Val Ala Leu Asn
3810                3815                3820

Lys Lys Tyr Glu Val Tyr Phe Thr Gly Thr Ser Pro Gln Asn Leu Arg
3825                3830                3835                3840

Leu Met Leu Leu Asn Val Glu His Asn Lys Ala Val Leu Val Gly Ile
            3845                3850                3855

Phe Phe Ser Thr Leu Gln Arg Leu Asp Val Tyr Val Asn Asn Ser Leu
        3860                3865                3870

Val Cys Pro Lys Asn Thr Ala Trp Asn Ala Gln Lys Lys His Cys Glu
        3875                3880                3885

Leu Glu Arg His Leu Ser Thr Glu Gln Phe Leu Pro Asn Leu Gly Ser
    3890                3895                3900

Thr Val Pro Gly Glu Asn Tyr Phe Asp Arg Thr Tyr Gln Met Leu Tyr
3905                3910                3915                3920

Leu Phe Leu Lys Gly Thr Thr Pro Val Glu Val His Thr Ala Thr Val
```

```
                              3925                3930                3935
Ile Phe Val Ser Phe His Leu Pro Val Met Thr Ala Asp Glu Phe Phe
            3940                3945                3950

Ser Ser His Asn Leu Val Arg Asn Leu Ala Leu Phe Leu Lys Ile Pro
            3955                3960                3965

Ser Asp Lys Ile Arg Val Ser Arg Ile Ile Gly Ala Ser Leu Arg Lys
            3970                3975                3980

Lys Arg Ser Thr Gly His Ile Met Glu Phe Glu Ile Gly Ala Ala Pro
3985                3990                3995                4000

Thr Gln Phe Leu Ser Asn Ser Thr Thr Gly Gln Met Gln Leu Ser Glu
            4005                4010                4015

Leu Gln Glu Ile Thr Asp Ser Leu Gly Gln Ala Val Val Leu Gly Lys
            4020                4025                4030

Ile Ser Thr Ile Leu Gly Phe Asn Ile Ser Ser Met Ser Ile Thr Ser
            4035                4040                4045

Pro Ile Pro Gln Pro Thr Asp Ser Gly Trp Ile Lys Val Thr Ala Gln
            4050                4055                4060

Pro Val Glu Arg Ser Ala Phe Pro Val His Tyr Leu Ala Leu Val Ser
4065                4070                4075                4080

Ser Leu Ser Val Val Ala Gln Pro Val Ala Ala Gln Pro Gly Gln Pro
            4085                4090                4095

Phe Pro Gln Gln Pro Ser Val Lys Ala Val Asp Pro Glu Gly Asn Cys
            4100                4105                4110

Val Ser Val Gly Ile Thr Ser Leu Thr Leu Lys Ala Ile Leu Lys Asp
            4115                4120                4125

Ser Asn Asn Gln Val Gly Gly Leu Ser Gly Asn Thr Thr Ile Pro
            4130                4135                4140

Phe Ser Thr Cys Trp Ala Asn Tyr Thr Asp Leu Thr Pro His Arg Thr
4145                4150                4155                4160

Gly Lys Asn Tyr Lys Ile Glu Phe Val Leu Asp Asn Thr Val Arg Val
            4165                4170                4175

Asp Ser Arg Pro Phe Ser Leu Ser Ala Gln Ser Val Pro Gly Gly Ser
            4180                4185                4190

Gly Ser Ser Pro Gly Ser Gly Ser Ser Ser Gly His Ser Lys Ala
            4195                4200                4205

Ser Ser Val Gly Thr Pro Val Gln Thr Leu Ala Val Ile Thr Ala Cys
            4210                4215                4220

Leu Val Gly Arg Leu Leu Leu Leu Glu Val Phe Met Ala Ala Val Phe
4225                4230                4235                4240

Ile Leu Asn Thr Thr Val Gly Ile Asn
            4245

<210> SEQ ID NO 5
<211> LENGTH: 3849
<212> TYPE: PRT
<213> ORGANISM: Homo sapiens

<400> SEQUENCE: 5

Met Thr Ala Trp Leu Ile Ser Leu Met Ser Ile Glu Val Leu Leu Leu
1               5                   10                  15

Ala Val Arg His Leu Ser Leu His Ile Glu Pro Glu Glu Gly Ser Leu
            20                  25                  30

Ala Gly Gly Thr Trp Ile Thr Val Ile Phe Asp Gly Leu Glu Leu Gly
        35                  40                  45

Val Leu Tyr Pro Asn Asn Gly Ser Gln Leu Glu Ile His Leu Val Asn
```

```
            50                  55                  60
Val Asn Met Val Val Pro Ala Leu Arg Ser Val Pro Cys Asp Val Phe
 65                  70                  75                  80

Pro Val Phe Leu Asp Leu Pro Val Val Thr Cys Arg Thr Arg Ser Val
                 85                  90                  95

Leu Ser Glu Ala His Glu Gly Leu Tyr Phe Leu Glu Ala Tyr Phe Gly
                100                 105                 110

Gly Gln Leu Val Ser Ser Pro Asn Pro Gly Pro Arg Asp Ser Cys Thr
                115                 120                 125

Phe Lys Phe Ser Lys Ala Gln Thr Pro Ile Val His Gln Val Tyr Pro
                130                 135                 140

Pro Ser Gly Val Pro Gly Lys Leu Ile His Val Tyr Gly Trp Ile Ile
145                 150                 155                 160

Thr Gly Arg Leu Glu Thr Phe Asp Phe Asp Ala Glu Tyr Ile Asp Ser
                165                 170                 175

Pro Val Ile Leu Glu Ala Gln Gly Asp Lys Trp Val Thr Pro Cys Ser
                180                 185                 190

Leu Ile Asn Arg Gln Met Gly Ser Cys Tyr Pro Ile Gln Glu Asp His
                195                 200                 205

Gly Leu Gly Thr Leu Gln Cys His Val Glu Gly Asp Tyr Ile Gly Ser
                210                 215                 220

Gln Asn Val Ser Phe Ser Val Phe Asn Lys Gly Lys Ser Met Val His
225                 230                 235                 240

Lys Lys Ala Trp Leu Ile Ser Ala Lys Gln Asp Leu Phe Leu Tyr Gln
                245                 250                 255

Thr His Ser Glu Ile Leu Ser Val Phe Pro Glu Thr Gly Ser Leu Gly
                260                 265                 270

Gly Arg Thr Asn Ile Thr Ile Thr Gly Asp Phe Phe Asp Asn Ser Ala
                275                 280                 285

Gln Val Thr Ile Ala Gly Ile Pro Cys Asp Ile Arg His Val Ser Pro
                290                 295                 300

Arg Lys Ile Glu Cys Thr Thr Arg Ala Pro Gly Lys Asp Val Arg Leu
305                 310                 315                 320

Thr Thr Pro Gln Pro Gly Asn Arg Gly Leu Leu Phe Glu Val Gly Asp
                325                 330                 335

Ala Val Glu Gly Leu Glu Leu Thr Glu Ala Thr Pro Gly Tyr Arg Trp
                340                 345                 350

Gln Ile Val Pro Asn Ala Ser Ser Pro Phe Gly Phe Trp Ser Gln Glu
                355                 360                 365

Gly Gln Pro Phe Arg Ala Arg Leu Ser Gly Phe Phe Val Ala Pro Glu
                370                 375                 380

Thr Asn Asn Tyr Thr Phe Trp Ile Gln Ala Asp Ser Gln Ala Ser Leu
385                 390                 395                 400

His Phe Ser Trp Ser Glu Pro Arg Thr Lys Val Lys Val Ala Ser
                405                 410                 415

Ile Ser Val Gly Thr Ala Asp Trp Phe Asp Ser Trp Glu Gln Asn Arg
                420                 425                 430

Asp Glu Gly Thr Trp Gln Gln Lys Thr Pro Lys Leu Glu Leu Leu Gly
                435                 440                 445

Gly Ala Met Tyr Tyr Leu Glu Ala Glu His His Gly Ile Ala Pro Ser
                450                 455                 460

Arg Gly Met Arg Ile Gly Val Gln Ile His Asn Thr Trp Leu Asn Pro
465                 470                 475                 480
```

```
Asp Val Val Thr Thr Tyr Leu Arg Glu Lys His Gln Ile Arg Val Arg
            485                 490                 495

Ala Gln Arg Leu Pro Glu Val Gln Val Leu Asn Val Ser Gly Arg Gly
        500                 505                 510

Asn Phe Phe Leu Thr Trp Asp Asn Val Ser Ser Gln Pro Ile Pro Ala
            515                 520                 525

Asn Ala Thr Ala His Leu Ile Gln Thr Thr Ile Glu Glu Leu Leu Ala
        530                 535                 540

Val Lys Cys Lys Leu Glu Pro Leu Trp Ser Asn Ile Leu Leu Arg Leu
545                 550                 555                 560

Gly Phe Glu Arg Gly Pro Glu Val Ser Asn Ser Asp Gly Asp Leu Thr
                565                 570                 575

Ser Gly Thr Glu Pro Phe Cys Gly Arg Phe Ser Leu Arg Gln Pro Arg
            580                 585                 590

His Leu Val Leu Thr Pro Pro Ala Ala Gln Lys Gly Tyr Arg Leu Asp
        595                 600                 605

Gln Tyr Thr His Leu Cys Leu Ala Tyr Lys Gly His Met Asn Lys Ile
        610                 615                 620

Leu Lys Met Ile Val Ser Phe Thr Ile Gly Phe Gln Asn Met Val Lys
625                 630                 635                 640

Asn Thr Thr Cys Asp Trp Ser Leu Thr Arg Thr Ser Pro Glu Ser Trp
                645                 650                 655

Gln Phe Asp Cys Thr Asp Leu Trp Glu Thr Cys Val Arg Cys Phe Gly
            660                 665                 670

Asp Leu Gln Pro Pro Ala Asn Ser Pro Val Leu Val His Gln Ile
        675                 680                 685

Asn Leu Leu Pro Leu Ala Gln Glu Thr Gly Leu Phe Tyr Val Asp Glu
        690                 695                 700

Ile Ile Ile Ala Asp Thr Asn Val Thr Val Ser Gln Ala Asp Ser Gly
705                 710                 715                 720

Thr Ala Arg Pro Gly Gly Asn Leu Val Glu Ser Val Ser Val Val Gly
                725                 730                 735

Ser Pro Pro Val Tyr Ser Val Ser Trp Leu Ala Gly Cys Gly Thr
            740                 745                 750

Glu Leu Pro Leu Ile Thr Ala Arg Ser Val Pro Thr Glu Gly Thr Glu
        755                 760                 765

Glu Gly Ser Gly Leu Val Leu Val Thr Thr Gln Arg Arg Gln Arg Thr
770                 775                 780

Ser Pro Pro Leu Gly Gly His Phe Arg Ile Gln Leu Pro Asn Thr Val
785                 790                 795                 800

Ile Ser Asp Val Pro Val Gln Ile Ser Ala His His Leu His Gln Leu
            805                 810                 815

Leu Gln Asn Asn Ala Asp Asp Phe Thr Ser Arg Tyr Leu Asn Ala Ser
        820                 825                 830

Asp Phe Thr Val Lys Glu Asp Leu Tyr Thr Cys Tyr Glu His Val Trp
        835                 840                 845

Thr Leu Ser Trp Ser Thr Gln Ile Gly Asp Leu Pro Asn Phe Ile Arg
        850                 855                 860

Val Ser Asp Glu Asn Leu Thr Gly Val Asn Pro Ala Ala Ala Thr Arg
865                 870                 875                 880

Val Val Tyr Asp Gly Gly Val Phe Leu Gly Pro Ile Phe Gly Asp Met
                885                 890                 895

Leu Ala Thr Ala Asn Gln His Thr Gln Val Val Arg Val Asn Asp
        900                 905                 910
```

```
Val Pro Ala His Cys Pro Gly Ser Cys Ser Phe Gln Tyr Leu Gln Gly
            915                 920                 925

Ser Thr Pro Cys Val His Ser Val Trp Tyr Ser Ile Asp Gly Asp Ile
        930                 935                 940

Asn Leu Met Ile Tyr Ile Thr Gly Thr Gly Phe Ser Gly Asp Ser Gln
945                 950                 955                 960

Phe Leu Gln Val Thr Val Asn Lys Thr Ser Cys Lys Val Ile Phe Ser
                965                 970                 975

Asn Gln Thr Asn Val Val Cys Gln Thr Asp Leu Leu Pro Val Gly Met
            980                 985                 990

His Arg Ile Leu Met Leu Val Arg Pro Ser Gly Leu Ala Ile Ser Ala
        995                 1000                1005

Thr Gly Glu Asp Leu Phe Leu Asn Val Lys Pro Arg Leu Asp Met Val
    1010                1015                1020

Glu Pro Ser Arg Ala Ala Asp Ile Gly Gly Leu Trp Ala Thr Ile Arg
1025                1030                1035                1040

Gly Ser Ser Leu Glu Gly Val Ser Leu Ile Leu Phe Gly Ser Tyr Ser
                1045                1050                1055

Cys Ala Ile Asn Val Ala Thr Ser Asn Ser Ser Arg Ile Gln Cys Lys
                1060                1065                1070

Val Pro Pro Arg Gly Lys Asp Gly Arg Ile Val Asn Val Thr Val Ile
            1075                1080                1085

Arg Gly Asp Tyr Ser Ala Val Leu Pro Arg Ala Phe Thr Tyr Val Ser
            1090                1095                1100

Ser Leu Asn Pro Val Ile Val Thr Leu Ser Arg Asn Ile Ser Asn Ile
1105                1110                1115                1120

Ala Gly Gly Glu Thr Leu Val Ile Gly Val Ala Arg Leu Met Asn Tyr
                1125                1130                1135

Thr Asp Leu Asp Val Glu Val His Val Gln Asp Ala Leu Ala Pro Val
            1140                1145                1150

His Thr Gln Ser Ala Trp Gly Leu Glu Val Ala Leu Pro Pro Leu Pro
            1155                1160                1165

Ala Gly Leu His Arg Ile Ser Val Ser Ile Asn Gly Val Ser Ile His
        1170                1175                1180

Ser Gln Gly Val Asp Leu His Ile Gln Tyr Leu Thr Glu Val Phe Ser
1185                1190                1195                1200

Ile Glu Pro Cys Cys Gly Ser Leu Leu Gly Gly Thr Ile Leu Ser Ile
            1205                1210                1215

Ser Gly Ile Gly Phe Ser Arg Asp Pro Ala Leu Val Trp Val Leu Val
            1220                1225                1230

Gly Asn Arg Ser Cys Asp Ile Val Asn Leu Thr Glu Ala Ser Ile Trp
        1235                1240                1245

Cys Glu Thr Leu Pro Ala Pro Gln Ile Pro Asp Ala Gly Ala Pro Thr
    1250                1255                1260

Val Pro Ala Ala Val Glu Val Trp Ala Gly Asn Arg Phe Phe Ala Arg
1265                1270                1275                1280

Gly Pro Ser Pro Ser Leu Val Gly Lys Gly Phe Thr Phe Met Tyr Glu
                1285                1290                1295

Ala Ala Ala Thr Pro Val Val Thr Ala Met Gln Gly Glu Ile Thr Asn
            1300                1305                1310

Ser Ser Leu Ser Leu His Val Gly Gly Ser Asn Leu Ser Asn Ser Val
        1315                1320                1325

Ile Leu Leu Gly Asn Leu Asn Cys Asp Val Glu Thr Gln Ser Phe Gln
```

-continued

```
             1330              1335              1340
Gly Asn Val Ser Leu Ser Gly Cys Ser Ile Pro Leu His Ser Leu Glu
1345              1350              1355              1360

Ala Gly Ile Tyr Pro Leu Gln Val Arg Gln Lys Gln Met Gly Phe Ala
             1365              1370              1375

Asn Met Ser Val Val Leu Gln Gln Phe Ala Val Met Pro Arg Ile Met
             1380              1385              1390

Ala Ile Phe Pro Ser Gln Gly Ser Ala Cys Gly Gly Thr Ile Leu Thr
             1395              1400              1405

Val Arg Gly Leu Leu Leu Asn Ser Arg Arg Ser Val Arg Val Asp
             1410              1415              1420

Leu Ser Gly Pro Phe Thr Cys Val Ile Leu Ser Leu Gly Asp His Thr
1425              1430              1435              1440

Ile Leu Cys Gln Val Ser Leu Glu Gly Asp Pro Leu Pro Gly Ala Ser
                  1445              1450              1455

Phe Ser Leu Asn Val Thr Val Leu Val Asn Gly Leu Thr Ser Glu Cys
             1460              1465              1470

Gln Gly Asn Cys Thr Leu Phe Ile Arg Glu Glu Ala Ser Pro Val Met
             1475              1480              1485

Asp Ala Leu Ser Thr Asn Thr Ser Gly Ser Leu Thr Thr Val Leu Ile
             1490              1495              1500

Arg Gly Gln Arg Leu Ala Thr Thr Ala Asp Glu Pro Met Val Phe Val
1505              1510              1515              1520

Asp Asp Gln Leu Pro Cys Asn Val Thr Phe Phe Asn Ala Ser His Val
                  1525              1530              1535

Val Cys Gln Thr Arg Asp Leu Ala Pro Gly Pro His Tyr Leu Ser Val
             1540              1545              1550

Phe Tyr Thr Arg Asn Gly Tyr Ala Cys Ser Gly Asn Val Ser Arg His
             1555              1560              1565

Phe Tyr Ile Met Pro Gln Val Phe His Tyr Phe Pro Lys Asn Phe Ser
             1570              1575              1580

Leu His Gly Gly Ser Leu Leu Thr Ile Glu Gly Thr Gly Leu Arg Gly
1585              1590              1595              1600

Gln Asn Thr Thr Ser Val Tyr Ile Asp Gln Gln Thr Cys Leu Thr Val
                  1605              1610              1615

Asn Ile Gly Ala Glu Leu Ile Arg Cys Ile Val Pro Thr Gly Asn Gly
             1620              1625              1630

Ser Val Ala Leu Glu Ile Glu Val Asp Gly Leu Trp Tyr His Ile Gly
             1635              1640              1645

Val Ile Gly Tyr Asn Lys Ala Phe Thr Pro Glu Leu Ile Ser Ile Ser
1650              1655              1660

Gln Ser Asp Asp Ile Leu Thr Phe Ala Val Ala Gln Ile Ser Gly Ala
1665              1670              1675              1680

Ala Asn Ile Asp Ile Phe Ile Gly Met Ser Pro Cys Val Gly Val Ser
                  1685              1690              1695

Gly Asn His Thr Val Leu Gln Cys Val Val Pro Ser Leu Pro Ala Gly
             1700              1705              1710

Glu Tyr His Val Arg Gly Tyr Asp Cys Ile Arg Gly Trp Ala Ser Ser
             1715              1720              1725

Ala Leu Val Phe Thr Ser Arg Val Ile Ile Thr Ala Val Thr Glu Asn
             1730              1735              1740

Phe Gly Cys Leu Gly Gly Arg Leu Val His Val Phe Gly Ala Gly Phe
1745              1750              1755              1760
```

-continued

```
Ser Pro Gly Asn Val Ser Ala Val Cys Gly Ala Pro Cys Arg Val
            1765                1770                1775

Leu Ala Asn Ala Thr Val Ser Ala Phe Ser Cys Leu Val Pro Leu
            1780                1785                1790

Asp Val Ser Leu Ala Phe Leu Cys Gly Leu Lys Arg Glu Glu Asp Ser
        1795                1800                1805

Cys Glu Ala Ala Arg His Thr Tyr Val Gln Cys Asp Leu Thr Val Ala
        1810                1815                1820

Met Ala Thr Glu Gln Leu Leu Glu Ser Trp Pro Tyr Leu Tyr Ile Cys
1825                1830                1835                1840

Glu Glu Ser Ser Gln Cys Leu Phe Val Pro Asp His Trp Ala Glu Ser
            1845                1850                1855

Met Phe Pro Ser Phe Ser Gly Leu Phe Ile Ser Pro Lys Leu Glu Arg
            1860                1865                1870

Asp Glu Val Leu Ile Tyr Asn Ser Ser Cys Asn Ile Thr Met Glu Thr
            1875                1880                1885

Glu Ala Glu Met Glu Cys Glu Thr Pro Asn Gln Pro Ile Thr Val Lys
            1890                1895                1900

Ile Thr Glu Ile Arg Lys Arg Trp Gly Gln Asn Thr Gln Gly Asn Phe
1905                1910                1915                1920

Ser Leu Gln Phe Cys Arg Arg Trp Ser Arg Thr His Ser Trp Phe Pro
            1925                1930                1935

Glu Arg Leu Pro Gln Asp Gly Asp Asn Val Thr Val Glu Asn Gly Gln
            1940                1945                1950

Leu Leu Leu Leu Asp Thr Asn Thr Ser Ile Leu Asn Leu Leu His Ile
            1955                1960                1965

Lys Gly Gly Lys Leu Ile Phe Met Ala Pro Gly Pro Ile Glu Leu Arg
    1970                1975                1980

Ala His Ala Ile Leu Val Ser Asp Gly Gly Glu Leu Arg Ile Gly Ser
1985                1990                1995                2000

Glu Asp Lys Pro Phe Gln Gly Arg Ala Gln Ile Thr Leu Tyr Gly Ser
            2005                2010                2015

Ser Tyr Ser Thr Pro Phe Phe Pro Tyr Gly Val Lys Phe Leu Ala Val
            2020                2025                2030

Arg Asn Gly Thr Leu Ser Leu His Gly Ser Leu Pro Glu Val Ile Val
            2035                2040                2045

Thr Cys Leu Arg Ala Thr Ala His Ala Leu Asp Thr Val Leu Ala Leu
    2050                2055                2060

Glu Asp Ala Val Asp Trp Asn Pro Gly Asp Glu Val Val Ile Ile Ser
2065                2070                2075                2080

Gly Thr Gly Val Lys Gly Ala Lys Pro Met Glu Glu Ile Val Thr Val
            2085                2090                2095

Glu Thr Val Gln Asp Thr Asp Leu Tyr Leu Lys Ser Pro Leu Arg Tyr
            2100                2105                2110

Ser His Asn Phe Thr Glu Asn Trp Val Ala Gly Glu His His Ile Leu
            2115                2120                2125

Lys Ala Thr Val Ala Leu Leu Ser Arg Ser Ile Thr Ile Gln Gly Asn
    2130                2135                2140

Leu Thr Asn Glu Arg Glu Lys Leu Leu Val Ser Cys Gln Glu Ala Asn
2145                2150                2155                2160

Ala Pro Glu Gly Asn Leu Gln His Cys Leu Tyr Ser Met Ser Glu Lys
            2165                2170                2175

Met Leu Gly Ser Arg Asp Met Gly Ala Arg Val Ile Val Gln Ser Phe
            2180                2185                2190
```

-continued

```
Pro Glu Glu Pro Ser Gln Val Gln Leu Lys Gly Val Gln Phe Gln Val
        2195                2200                2205

Leu Gly Gln Ala Phe His Lys His Leu Ser Ser Leu Thr Leu Val Gly
        2210                2215                2220

Ala Met Arg Glu Ser Phe Ile Gln Gly Cys Thr Val Arg Asn Ser Phe
2225                2230                2235                2240

Ser Arg Gly Leu Ser Met Cys Gly Thr Leu Gly Leu Lys Val Asp Ser
        2245                2250                2255

Asn Val Phe Tyr Asn Ile Leu Gly His Ala Leu Leu Val Gly Thr Cys
        2260                2265                2270

Thr Glu Met Arg Tyr Ile Ser Trp Glu Ala Ile His Gly Arg Lys Asp
        2275                2280                2285

Asp Trp Ser Gly His Gly Asn Ile Ile Arg Asn Asn Val Ile Ile Gln
        2290                2295                2300

Val Ser Gly Ala Glu Gly Leu Ser Asn Pro Glu Met Leu Thr Pro Ser
2305                2310                2315                2320

Gly Ile Tyr Ile Cys Ser Pro Thr Asn Val Ile Glu Gly Asn Arg Val
        2325                2330                2335

Cys Gly Ala Gly Tyr Gly Tyr Phe Phe His Leu Met Thr Asn Gln Thr
        2340                2345                2350

Ser Gln Ala Pro Leu Leu Ser Phe Thr Gln Asn Ile Ala His Ser Cys
        2355                2360                2365

Thr Arg Tyr Gly Leu Phe Val Tyr Pro Lys Phe Gln Pro Pro Trp Asp
        2370                2375                2380

Asn Val Thr Gly Thr Thr Leu Phe Gln Ser Phe Thr Val Trp Glu Ser
2385                2390                2395                2400

Ala Gly Gly Ala Gln Ile Phe Arg Ser Ser Asn Leu Arg Leu Lys Asn
        2405                2410                2415

Phe Lys Val Tyr Ser Cys Arg Asp Phe Gly Ile Asp Val Leu Glu Ser
        2420                2425                2430

Asp Ala Asn Thr Ser Val Thr Asp Ser Leu Leu Leu Gly His Phe Ala
        2435                2440                2445

His Lys Gly Ser Leu Cys Met Ser Ser Gly Ile Lys Thr Pro Lys Arg
        2450                2455                2460

Trp Glu Leu Met Val Ser Asn Thr Thr Phe Val Asn Phe Asp Leu Ile
2465                2470                2475                2480

Asn Cys Val Ala Ile Arg Thr Cys Ser Asp Cys Ser Gln Gly Gln Gly
        2485                2490                2495

Gly Phe Thr Val Lys Thr Ser Gln Leu Lys Phe Thr Asn Ser Ser Asn
        2500                2505                2510

Leu Val Ala Phe Pro Phe Pro His Ala Ala Ile Leu Glu Asp Leu Asp
        2515                2520                2525

Gly Ser Leu Ser Gly Lys Asn Arg Ser His Ile Leu Ala Ser Met Glu
        2530                2535                2540

Thr Leu Ser Ala Ser Cys Leu Val Asn Ser Ser Phe Gly Arg Val Val
2545                2550                2555                2560

His Gly Ser Ala Cys Gly Gly Val Leu Phe His Arg Met Ser Ile
        2565                2570                2575

Gly Leu Ala Asn Thr Pro Glu Val Ser Tyr Asp Leu Met Thr Asp
        2580                2585                2590

Ser Arg Asn Lys Thr Thr Thr Val Asn Tyr Val Arg Asp Thr Leu Ser
        2595                2600                2605

Asn Pro Arg Gly Trp Met Ala Leu Leu Leu Asp Gln Glu Thr Tyr Ser
```

```
              2610                2615                2620
Leu Gln Ser Glu Asn Leu Trp Ile Asn Arg Ser Leu Gln Tyr Ser Ala
2625                2630                2635                2640

Thr Phe Asp Asn Phe Ala Pro Gly Asn Tyr Leu Leu Val His Thr
                2645                2650                2655

Asp Leu Pro Pro Tyr Pro Asp Ile Leu Leu Arg Cys Gly Ser Arg Val
                2660                2665                2670

Gly Leu Ser Phe Pro Phe Leu Pro Ser Pro Gly Gln Asn Gln Gly Cys
                2675                2680                2685

Asp Trp Phe Phe Asn Ser Gln Leu Arg Gln Leu Thr Tyr Leu Val Ser
                2690                2695                2700

Gly Glu Gly Gln Val Gln Val Ile Leu Arg Val Lys Glu Gly Met Pro
2705                2710                2715                2720

Pro Thr Ile Ser Ala Ser Thr Ser Ala Pro Glu Ser Ala Leu Lys Trp
                2725                2730                2735

Ser Leu Pro Glu Thr Trp Gln Gly Val Glu Glu Gly Trp Gly Gly Tyr
                2740                2745                2750

Asn Asn Thr Ile Pro Gly Pro Gly Asp Asp Val Leu Ile Leu Pro Asn
                2755                2760                2765

Arg Thr Val Leu Val Asp Thr Asp Leu Pro Phe Phe Lys Gly Leu Tyr
                2770                2775                2780

Val Met Gly Thr Leu Asp Phe Pro Val Asp Arg Ser Asn Val Leu Ser
2785                2790                2795                2800

Val Ala Cys Met Val Ile Ala Gly Gly Glu Leu Lys Val Gly Thr Leu
                2805                2810                2815

Glu Asn Pro Leu Glu Lys Glu Gln Lys Leu Leu Ile Leu Leu Arg Ala
                2820                2825                2830

Ser Glu Gly Val Phe Cys Asp Arg Met Asn Gly Ile His Ile Asp Pro
                2835                2840                2845

Gly Thr Ile Gly Val Tyr Gly Lys Val His Leu Tyr Ser Ala Tyr Pro
                2850                2855                2860

Lys Asn Ser Trp Thr His Leu Gly Ala Asp Ile Ala Ser Gly Asn Glu
2865                2870                2875                2880

Arg Ile Ile Val Glu Asp Ala Val Asp Trp Arg Pro His Asp Lys Ile
                2885                2890                2895

Val Leu Ser Ser Ser Tyr Glu Pro His Glu Ala Glu Val Leu Thr
                2900                2905                2910

Val Lys Glu Val Lys Gly His His Val Arg Ile Tyr Glu Arg Leu Lys
                2915                2920                2925

His Arg His Ile Gly Ser Val His Val Thr Glu Asp Gly Arg His Ile
                2930                2935                2940

Arg Leu Ala Ala Glu Val Gly Leu Leu Thr Arg Asn Ile Gln Ile Gln
2945                2950                2955                2960

Pro Asp Val Ser Cys Arg Gly Arg Leu Phe Val Gly Ser Phe Arg Lys
                2965                2970                2975

Ser Ser Arg Glu Glu Phe Ser Gly Val Leu Gln Leu Leu Asn Val Glu
                2980                2985                2990

Ile Gln Asn Phe Gly Ser Pro Leu Tyr Ser Ser Val Glu Phe Ser Asn
                2995                3000                3005

Val Ser Ala Gly Ser Trp Ile Ile Ser Ser Thr Leu His Gln Ser Cys
                3010                3015                3020

Gly Gly Gly Ile His Ala Ala Ala Ser His Gly Val Leu Leu Asn Asp
3025                3030                3035                3040
```

```
Asn Ile Val Phe Gly Thr Ala Gly His Gly Ile Asp Leu Glu Gly Gln
            3045                3050                3055

Ala Tyr Thr Val Thr Asn Asn Leu Val Val Leu Met Thr Gln Pro Ala
            3060                3065                3070

Trp Ser Thr Ile Trp Val Ala Gly Ile Lys Val Asn Gln Val Lys Asp
            3075                3080                3085

Ile Asn Leu His Gly Asn Val Val Ala Gly Ser Glu Arg Leu Gly Phe
            3090                3095                3100

His Ile Arg Gly His Lys Cys Ser Ser Cys Glu Leu Leu Trp Ser Asp
3105                3110                3115                3120

Asn Val Ala His Ser Ser Leu His Gly Leu His Leu Tyr Lys Glu Ser
            3125                3130                3135

Gly Leu Asp Asn Cys Thr Arg Ile Ser Gly Phe Leu Ala Phe Lys Asn
            3140                3145                3150

Phe Asp Tyr Gly Ala Met Leu His Val Glu Asn Ser Val Glu Ile Glu
            3155                3160                3165

Asn Ile Thr Leu Val Asp Asn Thr Ile Gly Leu Leu Ala Val Val Tyr
            3170                3175                3180

Val Phe Ser Ala Pro Gln Asn Ser Val Lys Lys Val Gln Ile Val Leu
3185                3190                3195                3200

Arg Asn Ser Val Ile Val Ala Thr Ser Ser Ser Phe Asp Cys Ile Gln
            3205                3210                3215

Asp Lys Val Lys Pro His Ser Ala Asn Leu Thr Ser Thr Asp Arg Ala
            3220                3225                3230

Pro Ser Asn Pro Arg Gly Gly Arg Ile Gly Ile Leu Trp Pro Val Phe
            3235                3240                3245

Thr Ser Glu Pro Asn Gln Trp Pro Gln Glu Pro Trp His Lys Val Arg
            3250                3255                3260

Asn Asp His Ser Ile Ser Gly Ile Met Lys Leu Gln Asp Val Thr Phe
3265                3270                3275                3280

Ser Ser Phe Val Lys Ser Cys Tyr Ser Asp Asp Leu Asp Val Cys Ile
            3285                3290                3295

Leu Pro Asn Ala Glu Asn Ser Gly Ile Met His Pro Ile Thr Ala Glu
            3300                3305                3310

Arg Thr Arg Met Leu Lys Ile Lys Asp Lys Asn Lys Phe Tyr Phe Pro
            3315                3320                3325

Ser Leu Gln Pro Arg Lys Asp Leu Gly Lys Val Val Cys Pro Glu Leu
            3330                3335                3340

Asp Cys Ala Ser Pro Arg Lys Tyr Leu Phe Lys Asp Leu Asp Gly Arg
3345                3350                3355                3360

Ala Leu Gly Leu Pro Pro Pro Val Ser Val Phe Pro Lys Thr Glu Ala
            3365                3370                3375

Glu Trp Thr Ala Ser Phe Phe Asn Ala Gly Thr Phe Arg Glu Glu Gln
            3380                3385                3390

Lys Cys Thr Tyr Gln Phe Leu Met Gln Gly Phe Ile Cys Lys Gln Thr
            3395                3400                3405

Asp Gln Val Val Leu Ile Leu Asp Ser Ala Asp Ala Ile Trp Ala Ile
            3410                3415                3420

Gln Lys Leu Tyr Pro Val Val Ser Val Thr Ser Gly Phe Val Asp Val
3425                3430                3435                3440

Phe Ser Ser Val Asn Ala Asn Ile Pro Cys Ser Thr Ser Gly Ser Val
            3445                3450                3455

Ser Thr Phe Tyr Ser Ile Leu Pro Ile Arg Gln Ile Thr Lys Val Cys
            3460                3465                3470
```

-continued

Phe Met Asp Gln Thr Pro Gln Val Leu Arg Phe Phe Leu Leu Gly Asn
        3475                3480                3485

Lys Ser Thr Ser Lys Leu Leu Leu Ala Val Phe Tyr His Glu Leu Gln
        3490                3495                3500

Ser Pro His Val Phe Leu Gly Glu Ser Phe Ile Pro Pro Thr Leu Val
3505                3510                3515                3520

Gln Ser Ala Ser Leu Leu Leu Asn Glu Ser Ile Gly Ala Asn Tyr Phe
            3525                3530                3535

Asn Ile Met Asp Asn Leu Leu Tyr Val Val Leu Gln Gly Glu Glu Pro
            3540                3545                3550

Ile Glu Ile Arg Ser Gly Val Ser Ile His Leu Ala Leu Thr Val Met
        3555                3560                3565

Val Ser Val Leu Glu Lys Gly Trp Glu Ile Val Ile Leu Glu Arg Leu
        3570                3575                3580

Thr Asn Phe Leu Gln Ile Gly Gln Asn Gln Ile Arg Phe Ile His Glu
3585                3590                3595                3600

Met Pro Gly His Glu Glu Thr Leu Lys Ala Ile Ala Asp Ser Arg Ala
            3605                3610                3615

Lys Arg Lys Arg Asn Cys Pro Thr Val Thr Cys Thr Ser His Tyr Arg
            3620                3625                3630

Arg Val Gly Gln Arg Arg Pro Leu Met Met Glu Met Asn Ser His Arg
        3635                3640                3645

Ala Ser Pro Pro Met Thr Val Glu Thr Ile Ser Lys Val Ile Val Ile
        3650                3655                3660

Glu Ile Gly Asp Ser Pro Thr Val Arg Ser Thr Gly Met Ile Ser Ser
3665                3670                3675                3680

Leu Ser Ser Asn Lys Leu Gln Asn Leu Ala His Arg Val Ile Thr Ala
            3685                3690                3695

Gln Gln Thr Gly Val Leu Glu Asn Val Leu Asn Met Thr Ile Gly Ala
            3700                3705                3710

Leu Leu Val Thr Gln Ser Lys Gly Val Ile Gly Tyr Gly Asn Thr Ser
        3715                3720                3725

Ser Phe Lys Thr Gly Asn Leu Ile Tyr Ile Arg Pro Tyr Ala Leu Ser
        3730                3735                3740

Ile Leu Val Gln Pro Ser Asp Gly Glu Val Gly Asn Glu Leu Pro Val
3745                3750                3755                3760

Gln Pro Gln Leu Val Phe Leu Asp Glu Gln Asn Arg Arg Val Glu Ser
            3765                3770                3775

Leu Gly Pro Pro Ser Glu Pro Trp Thr Ile Ser Ala Ser Leu Glu Gly
            3780                3785                3790

Ala Ser Asp Ser Val Leu Lys Gly Cys Thr Gln Ala Glu Thr Gln Asp
            3795                3800                3805

Gly Tyr Val Ser Phe Tyr Asn Leu Ala Val Leu Ile Ser Gly Ser Asn
            3810                3815                3820

Trp His Phe Ile Phe Thr Val Thr Ser Pro Pro Gly Val Asn Phe Thr
3825                3830                3835                3840

Ala Arg Ser Lys Pro Phe Ala Val Leu
            3845

<210> SEQ ID NO 6
<211> LENGTH: 102
<212> TYPE: PRT
<213> ORGANISM: Homo sapiens

<400> SEQUENCE: 6

Pro Lys Val Thr Glu Ile Ile Pro Lys Tyr Gly Ser Ile Asn Gly Ala
1               5                   10                  15

Thr Arg Leu Thr Ile Arg Gly Glu Gly Phe Ser Gln Ala Asn Gln Phe
            20                  25                  30

Asn Tyr Gly Val Asp Asn Ala Glu Leu Gly Asn Ser Val Gln Leu Ile
            35                  40                  45

Ser Ser Phe Gln Ser Ile Thr Cys Asp Val Glu Lys Asp Ala Ser His
50                  55                  60

Ser Thr Gln Ile Thr Cys Tyr Thr Arg Ala Met Pro Glu Asp Ser Tyr
65                  70                  75                  80

Thr Val Arg Val Ser Val Asp Gly Val Pro Val Thr Glu Asn Asn Thr
                85                  90                  95

Cys Lys Gly His Ile Asn
            100

<210> SEQ ID NO 7
<211> LENGTH: 113
<212> TYPE: PRT
<213> ORGANISM: Homo sapiens

<400> SEQUENCE: 7

Pro Thr Ile Arg Ser Ile Thr Pro Leu Ser Gly Thr Pro Gly Thr Leu
1               5                   10                  15

Ile Thr Ile Gln Gly Arg Ile Phe Thr Asp Val Tyr Gly Ser Asn Ile
            20                  25                  30

Ala Leu Ser Ser Asn Gly Lys Asn Val Arg Ile Leu Arg Val Tyr Ile
            35                  40                  45

Gly Gly Met Pro Cys Glu Leu Leu Ile Pro Gln Ser Asp Asn Leu Tyr
50                  55                  60

Gly Leu Lys Leu Asp His Pro Asn Gly Asp Met Gly Ser Met Val Cys
65                  70                  75                  80

Lys Thr Thr Gly Thr Phe Ile Gly His His Asn Val Ser Phe Ile Leu
                85                  90                  95

Asp Asn Asp Tyr Gly Arg Ser Phe Pro Gln Lys Met Ala Tyr Phe Val
            100                 105                 110

Ser

<210> SEQ ID NO 8
<211> LENGTH: 93
<212> TYPE: PRT
<213> ORGANISM: Homo sapiens

<400> SEQUENCE: 8

Ala Glu Val Thr Met Ile Phe Pro Ser Gln Gly Ser Ile Arg Gly Gly
1               5                   10                  15

Thr Thr Leu Thr Ile Ser Gly Arg Phe Phe Asp Gln Thr Asp Phe Pro
            20                  25                  30

Val Arg Val Leu Val Gly Gly Glu Pro Cys Asp Ile Leu Asn Val Thr
            35                  40                  45

Glu Asn Ser Ile Cys Cys Lys Thr Pro Pro His Ile Leu Lys
50                  55                  60

Thr Val Tyr Pro Gly Gly Arg Gly Leu Lys Leu Glu Val Trp Asn Asn
65                  70                  75                  80

Ser Arg Pro Ile Arg Leu Glu Glu Ile Leu Glu Tyr Asn
            85                  90

<210> SEQ ID NO 9
<211> LENGTH: 86
<212> TYPE: PRT
<213> ORGANISM: Homo sapiens

<400> SEQUENCE: 9

Pro Leu Val Leu Ala Ile Ser Pro Ser Gln Gly Ser Tyr Glu Glu Gly
1               5                   10                  15

Thr Ile Leu Thr Ile Val Gly Ser Gly Phe Ser Pro Ser Ser Ala Val
            20                  25                  30

Thr Val Ser Val Gly Pro Val Gly Cys Ser Leu Leu Ser Val Asp Glu
        35                  40                  45

Lys Glu Leu Lys Cys Gln Ile Leu Asn Gly Ser Ala Gly His Ala Pro
50                  55                  60

Val Ala Val Ser Met Ala Asp Val Gly Leu Ala Gln Asn Val Gly Gly
65                  70                  75                  80

Glu Glu Phe Tyr Phe Val
                85

<210> SEQ ID NO 10
<211> LENGTH: 81
<212> TYPE: PRT
<213> ORGANISM: Homo sapiens

<400> SEQUENCE: 10

Ser Gln Ile Ser His Ile Trp Pro Asp Ser Gly Ser Ile Ala Gly Gly
1               5                   10                  15

Thr Leu Leu Thr Leu Ser Gly Phe Gly Phe Asn Glu Asn Ser Lys Val
            20                  25                  30

Leu Val Gly Asn Glu Thr Cys Asn Val Ile Glu Gly Asp Leu Asn Arg
        35                  40                  45

Ile Thr Cys Arg Thr Pro Lys Lys Thr Glu Gly Thr Val Asp Ile Ser
    50                  55                  60

Val Thr Thr Asn Gly Phe Gln Ala Thr Ala Arg Asp Ala Phe Ser Tyr
65                  70                  75                  80

Asn

<210> SEQ ID NO 11
<211> LENGTH: 86
<212> TYPE: PRT
<213> ORGANISM: Homo sapiens

<400> SEQUENCE: 11

Pro Ile Ile Thr Asp Phe Ser Pro Lys Val Arg Thr Ile Leu Gly Glu
1               5                   10                  15

Val Asn Leu Thr Ile Lys Gly Tyr Asn Phe Gly Asn Glu Leu Thr Gln
            20                  25                  30

Asn Met Ala Val Tyr Val Gly Gly Lys Thr Cys Gln Ile Leu His Trp
        35                  40                  45

Asn Phe Thr Asp Ile Arg Cys Leu Leu Pro Lys Leu Ser Pro Gly Lys
    50                  55                  60

His Asp Ile Tyr Val Glu Val Arg Asn Trp Gly Phe Ala Ser Thr Arg
65                  70                  75                  80

Asp Lys Leu Asn Ser Ser
                85

<210> SEQ ID NO 12

```
<211> LENGTH: 81
<212> TYPE: PRT
<213> ORGANISM: Homo sapiens

<400> SEQUENCE: 12

Leu Glu Val Thr Ser Met Phe Pro Gln Arg Gly Ser Leu Phe Gly Gly
1               5                   10                  15

Thr Glu Ile Thr Ile Arg Gly Phe Gly Phe Ser Thr Ile Pro Ala Glu
            20                  25                  30

Asn Thr Val Leu Leu Gly Ser Ile Pro Cys Asn Val Thr Ser Ser Ser
        35                  40                  45

Glu Asn Val Ile Lys Cys Ile Leu His Ser Thr Gly Asn Ile Phe Arg
    50                  55                  60

Ile Thr Asn Asn Gly Lys Asp Ser Val His Gly Leu Gly Tyr Ala Trp
65                  70                  75                  80

Ser

<210> SEQ ID NO 13
<211> LENGTH: 83
<212> TYPE: PRT
<213> ORGANISM: Homo sapiens

<400> SEQUENCE: 13

Pro Ser Ile Ser Asn Ile Thr Pro Ser Thr Gly Thr Val Asn Glu Leu
1               5                   10                  15

Ile Thr Ile Ile Gly His Gly Phe Ser Asn Leu Pro Trp Ala Asn Lys
            20                  25                  30

Val Thr Ile Gly Ser Tyr Pro Cys Val Val Glu Glu Ser Ser Glu Asp
        35                  40                  45

Ser Ile Thr Cys His Ile Asp Pro Gln Asn Ser Met Asp Val Gly Ile
    50                  55                  60

Arg Glu Thr Val Thr Leu Thr Val Tyr Asn Leu Gly Thr Ala Ile Asn
65                  70                  75                  80

Thr Leu Ser

<210> SEQ ID NO 14
<211> LENGTH: 86
<212> TYPE: PRT
<213> ORGANISM: Homo sapiens

<400> SEQUENCE: 14

Pro Asn Ile Asp Leu Val Leu Pro Asn Ala Gly Ser Thr Thr Gly Met
1               5                   10                  15

Thr Ser Val Thr Ile Lys Gly Ser Gly Phe Ala Val Ser Ser Ala Gly
            20                  25                  30

Val Lys Val Leu Met Gly His Phe Pro Cys Lys Val Leu Ser Val Asn
        35                  40                  45

Tyr Thr Ala Ile Glu Cys Glu Thr Ser Pro Ala Ala Gln Gln Leu Val
    50                  55                  60

Asp Val Asp Leu Leu Ile His Gly Val Pro Ala Gln Cys Gln Gly Asn
65                  70                  75                  80

Cys Thr Phe Ser Tyr Leu
                85

<210> SEQ ID NO 15
<211> LENGTH: 82
<212> TYPE: PRT
<213> ORGANISM: Homo sapiens
```

<400> SEQUENCE: 15

Pro Tyr Ile Thr Gly Val Phe Pro Asn Ser Val Ile Gly Ser Val Lys
1               5                   10                  15

Val Leu Ile Glu Gly Glu Gly Leu Gly Thr Val Leu Glu Asp Ile Ala
            20                  25                  30

Val Phe Ile Gly Asn Gln Gln Phe Arg Ala Ile Glu Val Asn Glu Asn
        35                  40                  45

Asn Ile Thr Ala Leu Val Thr Pro Leu Pro Val Gly His His Ser Val
    50                  55                  60

Ser Val Val Val Gly Ser Lys Gly Leu Ala Leu Gly Asn Leu Thr Val
65                  70                  75                  80

Ser Ser

<210> SEQ ID NO 16
<211> LENGTH: 81
<212> TYPE: PRT
<213> ORGANISM: Homo sapiens

<400> SEQUENCE: 16

Pro Pro Val Ala Ser Leu Ser Pro Thr Ser Gly Ser Ile Gly Gly Gly
1               5                   10                  15

Thr Thr Leu Val Ile Thr Gly Asn Gly Phe Tyr Pro Gly Asn Thr Thr
            20                  25                  30

Val Thr Ile Gly Asp Glu Pro Cys Gln Ile Ile Ser Ile Asn Pro Asn
        35                  40                  45

Glu Val Tyr Cys Arg Thr Pro Ala Gly Thr Thr Gly Met Val Asp Val
    50                  55                  60

Lys Ile Phe Val Asn Thr Ile Ala Tyr Pro Pro Leu Leu Phe Thr Tyr
65                  70                  75                  80

Ala

<210> SEQ ID NO 17
<211> LENGTH: 83
<212> TYPE: PRT
<213> ORGANISM: Homo sapiens

<400> SEQUENCE: 17

Pro Phe Leu Arg Gly Ile Ile Pro Ser Arg Gly Pro Pro Gly Thr Glu
1               5                   10                  15

Ile Glu Ile Thr Gly Ser Asn Phe Gly Phe Glu Ile Leu Glu Ile Ser
            20                  25                  30

Val Met Ile Asn Asn Ile Gln Cys Asn Val Thr Met Ala Asn Asp Ser
        35                  40                  45

Val Leu Gln Cys Ile Val Gly Asp His Ala Gly Thr Phe Pro Val
    50                  55                  60

Met Met His His Lys Thr Lys Gly Ser Ala Met Ser Thr Val Val Phe
65                  70                  75                  80

Glu Tyr Pro

<210> SEQ ID NO 18
<211> LENGTH: 88
<212> TYPE: PRT
<213> ORGANISM: Homo sapiens

<400> SEQUENCE: 18

Leu Asn Ile Gln Asn Ile Asn Pro Ser Gln Gly Ser Phe Gly Gly Gly
1               5                   10                  15

```
Gln Thr Met Thr Val Thr Gly Thr Gly Phe Asn Pro Gln Asn Ser Ile
             20                  25                  30

Ile Leu Val Cys Gly Ser Glu Cys Ala Ile Asp Arg Leu Arg Ser Asp
             35                  40                  45

Tyr Thr Thr Leu Leu Cys Glu Ile Pro Ser Asn Asn Gly Thr Gly Ala
             50                  55                  60

Glu Gln Ala Cys Glu Val Ser Val Val Asn Gly Lys Asp Leu Ser Gln
 65                  70                  75                  80

Ser Met Thr Pro Phe Thr Tyr Ala
             85

<210> SEQ ID NO 19
<211> LENGTH: 87
<212> TYPE: PRT
<213> ORGANISM: Homo sapiens

<400> SEQUENCE: 19

Pro Leu Ile Thr Ala Val Ser Pro Lys Arg Gly Ser Thr Ala Gly Gly
 1               5                  10                  15

Thr Arg Leu Thr Val Val Gly Ser Gly Phe Ser Glu Asn Met Glu Asp
             20                  25                  30

Val His Ile Thr Ile Ala Glu Ala Lys Cys Asp Val Glu Tyr Ser Asn
             35                  40                  45

Lys Thr His Ile Ile Cys Met Thr Asp Ala His Thr Leu Ser Gly Trp
 50                  55                  60

Ala Pro Val Cys Val His Ile Arg Gly Val Gly Met Ala Lys Leu Asp
 65                  70                  75                  80

Asn Ala Asp Phe Leu Tyr Val
             85

<210> SEQ ID NO 20
<211> LENGTH: 93
<212> TYPE: PRT
<213> ORGANISM: Homo sapiens

<400> SEQUENCE: 20

Pro Arg Ile Met Ala Ile Phe Pro Ser Gln Gly Ser Ala Cys Gly Gly
 1               5                  10                  15

Thr Ile Leu Thr Val Arg Gly Leu Leu Leu Asn Ser Arg Arg Arg Ser
             20                  25                  30

Val Arg Val Asp Leu Ser Gly Pro Phe Thr Cys Val Ile Leu Ser Leu
             35                  40                  45

Gly Asp His Thr Ile Leu Cys Gln Val Ser Leu Glu Gly Asp Pro Leu
 50                  55                  60

Pro Gly Ala Ser Phe Ser Leu Asn Val Thr Val Leu Val Asn Gly Leu
 65                  70                  75                  80

Thr Ser Glu Cys Gln Gly Asn Cys Thr Leu Phe Ile Arg
             85                  90

<210> SEQ ID NO 21
<211> LENGTH: 93
<212> TYPE: PRT
<213> ORGANISM: Mus musculus

<400> SEQUENCE: 21

Pro Ala Val Tyr Lys Val Phe Pro Thr Ser Ala Pro Leu Glu Gly Gly
 1               5                  10                  15

Thr Val Leu Thr Ile Cys Gly Trp Asp Phe Gly Phe Arg Lys Asn Asn
```

```
                    20                  25                  30
Lys Phe Asp Leu Arg Lys Thr Lys Val Leu Leu Gly Asn Glu Ser Cys
            35                  40                  45

Thr Leu Thr Leu Ser Glu Ser Thr Thr Asn Thr Leu Lys Cys Thr Val
        50                  55                  60

Gly Pro Ala Met Ser Glu His Phe Asn Val Ser Val Ile Ile Ser Asn
65                  70                  75                  80

Ser Arg Glu Thr Thr Gln Tyr Ser Ala Phe Ser Tyr Val
                85                  90

<210> SEQ ID NO 22
<211> LENGTH: 85
<212> TYPE: PRT
<213> ORGANISM: Mus musculus

<400> SEQUENCE: 22

Pro Thr Phe Tyr Arg Val Ser Pro Ser Arg Gly Pro Leu Ser Gly Gly
1               5                   10                  15

Thr Trp Ile Gly Ile Glu Gly Ser His Leu Asn Ala Gly Ser Asp Val
            20                  25                  30

Ala Val Ser Ile Gly Gly Arg Pro Cys Ser Phe Ser Trp Arg Asn Ser
        35                  40                  45

Arg Glu Ile Arg Cys Leu Thr Pro Pro Gly His Thr Pro Gly Ser Ala
    50                  55                  60

Pro Ile Val Ile Asn Ile Asn Arg Ala Gln Leu Ser Asn Pro Glu Val
65                  70                  75                  80

Lys Tyr Asn Tyr Thr
                85

<210> SEQ ID NO 23
<211> LENGTH: 88
<212> TYPE: PRT
<213> ORGANISM: Artificial Sequence
<220> FEATURE:
<223> OTHER INFORMATION: consensus

<400> SEQUENCE: 23

Pro Val Ile Thr Ser Ile Ser Pro Ser Ser Gly Pro Leu Ser Gly Gly
1               5                   10                  15

Thr Glu Ile Thr Ile Thr Gly Ser Asn Leu Gly Ser Gly Ser Glu Asp
            20                  25                  30

Ile Lys Val Thr Phe Gly Gly Thr Glu Cys Asp Val Ile Ser Ser Ser
            35                  40                  45

Ser Ser Thr Gln Ile Val Cys Lys Thr Pro Pro Val Ala Gly Gly Pro
    50                  55                  60

Ser Pro Pro Val Val Thr Val Ser Leu Asp Gly Asp Gly Leu Ser Ser
65                  70                  75                  80

Ser Pro Val Thr Phe Thr Tyr Val
                85

<210> SEQ ID NO 24
<211> LENGTH: 448
<212> TYPE: PRT
<213> ORGANISM: Homo sapiens

<400> SEQUENCE: 24

Trp Ser Arg Thr His Ser Trp Phe Pro Glu Arg Leu Pro Gln Asp Gly
1               5                   10                  15

Asp Asn Val Thr Val Glu Asn Gly Gln Leu Leu Leu Leu Asp Thr Asn
```

-continued

```
                 20                  25                  30
Thr Ser Ile Leu Asn Leu Leu His Ile Lys Gly Gly Lys Leu Ile Phe
             35                  40                  45
Met Ala Pro Gly Pro Ile Glu Leu Arg Ala His Ala Ile Leu Val Ser
 50                  55                  60
Asp Gly Gly Glu Leu Arg Ile Gly Ser Glu Asp Lys Pro Phe Gln Gly
 65                  70                  75                  80
Arg Ala Gln Ile Thr Leu Tyr Gly Ser Ser Tyr Ser Thr Pro Phe Phe
                 85                  90                  95
Pro Tyr Gly Val Lys Phe Leu Ala Val Arg Asn Gly Thr Leu Ser Leu
             100                 105                 110
His Gly Ser Leu Pro Glu Val Ile Val Thr Cys Leu Arg Ala Thr Ala
             115                 120                 125
His Ala Leu Asp Thr Val Leu Ala Leu Glu Asp Ala Val Asp Trp Asn
 130                 135                 140
Pro Gly Asp Glu Val Val Ile Ser Gly Thr Gly Val Lys Gly Ala
 145                 150                 155                 160
Lys Pro Met Glu Glu Ile Val Thr Val Glu Thr Val Gln Asp Thr Asp
             165                 170                 175
Leu Tyr Leu Lys Ser Pro Leu Arg Tyr Ser His Asn Phe Thr Glu Asn
             180                 185                 190
Trp Val Ala Gly Glu His His Ile Leu Lys Ala Thr Val Ala Leu Leu
             195                 200                 205
Ser Arg Ser Ile Thr Ile Gln Gly Asn Leu Thr Asn Glu Arg Glu Lys
             210                 215                 220
Leu Leu Val Ser Cys Gln Glu Ala Asn Ala Pro Glu Gly Asn Leu Gln
 225                 230                 235                 240
His Cys Leu Tyr Ser Met Ser Glu Lys Met Leu Gly Ser Arg Asp Met
                 245                 250                 255
Gly Ala Arg Val Ile Val Gln Ser Phe Pro Glu Glu Pro Ser Gln Val
             260                 265                 270
Gln Leu Lys Gly Val Gln Phe Gln Val Leu Gly Gln Ala Phe His Lys
             275                 280                 285
His Leu Ser Ser Leu Thr Leu Val Gly Ala Met Arg Glu Ser Phe Ile
             290                 295                 300
Gln Gly Cys Thr Val Arg Asn Ser Phe Ser Arg Gly Leu Ser Met Cys
 305                 310                 315                 320
Gly Thr Leu Gly Leu Lys Val Asp Ser Asn Val Phe Tyr Asn Ile Leu
             325                 330                 335
Gly His Ala Leu Leu Val Gly Thr Cys Thr Glu Met Arg Tyr Ile Ser
             340                 345                 350
Trp Glu Ala Ile His Gly Arg Lys Asp Asp Trp Ser Gly His Gly Asn
             355                 360                 365
Ile Ile Arg Asn Asn Val Ile Ile Gln Val Ser Gly Ala Glu Gly Leu
             370                 375                 380
Ser Asn Pro Glu Met Leu Thr Pro Ser Gly Ile Tyr Ile Cys Ser Pro
 385                 390                 395                 400
Thr Asn Val Ile Glu Gly Asn Arg Val Cys Gly Ala Gly Tyr Gly Tyr
             405                 410                 415
Phe Phe His Leu Met Thr Asn Gln Thr Ser Gln Ala Pro Leu Leu Ser
             420                 425                 430
Phe Thr Gln Asn Ile Ala His Ser Cys Thr Arg Tyr Gly Leu Phe Val
             435                 440                 445
```

<210> SEQ ID NO 25
<211> LENGTH: 341
<212> TYPE: PRT
<213> ORGANISM: Homo sapiens

<400> SEQUENCE: 25

Trp Ser Leu Pro Glu Thr Trp Gln Gly Val Glu Gly Trp Gly Gly
1               5                   10                  15

Tyr Asn Asn Thr Ile Pro Gly Pro Gly Asp Asp Val Leu Ile Leu Pro
            20                  25                  30

Asn Arg Thr Val Leu Val Asp Thr Asp Leu Pro Phe Phe Lys Gly Leu
            35                  40                  45

Tyr Val Met Gly Thr Leu Asp Phe Pro Val Asp Arg Ser Asn Val Leu
        50                  55                  60

Ser Val Ala Cys Met Val Ile Ala Gly Gly Glu Leu Lys Val Gly Thr
65                  70                  75                  80

Leu Glu Asn Pro Leu Glu Lys Glu Gln Lys Leu Leu Ile Leu Leu Arg
                85                  90                  95

Ala Ser Glu Gly Val Phe Cys Asp Arg Met Asn Gly Ile His Ile Asp
            100                 105                 110

Pro Gly Thr Ile Gly Val Tyr Gly Lys Val His Leu Tyr Ser Ala Tyr
        115                 120                 125

Pro Lys Asn Ser Trp Thr His Leu Gly Ala Asp Ile Ala Ser Gly Asn
130                 135                 140

Glu Arg Ile Ile Val Glu Asp Ala Val Asp Trp Arg Pro His Asp Lys
145                 150                 155                 160

Ile Val Leu Ser Ser Ser Tyr Glu Pro His Glu Ala Glu Val Leu
                165                 170                 175

Thr Val Lys Glu Val Lys Gly His His Val Arg Ile Tyr Glu Arg Leu
            180                 185                 190

Lys His Arg His Ile Gly Ser Val His Val Thr Glu Asp Gly Arg His
        195                 200                 205

Ile Arg Leu Ala Ala Glu Val Gly Leu Leu Thr Arg Asn Ile Gln Ile
210                 215                 220

Gln Pro Asp Val Ser Cys Arg Gly Arg Leu Phe Val Gly Ser Phe Arg
225                 230                 235                 240

Lys Ser Ser Arg Glu Glu Phe Ser Gly Val Leu Gln Leu Leu Asn Val
                245                 250                 255

Glu Ile Gln Asn Phe Gly Ser Pro Leu Tyr Ser Ser Val Glu Phe Ser
            260                 265                 270

Asn Val Ser Ala Gly Ser Trp Ile Ile Ser Ser Thr Leu His Gln Ser
        275                 280                 285

Cys Gly Gly Gly Ile His Ala Ala Ser His Gly Val Leu Leu Asn
290                 295                 300

Asp Asn Ile Val Phe Gly Thr Ala Gly His Gly Ile Asp Leu Glu Gly
305                 310                 315                 320

Gln Ala Tyr Thr Val Thr Asn Asn Leu Val Val Leu Met Thr Gln Pro
                325                 330                 335

Ala Trp Ser Thr Ile
            340

<210> SEQ ID NO 26
<211> LENGTH: 447
<212> TYPE: PRT
<213> ORGANISM: Homo sapiens -continued

```
<400> SEQUENCE: 26

Trp Ser Ser Asn Phe Ser Trp Gly Gly Lys Ser Pro Glu Glu Gly
1               5                   10                  15

Ser Leu Val Val Ile Thr Lys Gly Gln Thr Ile Leu Leu Asp Gln Ser
            20                  25                  30

Thr Pro Ile Leu Lys Met Leu Leu Ile Gln Gly Gly Thr Leu Ile Phe
            35                  40                  45

Asp Glu Ala Asp Ile Glu Leu Gln Ala Glu Asn Ile Leu Ile Thr Asp
        50                  55                  60

Gly Gly Val Leu Gln Ile Gly Thr Glu Thr Ser Pro Phe Gln His Lys
65                  70                  75                  80

Ala Val Ile Thr Leu His Gly His Leu Arg Ser Pro Glu Leu Pro Val
                85                  90                  95

Tyr Gly Ala Lys Thr Leu Ala Val Arg Glu Gly Ile Leu Asp Leu His
            100                 105                 110

Gly Val Pro Val Pro Val Thr Trp Thr Arg Leu Ala His Thr Ala Lys
        115                 120                 125

Ala Gly Glu Arg Ile Leu Ile Leu Gln Glu Ala Val Thr Trp Lys Pro
130                 135                 140

Gly Asp Asn Ile Val Ile Ala Ser Thr Gly His Arg His Ser Gln Gly
145                 150                 155                 160

Glu Asn Glu Lys Met Thr Ile Ala Ser Val Ser Ala Asp Gly Ile Asn
                165                 170                 175

Ile Thr Leu Ser Asn Pro Leu Asn Tyr Thr His Leu Gly Ile Thr Val
            180                 185                 190

Thr Leu Pro Asp Gly Thr Leu Phe Glu Ala Arg Ala Glu Val Gly Ile
        195                 200                 205

Leu Thr Arg Asn Ile Leu Ile Arg Gly Ser Asp Asn Val Glu Trp Asn
210                 215                 220

Asn Lys Ile Pro Ala Cys Pro Asp Gly Phe Asp Thr Gly Glu Phe Ala
225                 230                 235                 240

Thr Gln Thr Cys Leu Gln Gly Lys Phe Gly Glu Glu Ile Gly Ser Asp
                245                 250                 255

Gln Phe Gly Gly Cys Val Met Phe His Ala Pro Val Pro Gly Ala Asn
            260                 265                 270

Met Val Thr Gly Arg Ile Glu Tyr Val Glu Val Phe His Ala Gly Gln
        275                 280                 285

Ala Phe Arg Leu Gly Arg Tyr Pro Ile His Trp His Leu Leu Gly Asp
290                 295                 300

Leu Gln Phe Lys Ser Tyr Val Arg Gly Cys Ala Ile His Gln Ala Tyr
305                 310                 315                 320

Asn Arg Ala Val Thr Ile His Asn Thr His Leu Leu Val Glu Arg
                325                 330                 335

Asn Ile Ile Tyr Asp Ile Lys Gly Gly Ala Phe Phe Ile Glu Asp Gly
            340                 345                 350

Ile Glu His Gly Asn Ile Leu Gln Tyr Asn Leu Ala Val Phe Val Gln
        355                 360                 365

Gln Ser Thr Ser Leu Leu Asn Asp Asp Val Thr Pro Ala Ala Phe Trp
370                 375                 380

Val Thr Asn Pro Asn Asn Thr Ile Arg His Asn Ala Val Ala Gly Gly
385                 390                 395                 400

Thr His Phe Gly Phe Trp Tyr Arg Met Asn Asn His Pro Asp Gly Pro
                405                 410                 415
```

```
Ser Tyr Asp Arg Asn Ile Cys Gln Lys Arg Val Pro Leu Gly Glu Phe
            420                 425                 430

Phe Asn Asn Thr Val His Ser Gln Gly Trp Phe Gly Met Trp Ile
        435                 440                 445

<210> SEQ ID NO 27
<211> LENGTH: 344
<212> TYPE: PRT
<213> ORGANISM: Homo sapiens

<400> SEQUENCE: 27

Trp Ser Asn Asp Ser Phe Trp Gln Ser Ser Arg Glu Asn Asn Tyr Thr
1               5                   10                  15

Tyr Pro His Pro Gly Ala Asn Val Ile Ile Pro Glu Gly Thr Trp Ile
            20                  25                  30

Val Ala Asp Ile Asp Met Pro Ser Met Glu Arg Leu Ile Ile Trp Gly
        35                  40                  45

Val Leu Glu Leu Glu Asp Lys Tyr Asn Val Ala Ala Glu Ser Ser
    50                  55                  60

Tyr Arg Glu Val Val Leu Asn Ala Thr Tyr Ile Ser Leu Gln Gly Gly
65                  70                  75                  80

Arg Leu Ile Gly Gly Trp Glu Asp Asn Pro Phe Lys Gly Asp Leu Lys
                85                  90                  95

Ile Val Leu Arg Gly Asn His Thr Thr Gln Asp Trp Ala Leu Pro Glu
            100                 105                 110

Gly Pro Asn Gln Gly Ala Lys Val Leu Gly Val Phe Gly Glu Leu Asp
        115                 120                 125

Leu His Gly Ile Pro His Ser Ile Tyr Lys Thr Lys Leu Ser Glu Thr
    130                 135                 140

Ala Phe Ala Gly Ser Lys Val Leu Ser Leu Met Asp Ala Val Asp Trp
145                 150                 155                 160

Gln Glu Gly Glu Glu Ile Val Ile Thr Thr Ser Tyr Asp Phe His
                165                 170                 175

Gln Thr Glu Thr Arg Ser Ile Val Lys Ile Leu His Asp His Lys Ile
            180                 185                 190

Leu Ile Leu Asn Asp Ser Leu Ser Tyr Thr His Phe Ala Glu Lys Tyr
        195                 200                 205

His Val Pro Gly Thr Gly Glu Ser Tyr Thr Leu Ala Ala Asp Val Gly
    210                 215                 220

Ile Leu Ser Arg Asn Ile Lys Ile Val Gly Glu Asp Tyr Pro Gly Trp
225                 230                 235                 240

Ser Glu Asp Ser Phe Gly Ala Arg Val Leu Val Gly Ser Phe Thr Glu
                245                 250                 255

Asn Met Met Thr Phe Lys Gly Asn Ala Arg Ile Ser Asn Val Glu Phe
            260                 265                 270

Tyr His Ser Gly Gln Glu Gly Phe Arg Asp Ser Thr Ala Pro Arg Tyr
        275                 280                 285

Ala Val Thr Phe Leu Asn Leu Gly Gln Ile Gln Glu His Gly Ser Ser
    290                 295                 300

Tyr Ile Arg Gly Cys Ala Phe His His Gly Phe Ser Pro Ala Ile Gly
305                 310                 315                 320

Val Phe Gly Thr Asp Gly Leu Asp Ile Asp Asn Ile Ile His Phe
                325                 330                 335

Thr Val Gly Glu Gly Ile Arg Ile
            340
```

<210> SEQ ID NO 28
<211> LENGTH: 432
<212> TYPE: PRT
<213> ORGANISM: Chloroflexus aurantiacus

<400> SEQUENCE: 28

Trp Ser Asp Pro Ala Thr Trp Gly Gly Arg Leu Pro Gln Ala Gly Asp
1               5                   10                  15

Ala Val Thr Ile Pro Ala Gly Lys Val Val Leu Leu Asp Val Ser Pro
            20                  25                  30

Pro Pro Leu Gln Ser Leu Leu Ile Glu Gly Glu Leu Arg Phe Asp Arg
        35                  40                  45

Gln Asn Leu Asn Leu Thr Val Gly Trp Ile Met Leu His Gly Arg Gly
    50                  55                  60

Arg Leu Gln Ile Gly Thr Pro Thr Glu Pro Phe Thr Gln Arg Ala Thr
65                  70                  75                  80

Ile Thr Leu Thr Ala Ala Asn Leu Asp Glu Asp Val Met Gly Met Gly
                85                  90                  95

Thr Arg Gly Ile Leu Leu Met Gly Gly Thr Phe Glu Ala Tyr Gly Gln
            100                 105                 110

Thr Pro Asp Arg Ile Trp Thr Arg Leu Ala Asp His Ala Ala Thr Gly
        115                 120                 125

Ser Thr Thr Leu Thr Leu Ala Glu Pro Val Asn Trp Gln Thr Gly Asp
    130                 135                 140

Gln Ile Val Ile Ala Pro Thr Asp Phe Tyr Gly Val Ala Glu Thr Glu
145                 150                 155                 160

Arg Leu Thr Val Gln Ala Ala Asn Glu Thr Gln Val Ala Leu Thr Thr
                165                 170                 175

Pro Leu Gln Lys Glu Arg Trp Gly Arg Leu Gln Tyr Val Ser Pro Thr
            180                 185                 190

Gly Met Thr Leu Thr Pro Thr Thr Glu Val Thr Pro Leu Val Leu Asp
        195                 200                 205

Glu Arg Ala Glu Val Gly Ile Leu Ser Arg Arg Ile Val Ile Gln Gly
    210                 215                 220

Ala Asp Asp Glu Arg Trp Arg Asn Asp Arg Phe Gly Ala His Ile Met
225                 230                 235                 240

Val Met Gly Asn Gly Val Leu Arg Leu Asn Gly Val Glu Leu Arg Arg
                245                 250                 255

Met Gly Gln Gly Gly Arg Phe Gly Arg Tyr Pro Ile His Phe His Met
            260                 265                 270

Leu Ser Tyr Ala Ala Asp Gly Ser Leu Ile Gly Asp Ala Thr Gln Gln
        275                 280                 285

Leu Val Ala Asn Ser Ser Ile Trp Asn Ser Ala Asn Arg Cys Ile Thr
    290                 295                 300

Ile His Gly Thr Asn Gly Thr Thr Ile Arg Asn Asn Ile Cys Tyr Asp
305                 310                 315                 320

Ile Ala Gly His Ala Ile Phe Leu Glu Asp Ala Val Glu Arg Arg Asn
                325                 330                 335

Leu Ile Glu Asn Asn Leu Val Leu Lys Val Arg Gln Pro Pro Val Leu
            340                 345                 350

Leu Leu Asn His Asp Arg Glu Ala Phe Arg Arg Gly Pro Ser Gly Phe
        355                 360                 365

Trp Ile Thr Asn Pro Asp Asn Ile Val Arg Gly Asn Val Ala Ala Asp
    370                 375                 380

```
Ala Ala Gly Asn Gly Phe Trp Leu Ala Phe Pro Glu Arg Pro Leu Gly
385                 390                 395                 400

Ser Asn Lys Leu Val Pro Ile Arg Pro Ala Asn Thr Arg Leu Gly Ile
                405                 410                 415

Phe Ser His Asn Val Ala His Ser Asn Gly Lys Pro Gly Ile Asn Leu
            420                 425                 430

<210> SEQ ID NO 29
<211> LENGTH: 451
<212> TYPE: PRT
<213> ORGANISM: Homo sapiens

<400> SEQUENCE: 29

Asn Pro Arg Leu Arg Asn Trp Asp Pro Gly Gln Asp Ser Ala Lys Gln
1               5                   10                  15

Val Val Ile Lys Glu Gly Asp Met Leu Arg Leu Thr Ser Asp Ala Thr
                20                  25                  30

Val His Ser Ile Val Ile Gln Asp Gly Gly Leu Leu Val Phe Gly Asp
            35                  40                  45

Asn Lys Asp Gly Ser Arg Asn Ile Thr Leu Arg Thr His Tyr Ile Leu
50                  55                  60

Ile Gln Asp Gly Gly Ala Leu His Ile Gly Ala Glu Lys Cys Arg Tyr
65                  70                  75                  80

Lys Ser Lys Ala Thr Ile Thr Leu Tyr Gly Lys Ser Asp Glu Gly Glu
                85                  90                  95

Ser Met Pro Thr Phe Gly Lys Lys Phe Ile Gly Val Glu Ala Gly Gly
                100                 105                 110

Thr Leu Glu Leu His Gly Ala Arg Lys Ala Ser Trp Thr Leu Leu Ala
            115                 120                 125

Arg Thr Leu Asn Ser Ser Gly Val Lys Leu Asn Leu Leu Asp Asp Val
130                 135                 140

Ser Ser Trp Lys Pro Gly Asp Gln Ile Val Val Ala Ser Thr Asp Tyr
145                 150                 155                 160

Ser Met Tyr Gln Ala Glu Glu Phe Thr Leu Leu Pro Cys Ser Glu Cys
                165                 170                 175

Ser His Phe Gln Val Lys Val Lys Glu Thr Pro Gln Phe Leu His Met
            180                 185                 190

Gly Glu Ile Ile Asp Gly Val Asp Met Arg Ala Glu Val Gly Ile Leu
        195                 200                 205

Thr Arg Asn Ile Val Ile Gln Gly Glu Val Glu Asp Ser Cys Tyr Ala
210                 215                 220

Glu Asn Gln Cys Gln Phe Phe Asp Tyr Asp Thr Phe Gly Gly His Ile
225                 230                 235                 240

Met Ile Met Lys Asn Phe Thr Ser Val His Leu Ser Tyr Val Glu Leu
                245                 250                 255

Lys His Met Gly Gln Gln Gln Met Gly Arg Tyr Pro Val His Phe His
            260                 265                 270

Leu Cys Gly Asp Val Asp Tyr Lys Gly Gly Tyr Arg His Ala Thr Phe
        275                 280                 285

Val Asp Gly Leu Ser Ile His His Ser Phe Ser Arg Cys Ile Thr Val
290                 295                 300

His Gly Thr Asn Gly Leu Leu Ile Lys Asp Thr Ile Gly Phe Asp Thr
305                 310                 315                 320

Leu Phe His Cys Phe Phe Leu Glu Asp Gly Ile Glu Gln Arg Asn Thr
                325                 330                 335
```

```
Leu Phe His Asn Leu Gly Leu Thr Lys Pro Gly Thr Leu Leu Pro
            340                 345                 350

Thr Asp Arg Asn Asn Ser Met Cys Thr Thr Met Arg Asp Lys Val Phe
            355                 360                 365

Gly Asn Tyr Ile Pro Val Pro Ala Thr Asp Cys Met Ala Val Ser Thr
370                 375                 380

Phe Trp Ile Ala His Pro Asn Asn Leu Ile Asn Asn Ala Ala Ala
385                 390                 395                 400

Gly Ser Gln Asp Ala Gly Ile Trp Tyr Leu Phe His Lys Glu Pro Thr
                405                 410                 415

Gly Glu Ser Ser Gly Leu Gln Leu Leu Ala Lys Pro Glu Leu Thr Pro
            420                 425                 430

Leu Gly Ile Phe Tyr Asn Asn Arg Val His Ser Asn Phe Lys Ala Gly
            435                 440                 445

Leu Phe Ile
        450

<210> SEQ ID NO 30
<211> LENGTH: 451
<212> TYPE: PRT
<213> ORGANISM: Homo sapiens

<400> SEQUENCE: 30

Ser Pro Glu Leu Gln Pro Trp Asn Pro Gly His Asp Gln Asp His His
1               5                   10                  15

Val His Ile Gly Gln Gly Lys Thr Leu Leu Thr Ser Ser Ala Thr
            20                  25                  30

Val Tyr Ser Ile His Ile Ser Glu Gly Gly Lys Leu Val Ile Lys Asp
            35                  40                  45

His Asp Glu Pro Ile Val Leu Arg Thr Arg His Ile Leu Ile Asp Asn
50                  55                  60

Gly Gly Glu Leu His Ala Gly Ser Ala Leu Cys Pro Phe Gln Gly Asn
65                  70                  75                  80

Phe Thr Ile Ile Leu Tyr Gly Arg Ala Asp Glu Gly Ile Gln Pro Asp
                85                  90                  95

Pro Tyr Tyr Gly Leu Lys Tyr Ile Gly Val Gly Lys Gly Ala Leu
            100                 105                 110

Glu Leu His Gly Gln Lys Lys Leu Ser Trp Thr Phe Leu Asn Lys Thr
            115                 120                 125

Leu His Pro Gly Gly Thr Ile Leu Asn Leu Glu Asp Asn Val Gln Ser
            130                 135                 140

Trp Lys Pro Gly Asp Thr Leu Val Ile Ala Ser Thr Asp Tyr Ser Met
145                 150                 155                 160

Tyr Gln Ala Glu Glu Phe Gln Val Leu Pro Cys Arg Ser Cys Ala Pro
                165                 170                 175

Asn Gln Val Lys Val Ala Gly Lys Pro Met Tyr Leu His Ile Gly Glu
            180                 185                 190

Glu Ile Asp Gly Val Asp Met Arg Ala Glu Val Gly Leu Leu Ser Arg
            195                 200                 205

Asn Ile Ile Val Met Gly Glu Met Glu Asp Lys Cys Tyr Pro Tyr Arg
            210                 215                 220

Asn His Ile Cys Asn Phe Asp Phe Asp Thr Phe Gly Gly His Ile
225                 230                 235                 240

Lys Phe Ala Leu Gly Phe Lys Ala Ala His Leu Glu Gly Thr Glu Leu
                245                 250                 255
```

```
Lys His Met Gly Gln Gln Leu Val Gly Gln Tyr Pro Ile His Phe His
            260                 265                 270
Leu Ala Gly Asp Val Asp Glu Arg Gly Gly Tyr Asp Pro Thr Tyr
        275                 280                 285
Ile Arg Asp Leu Ser Ile His His Thr Phe Ser Arg Cys Val Thr Val
290                 295                 300
His Gly Ser Asn Gly Leu Leu Ile Lys Asp Val Val Gly Tyr Asn Ser
305                 310                 315                 320
Leu Gly His Cys Phe Phe Thr Glu Asp Gly Pro Glu Arg Asn Thr
                325                 330                 335
Phe Asp His Cys Leu Gly Leu Leu Val Lys Ser Gly Thr Leu Leu Pro
            340                 345                 350
Ser Asp Arg Asp Ser Lys Met Cys Lys Met Ile Thr Glu Asp Ser Tyr
        355                 360                 365
Pro Gly Tyr Ile Pro Lys Pro Arg Gln Asp Cys Asn Ala Val Ser Thr
    370                 375                 380
Phe Trp Met Ala Asn Pro Asn Asn Asn Leu Ile Asn Cys Ala Ala Ala
385                 390                 395                 400
Gly Ser Glu Glu Thr Gly Phe Trp Phe Ile Phe His His Val Pro Thr
                405                 410                 415
Gly Pro Ser Val Gly Met Tyr Ser Pro Gly Tyr Ser Glu His Ile Pro
            420                 425                 430
Leu Gly Lys Phe Tyr Asn Asn Arg Ala His Ser Asn Tyr Arg Ala Gly
        435                 440                 445
Met Ile Ile
    450

<210> SEQ ID NO 31
<211> LENGTH: 28
<212> TYPE: DNA
<213> ORGANISM: Artificial Sequence
<220> FEATURE:
<223> OTHER INFORMATION: Primer

<400> SEQUENCE: 31
ctggcaccac accttctaca atgagctg                                        28

<210> SEQ ID NO 32
<211> LENGTH: 32
<212> TYPE: DNA
<213> ORGANISM: Artificial Sequence
<220> FEATURE:
<223> OTHER INFORMATION: Primer

<400> SEQUENCE: 32
gcacagcttc tctttgatgt cacgcacgat tt                                   32

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
gaccacagtc catgccatca ct                                              22

<210> SEQ ID NO 34
<211> LENGTH: 20
<212> TYPE: DNA
<213> ORGANISM: Artificial Sequence
```

```
<220> FEATURE:
<223> OTHER INFORMATION: Primer

<400> SEQUENCE: 34
tccaccaccc tgttgctgta                                              20

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
tccatttagc acctgttggg c                                            21

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
agtcttccta caaggcacgc tg                                           22

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37
caccagtcct aatgtgtctg tgg                                          23

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
tggagaaaaa tggagtgagc ctc                                          23

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
gcaccaactc cgcagaac                                                18

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
tgtctacgcg ggcctctcct gcttg                                        25
```

```
<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
ggcagagcca aaataaaac ctg                                              23

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
ataggcttga aaatacctca acc                                             23

<210> SEQ ID NO 43
<211> LENGTH: 18
<212> TYPE: DNA
<213> ORGANISM: Artificial Sequence
<220> FEATURE:
<223> OTHER INFORMATION: Primer

<400> SEQUENCE: 43
ctctgaagat agaatacc                                                   18

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
tctgatatga tgaaaatg                                                   18

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
gaatggaact taactagaca tcag                                            24

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
gcaggaaaga aagcaagatc aac                                             23

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
```
aactagaaac aaaacagag                                              19

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
attatttacc atgaaacc                                               18

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
cttacacaga atcttttg                                               19

<210> SEQ ID NO 50
<211> LENGTH: 18
<212> TYPE: DNA
<213> ORGANISM: Artificial Sequence
<220> FEATURE:
<223> OTHER INFORMATION: Primer

<400> SEQUENCE: 50
tttaatatca ttggaccc                                               18

<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51
tttaagggaa ccagtgag                                               18

<210> SEQ ID NO 52
<211> LENGTH: 18
<212> TYPE: DNA
<213> ORGANISM: Artificial Sequence
<220> FEATURE:
<223> OTHER INFORMATION: Primer

<400> SEQUENCE: 52
atctgctatt tgttttg                                                18

<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53
tgagtagttt ttaagagaaa c                                           21

<210> SEQ ID NO 54
<211> LENGTH: 18
<212> TYPE: DNA
<213> ORGANISM: Artificial Sequence

```
<220> FEATURE:
<223> OTHER INFORMATION: Primer

<400> SEQUENCE: 54
tctgtgagca ttatgaag                                              18

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
attttgtact ttttctctg                                             19

<210> SEQ ID NO 56
<211> LENGTH: 18
<212> TYPE: DNA
<213> ORGANISM: Artificial Sequence
<220> FEATURE:
<223> OTHER INFORMATION: Primer

<400> SEQUENCE: 56
tatttaccct gttgaatc                                              18

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
ctgaagttaa aaaaatgttc                                            20

<210> SEQ ID NO 58
<211> LENGTH: 24
<212> TYPE: DNA
<213> ORGANISM: Artificial Sequence
<220> FEATURE:
<223> OTHER INFORMATION: Primer

<400> SEQUENCE: 58
ttatacactg ccttcccacc accc                                       24

<210> SEQ ID NO 59
<211> LENGTH: 18
<212> TYPE: DNA
<213> ORGANISM: Artificial Sequence
<220> FEATURE:
<223> OTHER INFORMATION: Primer

<400> SEQUENCE: 59
aaaaatcagg tatttggg                                              18

<210> SEQ ID NO 60
<211> LENGTH: 19
<212> TYPE: DNA
<213> ORGANISM: Artificial Sequence
<220> FEATURE:
<223> OTHER INFORMATION: Primer

<400> SEQUENCE: 60
agaatttgtg gtaataaag                                             19
```

```
<210> SEQ ID NO 61
<211> LENGTH: 19
<212> TYPE: DNA
<213> ORGANISM: Artificial Sequence
<220> FEATURE:
<223> OTHER INFORMATION: Primer

<400> SEQUENCE: 61
gatacactga tgtgatttg                                                    19

<210> SEQ ID NO 62
<211> LENGTH: 18
<212> TYPE: DNA
<213> ORGANISM: Artificial Sequence
<220> FEATURE:
<223> OTHER INFORMATION: Primer

<400> SEQUENCE: 62
tgtgaatata gaaatggc                                                     18

<210> SEQ ID NO 63
<211> LENGTH: 18
<212> TYPE: DNA
<213> ORGANISM: Artificial Sequence
<220> FEATURE:
<223> OTHER INFORMATION: Primer

<400> SEQUENCE: 63
ttatgatcct gatgaaag                                                     18

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
acagtatcaa atagtattct g                                                 21

<210> SEQ ID NO 65
<211> LENGTH: 18
<212> TYPE: DNA
<213> ORGANISM: Artificial Sequence
<220> FEATURE:
<223> OTHER INFORMATION: Primer

<400> SEQUENCE: 65
ataaatgttg aaaaggtc                                                     18

<210> SEQ ID NO 66
<211> LENGTH: 18
<212> TYPE: DNA
<213> ORGANISM: Artificial Sequence
<220> FEATURE:
<223> OTHER INFORMATION: Primer

<400> SEQUENCE: 66
taatgacagg aaaaagcc                                                     18

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
```

```
ctggaaaaaa gttatattca ttag                                            24

<210> SEQ ID NO 68
<211> LENGTH: 18
<212> TYPE: DNA
<213> ORGANISM: Artificial Sequence
<220> FEATURE:
<223> OTHER INFORMATION: Primer

<400> SEQUENCE: 68
attgagatcc tgccttcg                                                   18

<210> SEQ ID NO 69
<211> LENGTH: 18
<212> TYPE: DNA
<213> ORGANISM: Artificial Sequence
<220> FEATURE:
<223> OTHER INFORMATION: Primer

<400> SEQUENCE: 69
ttgaatagct gaattatg                                                   18

<210> SEQ ID NO 70
<211> LENGTH: 18
<212> TYPE: DNA
<213> ORGANISM: Artificial Sequence
<220> FEATURE:
<223> OTHER INFORMATION: Primer

<400> SEQUENCE: 70
acagaaacag tatctccc                                                   18

<210> SEQ ID NO 71
<211> LENGTH: 18
<212> TYPE: DNA
<213> ORGANISM: Artificial Sequence
<220> FEATURE:
<223> OTHER INFORMATION: Primer

<400> SEQUENCE: 71
gaaagatttc aacttttc                                                   18

<210> SEQ ID NO 72
<211> LENGTH: 18
<212> TYPE: DNA
<213> ORGANISM: Artificial Sequence
<220> FEATURE:
<223> OTHER INFORMATION: Primer

<400> SEQUENCE: 72
gcacaggata tacatttg                                                   18

<210> SEQ ID NO 73
<211> LENGTH: 19
<212> TYPE: DNA
<213> ORGANISM: Artificial Sequence
<220> FEATURE:
<223> OTHER INFORMATION: Primer

<400> SEQUENCE: 73
agttaatgtc tacaaattc                                                  19

<210> SEQ ID NO 74
<211> LENGTH: 20
<212> TYPE: DNA
<213> ORGANISM: Artificial Sequence
```

```
<220> FEATURE:
<223> OTHER INFORMATION: Primer

<400> SEQUENCE: 74
agagggtgca gggaaaatgc                                               20

<210> SEQ ID NO 75
<211> LENGTH: 18
<212> TYPE: DNA
<213> ORGANISM: Artificial Sequence
<220> FEATURE:
<223> OTHER INFORMATION: Primer

<400> SEQUENCE: 75
cgagtgttct aactttc                                                  18

<210> SEQ ID NO 76
<211> LENGTH: 18
<212> TYPE: DNA
<213> ORGANISM: Artificial Sequence
<220> FEATURE:
<223> OTHER INFORMATION: Primer

<400> SEQUENCE: 76
aggtcagttt cacagttc                                                 18

<210> SEQ ID NO 77
<211> LENGTH: 18
<212> TYPE: DNA
<213> ORGANISM: Artificial Sequence
<220> FEATURE:
<223> OTHER INFORMATION: Primer

<400> SEQUENCE: 77
ttgggggaaa accagaac                                                 18

<210> SEQ ID NO 78
<211> LENGTH: 18
<212> TYPE: DNA
<213> ORGANISM: Artificial Sequence
<220> FEATURE:
<223> OTHER INFORMATION: Primer

<400> SEQUENCE: 78
agattcaatt agcatatc                                                 18

<210> SEQ ID NO 79
<211> LENGTH: 18
<212> TYPE: DNA
<213> ORGANISM: Artificial Sequence
<220> FEATURE:
<223> OTHER INFORMATION: Primer

<400> SEQUENCE: 79
tctctgtgtt ctggtacg                                                 18

<210> SEQ ID NO 80
<211> LENGTH: 24
<212> TYPE: DNA
<213> ORGANISM: Artificial Sequence
<220> FEATURE:
<223> OTHER INFORMATION: Primer

<400> SEQUENCE: 80
cccaagaaat ggatttgtct tatc                                          24
```

```
<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
gctttctaaa gtgtatttgc                                               20

<210> SEQ ID NO 82
<211> LENGTH: 18
<212> TYPE: DNA
<213> ORGANISM: Artificial Sequence
<220> FEATURE:
<223> OTHER INFORMATION: Primer

<400> SEQUENCE: 82
tgtttctatc catactgc                                                 18

<210> SEQ ID NO 83
<211> LENGTH: 18
<212> TYPE: DNA
<213> ORGANISM: Artificial Sequence
<220> FEATURE:
<223> OTHER INFORMATION: Primer

<400> SEQUENCE: 83
ttacatggca aaaccac                                                  18

<210> SEQ ID NO 84
<211> LENGTH: 18
<212> TYPE: DNA
<213> ORGANISM: Artificial Sequence
<220> FEATURE:
<223> OTHER INFORMATION: Primer

<400> SEQUENCE: 84
tagttagctg tcttttcc                                                 18

<210> SEQ ID NO 85
<211> LENGTH: 18
<212> TYPE: DNA
<213> ORGANISM: Artificial Sequence
<220> FEATURE:
<223> OTHER INFORMATION: Primer

<400> SEQUENCE: 85
acatgaggct catttatg                                                 18

<210> SEQ ID NO 86
<211> LENGTH: 18
<212> TYPE: DNA
<213> ORGANISM: Artificial Sequence
<220> FEATURE:
<223> OTHER INFORMATION: Primer

<400> SEQUENCE: 86
tgtgtgtgcg tatacacc                                                 18

<210> SEQ ID NO 87
<211> LENGTH: 18
<212> TYPE: DNA
<213> ORGANISM: Artificial Sequence
<220> FEATURE:
<223> OTHER INFORMATION: Primer

<400> SEQUENCE: 87
```
aagattacag gcgtgaac					18

<210> SEQ ID NO 88
<211> LENGTH: 18
<212> TYPE: DNA
<213> ORGANISM: Artificial Sequence
<220> FEATURE:
<223> OTHER INFORMATION: Primer

<400> SEQUENCE: 88
gcacatagaa gaaaagag					18

<210> SEQ ID NO 89
<211> LENGTH: 18
<212> TYPE: DNA
<213> ORGANISM: Artificial Sequence
<220> FEATURE:
<223> OTHER INFORMATION: Primer

<400> SEQUENCE: 89 gactttatt cacctttg					18

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
gtctttaaca tattacaaac					20

<210> SEQ ID NO 91
<211> LENGTH: 19
<212> TYPE: DNA
<213> ORGANISM: Artificial Sequence
<220> FEATURE:
<223> OTHER INFORMATION: Primer

<400> SEQUENCE: 91
cttttgttaa aacctattc					19

<210> SEQ ID NO 92
<211> LENGTH: 18
<212> TYPE: DNA
<213> ORGANISM: Artificial Sequence
<220> FEATURE:
<223> OTHER INFORMATION: Primer

<400> SEQUENCE: 92
ctttcacacc cagtatag					18

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
tgtctgattt cataacaaca gg					22

<210> SEQ ID NO 94
<211> LENGTH: 25
<212> TYPE: DNA
<213> ORGANISM: Artificial Sequence

```
<220> FEATURE:
<223> OTHER INFORMATION: Primer

<400> SEQUENCE: 94
cctttgattc cactttatct tagag                                 25

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95 catcttttc ttttttcac                                         20

<210> SEQ ID NO 96
<211> LENGTH: 18
<212> TYPE: DNA
<213> ORGANISM: Artificial Sequence
<220> FEATURE:
<223> OTHER INFORMATION: Primer

<400> SEQUENCE: 96
catgcaattt tctctctg                                         18

<210> SEQ ID NO 97
<211> LENGTH: 18
<212> TYPE: DNA
<213> ORGANISM: Artificial Sequence
<220> FEATURE:
<223> OTHER INFORMATION: Primer

<400> SEQUENCE: 97
tatagttgaa ctgttttg                                         18

<210> SEQ ID NO 98
<211> LENGTH: 18
<212> TYPE: DNA
<213> ORGANISM: Artificial Sequence
<220> FEATURE:
<223> OTHER INFORMATION: Primer

<400> SEQUENCE: 98
aggaggaaaa agtgactg                                         18

<210> SEQ ID NO 99
<211> LENGTH: 18
<212> TYPE: DNA
<213> ORGANISM: Artificial Sequence
<220> FEATURE:
<223> OTHER INFORMATION: Primer

<400> SEQUENCE: 99
gcatttctgt atctcaac                                         18

<210> SEQ ID NO 100
<211> LENGTH: 18
<212> TYPE: DNA
<213> ORGANISM: Artificial Sequence
<220> FEATURE:
<223> OTHER INFORMATION: Primer

<400> SEQUENCE: 100
tgaccaatct tattgaag                                         18
```

```
<210> SEQ ID NO 101
<211> LENGTH: 18
<212> TYPE: DNA
<213> ORGANISM: Artificial Sequence
<220> FEATURE:
<223> OTHER INFORMATION: Primer

<400> SEQUENCE: 101
aagatgagag atgaattg                                                   18

<210> SEQ ID NO 102
<211> LENGTH: 18
<212> TYPE: DNA
<213> ORGANISM: Artificial Sequence
<220> FEATURE:
<223> OTHER INFORMATION: Primer

<400> SEQUENCE: 102
aactccatca agtttatg                                                   18

<210> SEQ ID NO 103
<211> LENGTH: 18
<212> TYPE: DNA
<213> ORGANISM: Artificial Sequence
<220> FEATURE:
<223> OTHER INFORMATION: Primer

<400> SEQUENCE: 103
gaagctcatt gaaaaatc                                                   18

<210> SEQ ID NO 104
<211> LENGTH: 18
<212> TYPE: DNA
<213> ORGANISM: Artificial Sequence
<220> FEATURE:
<223> OTHER INFORMATION: Primer

<400> SEQUENCE: 104
gataatcact ttcctatg                                                   18

<210> SEQ ID NO 105
<211> LENGTH: 18
<212> TYPE: DNA
<213> ORGANISM: Artificial Sequence
<220> FEATURE:
<223> OTHER INFORMATION: Primer

<400> SEQUENCE: 105
atttgacaaa atgtttgc                                                   18

<210> SEQ ID NO 106
<211> LENGTH: 18
<212> TYPE: DNA
<213> ORGANISM: Artificial Sequence
<220> FEATURE:
<223> OTHER INFORMATION: Primer

<400> SEQUENCE: 106
tcaggtttca gtgcttcc                                                   18

<210> SEQ ID NO 107
<211> LENGTH: 18
<212> TYPE: DNA
<213> ORGANISM: Artificial Sequence
<220> FEATURE:
<223> OTHER INFORMATION: Primer

<400> SEQUENCE: 107
```

```
attgccatgt tgtcaaag                                               18

<210> SEQ ID NO 108
<211> LENGTH: 18
<212> TYPE: DNA
<213> ORGANISM: Artificial Sequence
<220> FEATURE:
<223> OTHER INFORMATION: Primer

<400> SEQUENCE: 108
catttaggaa aaagtgac                                               18

<210> SEQ ID NO 109
<211> LENGTH: 18
<212> TYPE: DNA
<213> ORGANISM: Artificial Sequence
<220> FEATURE:
<223> OTHER INFORMATION: Primer

<400> SEQUENCE: 109
gtacaatctc attttatg                                               18

<210> SEQ ID NO 110
<211> LENGTH: 18
<212> TYPE: DNA
<213> ORGANISM: Artificial Sequence
<220> FEATURE:
<223> OTHER INFORMATION: Primer

<400> SEQUENCE: 110
tatcacatac accctggg                                               18

<210> SEQ ID NO 111
<211> LENGTH: 18
<212> TYPE: DNA
<213> ORGANISM: Artificial Sequence
<220> FEATURE:
<223> OTHER INFORMATION: Primer

<400> SEQUENCE: 111
aaacagttat cattttgg                                               18

<210> SEQ ID NO 112
<211> LENGTH: 20
<212> TYPE: DNA
<213> ORGANISM: Artificial Sequence
<220> FEATURE:
<223> OTHER INFORMATION: Primer

<400> SEQUENCE: 112
catataatag aagtacaaag                                             20

<210> SEQ ID NO 113
<211> LENGTH: 22
<212> TYPE: DNA
<213> ORGANISM: Artificial Sequence
<220> FEATURE:
<223> OTHER INFORMATION: Primer

<400> SEQUENCE: 113
actggaggta tgtattgact tg                                          22

<210> SEQ ID NO 114
<211> LENGTH: 22
<212> TYPE: DNA
<213> ORGANISM: Artificial Sequence
```

```
<220> FEATURE:
<223> OTHER INFORMATION: Primer

<400> SEQUENCE: 114
tgacccataa ggactttac ac                                              22

<210> SEQ ID NO 115
<211> LENGTH: 18
<212> TYPE: DNA
<213> ORGANISM: Artificial Sequence
<220> FEATURE:
<223> OTHER INFORMATION: Primer

<400> SEQUENCE: 115
aaaaggctct ggatttgc                                                  18

<210> SEQ ID NO 116
<211> LENGTH: 23
<212> TYPE: DNA
<213> ORGANISM: Artificial Sequence
<220> FEATURE:
<223> OTHER INFORMATION: Primer

<400> SEQUENCE: 116
cattaacctc tattgctctg aac                                            23

<210> SEQ ID NO 117
<211> LENGTH: 18
<212> TYPE: DNA
<213> ORGANISM: Artificial Sequence
<220> FEATURE:
<223> OTHER INFORMATION: Primer

<400> SEQUENCE: 117
ggtttgggga ctgttttg                                                  18

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
agtagacttc attggggttg                                                20

<210> SEQ ID NO 119
<211> LENGTH: 19
<212> TYPE: DNA
<213> ORGANISM: Artificial Sequence
<220> FEATURE:
<223> OTHER INFORMATION: Primer

<400> SEQUENCE: 119
ggaaatggct tctatccag                                                 19

<210> SEQ ID NO 120
<211> LENGTH: 23
<212> TYPE: DNA
<213> ORGANISM: Artificial Sequence
<220> FEATURE:
<223> OTHER INFORMATION: Primer

<400> SEQUENCE: 120
aggtattaag tgtaagtggg aac                                            23
```

```
<210> SEQ ID NO 121
<211> LENGTH: 23
<212> TYPE: DNA
<213> ORGANISM: Artificial Sequence
<220> FEATURE:
<223> OTHER INFORMATION: Primer

<400> SEQUENCE: 121
agactgtagg gtatattgta gtc                                              23

<210> SEQ ID NO 122
<211> LENGTH: 22
<212> TYPE: DNA
<213> ORGANISM: Artificial Sequence
<220> FEATURE:
<223> OTHER INFORMATION: Primer

<400> SEQUENCE: 122
gaaacaaaat atctgcaggt tc                                               22

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
atcaaaagag attcagttgc                                                  20

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
ctgccattac tttttctgac                                                  20

<210> SEQ ID NO 125
<211> LENGTH: 22
<212> TYPE: DNA
<213> ORGANISM: Artificial Sequence
<220> FEATURE:
<223> OTHER INFORMATION: Primer

<400> SEQUENCE: 125
ggaggttttg gaaatgaatc ag                                               22

<210> SEQ ID NO 126
<211> LENGTH: 22
<212> TYPE: DNA
<213> ORGANISM: Artificial Sequence
<220> FEATURE:
<223> OTHER INFORMATION: Primer

<400> SEQUENCE: 126
tggaaatgca caatgatgcg tg                                               22

<210> SEQ ID NO 127
<211> LENGTH: 24
<212> TYPE: DNA
<213> ORGANISM: Artificial Sequence
<220> FEATURE:
<223> OTHER INFORMATION: Primer

<400> SEQUENCE: 127
```

-continued

```
aaagggtttg acagtgtgat ctag                                              24

<210> SEQ ID NO 128
<211> LENGTH: 22
<212> TYPE: DNA
<213> ORGANISM: Artificial Sequence
<220> FEATURE:
<223> OTHER INFORMATION: Primer

<400> SEQUENCE: 128
atgctggttt tctattgctg tg                                                22

<210> SEQ ID NO 129
<211> LENGTH: 25
<212> TYPE: DNA
<213> ORGANISM: Artificial Sequence
<220> FEATURE:
<223> OTHER INFORMATION: Primer

<400> SEQUENCE: 129
cgaatgaaaa actctggtaa aatcc                                             25

<210> SEQ ID NO 130
<211> LENGTH: 22
<212> TYPE: DNA
<213> ORGANISM: Artificial Sequence
<220> FEATURE:
<223> OTHER INFORMATION: Primer

<400> SEQUENCE: 130
tcaggcagag tccaatgaac ag                                                22

<210> SEQ ID NO 131
<211> LENGTH: 25
<212> TYPE: DNA
<213> ORGANISM: Artificial Sequence
<220> FEATURE:
<223> OTHER INFORMATION: Primer

<400> SEQUENCE: 131
tgtaatgaat aatttaatag gtaac                                             25

<210> SEQ ID NO 132
<211> LENGTH: 22
<212> TYPE: DNA
<213> ORGANISM: Artificial Sequence
<220> FEATURE:
<223> OTHER INFORMATION: Primer

<400> SEQUENCE: 132
aagataaact taggagaggt tg                                                22

<210> SEQ ID NO 133
<211> LENGTH: 22
<212> TYPE: DNA
<213> ORGANISM: Artificial Sequence
<220> FEATURE:
<223> OTHER INFORMATION: Primer

<400> SEQUENCE: 133
tggatttggg gttttaattt tc                                                22

<210> SEQ ID NO 134
<211> LENGTH: 22
<212> TYPE: DNA
<213> ORGANISM: Artificial Sequence
```

```
<220> FEATURE:
<223> OTHER INFORMATION: Primer

<400> SEQUENCE: 134
gagtcttcct ctaccaactc cc                                              22

<210> SEQ ID NO 135
<211> LENGTH: 22
<212> TYPE: DNA
<213> ORGANISM: Artificial Sequence
<220> FEATURE:
<223> OTHER INFORMATION: Primer

<400> SEQUENCE: 135
agttctcaat aacaaatcaa ac                                              22

<210> SEQ ID NO 136
<211> LENGTH: 24
<212> TYPE: DNA
<213> ORGANISM: Artificial Sequence
<220> FEATURE:
<223> OTHER INFORMATION: Primer

<400> SEQUENCE: 136
cttttctaaa tacacatcat taag                                            24

<210> SEQ ID NO 137
<211> LENGTH: 22
<212> TYPE: DNA
<213> ORGANISM: Artificial Sequence
<220> FEATURE:
<223> OTHER INFORMATION: Primer

<400> SEQUENCE: 137
taccaaaaca atatgttatg tc                                              22

<210> SEQ ID NO 138
<211> LENGTH: 22
<212> TYPE: DNA
<213> ORGANISM: Artificial Sequence
<220> FEATURE:
<223> OTHER INFORMATION: Primer

<400> SEQUENCE: 138
gcatgattat accaaccacg ag                                              22

<210> SEQ ID NO 139
<211> LENGTH: 22
<212> TYPE: DNA
<213> ORGANISM: Artificial Sequence
<220> FEATURE:
<223> OTHER INFORMATION: Primer

<400> SEQUENCE: 139
tcttcaatat aagaggattc cg                                              22

<210> SEQ ID NO 140
<211> LENGTH: 22
<212> TYPE: DNA
<213> ORGANISM: Artificial Sequence
<220> FEATURE:
<223> OTHER INFORMATION: Primer

<400> SEQUENCE: 140
taaccttgag caaaccactg tg                                              22
```

```
<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
ctaaataact gtgatttctg gg                                              22

<210> SEQ ID NO 142
<211> LENGTH: 22
<212> TYPE: DNA
<213> ORGANISM: Artificial Sequence
<220> FEATURE:
<223> OTHER INFORMATION: Primer

<400> SEQUENCE: 142
gaagactggt actttgctgt ac                                              22

<210> SEQ ID NO 143
<211> LENGTH: 23
<212> TYPE: DNA
<213> ORGANISM: Artificial Sequence
<220> FEATURE:
<223> OTHER INFORMATION: Primer

<400> SEQUENCE: 143
ccagtataac ttggcagtat ttg                                             23

<210> SEQ ID NO 144
<211> LENGTH: 22
<212> TYPE: DNA
<213> ORGANISM: Artificial Sequence
<220> FEATURE:
<223> OTHER INFORMATION: Primer

<400> SEQUENCE: 144
gtacaagatc ccgtttgcat gg                                              22

<210> SEQ ID NO 145
<211> LENGTH: 22
<212> TYPE: DNA
<213> ORGANISM: Artificial Sequence
<220> FEATURE:
<223> OTHER INFORMATION: Primer

<400> SEQUENCE: 145
atttccccat gcaaacggga tc                                              22

<210> SEQ ID NO 146
<211> LENGTH: 22
<212> TYPE: DNA
<213> ORGANISM: Artificial Sequence
<220> FEATURE:
<223> OTHER INFORMATION: Primer

<400> SEQUENCE: 146
cagaagagac agtcaagcct tc                                              22

<210> SEQ ID NO 147
<211> LENGTH: 22
<212> TYPE: DNA
<213> ORGANISM: Artificial Sequence
<220> FEATURE:
<223> OTHER INFORMATION: Primer

<400> SEQUENCE: 147
```
ggttctccca tttagtgaag gc                                    22

<210> SEQ ID NO 148
<211> LENGTH: 22
<212> TYPE: DNA
<213> ORGANISM: Artificial Sequence
<220> FEATURE:
<223> OTHER INFORMATION: Primer

<400> SEQUENCE: 148
caattcaatt ctgtgctaac ac                                    22

<210> SEQ ID NO 149
<211> LENGTH: 23
<212> TYPE: DNA
<213> ORGANISM: Artificial Sequence
<220> FEATURE:
<223> OTHER INFORMATION: Primer

<400> SEQUENCE: 149
ccttttttat gtttcttaat gtg                                   23

<210> SEQ ID NO 150
<211> LENGTH: 22
<212> TYPE: DNA
<213> ORGANISM: Artificial Sequence
<220> FEATURE:
<223> OTHER INFORMATION: Primer

<400> SEQUENCE: 150
atgatgacaa aagtttagga ag                                    22

<210> SEQ ID NO 151
<211> LENGTH: 18
<212> TYPE: DNA
<213> ORGANISM: Artificial Sequence
<220> FEATURE:
<223> OTHER INFORMATION: Primer

<400> SEQUENCE: 151
ggaggagttt attagagg                                         18

<210> SEQ ID NO 152
<211> LENGTH: 18
<212> TYPE: DNA
<213> ORGANISM: Artificial Sequence
<220> FEATURE:
<223> OTHER INFORMATION: Primer

<400> SEQUENCE: 152
atgtaggctg tgtttggg                                         18

<210> SEQ ID NO 153
<211> LENGTH: 23
<212> TYPE: DNA
<213> ORGANISM: Artificial Sequence
<220> FEATURE:
<223> OTHER INFORMATION: Primer

<400> SEQUENCE: 153
taaatcttaa cataatatag ggg                                   23

<210> SEQ ID NO 154
<211> LENGTH: 23
<212> TYPE: DNA
<213> ORGANISM: Artificial Sequence

```
<220> FEATURE:
<223> OTHER INFORMATION: Primer

<400> SEQUENCE: 154
ttagataaac tatcatttct gcc                                              23

<210> SEQ ID NO 155
<211> LENGTH: 23
<212> TYPE: DNA
<213> ORGANISM: Artificial Sequence
<220> FEATURE:
<223> OTHER INFORMATION: Primer

<400> SEQUENCE: 155
tttggtcact atgttcattt aac                                              23

<210> SEQ ID NO 156
<211> LENGTH: 23
<212> TYPE: DNA
<213> ORGANISM: Artificial Sequence
<220> FEATURE:
<223> OTHER INFORMATION: Primer

<400> SEQUENCE: 156
agatattgaa gggtatcaac tac                                              23

<210> SEQ ID NO 157
<211> LENGTH: 23
<212> TYPE: DNA
<213> ORGANISM: Artificial Sequence
<220> FEATURE:
<223> OTHER INFORMATION: Primer

<400> SEQUENCE: 157
catttttttt cttctctacc atg                                              23

<210> SEQ ID NO 158
<211> LENGTH: 23
<212> TYPE: DNA
<213> ORGANISM: Artificial Sequence
<220> FEATURE:
<223> OTHER INFORMATION: Primer

<400> SEQUENCE: 158
acatttcatt catttgtgtt tac                                              23

<210> SEQ ID NO 159
<211> LENGTH: 22
<212> TYPE: DNA
<213> ORGANISM: Artificial Sequence
<220> FEATURE:
<223> OTHER INFORMATION: Primer

<400> SEQUENCE: 159
aagttgtagt ttatggatta tg                                               22

<210> SEQ ID NO 160
<211> LENGTH: 22
<212> TYPE: DNA
<213> ORGANISM: Artificial Sequence
<220> FEATURE:
<223> OTHER INFORMATION: Primer

<400> SEQUENCE: 160
tgcttctttc ttattatttg ag                                               22
```

```
<210> SEQ ID NO 161
<211> LENGTH: 22
<212> TYPE: DNA
<213> ORGANISM: Artificial Sequence
<220> FEATURE:
<223> OTHER INFORMATION: Primer

<400> SEQUENCE: 161
gggtggattt tttttcctgg tc                                          22

<210> SEQ ID NO 162
<211> LENGTH: 22
<212> TYPE: DNA
<213> ORGANISM: Artificial Sequence
<220> FEATURE:
<223> OTHER INFORMATION: Primer

<400> SEQUENCE: 162
aactgatatg tactttagtg cc                                          22

<210> SEQ ID NO 163
<211> LENGTH: 22
<212> TYPE: DNA
<213> ORGANISM: Artificial Sequence
<220> FEATURE:
<223> OTHER INFORMATION: Primer

<400> SEQUENCE: 163
tttatactag cacctaactc ag                                          22

<210> SEQ ID NO 164
<211> LENGTH: 22
<212> TYPE: DNA
<213> ORGANISM: Artificial Sequence
<220> FEATURE:
<223> OTHER INFORMATION: Primer

<400> SEQUENCE: 164
ccactgtgta tattcatttt cc                                          22

<210> SEQ ID NO 165
<211> LENGTH: 22
<212> TYPE: DNA
<213> ORGANISM: Artificial Sequence
<220> FEATURE:
<223> OTHER INFORMATION: Primer

<400> SEQUENCE: 165
cataattgcc aatgagatat ac                                          22

<210> SEQ ID NO 166
<211> LENGTH: 22
<212> TYPE: DNA
<213> ORGANISM: Artificial Sequence
<220> FEATURE:
<223> OTHER INFORMATION: Primer

<400> SEQUENCE: 166
gtaaatgtga atctttcaac ac                                          22

<210> SEQ ID NO 167
<211> LENGTH: 22
<212> TYPE: DNA
<213> ORGANISM: Artificial Sequence
<220> FEATURE:
<223> OTHER INFORMATION: Primer

<400> SEQUENCE: 167
```
cttctcagca ttggcaataa tc                                           22

<210> SEQ ID NO 168
<211> LENGTH: 22
<212> TYPE: DNA
<213> ORGANISM: Artificial Sequence
<220> FEATURE:
<223> OTHER INFORMATION: Primer

<400> SEQUENCE: 168
gagctgacta catatagatg ag                                           22

<210> SEQ ID NO 169
<211> LENGTH: 22
<212> TYPE: DNA
<213> ORGANISM: Artificial Sequence
<220> FEATURE:
<223> OTHER INFORMATION: Primer

<400> SEQUENCE: 169
caaaaatgtt ttattccaac tg                                           22

<210> SEQ ID NO 170
<211> LENGTH: 22
<212> TYPE: DNA
<213> ORGANISM: Artificial Sequence
<220> FEATURE:
<223> OTHER INFORMATION: Primer

<400> SEQUENCE: 170
aagatgtggc tatttagaag tc                                           22

<210> SEQ ID NO 171
<211> LENGTH: 23
<212> TYPE: DNA
<213> ORGANISM: Artificial Sequence
<220> FEATURE:
<223> OTHER INFORMATION: Primer

<400> SEQUENCE: 171
tgagtattga ttattgataa agg                                          23

<210> SEQ ID NO 172
<211> LENGTH: 23
<212> TYPE: DNA
<213> ORGANISM: Artificial Sequence
<220> FEATURE:
<223> OTHER INFORMATION: Primer

<400> SEQUENCE: 172
ccacaggatg tgtaatttga acc                                          23

<210> SEQ ID NO 173
<211> LENGTH: 25
<212> TYPE: DNA
<213> ORGANISM: Artificial Sequence
<220> FEATURE:
<223> OTHER INFORMATION: Primer

<400> SEQUENCE: 173
gcaaattgac ttatgttttt tgggg                                        25

<210> SEQ ID NO 174
<211> LENGTH: 22
<212> TYPE: DNA
<213> ORGANISM: Artificial Sequence

```
<220> FEATURE:
<223> OTHER INFORMATION: Primer

<400> SEQUENCE: 174
cattcactcc tttagttagc tc                                              22

<210> SEQ ID NO 175
<211> LENGTH: 25
<212> TYPE: DNA
<213> ORGANISM: Artificial Sequence
<220> FEATURE:
<223> OTHER INFORMATION: Primer

<400> SEQUENCE: 175
gtgtattgtc atatacttac tctcg                                           25

<210> SEQ ID NO 176
<211> LENGTH: 20
<212> TYPE: DNA
<213> ORGANISM: Artificial Sequence
<220> FEATURE:
<223> OTHER INFORMATION: Primer

<400> SEQUENCE: 176
ctagttttag cgattcctgg                                                 20

<210> SEQ ID NO 177
<211> LENGTH: 20
<212> TYPE: DNA
<213> ORGANISM: Artificial Sequence
<220> FEATURE:
<223> OTHER INFORMATION: Primer

<400> SEQUENCE: 177
ttctctggtt ctatatttcc                                                 20

<210> SEQ ID NO 178
<211> LENGTH: 22
<212> TYPE: DNA
<213> ORGANISM: Artificial Sequence
<220> FEATURE:
<223> OTHER INFORMATION: Primer

<400> SEQUENCE: 178
caggttacat aatactaagg ac                                              22

<210> SEQ ID NO 179
<211> LENGTH: 22
<212> TYPE: DNA
<213> ORGANISM: Artificial Sequence
<220> FEATURE:
<223> OTHER INFORMATION: Primer

<400> SEQUENCE: 179
tttggacatg ctgggattat gg                                              22

<210> SEQ ID NO 180
<211> LENGTH: 22
<212> TYPE: DNA
<213> ORGANISM: Artificial Sequence
<220> FEATURE:
<223> OTHER INFORMATION: Primer

<400> SEQUENCE: 180
ttcagaaatt ccacccttct cc                                              22
```

```
<210> SEQ ID NO 181
<211> LENGTH: 24
<212> TYPE: DNA
<213> ORGANISM: Artificial Sequence
<220> FEATURE:
<223> OTHER INFORMATION: Primer

<400> SEQUENCE: 181
cccatgtttt cttttagtaa gagc                                              24

<210> SEQ ID NO 182
<211> LENGTH: 22
<212> TYPE: DNA
<213> ORGANISM: Artificial Sequence
<220> FEATURE:
<223> OTHER INFORMATION: Primer

<400> SEQUENCE: 182
atgagctgaa gcaaaggtag gc                                                22

<210> SEQ ID NO 183
<211> LENGTH: 22
<212> TYPE: DNA
<213> ORGANISM: Artificial Sequence
<220> FEATURE:
<223> OTHER INFORMATION: Primer

<400> SEQUENCE: 183
tgaactcact gctgctcatc gg                                                22

<210> SEQ ID NO 184
<211> LENGTH: 23
<212> TYPE: DNA
<213> ORGANISM: Artificial Sequence
<220> FEATURE:
<223> OTHER INFORMATION: Primer

<400> SEQUENCE: 184
tatcctctac atattcttta cag                                               23

<210> SEQ ID NO 185
<211> LENGTH: 22
<212> TYPE: DNA
<213> ORGANISM: Artificial Sequence
<220> FEATURE:
<223> OTHER INFORMATION: Primer

<400> SEQUENCE: 185
ggcagaatgt gcattaaatc tg                                                22

<210> SEQ ID NO 186
<211> LENGTH: 22
<212> TYPE: DNA
<213> ORGANISM: Artificial Sequence
<220> FEATURE:
<223> OTHER INFORMATION: Primer

<400> SEQUENCE: 186
ggaggaagtg agaatgaaaa ac                                                22

<210> SEQ ID NO 187
<211> LENGTH: 25
<212> TYPE: DNA
<213> ORGANISM: Artificial Sequence
<220> FEATURE:
<223> OTHER INFORMATION: Primer

<400> SEQUENCE: 187
```
caagtgtatt catattgctc tctag                                          25

<210> SEQ ID NO 188
<211> LENGTH: 22
<212> TYPE: DNA
<213> ORGANISM: Artificial Sequence
<220> FEATURE:
<223> OTHER INFORMATION: Primer

<400> SEQUENCE: 188
gcctaatgac agattaagca ag                                             22

<210> SEQ ID NO 189
<211> LENGTH: 22
<212> TYPE: DNA
<213> ORGANISM: Artificial Sequence
<220> FEATURE:
<223> OTHER INFORMATION: Primer

<400> SEQUENCE: 189
ctagcataac aagaaataga tg                                             22

<210> SEQ ID NO 190
<211> LENGTH: 22
<212> TYPE: DNA
<213> ORGANISM: Artificial Sequence
<220> FEATURE:
<223> OTHER INFORMATION: Primer

<400> SEQUENCE: 190
aatttatgag atggcttcat gc                                             22

<210> SEQ ID NO 191
<211> LENGTH: 22
<212> TYPE: DNA
<213> ORGANISM: Artificial Sequence
<220> FEATURE:
<223> OTHER INFORMATION: Primer

<400> SEQUENCE: 191
ggagtatgca ctttcatttt gc                                             22

<210> SEQ ID NO 192
<211> LENGTH: 22
<212> TYPE: DNA
<213> ORGANISM: Artificial Sequence
<220> FEATURE:
<223> OTHER INFORMATION: Primer

<400> SEQUENCE: 192
atgagctgta aggctgacaa tg                                             22

<210> SEQ ID NO 193
<211> LENGTH: 22
<212> TYPE: DNA
<213> ORGANISM: Artificial Sequence
<220> FEATURE:
<223> OTHER INFORMATION: Primer

<400> SEQUENCE: 193
atattgaagg acggtttaag tg                                             22

<210> SEQ ID NO 194
<211> LENGTH: 22
<212> TYPE: DNA
<213> ORGANISM: Artificial Sequence

```
<220> FEATURE:
<223> OTHER INFORMATION: Primer

<400> SEQUENCE: 194
taagtacatt ttccatgtgt ac                                              22

<210> SEQ ID NO 195
<211> LENGTH: 22
<212> TYPE: DNA
<213> ORGANISM: Artificial Sequence
<220> FEATURE:
<223> OTHER INFORMATION: Primer

<400> SEQUENCE: 195
ctgtgatgtt ctggcttttt tc                                              22

<210> SEQ ID NO 196
<211> LENGTH: 22
<212> TYPE: DNA
<213> ORGANISM: Artificial Sequence
<220> FEATURE:
<223> OTHER INFORMATION: Primer

<400> SEQUENCE: 196
attgcattcc tccatctcaa ac                                              22

<210> SEQ ID NO 197
<211> LENGTH: 22
<212> TYPE: DNA
<213> ORGANISM: Artificial Sequence
<220> FEATURE:
<223> OTHER INFORMATION: Primer

<400> SEQUENCE: 197
agaatgctaa agtgaaaaac tc                                              22

<210> SEQ ID NO 198
<211> LENGTH: 22
<212> TYPE: DNA
<213> ORGANISM: Artificial Sequence
<220> FEATURE:
<223> OTHER INFORMATION: Primer

<400> SEQUENCE: 198
gttttgaaat agaaacagag ag                                              22

<210> SEQ ID NO 199
<211> LENGTH: 22
<212> TYPE: DNA
<213> ORGANISM: Artificial Sequence
<220> FEATURE:
<223> OTHER INFORMATION: Primer

<400> SEQUENCE: 199
ctgctgagtg tagtttatca tg                                              22

<210> SEQ ID NO 200
<211> LENGTH: 22
<212> TYPE: DNA
<213> ORGANISM: Artificial Sequence
<220> FEATURE:
<223> OTHER INFORMATION: Primer

<400> SEQUENCE: 200
gagtgaaact ggctcatcct tc                                              22
```

```
<210> SEQ ID NO 201
<211> LENGTH: 22
<212> TYPE: DNA
<213> ORGANISM: Artificial Sequence
<220> FEATURE:
<223> OTHER INFORMATION: Primer

<400> SEQUENCE: 201
tttaaaagca tggaaacagg ac                                              22

<210> SEQ ID NO 202
<211> LENGTH: 22
<212> TYPE: DNA
<213> ORGANISM: Artificial Sequence
<220> FEATURE:
<223> OTHER INFORMATION: Primer

<400> SEQUENCE: 202
tataattgtc tctatttatg gc                                              22

<210> SEQ ID NO 203
<211> LENGTH: 22
<212> TYPE: DNA
<213> ORGANISM: Artificial Sequence
<220> FEATURE:
<223> OTHER INFORMATION: Primer

<400> SEQUENCE: 203
aggaaatcaa acactatgat gc                                              22

<210> SEQ ID NO 204
<211> LENGTH: 22
<212> TYPE: DNA
<213> ORGANISM: Artificial Sequence
<220> FEATURE:
<223> OTHER INFORMATION: Primer

<400> SEQUENCE: 204
gatatcatgc acaagagctg tg                                              22

<210> SEQ ID NO 205
<211> LENGTH: 24
<212> TYPE: DNA
<213> ORGANISM: Artificial Sequence
<220> FEATURE:
<223> OTHER INFORMATION: Primer

<400> SEQUENCE: 205
tatgctattt ctacttaaaa attg                                            24

<210> SEQ ID NO 206
<211> LENGTH: 24
<212> TYPE: DNA
<213> ORGANISM: Artificial Sequence
<220> FEATURE:
<223> OTHER INFORMATION: Primer

<400> SEQUENCE: 206
tttgttggta caataactta gagg                                            24
```

METHOD OF DETECTING ENDOMETRIAL CANCER COMPRISING MEASURING LEVELS OF FIBROCYSTIN-L

CROSS-REFERENCE TO RELATED APPLICATIONS

This application is a divisional of U.S. Ser. No. 12/613,753, filed Nov. 6, 2009, now abandoned, which is a continuation of U.S. Ser. No. 11/202,548, filed Aug. 12, 2005, now abandoned, which is a continuation-in-part and claims benefit under 35 U.S.C. §120 of International Application No. PCT/US2004/004300 having an International Filing Date of Feb. 12, 2004, which claims benefit of priority from U.S. Provisional Application Ser. No. 60/446,860, filed Feb. 12, 2003.

STATEMENT AS TO FEDERALLY SPONSORED RESEARCH

This invention was made with government support under grant nos. DK058816, DK059597, and DK059505, awarded by the National Institutes of Health. The government has certain rights in the invention.

TECHNICAL FIELD

This document relates to PKHDL1, a homolog of the autosomal recessive kidney disease gene, and more particularly, to PKHDL1 nucleic acids and polypeptides, and variants thereof.

BACKGROUND

Autosomal recessive polycystic kidney disease (ARPKD) is an important renal cause of death in the perinatal period and of childhood renal failure. Neonatal disease presentation is typical, and characterized by greatly enlarged kidneys due to fusiform dilation of collecting ducts; congenital hepatic fibrosis is often a major complication in older patients. Progress toward understanding this complex disorder has recently been made by the identification of the disease-causing gene, PKHD1, in chromosome region 6p12. PKHD1 is a very large gene (~470 kb) containing 67 exons and an open reading frame (ORF) of 12,222 bp. PKHD1 has a tissue-specific expression pattern with the highest levels in fetal and adult kidney and lower levels in liver, pancreas and lung. The murine ortholog, Pkhd1, has recently been described.

A notable feature of both the human and murine genes is that multiple different splice forms may be generated. Visualization of PKHD1 transcripts by northern analysis has proved difficult with a smear of products often detected. These may represent multiple splice forms, unusual sensitivity of this transcript to degradation, or a combination of these factors. In situ hybridization of the murine transcript showed expression in the developing kidney and mature collecting ducts, plus ductal plate and bile ducts in the liver. Other sites of expression during development detected by in situ analysis were: large vessels, testis, sympathetic ganglia, pancreas and trachea with evidence that some sites of expression may be of specific splice forms.

The PKHD1 encoded protein, fibrocystin, is large (4074 aa) and predicted to be an integral membrane protein with a large extracellular region and a short cytoplasmic tail. Fibrocystin is not closely related to any other characterized protein, although it contains multiple copies of a defined domain and has regions of homology to other proteins; it seems to represent the founder member of a new protein family. The only well characterized domain in fibrocystin is the TIG/IPT (immunoglobulin-like fold shared by plexins and transcription factors) that is also found in the hepatocyte growth factor receptor (HGFR), plexins and other receptor molecules. Although fibrocystin has many more copies of this domain than these other proteins, the presence of the TIG domain, along with the structure of the protein, suggested that it may also act as a receptor.

SUMMARY

The invention is based on the identification, cloning, and sequence analysis of PKHDL1 and Pkhdl1, human and murine homologs, respectively, of the ARPKD gene PKHD1. The PKHD1 homologs encode fibrocystin-L, a large receptor protein (approximately 466 kDa) that contains a signal peptide, a single transmembrane domain, and a short cytoplasmic tail. Fibrocystin-L has low, but highly significant, homology to fibrocystin over the entire length of the protein, except the extreme C-terminal region containing the predicted transmembrane domain and cytoplasmic tail. This level of homology is greater than that seen between polycystin homologs, establishing the fibrocystins as a new protein family. PKHDL1 expression is up-regulated specifically in T lymphocytes and may have a role in cellular immunity. PKHDL1 expression also is up-regulated in endometrial cancer and other cancers, including breast, ovarian, and colon cancers.

In one aspect, the invention features an isolated nucleic acid that includes a sequence encoding a fibrocystin-L polypeptide. The fibrocystin-L polypeptide can be encoded by SEQ ID NO:1 or SEQ ID NO:2, and can include the amino acid sequence of SEQ ID NO:3 or SEQ ID NO:4. The fibrocystin-L polypeptide can include an amino acid sequence variant at a position selected from the group consisting of: position 702, position 1192, position 1199, position 1223, position 1514, position 1607, position 1638, position 3050, position 3607, and position 4220 of SEQ ID NO:3. For example, the amino acid sequence variant can be selected from the group consisting of: Pro at position 702, Ala at position 1192, Ser at position 1199, Val at position 1223, Ser at position 1514, Ile at position 1607, Cys at position 1638, Gln at position 3050, Glu at position 3607, and Ile at position 4220. The isolated nucleic acid can include a sequence variant with respect to SEQ ID NO:1, e.g., a sequence variant at a position selected from the group consisting of: position 1227, position 1404, position 1920, position 1965, position 2105, position 3574, position 3599, position 3668, position 4540, position 4819, position 4913, position 6621, position 9084, position 9150, position 10821, and position 12658 of SEQ ID NO:1. The sequence variant can be selected from the group consisting of: A at position 1227, T at position 1404, C at position 1920, G at position 1965, C at position 2105, G at position 3574, C at position 3599, T at position 3668, A at position 4540, A at position 4819, G at position 4913, G at position 6621, T at position 9084, G at position 9150, A at position 10821, and A at position 12658.

In another aspect, the invention features an isolated nucleic acid encoding a fibrocystin polypeptide, wherein the nucleic acid includes at least 300 contiguous nucleotides of SEQ ID NO:1 or a sequence variant thereof. The invention also features a vector that includes such isolated nucleic acids and host cells including the vector.

The invention also features an isolated nucleic acid 10 to 1700 nucleotides in length, the nucleic acid including a sequence, the sequence including one or more sequence variants relative to the sequence of SEQ ID NO:1, wherein the sequence is at least 80% identical over its length to the corresponding sequence in SEQ ID NO:1. The sequence variant can be at a position selected from the group consisting of: position 1227, position 1404, position 1920, position 1965, position 2105, position 3574, position 3599, position 3668, position 4540, position 4819, position 4913, position 6621, position 9084, position 9150, position 10821, and position 12658 of SEQ ID NO:1.

In yet another aspect, the invention features a plurality of oligonucleotide primer pairs (e.g., at least three, 13, 16, or 23 primer pairs), wherein each primer is 10 to 50 nucleotides in length, and wherein each primer pair, in the presence of mammalian genomic DNA and under polymerase chain reaction conditions, produces a nucleic acid product corresponding to a region of an PKHDL1 nucleic acid molecule, wherein the product is 30 to 1700 nucleotides in length. The nucleic acid product can include a nucleotide sequence variant relative to SEQ ID NO:1.

The invention also features a composition that includes a first oligonucleotide primer and a second oligonucleotide primer, wherein the first oligonucleotide primer and the second oligonucleotide primer are each 10 to 50 nucleotides in length, and wherein the first and second primers, in the presence of mammalian genomic DNA and under polymerase chain reaction conditions, produce a nucleic acid product corresponding to a region of a PKHDL1 nucleic acid molecule, wherein the product is 30 to 1700 nucleotides in length. The nucleic acid product can include a nucleotide sequence variant relative to SEQ ID NO:1.

Isolated nucleic acids that include the nucleotide sequence of SEQ ID NO:1 or SEQ ID NO:2, or the complement of SEQ ID NO:1 or SEQ ID NO:2, also are featured.

In yet another aspect, the invention features an antibody having specific binding affinity for a fibrocystin-L polypeptide. Such antibodies can be used to detect fibrocystin-L in biological samples.

The invention also features a method for determining if a subject has altered cellular immunity. The method includes providing a nucleic acid sample (e.g., genomic DNA) from the subject, and determining whether the nucleic acid sample contains one or more sequence variants within the PKHDL1 gene of the subject relative to a wild-type PKHDL1 gene, wherein the presence of the one or more sequence variants is associated with altered cellular immunity in the subject. The determining step can be performed by denaturing high performance liquid chromatography or direct sequencing. The variant can be at position 2105, position 3574, position 3599, position 3668, position 4540, position 4913, or position 9150 of SEQ ID NO:1, or other positions. The method further can include identifying the sequence variant by DNA sequencing.

In yet another aspect, the invention features an article of manufacture that includes a substrate, wherein the substrate includes a population of isolated nucleic acid molecules, wherein each nucleic acid molecule is 10 to 1000 nucleotides in length, wherein each nucleic acid molecule includes a different nucleotide sequence variant relative to the sequence of SEQ ID NO:1, and wherein the nucleic acid molecule is at least 80% identical over its length to the corresponding sequence in SEQ ID NO:1.

The invention also features a method for monitoring the immune response of a patient after vaccination. The method includes a) providing a biological sample from the patient after vaccination; b) determining the number of fibrocystin-L expressing T-cells in the biological sample; and c) comparing the number of fibrocystin-L expressing T-cells to a baseline number of fibrocystin-L expressing T-cells before vaccination.

The invention also features a method for detecting endometrial cancer. The method includes detecting the level of fibrocystin-L expression in a biological sample (e.g., endometrial tissue sample) from a patient. An increase in the level of fibrocystin-L in the sample relative to the level in a corresponding control sample is indicative of the presence of endometrial cancer. Fibrocystin-L expression can be assessed by detecting the polypeptide (e.g., by immunohistochemistry, western blotting, or an ELISA) or by analysis of mRNA levels.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the description and drawings, and from the claims.

DESCRIPTION OF DRAWINGS

FIG. 1A is an autoradiograph of a murine, multiple tissue (adult) Northern blot, hybridized with Pkhdl1 and showing weak smears in most lanes. FIGS. 1B-1D are RT-PCR analyses of (B) newborn and adult murine tissues with Pkhdl1 and β-actin control showing widespread low level expression of Pkhdl1; (C) human cell-lines SW13, adrenal carcinoma; ACHN, renal adenocarcinoma; HEK293, embryonic kidney; HT29, colonic adenocarcinoma; G-CCM, astrocytoma; Fib, skin fibroblasts; G-401, renal Wilm's tumor; Hep 3B, hepatoma, HeLa, cervical carcinoma; K562, erythroleukemia; lymph, EBV-transformed B-lymphocytes and MCF-7, breast cancer, with PKHDL1 and GAPDH and (D) various murine leukocyte populations as indicated with 30 and 40 cycles of PCR for Pkhdl1, and β-actin control. NK=natural killer cells and DCs=dendritic cells.

FIGS. 2A-2D are a Clustal W alignment of human fibrocystin (fib) (SEQ ID NO: 5) and human fibrocystin-L (fibL) (SEQ ID NO: 3) from their N-termini to positions 3849 aa and 4185 aa, respectively. Bold italicized font indicates identities and bold non-italicized font indicates similarities. Conserved domains (TIG; thin lines) and defined regions of homology (TMEM; thick lines) are indicated by a dashed line for fibrocystin-L and a solid line for fibrocystin. A "♦" indicates the start and stop of the dashed line. The predicted signal peptide cleavage sites are indicated with arrowheads.

FIG. 2E is an alignment of the 14 TIG domains of fibrocystin-L (fibL) (SEQ ID NO: 6-19) compared to fibrocystin (fib) TIG 5 (SEQ ID NO: 20), HGFR (murine) TIG 1 (SEQ ID NO: 21), plexin (murine) TIG 2 (SEQ ID NO: 22) and a receptor TIG consensus (SEQ ID NO: 23).

FIG. 2F is an alignment of the TMEM-A (A) and -B (B) regions of fibrocystin (fib) (SEQ ID NOS: 24 and 25) and fibrocystin-L (fibL) (SEQ ID NOS: 26 and 27) to a hypothetical protein from the bacteria *Chloroflexus aurantiacus* (chlor) (SEQ ID NO: 28) and human proteins of unknown function, TMEM2 (TMEM) (SEQ ID NO: 29) and XP051860 (51860) (SEQ ID NO: 30). These human proteins are gapped by the removal of 165 aa and 251 aa, respectively, as shown.

FIGS. 4A-4F are the nucleotide sequence of the PKHDL1 cDNA (SEQ ID NO:1).

FIGS. 5A-5F are the nucleotide sequence of the Pkhdl1 cDNA (SEQ ID NO:2).

FIGS. 6A and 6B are the amino acid sequence of human fibrocystin-L polypeptide (SEQ ID NO:3).

FIGS. 7A and 7B are the amino acid sequence of murine fibrocystin-L polypeptide (SEQ ID NO:4).

DETAILED DESCRIPTION

Figure 1:
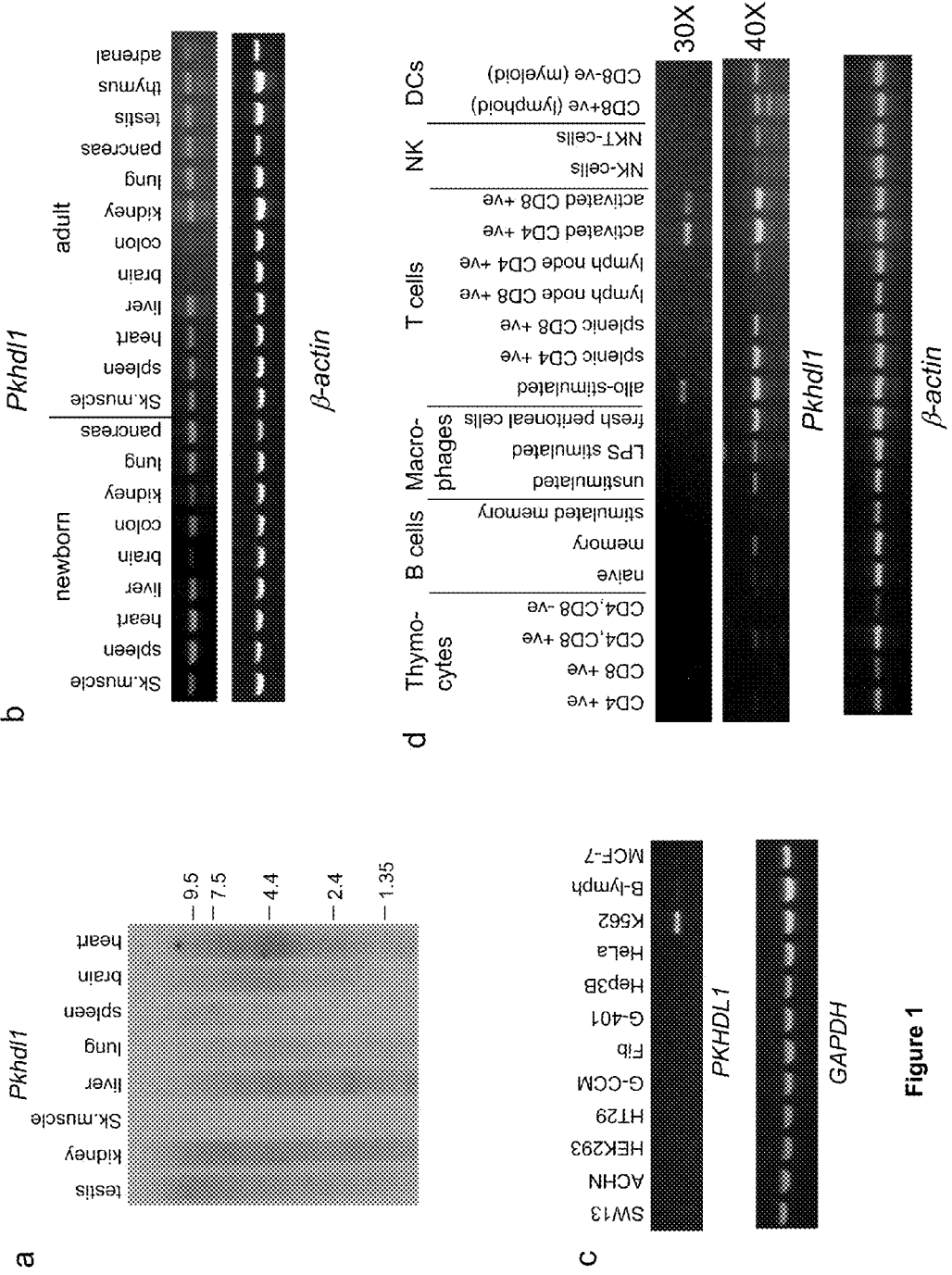
FIG. 1 depicts expression analysis of PKHDL1/Pkhdl1.

In general, the invention features PKHDL1 nucleic acids and polypeptides. As used herein "PKHDL1" nucleic acids refers to both the human PKHDL1 gene and the murine Pkhdl1 gene. PKHDL1 nucleic acids can encode fibrocystin-L polypeptides. Identification of fibrocystin-L should greatly aid the understanding of the structure and function of the fibrocystin protein family. Furthermore, PKHDL1 nucleic acids may have a role in cellular immunity as such nucleic acids can be specifically up-regulated in T lymphocytes following activation, and in cancers such as endometrial cancer as expressed PKHDL1 nucleic acids are overrepresented in endometrial adenocarcinomas and fibrocystin-L expression is up-regulated in endometrial cancer relative to normal endometrial tissue.

1. Isolated PKHDL1 Nucleic Acid Molecules

As used herein, the term "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that flank a PKHDL1 gene). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated PKHDL1 nucleic acid molecules are at least 10 nucleotides in length (e.g., 10, 20, 50, 100, 200, 300, 400, 500, 1000, or more nucleotides in length). As described in the Examples (below), the full-length human PKHDL1 transcript contains 78 exons and is 13081 nucleotides in length, with a coding region that is 12,729 nucleotides in length (FIGS. 4A-4F; SEQ ID NO:1). The full-length murine transcript has a coding region that is 12,747 nucleotides in length (FIGS. 5A-5F; SEQ ID NO:2). A PKHDL1 nucleic acid molecule therefore is not required to contain all of the coding region listed in SEQ ID NO:1 or 2 or all of the exons; in fact, a PKHDL1 nucleic acid molecule can contain as little as a single exon (as listed in Table 2, for example) or a portion of a single exon (e.g., 10 nucleotides from a single exon). In some embodiments, the PKHDL1 transcript is alternatively spliced, which can remove a portion of an exon, a single exon, or multiple exons from the transcript. Nucleic acid molecules that are less than full-length can be useful, for example, for diagnostic purposes.

Nucleic acid molecules of the invention may have sequences identical to those found in SEQ ID NO:1 or SEQ ID NO:2. Nucleic acid molecules also can have sequences identical to those found in the complement of SEQ ID NO:1 or SEQ ID NO:2. Alternatively, the sequence of a PKHDL1 nucleic acid molecule may contain one or more variants relative to the sequences set forth in SEQ ID NO:1 or SEQ ID NO:2, or the complement of SEQ ID NO:1 or SEQ ID NO:2. As used herein, a "sequence variant" refers to any mutation that results in a difference between nucleotides at one or more positions within the nucleic acid sequence of a particular nucleic acid molecule and the nucleotides at the same positions within the corresponding wild-type sequence set forth in SEQ ID NO:1 or SEQ ID NO:2. Nucleotides are referred to herein by the standard one-letter designation (A, C, G, or T). Sequence variants can be found in coding and non-coding regions, including exons, introns, promoters, and untranslated sequences. The presence of one or more sequence variants in the PKHDL1 nucleic acid sequence of a subject can be detected as set forth below in subsection 8.

Sequence variants can be, for example, deletions, insertions, or substitutions at one or more nucleotide positions (e.g., 1, 2, 3, 10, or more than 10 positions), provided that the nucleic acid is at least 80% identical (e.g., 80%, 85%, 90%, 95%, or 99% identical) over its length to the corresponding region of the wild-type sequences set forth in SEQ ID NO:1 or SEQ ID NO:2. The human and murine coding regions are 84.1% identical. Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from the State University of New York—Old Westbury campus library as well as at Fish & Richardson's web site (world wide web at fr.com/blast) or the U.S. government's National Center for Biotechnology Information web site (world wide web at ncbi.nlm.nih.gov/blast/executables). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to –1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 200 nucleotides from the target sequence aligned with a region of the sequence set forth in SEQ ID NO: 1 where the first and last nucleotides of that 200 nucleotide region are matches, and (3) the number of matches over those 200 aligned nucleotides is 180, then the 1000 nucleotide target sequence contains a length of 200 and a percent identity over that length of 90 (i.e., 180) 200×100=90).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Sequence variants that are deletions or insertions can create frame-shifts within the coding region that alter the amino acid sequence of the encoded polypeptide, and thus can affect its structure and function.

Substitutions include silent mutations that do not affect the amino acid sequence of the encoded polypeptide, missense mutations that alter the amino acid sequence of the encoded polypeptide, and nonsense mutations that prematurely terminate and therefore truncate the encoded polypeptide. Non-limiting examples of silent mutations are included in Table 5 (e.g., A substituted for G at position 1227 of SEQ ID NO:1, T substituted for C at position 1404 of SEQ ID NO:1, C substituted for T at position 1920 of SEQ ID NO:1, G substituted for A at position 1965 of SEQ ID NO:1, G substituted for C at position 6621 of SEQ ID NO:1, T substituted for A at position 9084 of SEQ ID NO:1). Non-limiting examples of missense mutations are included in Table 5 (e.g., G substituted for A at position 490, C substituted for A at position 2105 of SEQ ID NO:1, G substituted for A at position 3574 of SEQ ID NO:1, C substituted for T at position 3599 of SEQ ID NO:1, T substituted for G at position 3668 of SEQ ID NO:1, A substituted for C at position 4540 of SEQ ID NO:1, A substituted for G at position 4819 of SEQ ID NO:1, G substituted for A at position 4913 of SEQ ID NO:1, G substituted for C at position 9150 of SEQ ID NO:1, A substituted for C at position 10821 of SEQ ID NO:1, and A substituted for G at position 12658 of SEQ ID NO:1).

Deletion, insertion, and substitution sequence variants can create or destroy splice sites and thus alter the splicing of a PKHDL1 transcript, such that the encoded polypeptide contains a deletion or insertion relative to the polypeptide encoded by the corresponding wild-type nucleic acid sequences set forth in SEQ ID NO:1 or SEQ ID NO:2. Sequence variants that affect splice sites of PKHDL1 nucleic acid molecules can result in fibrocystin-L polypeptides that lack the amino acids encoded by particular exons or portions thereof.

Certain sequence variants described herein may be associated with ARPKD. Such sequence variants typically result in a change in the encoded polypeptide that can have a dramatic effect on the function of the polypeptide. These changes can include, for example, a truncation, a frame-shifting alteration, or a substitution at a highly conserved position. Conserved positions can be identified by inspection of a nucleotide or amino acid sequence alignment showing related nucleic acids or polypeptides from different species (e.g., the sequence alignments shown in FIGS. 2E and 2F). For example, the non-conservative substitution of a proline at amino acid 702 for a glutamine may be associated with ARPKD. In some ARPKD patients, the same ARPKD-associated sequence variant can be found on both alleles. In other patients, a combination of ARPKD-associated sequence variants can be found on separate alleles of an ARPKD gene.

Other sequence variants described herein include polymorphisms that occur within a normal population and typically are not associated with ARPKD. Sequence variants of this type can be, for example, nucleotide substitutions (e.g., silent mutations) that do not alter the amino acid sequence of the encoded fibrocystin-L polypeptide, or alterations that alter the amino acid sequence but that do not affect the overall function of the polypeptide. With respect to SEQ ID NO:1, sequence variants that are polymorphisms can include, for example, an A at position 4540 of SEQ ID NO:1 or an A at position 12658 of SEQ ID NO:1.

2. Production of Isolated PKHDL1 Nucleic Acid Molecules

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated PKHDL1 nucleic acid molecule. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in

*PCR Primer: A Laboratory Manual*, Ed. by Dieffenbach, C. and Dveksler, G., Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication or nucleic acid sequence-based amplification also can be used to obtain isolated nucleic acids. See, for example, Lewis (1992) *Genetic Engineering News* 12(9): 1; Guatelli et al. (1990) *Proc. Natl. Acad. Sci. USA* 87:1874-1878; and Weiss (1991) *Science* 254:1292-1293.

In one embodiment, a primer is a single-stranded or double-stranded oligonucleotide that typically is 10 to 50 nucleotides in length, and when combined with mammalian genomic DNA and subjected to PCR conditions, is capable of being extended to produce a nucleic acid product corresponding to a region of a PKHDL1 nucleic acid molecule. Typically, a PKHDL1 PCR product is 30 to 1700 nucleotides in length (e.g., 30, 35, 50, 100, 250, 500, 1000, 1500, or 1650 nucleotides in length). Specific regions of mammalian DNA can be amplified (i.e., replicated such that multiple exact copies are produced) when a pair of oligonucleotide primers is used in the same PCR reaction, wherein one primer contains a nucleotide sequence from the coding strand of a PKHDL1 nucleic acid and the other primer contains a nucleotide sequence from the non-coding strand of a PKHDL1 nucleic acid. The "coding strand" of a nucleic acid is the nontranscribed strand, which has the same nucleotide sequence as the specified RNA transcript (with the exception that the RNA transcript contains uracil in place of thymidine residues), while the "non-coding strand" of a nucleic acid is the strand that serves as the template for transcription.

A single PCR reaction mixture may contain one pair of oligonucleotide primers. Alternatively, a single reaction mixture may contain a plurality of oligonucleotide primer pairs, in which case multiple PCR products can be generated. Each primer pair can amplify, for example, one exon or a portion of one exon. Intron sequences also can be amplified.

Oligonucleotide primers can be incorporated into compositions. Typically, a composition of the invention will contain a first oligonucleotide primer and a second oligonucleotide primer, each 10 to 50 nucleotides in length, which can be combined with genomic DNA from a mammal and subjected to PCR conditions as set out below, to produce a nucleic acid product that corresponds to a region of a PKHDL1 nucleic acid molecule. A composition also may contain buffers and other reagents necessary for PCR (e.g., DNA polymerase or nucleotides). Furthermore, a composition may contain one or more additional pairs of oligonucleotide primers (e.g., 3, 13, 16, or 23 primer pairs), such that multiple nucleic acid products can be generated.

Specific PCR conditions typically are defined by the concentration of salts (e.g., $MgCl_2$) in the reaction buffer, and by the temperatures utilized for melting, annealing, and extension. Specific concentrations or amounts of primers, templates, deoxynucleotides (dNTPs), and DNA polymerase also may be set out. For example, PCR conditions with a buffer containing 2.5 mM $MgCl_2$, and melting, annealing, and extension temperatures of 94° C., 44-65° C., and 72° C., respectively, are particularly useful. Under such conditions, a PCR sample can include, for example, 60 ng genomic DNA, 8 mM each primer, 200 pM dNTPs, 1 U DNA polymerase (e.g., AmpliTaq Gold), and the appropriate amount of buffer as specified by the manufacturer of the polymerase (e.g., 1× AmpliTaq Gold buffer). Denaturation, annealing, and extension each may be carried out for 30 seconds per cycle, with a total of 25 to 35 cycles, for example. An initial denaturation step (e.g., 94° C. for 2 minutes) and a final elongation step (e.g., 72° C. for 10 minutes) also may be useful.

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequence depicted in FIGS. 4A-4F or 5A-5F can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, Edited by Ausubel et al., 1992. Examples of positions that can be modified are described above and in Table 5, as well as in the alignments of FIGS. 2E and 2F.

3. Vectors and Host Cells

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

In the expression vectors of the invention, the nucleic acid is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Suitable promoters can be tissue-specific (i.e., capable of directing expression of a nucleic acid preferentially in a particular cell type. Non-limiting examples of tissue-specific promoters include the lymphoid-specific promoters (Calame and Eaton (1988), *Adv. Immunol.*, 43:235-257) and T-cell specific promoters (Winoto and Baltimore (1989), *EMBO J.*, 8:729-733). Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.). For example, the pET-43a+ vector from Novagen can be used.

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* (2$^{nd}$ edition), Cold Spring Harbor Laboratory, New York (1989), and reagents for transformation and/or transfection are commercially available (e.g., Lipofectin (Invitrogen/Life Technologies); Fugene (Roche, Indianapolis, Ind.); and SuperFect (Qiagen, Valencia, Calif.)).

In one embodiment, host cells are T-cells that have been isolated from a subject. Such cells can be manipulated ex vivo (e.g., by transfecting with a vector that encodes a fibrocystin-L polypeptide as described above) then re-introduced into the subject to augment the subject's immune responses to, for example, an infectious disease or cancer, or as adjuvant therapy following an allogeneic bone marrow transplant (i.e., donor lymphocyte infusion). In other embodiments, the host cells are PEAK cells, a human embryonic kidney (HEK)-293 derivative selected for high transfection frequency (Edge Biosystems, Gaithersburg, Md.).

4. Fibrocystin-L Polypeptides

The invention provides purified fibrocystin-L polypeptides that are encoded by the PKHDL1 nucleic acid molecules of the invention. A "polypeptide" refers to a chain of at least 10 amino acid residues (e.g., 10, 20, 50, 75, 100, 200, or more than 200 residues), regardless of post-translational modification (e.g., phosphorylation or glycosylation). Typically, a fibrocystin-L polypeptide of the invention is capable of eliciting a fibrocystin-L-specific antibody response (i.e., is able to act as an immunogen that induces the production of antibodies capable of specific binding to fibrocystin-L).

A fibrocystin-L polypeptide may have an amino acid sequence that is identical to that of SEQ ID NO:3 or SEQ ID NO:4. Alternatively, a fibrocystin-L polypeptide can include an amino acid sequence variant. As used herein, an amino acid sequence variant refers to a deletion, insertion, or substitution at one or more amino acid positions (e.g., 1, 2, 3, 4, 5, 6, 7, 8, 9, 10, or more than 10 positions), provided that the polypeptide has an amino acid sequence that is at least 80% identical (e.g., 80%, 85%, 90%, 95%, or 99% identical) over its length to the corresponding region of the sequences set forth in SEQ ID NO:3 or SEQ ID NO:4.

Percent sequence identity is calculated by determining the number of matched positions in aligned amino acid sequences, dividing the number of matched positions by the total number of aligned amino acids, and multiplying by 100. The percent identity between amino acid sequences therefore is calculated in a manner analogous to the method for calculating the identity between nucleic acid sequences, using the Bl2seq program from the stand-alone version of BLASTZ containing BLASTN version 2.0.14 and BLASTP version 2.0.14; see subsection 1, above. A matched position refers to a position in which identical residues occur at the same position in aligned amino acid sequences. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. The following command will generate an output file containing a comparison between two amino acid sequences: C:\Bl2seq -i c:\seq1.txt -j c:\seq2.txt -p blastp -o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive amino acid residues from the target sequence presented in alignment with sequence from the identified sequence starting with any matched position and ending with any other matched position. A matched position is any position where an identical amino acid residue is presented in both the target and identified sequence. Gaps presented in the target sequence are not counted since gaps are not amino acid residues. Likewise, gaps presented in the identified sequence are not counted since target sequence amino acid residues are counted, not amino acid residues from the identified sequence.

The percent identity over a particular length is determined by counting the number of matched positions over that length and dividing that number by the length followed by multiplying the resulting value by 100. For example, if (1) a 1000 amino acid target sequence is compared to the sequence set forth in SEQ ID NO:3, (2) the Bl2seq program presents 200 amino acids from the target sequence aligned with a region of the sequence set forth in SEQ ID NO:3 where the first and last amino acids of that 200 amino acid region are matches, and (3) the number of matches over those 200 aligned amino acids is 180, then the 1000 amino acid target sequence contains a length of 200 and a percent identity over that length of 90 (i.e. 180) 200×100=90). As described for aligned nucleic acids in subsection 1, different regions within a single amino acid target sequence that aligns with an identified sequence can each have their own percent identity. It also is noted that the percent identity value is rounded to the nearest tenth, and the length value will always be an integer.

The deletion of amino acids from a fibrocystin-L polypeptide or the insertion of amino acids into a fibrocystin-L polypeptide can significantly affect the structure of the polypeptide. A deletion can result in a fibrocystin-L polypeptide that is truncated. Amino acids also may be deleted from a fibrocystin-L polypeptide as a result of altered splicing (see subsection 1, above).

Amino acid substitutions may be conservative or non-conservative. Conservative amino acid substitutions replace an amino acid with an amino acid of the same class, whereas non-conservative amino acid substitutions replace an amino acid with an amino acid of a different class. Conservative amino acid substitutions typically have little effect on the structure or function of a polypeptide. Examples of conservative substitutions include amino acid substitutions within the following groups: glycine and alanine; valine, isoleucine, and leucine; aspartic acid and glutamic acid; asparagine, glutamine, serine, and threonine; lysine, histidine, and arginine; and phenylalanine and tyrosine. Conservative substitutions within a fibrocystin-L polypeptide can include, for example, Ile substituted for Val at amino acid position 1607 of SEQ ID NO:3, Glu substituted for Asp at amino acid position 3607 of SEQ ID NO:3, and Ile substituted for Val at amino acid position 4220 of SEQ ID NO:3.

Non-conservative substitutions may result in a substantial change in the hydrophobicity of the polypeptide or in the bulk of a residue side chain. In addition, non-conservative substitutions may make a substantial change in the charge of the polypeptide, such as reducing electropositive charges or introducing electronegative charges. Examples of non-conservative substitutions include a basic amino acid for a non-polar amino acid, or a polar amino acid for an acidic amino acid. Non-conservative substitutions within a fibrocystin polypeptide can include, for example, Pro substituted for Gln at amino acid position 702 of SEQ ID NO:3, Ala substituted for Thr at amino acid position 1192 of SEQ ID NO:3, Ser substituted for Leu at amino acid position 1199 of SEQ ID NO:3, Val substituted for Gly at position 1223 of SEQ ID NO:3, Ser substituted for Arg at position 1514 of SEQ ID NO:3, Cys substituted for Tyr at position 1638 of SEQ ID NO:3, or Gln substituted for His at position 3050 of SEQ ID NO:1.

The term "purified" as used herein with reference to a polypeptide refers to a polypeptide that either has no naturally occurring counterpart (e.g., a peptidomimetic), has been chemically synthesized and is thus uncontaminated by other polypeptides, or has been separated or purified from other cellular components by which it is naturally accompanied (e.g., other cellular proteins, polynucleotides, or cellular components). Typically, the polypeptide is considered "purified" when it is at least 70% (e.g., 70%, 80%, 90%, 95%, or 99%), by dry weight, free from the proteins and naturally occurring organic molecules with which it naturally associates.

Fibrocystin-L polypeptides typically contain multiple functional domains (e.g., two or more regions that are responsible for a specific function of the polypeptide.) A fibrocystin-L polypeptide may contain one or more transmembrane (™) domains, such that part of the polypeptide is cytoplasmic and part is extracellular. Such a domain can be located, for example, between amino acid residues 4213 and 4235 of SEQ ID NO:3, such that the full length fibrocystin-L polypeptide has a large N-terminal extracellular region and a short, 8 amino acid C-terminal cytoplasmic tail. In order to facilitate insertion of the polypeptide into the cellular membrane, a fibrocystin-L polypeptide also may include a hydrophobic signal peptide (e.g., the 20 amino acid residues at the N-terminus). Additionally, a fibrocystin-L polypeptide can contain one or more (e.g., 3, 11, or 14) TIG/IPT domains (Transcription-associated ImmunoGlobulin domain/Immunoglobulin-like fold shared by Plexins and Transcription factors; referred to hereafter as TIG domains), similar to those found in fibrocystin, the hepatocyte growth factor receptor, plexins, and the macrophage-stimulating protein receptor. TIG domains can be located anywhere within the polypeptide, although localization within the N-terminal 50% of a fibrocystin-L polypeptide is particularly common. Fibrocystin-L polypeptides also can have one or more TMEM2 regions of homology (e.g., residues 2180-2375 or 3032-3376 of SEQ ID NO:3). Furthermore, a fibrocystin-L polypeptide can contain one or more sites for N-glycosylation (e.g., 56 N-glycosylation sites in the N-terminal region). A fibrocystin polypeptide also may contain sites (e.g., in the C-terminal tail) for phosphorylation by protein kinase A and/or protein kinase C.

5. Production of Fibrocystin-L Polypeptides

Fibrocystin-L polypeptides can be produced by a number of methods, many of which are well known in the art. By way of example and not limitation, fibrocystin-L polypeptides can be obtained by extraction from a natural source (e.g., from isolated cells, tissues or bodily fluids), by expression of a recombinant nucleic acid encoding the polypeptide, or by chemical synthesis.

Fibrocystin-L polypeptides of the invention can be produced by, for example, standard recombinant technology, using expression vectors encoding fibrocystin-L polypeptides. The resulting fibrocystin-L polypeptides then can be purified. Expression systems that can be used for small or large scale production of fibrocystin-L polypeptides include, without limitation, microorganisms such as bacteria (e.g., *E. coli* and *B. subtilis*) transformed with recombinant bacteriophage DNA, plasmid DNA, or cosmid DNA expression vectors containing the nucleic acid molecules of the invention; yeast (e.g., *S. cerevisiae*) transformed with recombinant yeast expression vectors containing the nucleic acid molecules of the invention; insect cell systems infected with recombinant virus expression vectors (e.g., baculovirus) containing the nucleic acid molecules of the invention; plant cell systems infected with recombinant virus expression vectors (e.g., tobacco mosaic virus) or transformed with recombinant plasmid expression vectors (e.g., Ti plasmid) containing the nucleic acid molecules of the invention; or mammalian cell systems (e.g., primary cells or immortalized cell lines such as COS cells, Chinese hamster ovary cells, HeLa cells, HEK-293 cells, PEAK cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids of the invention.

Suitable methods for purifying the polypeptides of the invention can include, for example, affinity chromatography, immunoprecipitation, size exclusion chromatography, and ion exchange chromatography. See, for example, Flohe et al. (1970) *Biochim. Biophys. Acta.* 220:469-476, or Tilgmann et al. (1990) *FEBS* 264:95-99. The extent of purification can be measured by any appropriate method, including but not limited to: column chromatography, polyacrylamide gel electrophoresis, or high-performance liquid chromatography. Fibrocystin-L polypeptides also can be "engineered" to contain a tag sequence described herein that allows the polypeptide to be purified (e.g., captured onto an affinity matrix). Immunoaffinity chromatography also can be used to purify fibrocystin-L polypeptides.

6. Anti-Fibrocystin-L Antibodies

The invention also provides antibodies having specific binding affinity for fibrocystin-L polypeptides. Such antibodies can be useful for diagnostic purposes (an antibody that recognizes a specific fibrocystin-L variant could be used to determine if a subject's cellular immunity is compromised or to detect endometrial cancer). An antibody having specific binding affinity for a fibrocystin-L polypeptide also can be used to prevent the development of an autoimmune disease in a subject at risk for autoimmunity or to treat an autoimmune disease (e.g., thyroiditis, inflammatory bowel disease, asthma, rheumatoid arthritis, systemic lupus erythematosis (SLE), or type I diabetes) in a subject. For example, an antibody such as a monoclonal antibody can be administered to a subject that contains antibodies against pancreatic islet antigens and a family history of type I diabetes to prevent the development of diabetes. An antibody having specific binding affinity for a fibrocystin-L polypeptide also can be administered to a subject to prevent or treat rejection of an organ or tissue transplant.

An "antibody" or "antibodies" includes intact molecules as well as fragments thereof that are capable of binding to an epitope of a fibrocystin-L polypeptide. The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids. The terms "antibody" and "antibodies" include polyclonal antibodies, monoclonal antibodies, humanized or chimeric antibodies, single chain Fv antibody fragments, Fab fragments, and $F(ab)_2$ fragments. Suitable "antibody" or "antibodies" can be of any isotype. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful.

In general, a fibrocystin-L polypeptide is produced as described above, i.e., recombinantly, by chemical synthesis, or by purification of the native protein, and then used to immunize animals. Various host animals including, for example, rabbits, chickens, mice, guinea pigs, and rats, can be immunized by injection of the protein of interest. Depending on the host species, adjuvants can be used to increase the immunological response and include Freund's adjuvant (complete and/or incomplete), mineral gels such as aluminum hydroxide, surface-active substances such as lysolecithin, pluronic polyols, polyanions, peptides, oil emulsions, keyhole limpet hemocyanin, and dinitrophenol. Polyclonal antibodies are contained in the sera of the immunized animals. Monoclonal antibodies can be prepared using standard hybridoma technology. In particular, monoclonal antibodies can be obtained by any technique that provides for the production of antibody molecules by continuous cell lines in culture as described, for example, by Kohler et al. (1975) *Nature* 256:495-497, the human B-cell hybridoma technique of Kosbor et al. (1983) *Immunology Today* 4:72, and Cote et al. (1983) *Proc. Natl. Acad. Sci. USA* 80:2026-2030, and the EBV-hybridoma technique of Cole et al., *Monoclonal Antibodies and Cancer Therapy*, Alan R. Liss, Inc. pp. 77-96 (1983). Such antibodies can be of any immunoglobulin class including IgM, IgG, IgE, IgA, IgD, and any subclass thereof. The hybridoma producing the monoclonal antibodies of the invention can be cultivated in vitro or in vivo.

A chimeric antibody is a molecule in which different portions are derived from different animal species, such as those having a variable region derived from a mouse monoclonal antibody and a human immunoglobulin constant region. Chimeric antibodies can be produced through standard techniques.

Antibody fragments that have specific binding affinity for fibrocystin-L polypeptides can be generated by known techniques. Such antibody fragments include, but are not limited to, $F(ab')_2$ fragments that can be produced by pepsin digestion of an antibody molecule, and Fab fragments that can be generated by deducing the disulfide bridges of $F(ab')_2$ fragments. Alternatively, Fab expression libraries can be constructed. See, for example, Huse et al. (1989) *Science* 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of a fibrocystin-L polypeptide by standard immunoassay methods including, for example, enzyme-linked immunosorbent assay (ELISA) or radioimmuno assay (RIA). See, *Short Protocols in Molecular Biology*, eds. Ausubel et al., Green Publishing Associates and John Wiley & Sons (1992). Suitable antibodies typically have equal binding affinities for recombinant and native proteins. As described herein, monoclonal antibodies FibLA-2, FibLA-10.1, FibLA-10.2, FibLA-4.1, FibLA-4.2, FibLA-11.1, FibLA-11.2, FibLA-11.3, FibLA-13.1, and FibLA-13.2 are useful for detecting fibrocystin-L in tissues and cell lines.

7. Methods for Using PKHDL1 Nucleic Acid Molecules, Fibrocystin-L Polypeptides, and Fibrocystin-L Expressing Cells As described herein, fibrocystin-L is widely expressed at a low level across many human tissues, including kidney (proximal and distal tubules), fallopian tube, thyroid, liver, adrenal cortex, gallbladder, testis, breast, and spleen. It is strongly expressed in fallopian tube, which is known to be heavily ciliated. It also appears to be upregulated in endometrial adenocarcinomas compared with levels detected in normal endometrium. Immunostaining of endometrium and fallopian tubes indicated the protein has an apical distribution and is present on endometrial epithelial apical cilia of these cells and appears to mislocalize apically in some cancers. Other hormone dependent cancers (e.g., breast and ovarian) also had up-regulated levels of fibrocystin-L, as did some lung and colon cancers. The tissue distribution of fibrocystin-L elsewhere seems to correlate with known ciliated epithelial surfaces (e.g., thyroid, kidney, lung, adrenal cortex, and pituitary). The findings of localized up-regulation (shown, for example, by increased immunoreactivity and relative protein expression levels by western, and confocal microscopy) as well as the abundance of PKHDL1 cDNAs in endometrial cancer demonstrates there is a connection between this gene and endometrial carcinogenesis and other cancers.

Fibrocystin-L also is expressed in both human and mouse T-lymphocytes (T-cells) and is up-regulated following human and mouse T-cell activation. Activated T-cells refers to cells that have been recently stimulated, accumulate at sites of ongoing immune activity, and are usually depleted once a disease process has been eliminated. In autoimmune diseases or rejection of a transplant, inappropriate accumulation and persistence of activated T-cells can result in tissue injury. Fibrocystin-L also is present in higher amounts in $CD4^+$ (helper) T-cells than in $CD8^+$ (killer) T-cells and present in higher amounts in memory T-cells than in naïve helper T-cells. Naive cells have not been previously activated, require a strong stimulus to undergo activation, typically require a period of days to become fully activated, and do not circulate through most organs. Memory T-cells are long-lasting T-cells that have been activated previously, are capable of rigid re-activation upon receipt of a new stimulus (e.g., re-exposure to the same infectious agent), and circulate through most organs and tissues. The generation of memory T-cells is essential for successful vaccination against many infections. As such, fibrocystin-L may play a role in the function of memory and activated T-cells. The genetic programs that are initiated by T-cell interactions with antigen-presenting cells (APCs) bearing cognate antigen regulate a host of specialized functions including T-cell proliferation, cytokine production, migration patterns, cytotoxicity, and cell survival. Coordination of these functions is essential for elimination of infection, immune surveillance against neoplasia, and generation of memory responses. Furthermore, aberrant T-cell activation underlies the pathogenesis of autoimmunity and rejection of transplanted organs and tissues. Fibrocystin-L may play a role in the regulation of the T-cell-APC interface structure or in adhesion and migration patterns.

Thus, detecting PKHDL1 nucleic acids or nucleic acid sequence variants thereof, or fibrocystin-L polypeptides, can be useful for characterizing immune responses in subjects, or for diagnosing, preventing, or treating autoimmune disease, transplant rejection, infectious disease, or cancer (e.g., endometrial, breast, ovarian, lung, or colon cancer). For example, PKHDL1 mutation and polymorphism analysis can be used to identify individuals at greater or lesser risk for, e.g., immune-mediated diseases or cancer.

PKHDL1 nucleic acids or nucleic acid sequence variants thereof, or fibrocystin-L polypeptides, also can be detected as a marker of endometrial cancer and other cancers, including breast, ovarian, lung, and colon cancer, or to grade endometrial or other cancers. For example, monoclonal antibody FibLA-2, FibLA-10.1, FibLA-10.2, FibLA-4.1, FibLA-4.2, FibLA-11.1, FibLA-11.2, FibLA-11.3, FibLA-13.1, or FibLA-13.2 can be used to detect fibrocystin L in a biological sample such as a tissue sample from the endometrium, breast, ovary, lung, or colon. In some embodiments, endometrial or other cancers can be graded by detecting the level of fibrocystin-L expression in tumor tissues using, for example, immunohistochemistry, western blotting, or an ELISA to detect the polypeptide or by analysis of mRNA levels. In other embodiments, endometrial or other cancers can be graded by detecting the level of secreted fibrocystin-L or fragments thereof in blood serum, urine or other bodily fluid. Fibrocystin L can be detected in combination with another marker for a particular cancer (e.g., PTEN or p53) or in combination with determining the status of a hormone receptor (e.g., estrogen or progesterone receptor status).

Furthermore, fibrocystin-L expressing T-cells can be detected and/or quantified in the blood to measure, for example, immune responses to vaccination or the nature and severity of autoimmune disease or transplant rejection. In general, the number of fibrocystin-L expressing T-cells in the blood will be increased after vaccination when compared with the baseline number of fibrocystin-L expressing T-cells in the blood before vaccination. Similarly, with respect to autoimmune disease or transplant rejection, the number of fibrocystin-L expressing T-cells will be increased relative to a baseline number of fibrocystin-L expressing T-cells in a control population (e.g., control subjects without autoimmune disease or subjects that have not undergone a transplant). Fibrocystin-L expressing T-cells also can be detected and/or quantified in tissue biopsy specimens to assess the nature and severity of autoimmune disease, transplant rejection, or a cancer-specific cellular immune response. Standard techniques can be used to detect and/or quantitate the number of fibrocystin-L expressing T-cells that are present in a biological sample (e.g., a blood or tissue sample).

8. Methods of Detecting Sequence Variants

Methods of the invention can be utilized to determine whether the PKHDL1 gene of a subject contains a sequence variant or combination of sequence variants. Furthermore, methods of the invention can be used to determine whether both PKHDL1 alleles of a subject contain sequence variants (either the same sequence variant(s) on both alleles or separate sequence variants on each allele), or whether only a single allele of a subject contains sequence variants.

Sequence variants within a PKHDL1 nucleic acid can be detected by a number of methods. Sequence variants can be detected by, for example, sequencing exons, introns, or untranslated sequences, denaturing high performance liquid chromatography (DHPLC; Underhill et al. (1997) *Genome Res.* 7:996-1005), allele-specific hybridization (Stoneking et al. (1991) *Am. J. Hum. Genet.* 48:370-382; and Prince et al. (2001) *Genome Res.* 11(1):152-162), allele-specific restriction digests, mutation specific polymerase chain reactions, single-stranded conformational polymorphism detection (Schafer et al. (1998) *Nat. Biotechnol.* 15:33-39), infrared matrix-assisted laser desorption/ionization mass spectrometry (WO 99/57318), and combinations of such methods.

Genomic DNA generally is used in the analysis of PKHDL1 sequence variants. Genomic DNA typically is extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), the Wizard® Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.).

Typically, an amplification step is performed before proceeding with the detection method. For example, exons or introns of the PKHDL1 gene can be amplified and then directly sequenced. Dye primer sequencing can be used to increase the accuracy of detecting heterozygous samples.

PKHDL1 sequence variants can be detected by, for example, DHPLC analysis of PKHDL1 nucleic acid molecules. Genomic DNA can be isolated from a subject (e.g., a human, a mouse, or a rat), and sequences from one or more regions of an ARPKD gene can be amplified (e.g., by PCR) using specific pairs of oligonucleotide primers (e.g., as described above in subsection 2). After amplification, PCR products can be denatured and reannealed, such that an allele containing a PKHDL1 sequence variant can reanneal with a wild-type allele to form a heteroduplex (i.e., a double-stranded nucleic acid with a mismatch at one or more positions). The reannealed products then can be subjected to DHPLC, which detects heteroduplexes based on their altered melting temperatures, as compared to homoduplexes that do not contain mismatches. Samples containing heteroduplexes can be sequenced by standard methods to specifically identify the variant nucleotides. Examples of specific sequence variants are provided in Table 5 below.

Allele specific hybridization also can be used to detect PKHDL1 nucleotide sequence variants, including complete haplotypes of a mammal. In practice, samples of DNA or RNA from one or more mammals are amplified using pairs of primers, and the resulting amplification products are immobilized on a substrate (e.g., in discrete regions). Hybridization conditions are selected such that a nucleic acid probe will specifically bind to the sequence of interest, e.g., the PKHDL1 nucleic acid molecule containing a particular sequence variant. Such hybridizations typically are performed under high stringency, as some nucleotide sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS)) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For PKHDL1 nucleotide sequence variants that introduce a restriction site, restriction digest with the particular restriction enzyme can differentiate the alleles. For PKHDL1 sequence variants that do not alter a common restriction site, mutagenic primers can be designed that introduce a restriction site when the variant allele is present or when the wild type allele is present. A portion of a PKHDL1 nucleic acid can be amplified using the mutagenic primer and a wild type primer, followed by digestion with the appropriate restriction endonuclease.

Certain sequence variants, such as insertions or deletions of one or more nucleotides, change the size of the DNA fragment encompassing the variant. The insertion or deletion of nucleotides can be assessed by amplifying the region encompassing the sequence variant and determining the size of the amplified products in comparison with size standards. For example, a region of a PKHDL1 nucleic acid can be amplified using a primer set from either side of the sequence variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

Other methods also can be used to detect sequence variants. For example, conventional and field-inversion electrophoresis are known in the art to be useful for visualizing basepair changes. Furthermore, Southern blotting and hybridization can be utilized to detect larger rearrangements such as deletions and insertions.

The association of certain sequence variants with susceptibility to APRKD or a diagnosis of ARPKD can be determined. An ARPKD-associated (or disease-associated) sequence variant is a sequence variant or combination of sequence variants within the PKHDL1 gene of a subject that is correlated with the presence of ARPKD in that subject. Sequence variants associated with the presence of ARPKD in a subject can include, for example, mutations that will result in truncation of a fibrocystin-L polypeptide or a substantial in-frame alteration within a PKHDL1 transcript from the subject, missense or small in-frame mutations found within a nucleic acid sample of a subject and not found at a significant level in the normal population, and mutations that segregate in ARPKD families in a fashion known in the art to be consistent with autosomal recessive inheritance. Other sequence variants may be identified that are not individually disease-associated, but which may be associated with ARPKD when combined with one or more additional sequence variants. Still other sequence variants can be identified that are simply polymorphisms within the normal population, and which are not associated with ARPKD.

9. Articles of Manufacture

PKHDL1 nucleic acid molecules (e.g., oligonucleotide primer pairs and probes) of the invention can be combined with packaging material and sold as kits for determining if a subject has altered cellular immunity, if a subject is susceptible to developing ARPKD, diagnosing a patient with ARPKD, for detecting endometrial cancer, based on the detection of PKHDL1 gene expression or sequence variants within the PKHDL1 gene of the subject. Components and methods for producing articles of manufacture such as kits are well known. An article of manufacture may include one pair of PKHDL1 oligonucleotide primers or a plurality of oligonucleotide primer pairs (e.g., 2, 3, 4, 10, or more than 10 primer pairs). In addition, the article of manufacture may include buffers or other solutions, or any other components necessary to assess whether the PKHDL1 gene of a subject contains one or more variants. Instructions describing how the PKHDL1 primer pairs are useful for detecting sequence variants within a PKHDL1 gene also can be included in such kits.

In other embodiments, articles of manufacture include populations of isolated PKHDL1 nucleic acid molecules immobilized on a substrate. Suitable substrates provide a base for the immobilization of the nucleic acids, and in some embodiments, allow immobilization of nucleic acids into discrete regions. In embodiments in which the substrate includes a plurality of discrete regions, different populations of isolated nucleic acids can be immobilized in each discrete region. Thus, each discrete region of the substrate can include a PKHDL1 nucleic acid molecule containing a different sequence variant (e.g., the sequence variants of Table 5). Such articles of manufacture can include two or more nucleic acid molecules with different sequence variants, or can include nucleic acid molecules with all of the sequence variants known for PKHDL1.

Suitable substrates can be of any shape or form and can be constructed from, for example, glass, silicon, metal, plastic, cellulose or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules typically are about 20 nucleotides in length, but can vary from about 10 nucleotides to about 1000 or more nucleotides in length.

In practice, a sample of DNA or RNA from a subject is amplified, the amplification product is hybridized to an article of manufacture containing populations of isolated nucleic acid molecules in discrete regions, and hybridization can be detected. Typically, the amplified product is labeled to facilitate detection of hybridization. See, for example, Hacia et al. (1996) *Nature Genet.*, 14:441-447; and U.S. Pat. Nos. 5,770, 722 and 5,733,729.

The invention will be further described in the following examples, which do not limit the scope of the invention described in the claims.

EXAMPLES

Materials and Methods

Preparation of Resting and Stimulated Immune Cell Sub-Populations

Spleens, thymuses and subcutaneous lymph nodes were dissected from B6 and BALB/C mice under sterile conditions. Cell suspensions were prepared by disruption of the organs in DMEM/10% FCS and passage through 45 µm nylon mesh. For spleen and thymus suspensions, erythrocytes were lysed by 5 min incubation in ACK buffer (0.15 M $NH_4Cl$, 1.0 mM $KHCO_3$, 0.1 mM $Na_2EDTA$, pH 7.2). For flow cytometric sorting, surface staining with a panel of fluorochrome-labeled monoclonal antibodies (BD Pharmingen, San Diego, Calif.) was carried out by incubating the cells in DMEM/10% FCS at 4° C. for 1 hour. Labeled cell suspensions were washed and re-suspended in DMEM/10% FCS at 4 to $8 \times 10^6$ cells/ml and flow sorted using a FACS Vantage sorter (Becton Dickinson Immunocytometry Systems, San Jose, Calif.). The antibody combinations were as follows: Splenic T-cell sub-populations: anti-mouse CD4-FITC (RM4-4), and anti-mouse CD8α-PE (53-6.7). Sorted populations: $CD4^{+ve}/CD8^{-ve}$ (CD4+ T-cells) and $CD4^{-ve}/CD8^{+ve}$ (CD8+ T-cells). Splenic dendritic cell sub-populations: anti-mouse CD11c-FITC (HL3) and anti-mouse CD8α-PE. Sorted populations: $CD11c^{+ve}/CD8^{-ve}$ (myeloid) and $CD11c^{+ve}/CD8^{+ve}$ (lymphoid). Thymocyte sub-populations: anti-mouse CD4-FITC, anti-mouse CD8α-PE. Sorted populations: $CD4^{-ve}/CD8^{-ve}$, $CD4^{+ve}/CD8^{+ve}$, $CD4^{+ve}/CD8^{-ve}$, and $CD4^{-ve}/CD8^{+ve}$. Splenic NK and NKT cells: anti-mouse CD3ε-FITC (145-2C11) and anti-NK 1.1-PE (PK136). Sorted populations: $NK1.1^{+ve}/CD3\epsilon^{-ve}$ (NK-cells) and $NK1.1^{+ve}/CD3\epsilon^{+ve}$ (NKT-cells). Splenic B-cell sub-populations: anti-mouse IgD-FITC (11-26c.2a) and anti-mouse CD19-PE (1D3). Sorted populations: $CD19^{+ve}/IgD^{+ve}$ (naïve B-cells) and $CD19^{+ve}/IgD^{-ve}$ (memory B-cells). An aliquot of the memory B-cells was stimulated for 96 hours (activated memory B-cells) with plate-bound goat-anti-mouse IgG (ICN Biomedicals Inc., Aurora, Ohio), 25 ng/ml lipopolysaccharide (LPS, Sigma Aldrich, St. Louis, Mo.), and 2.5 µg/ml purified anti-mouse CD40 (HM40-3, BD Pharmingen). Murine $CD4^{+ve}$ and $CD8^{ve}$ lymph node T-cells were purified by nylon wool column and complement-mediated depletion then activated for 72 hours in tissue culture plates coated with a combination of hamster anti-mouse CD3ε (145-2C11) and hamster anti-mouse CD28 (PV-1), as described by Griffin M. D., et al. (2000), *J Immunol.*, 164, 4433-42; or stimulated for 96 hours by co-culture with irradiated allogeneic (B6) bone marrow-derived dendritic cells (allo-stimulated T-cells).

Murine peritoneal inflammatory macrophages were generated from B6 mice by intraperitoneal injection (1 ml/animal) of sterile 3% thioglycollate (Becton Dickinson Microbiology Systems, Cockeysville, Md.). After 7 days, the animals were sacrificed and cells extracted by peritoneal lavage using sterile DMEM/10% FCS, washed and an aliquot retained for RNA preparation (fresh peritoneal inflammatory cells). The remainder of the cells were re-suspended in DMEM/10% FCS and allowed to adhere to tissue culture flasks at 37° C. for 2 hours. Non-adherent cells were removed by washing with sterile PBS and individual cell layers were exposed for 1 hour at 37° C. to PBS alone (unstimulated macrophages) or to PBS containing LPS 2 µg/ml (stimulated macrophages). These solutions then were removed, the cell layers washed with PBS, and culture medium re-applied for 24 hours.

Human lymphocytes were isolated from whole blood using 54% Percott (American Biosciences, Piscataway, N.J.) and the resulting PBS washed and pelleted cells were incubated in RPMI/10% FCS with concanavalin A (10 µg/ml) for 72 hours at 37° C.

RNA Analysis

RNA was isolated from snap frozen human tissues (adrenal, breast, colon, heart, kidney, liver, lung, pancreas, placenta and uterus, obtained as surgical waste), mouse tissues, cell-lines and the leukocyte populations described above (see FIG. 1) using the Trizol method (Invitrogen, Carlsbad, Calif.) or with the NucleoSpin (BD Biosciences, San Jose, Calif.) column system. Isolated RNA (1-5 µg) was used to make cDNA with the Clontech Powerscript™ Reverse Transcriptase cDNA Synthesis Kit (BD Biosystems, San Jose, Calif.) and 250 µg random primers (Invitrogen, Carlsbad, Calif.). PKHDL1 (Pkhdl1) expression was analyzed by RT-PCR using 50 ng cDNA and equalized by amplification of the control β-actin (mouse: F5'-CTGGCACCACACCTTCTA-CAATGAGCTG-3' (SEQ ID NO: 31): R-5'-GCACAGCT-TCTCTTTGATGTCACGCACGATTTC-3') (SEQ ID NO: 32)) or GAPDH (human: F5'-GACCACAGTCCATGCCAT-CACT-3'(SEQ ID NO: 33): R5'-TCCACCACCCTGTTGCT-GTA-3'(SEQ ID NO: 34); 453 bp product). For analysis of murine Pkhdl1, a 258 bp region from exons 76-77 (12429-12686 bp; F5'-TCCATTTAGCACCTGTTGGGC-3'(SEQ ID NO: 35); R5'-AGTCTTCCTACAAGGCACGCTG-3'(SEQ ID NO: 36)) was amplified and for human PKHDL1, a 247 bp region from exons 35-36 (4232-4478 bp; F5'-CACCAGTC-CTAATGTGTCTGTGG-3'(SEQ ID NO: 37); R5'-TG-GAGAAAAATGGAGTGAGCCTC-3'(SEQ ID NO: 38)) was assayed. PCR conditions were as follows: 0.125U AmpliTaq Gold (Applied Biosystems, Foster City, Calif.) in the supplied buffer, 2.0 mM $MgCl_2$, 0.2 mM each nucleotide, 4 pM each primer and 50 ng cDNA, and PCR conditions of: 4 min at 94° C.; 60 s at 94° C., 30 s at 56-64° C. and 30-60 s at 72° C. for 30-40 cycles; and finally 10 min at 72° C. The products were electrophoresed through 2.0% agarose gels and visualized by ethidium bromide staining Multi-Tissue Northern Blots (BD Biosciences, San Jose, Calif.) were hybridized and washed using standard methods with the probes: human PKHDL1, Ex 1-12, 979 bp (9-986 nt) and Ex 38-41, 1248 bp (5065-6312 nt) and murine Pkhdl1, ex32-38, 1048 bp (3788-4835 nt).

Cloning PKHDL1

The positions of likely human PKHDL1 exons were determined by comparison of genomic DNA (AC021001) to: the mouse D86 cDNA sequence, PKHD1, Genome Scan putative genes (Hs 8205 30 21 2; Hs 8205 30 23 1 and Hs 8205 30 23 2) and using the NIX suite of programs (world wide web at hgmp.mrc.ac.uk). The transcript was amplified as 16 overlapping fragments with primers positioned in the most strongly predicted exons (see Table 1) using PCR conditions as described above and human lung or adrenal cDNA. The mouse ORF from the cDNA D86 to the 3'UTR has been cloned as 14 cDNA clones (Table 2). Fragments were cloned into specific restriction site of pZERO using amplification primers with matching sites, or unmodified product was cloned into terminal transferase (New England Biolabs, Beverly, Mass.) treated, EcoRV cut vector using the Rapid DNA Ligation Kit (Roche Applied Science, Indianapolis, Ind.) and grown in *E. coli* XL-2MRF' (Stratagene, LaJolla, Calif.). The 5' and 3' regions were amplified and cloned using RACE strategies with the SMART RACE cDNA Amplification Kit (BD Biosciences, San Jose, Calif.). For the 5' RACE, human adrenal RNA was reverse transcribed with Powerscript RT and amplified with the 5' RACE CDS and SMART-II primers using touchdown PCR and nested gene specific primers. At the 3' end, cDNA synthesis was with the tailed and anchored oligo (dT) primer, 3'-CDS, and amplified as above with nested gene specific primers. Products were sequenced using the Big-Dye Terminator Kit (Applied Biosystems, Foster City, Calif.) and analyzed on ABI377 Sequencers. The sequence was assembled into a contig using the Sequencer 4.1.2 program.

TABLE 1

Details of PKHDL1 cDNA clones

| Clone | Size *bp) | Exons | Position in coding region | Comments |
|---|---|---|---|---|
| MH1 | 338 | 1-3 | −104:234 | 5' RACE |
| MH2 | 978 | 1-12 | 9:986 | |
| MH3 | 1291 | 11-20 | 852:2143 | |
| MH4 | 568 | 20-23 | 2086:2653 | |
| MH5 | 1097 | 23-31 | 2588:3684 | |
| MH6 | 934 | 29-36 | 3488:4421 | |
| MH7 | 925 | 35-38 | 4217:5141 | |
| MH8 | 1249 | 38-41 | 5065:6312 | |
| MH9 | 1233 | 40-48 | 6046:7278 | |
| MH10 | 1185 | 47-49 | 7124:8308 | |
| MH11 | 702 | 49-51 | 7980:8681 | |
| MH12 | 1158 | 50-59 | 8586:9743 | |
| MH13 | 705 | 58-63 | 9618:10322 | |
| MH14 | 1311 | 61-70 | 10051:11362 | |
| MH15 | 1038 | 70-75 | 11256:12293 | |
| MH16 | 961 | 73-78 | 12017:3' 339 | 3' RACE |

TABLE 2

Details of Pkhdl1 cDNA clones

| Clone | Size (bp) | Exons | Position in coding region (nt) | Comments |
|---|---|---|---|---|
| D86 | 5773 | 1-38 | 1:5773 | Alternative 3'UTR 62 bp into IVS 38 |
| MS1 | 563 | 38-41 | 5618:6180 | |
| MS2 | 690 | 39-43 | 5921:6610 | |
| MS3 | 606 | 42-47 | 6495:7100 | |
| MS4 | 640 | 46-49 | 6903:7542 | |
| MS5 | 1005 | 48-49 | 7343:8347 | |
| MS6 | 609 | 49-52 | 8244:8852 | |
| MS7 | 846 | 51-57 | 8698:9543 | |
| MS8 | 683 | 56-62 | 9452:10134 | |
| MS9 | 673 | 61-66 | 10010:10682 | |
| MS10 | 583 | 66-69 | 10603:11185 | |
| MS11 | 656 | 6-9-73 | 11114:11769 | |
| MS12 | 302 | 71-73 | 11509:11810 | |

TABLE 2-continued

Details of Pkhdl1 cDNA clones

| Clone | Size (bp) | Exons | Position in coding region (nt) | Comments |
|---|---|---|---|---|
| MS13 | 943 | 73-77 | 11771:12713 | |
| MS14 | 284 | 7778 | 12423:3'UTR, 56 | |

Mutation Analysis of PKHDL1

All patients in the study gave informed consent and the project was approved by the Institutional Review Board at Mayo Clinic. Five previously described ARPKD patients from families: M36, P244, M51, M52 and M55 (Ward C. J., et al. (2002), *Nature Genet.*, 30, 259-269), plus two additional typical ARPKD patients, in which no PKHD1 mutation was identified (n=4) or where only a single missense change was detected (M52, M52 and M55), were screened for PKHDL1 mutations. An additional thirteen typical ARPKD patients with no detected PKHD1 mutation were screened for changes in thirty-four PKHDL1 exons, but as no likely disease causing mutations were identified, the screening of the gene was not completed.

To screen for PKHDL1 mutations, all the 78 coding exons were amplified from genomic DNA as 85 fragments of ~150-350 bp. Primers were typically positioned in the intron ~20 bp from the intron/exon boundary. See Table 3 for the sequence of each of the primers. The fragments were amplified using the following protocol: genomic DNA (60 ng), primers (8 pmol each), dNTPs (200 µM each), MgCl$_2$ (2.5 mM) and 1U of Taq Gold in the supplied buffer (Applied Biosystems, Foster City, Calif.), in a total volume of 25 µl. The PCR program included: 120 s, 94° C., 35-40 cycles of 30 s at 94° C., 30 s at 50°-63° C. and 30 s at 72° C.; and 10 min 72° C. The PCR products were treated to form heteroduplexes and analyzed for base-pair changes using DHPLC on the WAVE Fragment Analysis System (Transgenomic, Omaha, Nebr.), as previously described (Ward C. J., et al. (2002) supra). See also Table 3 for DHPLC conditions. Briefly, crude PCR (300-500 ng) was injected into the chromatographic column (DNASep Cartridge, Transgenomic, Omaha, Nebr.) and eluted using calculated and empirically determined optimal conditions. Samples showing an abnormal chromatogram were further characterized by direct sequencing as previously described (Ward C. J., et al. (2002) supra). Potentially pathogenic changes were validated by DHPLC analysis of 25-100 normal controls (50-200 chromosomes).

TABLE 3

Details of PCR amplicons and DHPLC conditions to analyze the PKHDL1 gene

| Exon frag. | Size (bp) | PCR annealing temp (° C.) | Forward Primer Sequences (5'-3') | SEQ ID | Reverse Primer Sequences (5'-3') | SEQ ID | DHPLC conditions Temp (° C.) | Initial % buffer B |
|---|---|---|---|---|---|---|---|---|
| 1 | 152 | 57 | GCACCAACTCCGCAGAAC | 39 | TGTCTACGCGGGCCTCTCCTGCTTG | 40 | 63 | 47 |
| 2 | 302 | 48 | GGCAGAGCCAAAAATAAAACCTG | 41 | ATAGGCTTGAAAATACCTCAACC | 42 | 51 | 54 |
| 3 | 242 | 43 | CTCTGAAGATAGAATACC | 43 | TCTGATATGATGAAAATG | 44 | 53 | 52 |
| 4 | 311 | 48 | GAATGGAACTTAACTAGACATCAG | 45 | GCAGGAAAGAAAGCAAGATCAAC | 46 | 56 | 55 |
| 5 | 159 | 43 | AACTAGAAACAAAACAGAG | 47 | ATTATTTACCATGAAACC | 48 | 53 | 48 |
| 6 | 217 | 42 | CTTACACAGAATCTTTTTG | 49 | TTTAATATCATTGGACCC | 50 | 53 | 51 |
| 7 | 191 | 44 | TTTAAGGGAACCAGTGAG | 51 | ATCTGCTATTTGTTTTG | 52 | 54 | 50 |

TABLE 3-continued

Details of PCR amplicons and DHPLC conditions to analyze the PKHDL1 gene

| Exon frag. | Size (bp) | PCR annealing temp (° C.) | Forward Primer Sequences (5'-3') | SEQ ID | Reverse Primer Sequences (5'-3') | SEQ ID | DHPLC Temp (° C.) | DHPLC Initial % buffer B |
|---|---|---|---|---|---|---|---|---|
| 8 | 191 | 45 | TGAGTAGTTTTTAAGAGAAAC | 53 | TCTGTGAGCATTATGAAG | 54 | 54 | 50 |
| 9 | 198 | 43 | ATTTTGTACTTTTTCTCTG | 55 | TATTTACCCTGTTGAATC | 56 | 53 | 50 |
| 10 | 193 | 45 | CTGAAGTTAAAAAATGTTC | 57 | TTATACACTGCCTTCCCACCACCC | 58 | 53, 55 | 51 |
| 11 | 223 | 46 | AAAAATCAGGTATTTGGG | 59 | AGAATTTGTGGTAATAAAG | 60 | 52, 56 | 51 |
| 12 | 198 | 46 | GATACACTGATGTGATTTG | 61 | TGTGAATATAGAAATGGC | 62 | 56 | 50 |
| 13 | 345 | 45 | TTATGATCCTGATGAAAG | 63 | ACAGTATCAAATAGTATTCTG | 64 | 57 | 55 |
| 14 | 179 | 44 | ATAAATGTTGAAAAGGTC | 65 | TAATGACAGGAAAAAGCC | 66 | 54 | 49 |
| 15 | 259 | 49 | CTGGAAAAAAGTTATATTCATTAG | 67 | ATTGAGATCCTGCCTTCG | 68 | 54, 57 | 53 |
| 16 | 249 | 43 | TTGAATAGCTGAATTATG | 69 | ACAGAAACAGTATCTCCC | 70 | 51 | 52 |
| 17 | 251 | 46 | GAAAGATTTCAACTTTTC | 71 | GCACAGGATATACATTTG | 72 | 56 | 53 |
| 18 | 243 | 46 | AGTTAATGTCTACAAATTC | 73 | AGAGGGTGCAGGGAAAATGC | 74 | 56 | 52 |
| 19 | 204 | 44 | CGAGTGTTCTAACTTTTC | 75 | AGGTCAGTTCACAGTTC | 76 | 52, 54 | 50 |
| 20 | 243 | 45 | TTGGGGGAAAACCAGAAC | 77 | AGATTCAATTAGCATATC | 78 | 55 | 52 |
| 21 | 336 | 45 | TCTCTGTGTTCTGGTACG | 79 | CCCAAGAAATGGATTTGTCTTATC | 80 | 52 | 55 |
| 22 | 326 | 46 | GCTTTCTAAAGTGTATTTGC | 81 | TGTTTCTATCCATACTGC | 82 | 52, 55 | 55 |
| 23 | 343 | 46 | TTACATGGCAAAAACCAC | 83 | TAGTTAGCTGTCTTTTCC | 84 | 52 | 55 |
| 24 | 300 | 46 | ACATGAGGCTCATTTATG | 85 | TGTGTGTGCGTATACACC | 86 | 54, 55 | 54 |
| 25 | 276 | 51 | AAGATTACAGGCGTGAAC | 87 | GCACATAGAAGAAAAGAG | 88 | 62 | 53 |
| 26 | 297 | 44 | GACTTTTATTCACCTTTG | 89 | GTCTTTAACATATTACAAAC | 90 | 54 | 54 |
| 27 | 221 | 47 | CTTTTGTTAAAACCTATTC | 91 | CTTTCACACCCAGTATAG | 92 | 57 | 51 |
| 28 | 244 | 49 | TGTCTGATTTCATAACAACAGG | 93 | CCTTTGATTCCACTTTATCTTAGAG | 94 | 55 | 50 |
| 29 | 226 | 49 | CATCTTTTTCTTTTTTCAC | 95 | CATGCAATTTTCTCTCTG | 96 | 58 | 52 |
| 30 | 204 | 44 | TATAGTTGAACTGTTTTG | 97 | AGGAGGAAAAAGTGACTG | 98 | 55 | 50 |
| 31 | 215 | 44 | GCATTTCTGTATCTCAAC | 99 | TGACCAATCTTATTGAAG | 100 | 54 | 51 |
| 32 | 322 | 47 | AAGATGAGAGATGAATTG | 101 | AACTCCATCAAGTTTATG | 102 | 54 | 55 |
| 33 | 212 | 45 | GAAGCTCATTGAAAAATC | 103 | GATAATCACTTTCCTATG | 104 | 55 | 51 |
| 34 | 204 | 45 | ATTTGACAAAATGTTTGC | 105 | TCAGGTTTCAGTGCTTCC | 106 | 55 | 50 |
| 35 | 313 | 47 | ATTGCCATGTTGTCAAAG | 107 | CATTTAGGAAAAAGTGAC | 108 | 52, 57 | 55 |
| 36 | 250 | 46 | GTACAATCTCATTTTATG | 109 | TATCACATACACCCTGGG | 110 | 57 | 53 |
| 37 | 325 | 45 | AAACAGTTATCATTTTGG | 111 | CATATAATAGAAGTACAAAG | 112 | 56 | 55 |
| 38a | 349 | 50 | ACTGGAGGTATGTATTGACTTG | 113 | TGACCCATAAGGACTTTTACAC | 114 | 56 | 55 |
| 38b | 347 | 50 | AAAAGGCTCTGGATTTGC | 115 | CATTAACCTCTATTGCTCTGAAC | 116 | 58 | 55 |
| 38c | 334 | 50 | GGTTTGGGGACTGTTTTG | 117 | AGTAGACTTCATTGGGGTTG | 118 | 58 | 55 |
| 38d | 350 | 50 | GGAAATGGCTTCTATCCAG | 119 | AGGTATTAAGTGTAAGTGGGAAC | 120 | 52, 56 | 56 |
| 39 | 472 | 48 | AGACTGTAGGGTATATTGTAGTC | 121 | GAAACAAAATATCTGCAGGTTC | 122 | 52 | 55 |
| 40 | 350 | 47 | ATCAAAAGAGATTCAGTTGC | 123 | CTGCCATTACTTTTTCTGAC | 124 | 52 | 55 |

TABLE 3-continued

Details of PCR amplicons and DHPLC conditions to analyze the PKHDL1 gene

| Exon frag. | Size (bp) | PCR annealing temp (° C.) | Forward Primer Sequences (5'-3') | SEQ ID | Reverse Primer Sequences (5'-3') | SEQ ID | DHPLC conditions Temp (° C.) | Initial % buffer B |
|---|---|---|---|---|---|---|---|---|
| 41 | 281 | 55 | GGAGGTTTTGGAAATGAATCAG | 125 | TGGAAATGCACAATGATGCGTG | 126 | 60 | 54 |
| 42 | 275 | 52 | AAAGGGTTTGACAGTGTGATCTAG | 127 | ATGCTGGTTTTCTATTGCTGTG | 128 | 56 | 53 |
| 43 | 253 | 52 | CGAATGAAAAACTCTGGTAAAATCC | 129 | TCAGGCAGAGTCCAATGAACAG | 130 | 55 | 53 |
| 44 | 268 | 46 | TGTAATGAATAATTTAATAGGTAAC | 131 | AAGATAAACTTAGGAGAGGTTG | 132 | 53 | 53 |
| 45 | 223 | 54 | TGGATTTGGGGTTTTAATTTTC | 133 | GAGTCTTCCTCTACCAACTCCC | 134 | 60 | 51 |
| 46 | 231 | 49 | AGTTCTCAATAACAAATCAAAC | 135 | CTTTTCTAAATACACATCATTAAG | 136 | 57 | 52 |
| 47 | 344 | 48 | TACCAAAACAATATGTTATGTC | 137 | GCATGATTATACCAACCACGAG | 138 | 56 | 55 |
| 48 | 241 | 50 | TCTTCAATATAAGAGGATTCCG | 139 | TAACCTTGAGCAAACCACTGTG | 140 | 55 | 52 |
| 49a | 304 | 50 | CTAAATAACTGTGATTTCTGGG | 141 | GAAGACTGGTACTTTGCTGTAC | 142 | 56 | 54 |
| 49b | 303 | 53 | CCAGTATAACTTGGCAGTATTTG | 143 | GTACAAGATCCCGTTTGCATGG | 144 | 58 | 54 |
| 49c | 333 | 53 | ATTTCCCCATGCAAACGGGATC | 145 | CAGAAGAGACAGTCAAGCCTTC | 146 | 59 | 55 |
| 49d | 300 | 41 | GGTTCTCCCATTTAGTGAAGGC | 147 | CAATTCAATTCTGTGCTAACAC | 148 | 53, 58 | 54 |
| 50 | 314 | 50 | CCTTTTTTATGTTTCTTAATGTG | 149 | ATGATGACAAAAGTTTAGGAAG | 150 | 52, 58 | 55 |
| 51 | 269 | 46 | GGAGGAGTTTATTAGAGG | 151 | ATGTAGGCTGTGTTGGG | 152 | 54 | 53 |
| 52 | 299 | 47 | TAAATCTTAACATAATATAGGGG | 153 | TTAGATAAACTATCATTTCTGCC | 154 | 52, 53 | 54 |
| 53 | 254 | 50 | TTTGGTCACTATGTTCATTTAAC | 155 | AGATATTGAAGGGTATCAACTAC | 156 | 57 | 51 |
| 54 | 240 | 48 | CATTTTTTTCTTCTCTACCATG | 157 | ACATTTCATTCATTTGTGTTTAC | 158 | 55 | 52 |
| 55 | 281 | 47 | AAGTTGTAGTTTATGGATTATG | 159 | TGCTTCTTTCTTATTATTTGAG | 160 | 51, 56 | 54 |
| 56 | 272 | 49 | GGGTGGATTTTTTTTCCTGGTC | 161 | AACTGATATGTACTTTAGTGCC | 162 | 55 | 53 |
| 57 | 227 | 48 | TTTATACTAGCACCTAACTCAG | 163 | CCACTGTGTATATTCATTTTCC | 164 | 57 | 52 |
| 58 | 300 | 47 | CATAATTGCCAATGAGATATAC | 165 | GTAAATGTGAATCTTTCAACAC | 166 | 53 | 54 |
| 59 | 284 | 49 | CTTCTCAGCATTGGCAATAATC | 167 | GAGCTGACTACATATAGATGAG | 168 | 55 | 54 |
| 60 | 250 | 47 | CAAAAATGTTTTATTCCAACTG | 169 | AAGATGTGGCTATTTAGAAGTC | 170 | 52 | 53 |
| 61 | 283 | 47 | TGAGTATTGATTATTGATAAAGG | 171 | CCACAGGATGTGTAATTTGAACC | 172 | 52 | 54 |
| 62 | 270 | 48 | GCAAATTGACTTATGTTTTTGGGG | 173 | CATTCACTCCTTTAGTTAGCTC | 174 | 52 | 53 |
| 63 | 208 | 48 | GTGTATTGTCATATACTTACTCTCG | 175 | CTAGTTTTAGCGATTCCTGG | 176 | 55 | 51 |
| 64 | 243 | 47 | TTCTCTGGTTCTATATTTCC | 177 | CAGGTTACATAATACTAAGGAC | 178 | 54 | 52 |
| 65 | 305 | 51 | TTTGGACATGCTGGGATTATGG | 179 | TTCAGAAATTCCACCCTTCTCC | 180 | 55 | 54 |
| 66 | 300 | 51 | CCCATGTTTTCTTTTAGTAAGAGC | 181 | ATGAGCTGAAGCAAAGGTAGGC | 182 | 56 | 54 |
| 67 | 301 | 48 | TGAACTCACTGCTGCTCATCGG | 183 | TATCCTCTACATATTCTTTACAG | 184 | 56 | 55 |
| 68 | 302 | 48 | GGCAGAATGTGCATTAAATCTG | 185 | GGAGGAAGTGAGAATGAAAAAC | 186 | 52 | 54 |
| 69 | 327 | 51 | CAAGTGTATTCATATTGCTCTCTAG | 187 | GCCTAATGACAGATTAAGCAAG | 188 | 57 | 55 |
| 70 | 333 | 48 | CTAGCATAACAAGAAATAGATG | 189 | AATTTATGAGATGGCTTCATGC | 190 | 53 | 55 |
| 71 | 301 | 53 | GGAGTATGCACTTTCATTTTGC | 191 | ATGAGCTGTAAGGCTGACAATG | 192 | 58 | 54 |
| 72 | 258 | 47 | ATATTGAAGGACGGTTTAAGTG | 193 | TAAGTACATTTTCCATGTGTAC | 194 | 54 | 53 |
| 73 | 409 | 52 | CTGTGATGTTCTGGCTTTTTTC | 195 | ATTGCATTCCTCCATCTCAAAC | 196 | 55 | 57 |

TABLE 3-continued

Details of PCR amplicons and DHPLC conditions to analyze the PKHDL1 gene

| Exon frag. | Size (bp) | PCR annealing temp (° C.) | Forward Primer Sequences (5'-3') | SEQ ID | Reverse Primer Sequences (5'-3') | SEQ ID | DHPLC conditions Temp (° C.) | Initial % buffer B |
|---|---|---|---|---|---|---|---|---|
| 74 | 327 | 48 | AGAATGCTAAAGTGAAAAACTC | 197 | GTTTTGAAATAGAAACAGAGAG | 198 | 54 | 55 |
| 75 | 276 | 52 | CTGCTGAGTGTAGTTTATCATG | 199 | GAGTGAAACTGGCTCATCCTTC | 200 | 56, 58 | 53 |
| 76 | 267 | 48 | TTTAAAAGCATGGAAACAGGAC | 201 | TATAATTGTCTCTATTTATGGC | 202 | 54, 55 | 53 |
| 77 | 367 | 51 | AGGAAATCAAACACTATGATGC | 203 | GATATCATGCACAAGAGCTGTG | 204 | 56 | 56 |
| 78 | 342 | 46 | TATGCTATTTCTACTTAAAAATTG | 205 | TTTGTTGGTACAATAACTTAGAGG | 206 | 52 | 55 |

Sequence Analysis

The intron/exon structure of PKHDL1 was determined by comparison with genomic sequence using MacVector 7.0 and SIM4 (pbil.univ-lyon1.fr/sim4.html). The sequence of the murine Pkhdl1 transcript was determined by comparison of human PKHDL1 sequence and the Pkhdl1 cDNA clone, D86, to mouse genomic sequence using MacVector. The genomic sequence was used as the authentic sequence for the human and murine transcripts and the numbering of the transcript was from the start codon.

BLAST was used to screen for homologous sequences in the GenBank database. Comparison between orthologs, and fibrocystin and fibrocystin-L, was made by BLAST2 and the Pustell protein/DNA sequence alignment tool of MacVector. Protein domains were defined using the Pfam database (pfam.wustl.edu). To analyze protein topology the programs SOSUI (sosui.proteome.bio.tuat.ac.jp/sosuiframe0.html); TMHMM (v2.0) (cbs.dtn.dk/services/TMHMM-2.0) and SignalP (v2.0) (cbs.dtn.dk/services/SignalP/) were used. Potential N-glycosylation sites and phosphorylation sites were identified with MacVector and alignments made with the ClustalW (v1.4) program, within MacVector.

GenBank Accession Numbers

Fibrocystin (human) AAL74290; (mouse) AAN05018; D86 (mouse), NP_619615; DKF2p586C1021, XP_488444; PKHDL1 cDNA clone ADBBEB10 (5'), AV706327; PKHDL1 genomic sequence (human) RP11-419L20, AC02001; (mouse) NW_000106 (44,650K-44,800K). Fibrocystin-L related proteins: HGFR (mouse), NP_032617; plexin 1 (mouse), NP_032901; TMEM2 (human) NP_037522; XP_051860 (human) XP051860; hypothetical protein from *C. aurantiacus*, ZP_00018581 and hypothetical protein from *T. Tengeongensis*, NP_621862. GenomeScan and other predicted proteins similar to fibrocystin-L: Hs8 8205 30 32 2; Hs 8205 30231; Hs 8205 30 232 (human); LOC271264 (mouse) XP_194970. Fugu PKHDL1, genomic sequence Scaffold 2621, CAAB01002621. PKHDL1 and Pkhdl1 cDNA sequences, AY219181 and AY219182, respectively.

Example 1

Identification and cloning of PKHDL1 and Pkhdl1

To identify the human ortholog of D86, the 1945 aa protein sequence was analyzed against the human genomic sequence by BLAST. The likely human ortholog was identified by a strong hit in genomic sequence from chromosome region 8q23 in the BAC clone RP11-419L20. Comparison of the genomic sequence to full-length fibrocystin using Pustell protein/DNA sequence alignment and BLAST showed that the homology on chromosome 8 extended over most of the length of the disease related protein, covering at least 150 kb of genomic DNA. This region not only contained homology to D86 but also matched the previously described cDNA, DKFZp586C1021, that is similar to the 3' region of PKHD1, indicating that these cDNAs are part of the same large gene.

To clone the full-length human D86 ortholog, (the PKHD-like 1 gene, PKHDL1), a RT-PCR exon linking approach was used with primers located in exons strongly predicted by GenomeScan and NIX analysis, and by homology with fibrocystin. The full-length transcript was cloned as 16 overlapping fragments (see Table 1 for details) and the 5' and 3' ends of the mRNA identified and cloned by RACE strategies (as described above). RNA from human lung and adrenal was used for the RT-PCR and all products were cloned and sequenced. There was some evidence of alternative splicing, but sequence from the largest amplified fragment in each case was assembled into a contig containing an ORF of 12,729 bp. PKHDL1 has a 5' untranslated region (UTR) of 104 bp and the putative start codon is the first in-frame ATG in the sequence. The start codon does not strongly match the Kozak consensus, but overall 5 of 13 sites, including +4 and −2, match the consensus. The 3' UTR is 248 bp and has a typical polyadenylation signal preceding the site of polyA addition by 21 bp. The total transcript is 13081 bp.

Comparison of the PKHDL1 transcript to the genomic sequence showed that the gene contains 78 exons (see Table 4 for details) and the total genomic size of the gene is 167,918 bp. Two splice donor sites (for IVS 8 and 67) have the non-canonical GC sequence rather than the typical GT. As is often found in the ~0.5% of splice donor sites that have a GC, the rest of the donor sequence (at both exons) closely matches the splice site consensus. The transcriptional start of PKHDL1 is associated with a CpG island.

Many PKHDL1 exons were identified by gene prediction programs and GenomeScan defined the human and murine gene as three and two different genes, respectively (see Methods for details). Of the 78 PKHDL1 exons, 53 were predicted correctly, 3 exons had one different splice junction (one associated with the GC splice donor) and 22 exons were not predicted. A further 6 exons were predicted that were not found in the final transcript. Therefore, although these prediction programs are helpful to identify exons, RT-PCR and sequencing were required to define the most likely gene sequence. In this case, the availability of the D86 murine cDNA of Pkhdl1 (exons 1-38) and human cDNA DKFZp586C1021 (exons 69-78) helped determine the structure of the gene.

TABLE 4

Intron/exon structure of human and murine PKHDL1

| Exon▲ Number | size (nt) | Coding region position□ nt | aa | Human IVS size (nt) | Mouse IVS size (nt) |
|---|---|---|---|---|---|
| 1 | 177* | 1-73 | 1-25 | 1893 | 1767 |
| 2 | 90 | 74-163 | 25-55 | 16733 | 6795 |
| 3 | 145 | 164-308 | 55-103 | 948 | 916 |
| 4 | 109 | 309-417 | 103-139 | 1498 | ? |
| 5 | 58 | 418-475 | 140-159 | 1409 | 1994 |
| 6 | 94 | 476-569 | 159-190 | 2866 | 4111 |
| 7 | 54 | 570-623 | 190-208 | 528 | 491 |
| 8 | 74 | 624-697 | 208-233 | 1299† | 980 |
| 9 | 43 | 698-740 | 233-247 | 3920 | 4065 |
| 10 | 71 | 741-811 | 247-271 | 1541 | 1440 |
| 11 | 111 | 812-922 | 271-308 | 2321 | 1926 |
| 12 | 90 | 923-1012 | 308-339 | 1527 | 2256 |
| 13 | 269 | 1013-1281 | 338-427 | 1152 | 464 |
| 14 | 92 | 1282-1373 | 428-458 | 2965 | 1695 |
| 15 | 160 | 1374-1533 | 458-511 | 281 | 377 |
| 16 | 136 | 1534-1669 | 512-557 | 1204 | 647 |
| 17 | 144 | 1670-1813 | 557-605 | 1570 | 606 |
| 18 | 158 | 1814-1971 | 605-657 | 1658 | 1281 |
| 19 | 114 | 1972-2085 | 658-695 | 2286 | 1661 |
| 20 | 150 | 2086-2235 | 696-745 | 1006 | 580 |
| 21 | 125 | 2236-2360 | 746-787 | 5551 | 1080 |
| 22 | 164 | 2361-2524 | 787-842 | 1257 | 173 |
| 23 | 173 | 2525-2697 | 842-899 | 4394 | 5891 |
| 24 | 148 | 2698-2845 | 900-949 | 1769 | 1093 |
| 25 | 155 | 2846-3000 | 949-1000 | 2183 | 1908 |
| 26 | 123 | 3001-3123 | 1001-1041 | 469 | 1128 |
| 27 | 106 | 3124-3229 | 1042-1077 | 3086 | 1900 |
| 28 | 111 | 3230-3340 | 1077-1114 | 1973 | 1467 |
| 29 | 165 | 3341-3505 | 1114-1169 | 983 | 869 |
| 30 | 122 | 3506-3627 | 1169-1209 | 1864 | 1753 |
| 31 | 133 | 3628-3760 | 1210-1254 | 440 | 764 |
| 32 | 196 (193) | 3761-3956 | 1254-1319 | 1617 | 1516 |
| 33 | 143 | 3957-4099 | 1319-1367 | 422 | 602 |
| 34 | 105 | 4100-4204 | 1367-1402 | 627 | 639 |
| 35 | 189 | 4205-4393 | 1402-1465 | 750 | 739 |
| 36 | 171 | 4394-4564 | 1465-1522 | 559 | 312 |
| 37 | 227 | 4565-4791 | 1522-1597 | 758 | 731 |
| 38 | 985 | 4792-5776 | 1598-1926 | 2497 | 2813 |
| 39 | 249 | 5777-6025 | 1926-2009 | 946 | 637 |
| 40 | 150 | 6026-6175 | 2009-2059 | 1487 | 1821 |
| 41 | 175 | 6176-6350 | 2059-2117 | 974 | 921 |
| 42 | 157 | 6351-6507 | 2117-2169 | 437 | 370 |
| 43 | 157 | 6508-6664 | 2170-2222 | 1292 | 1402 |
| 44 | 80 | 6665-6744 | 2222-2248 | 476 | 670 |
| 45 | 130 | 6745-6874 | 2249-2292 | 1409 | 1073 |
| 46 | 130 | 6875-7004 | 2292-2335 | 3203 | 2392 |
| 47 | 242 | 7005-7246 | 2335-2416 | 1935 | 1750 |
| 48 | 137 | 7247-7383 | 2416-2461 | 2307 | 980 |
| 49 | 1030 | 7384-8413 | 2462-2805 | 1332 | ? |
| 50 | 192 | 8414-8605 | 2805-2869 | 8348 | 3611 |
| 51 | 152 | 8605-8757 | 2869-2919 | 1238 | 1191 |
| 52 | 160 | 8758-8917 | 2920-2973 | 557 | 727 |
| 53 | 172 | 8918-9089 | 2973-3030 | 2154 | 970 |
| 54 | 89 | 9090-9178 | 3033-3060 | 351 | 498 |
| 55 | 149 | 9179-9327 | 3060-3109 | 1293 | 1728 |
| 56 | 130 | 9328-9457 | 3110-3153 | 1424 | 1253 |
| 57 | 119 | 9458-9576 | 3153-3192 | 1938 | 728 |
| 58 | 130 | 9577-9706 | 3193-3236 | 1474 | 1504 |
| 59 | 174 | 9707-9880 | 3236-3294 | 3130 | 1839 |
| 60 | 104 | 9881-9984 | 3294-3328 | 916 | 1864 |
| 61 | 130 | 9985-10114 | 3329-3372 | 771 | 1099 |
| 62 | 122 | 10115-10236 | 3372-3412 | 1666 | 375 |
| 63 | 91 | 10237-10327 | 3413-3443 | 3167 | 3522 |
| 64 | 149 | 10328-10476 | 3443-3492 | 82 | 83 |
| 65 | 123 | 10477-10599 | 3493-3533 | 1189 | 480 |
| 66 | 112 | 10600-10711 | 3534-3571 | 81 | 80 |
| 67 | 117 | 10712-10828 | 3571-3610 | 5555† | 3776† |
| 68 | 166 | 10829-10994 | 3610-3665 | 3170 | 3067 |
| 69 | 233 | 10995-11227 | 3665-3743 | 201 | 190 |
| 70 | 168 | 11228-11395 | 3743-3799 | 2512 | 2503 |
| 71 | 158 | 11396-11553 | 3799-3851 | 4235 | 1416 |
| 72 | 136 | 11554-11689 | 3852-3897 | 2861 | 2838 |
| 73 | 342 | 11690-12031 | 3897-4011 | 3677 | 2164 |
| 74 | 152 | 12032-12183 | 4011-4061 | 406 | 2434 |
| 75 | 147 | 12184-12330 | 4062-411- | 342 | 283 |
| 76 | 154 | 12331-12484 | 411-4162 | 3397 | 1837 |
| 77 | 237 (258) | 12485-12721 | 4162-4241 | 3059 | 4026 |
| 78 | 254● (209)■ | 12722-12729 | 4241-4243 | | |

▲mouse size in brackets if different from human;
*human 5' UTR = 104; mouse 5' UTR not determined;
†atypical GC splice donor;
□in human and mouse to exon 32.
Exon 32-77 mouse position 1 codon less.
Exon 77-78 mouse position 6 codons more;
●human 3' UTR = 248;
■mouse 3'UTR = 201

To confirm the structure of PKHDL1 and determine if the D86 cDNA contained the entire mouse ortholog, the sequence of the mouse transcript was determined. The human transcript was compared to murine genomic sequence by BLAST and the NW000106 Mouse Supercontig was identified, indicating that Pkhdl1 is located in mouse chromosome region 15B3. Strong similarity between PKHDL1 and the murine genomic sequence (and also using the D86 cDNA) enabled the full-length Pkhdl1 ORF of 12,747 bp to be predicted. The mouse ORF from the D86 cDNA to the 3'UTR also was cloned as 14 RT-PCR fragments (see Table 2), confirming the structure of the gene. The intron/exon structure of Pkhdl1 is the same as its human counterpart with 78 exons and all exon sizes, except 1, 32, 77 and 78, the same in human in mouse (see Table 2 for details). The atypical GC splice donor to exon 67 is conserved in the mouse, but the exon 8 donor is GT in this organism. The murine Pkhdl1 gene is also associated with a CpG island.

Example 2

Tissue expression of PKHDL1

Initially, PKHDL1 cDNAs of human and mouse were hybridized to multiple tissue northern blots but no clear bands were visualized. Faint smears were seen in many lanes (FIG. 1A). The problem of visualizing PKHDL1 as a specific transcript by northern blotting appeared similar to that seen with PKHD1. In the case of PKHDL1, the problem of resolving the transcript as a discrete fragment was compounded by its low level of expression. Faint smears on the Northern blot may reflect particular sensitivity of this transcript to degradation or, as for PKHD1, the presence of multiple alternatively spliced transcripts. Therefore, RT-PCR was used to examine the tissue expression of this gene.

Analysis of human adult material showed expression in most tissues. Analysis of a fuller range of tissues was possible in mouse and this also showed that expression levels were low, with the product found in most tissues, both newborn and adult, after multiple cycle PCR (see FIG. 1B). PKHDL1/Pkhdl1 therefore appeared to be expressed at a low level in most tissue types. The widespread low level of expression of PKHDL1 may reflect the association of a CpG island with the promoter of this gene. CpG islands often are associated with more widely expressed genes.

There was evidence of possible alternative splicing of PKHDL1 as several RT-PCR reactions generated more than one product. The GC splice donor found at two exon junctions is also often associated with alternative splicing. Furthermore, one human adrenal gland cDNA clone, ADBBEB10, that was fully sequenced, extends exon 18 a further 886 bp and leads to a novel 3' UTR with an atypical, ATTAAA polyadenylation signal shortly before the site of polyA addition. D86, the originally described transcript of the 5' part of Pkhdl1, has an extension of exon 38 into IVS38, producing a 3' UTR of 62 bp, although no clear polyadenylation site is present in this sequence. It therefore seems likely that PKHDL1, like PKHD1, will generate many alternatively spliced transcripts, some predicted to produce secreted proteins (such as ADBBEB10 and D86), as well as the membrane bound form indicated by the longest ORF. There are significant regions of breakdown in homology between the two proteins (see FIGS. 2A-2D). Alternative splice forms of the fibrocystin and fibrocystin-L proteins may match the other homolog better.

Example 3

Are Mutations to PKHDL1 Associated with ARPKD?

Previously, mutation analysis of PKHD1 revealed a population of clinically well-characterized ARPKD patients in which no mutation was identified. The homology of PKHDL1 to PKHD1 and expression in kidney and liver suggested that it could be a candidate as a second ARPKD gene. To test this hypothesis, ARPKD patients from seven families without definite PKHD1 mutations were screened for basepair changes throughout the gene. The gene was partially screened in a further 13 PKHD1 mutation negative ARPKD patients (see Methods for details). The 78 PKHDL1 coding exons and flanking intronic sequences were amplified from genomic DNA and analyzed for base-pair mismatches by denaturing high-performance liquid chromatography (DH-PLC; see Methods for details). This analysis revealed 17 exonic changes (see Table 5 for details), including silent changes at the amino acid level and conservative and non-conservative substitutions. No nonsense or deletion/insertion mutations were found. Seven non-conservative changes were screened in normal controls; five of these were found in that population (see Table 5), but two, Q/P702 and L/S 1199, were not detected. Analysis to determine whether these two substitutions segregated with the disease was uninformative. The L/S 1199 change, however, is probably not ARPKD associated as the family in which this change was detected (M52) also has the PKHD1 substitution, T36M. Although initially the significance of T36M was unclear, finding this change in other ARPKD families showed that M52 is a typical (PKHD1 mutated) ARPKD family. Q/P702 is conserved in the mouse ortholog, but not fibrocystin (where it is aspartic acid), and the pathogenic significance of this change remains unclear.

In summary, analysis of PKHDL1 in a group of ARPKD patients without detected PKHD1 mutations revealed a number of missense changes but no inactivating mutations (see Table 5). Although one non-conservative change was found only in an ARPKD family, overall the data did not provide compelling evidence associating this gene with ARPKD, even if this possibility cannot be entirely excluded. The lack of association of PKHDL1 with ARPKD is consistent with the major sites of expression of this gene in blood cell lineages.

TABLE 5

Detected variants in PKHDL1

| Designation | Amino Acid Position/ Nucleotide Change | Exon | Allele Frequency ARPKD Population | Allele Frequency Normal Controls |
|---|---|---|---|---|
| 1/V164 | 490A/G | 6 | 3/14 | |
| 1227G/A | K409 | 13 | 3/14 | |
| 1404C/T | Y468 | 15 | 2/14 | |
| 1920T/C | N640 | 18 | 1/14 | |
| 1965A/G | E655 | 18 | 1/14 | |
| Q/P702 | 2105A/C | 20 | 1/14 | 0/200 |
| T/A1192 | 3574A/G | 30 | 4/14 | 13/100 |
| L/S1199 | 3599T/C | 30 | 1/14 | 0/100 |
| G/V1223 | 3668G/T | 31 | 1/14 | 1/200 |
| R/S1514* | 4540C/A | 36 | 4/14 | 17/100 |
| V/I1607 | 4819/G/A | 38 | 1/14 | |
| Y/C1638 | 4913A/G | 38 | 3/14 | 12/100 |
| 6621C/G | L2207 | 43 | 3/14 | |
| 9084A/T | T3028 | 53 | 3/14 | |
| H/Q3050 | 9150C/G | 54 | 4/14 | 14/64 |
| D/E3607 | 10821C/A | 67 | 1/14 | |
| V/I4220* | 12658G/A | 77 | 1/14 | |

*Polymorphic change detected in cDNA sequence

Example 4

Cellular Expression of PKHDL1

To determine the cell types that express PKHDL1, tissue-specific cell lines were analyzed by RT-PCR (FIG. 1C). These showed the highest level of expression in K562, an erythroleukemia cell line and stimulated T-cells, with the only other expressing cells being EBV transformed lymphoblasts. Expression limited to blood-derived cells is consistent with the database description of D86 as a lymphocyte-secreted protein. Furthermore, the tissue origin of described murine Pkhdl1 ESTs is in thymus (n=5) and lymph node (n=2), as well as adrenal (n=2).

Detection of the PKHDL1 transcript in organs that are composed entirely of immune cell subtypes (spleen and thymus) as well as in activated T-cells and B lymphoblasts suggested that expression of PKHDL1 may be important within cells of the immune system. To determine whether the expression is confined to specific immune cell populations or to states of immune activity, flow cytometric sorting from murine lymphoid organs and in vitro activation protocols were carried out (see Methods for details). RT-PCR analysis of RNA isolated from these cells resulted in detection of Pkhdl1 at low cycle number only in activated bulk T-cells and purified CD4$^{+ve}$ (helper) and CD8$^{+ve}$ (cytotoxic) T-cells (FIG. 1D). Strong in vitro stimulation of B-cells and inflammatory macrophages did not result in high-level expression. At high cycle number expression was also detectable in CD4$^{++ve}$, CD8$^{+ve}$ (double positive) thymocytes, resting naïve and memory B-cells, unstimulated and stimulated peritoneal macrophages, resting CD4$^{+ve}$ and CD8$^{+ve}$ T-cells, NKT-cells, and both CD8$^{+ve}$ and CD8$^{-ve}$ dendritic cells.

In summary, analysis of highly purified cell populations from murine lymphoid organs indicated that fibrocystin-L is up-regulated in T-cells following activation and, therefore, may serve a specific function in cellular immunity. Increased expression of mRNA in purified helper (CD4$^{+ve}$) and cytotoxic (CD8$^{+ve}$) T-cells was detected following activating stimuli delivered by lectins, allogeneic antigen presenting cells (APCs), and immobilized antibodies to the T-cell receptor and the co-stimulatory receptor CD28. In contrast, strong activation stimuli failed to induce up-regulation of Pkhdl1 in memory phenotype B-cells and inflammatory macrophages.

Example 5

The Structure of Fibrocystin-L

Figure 3:
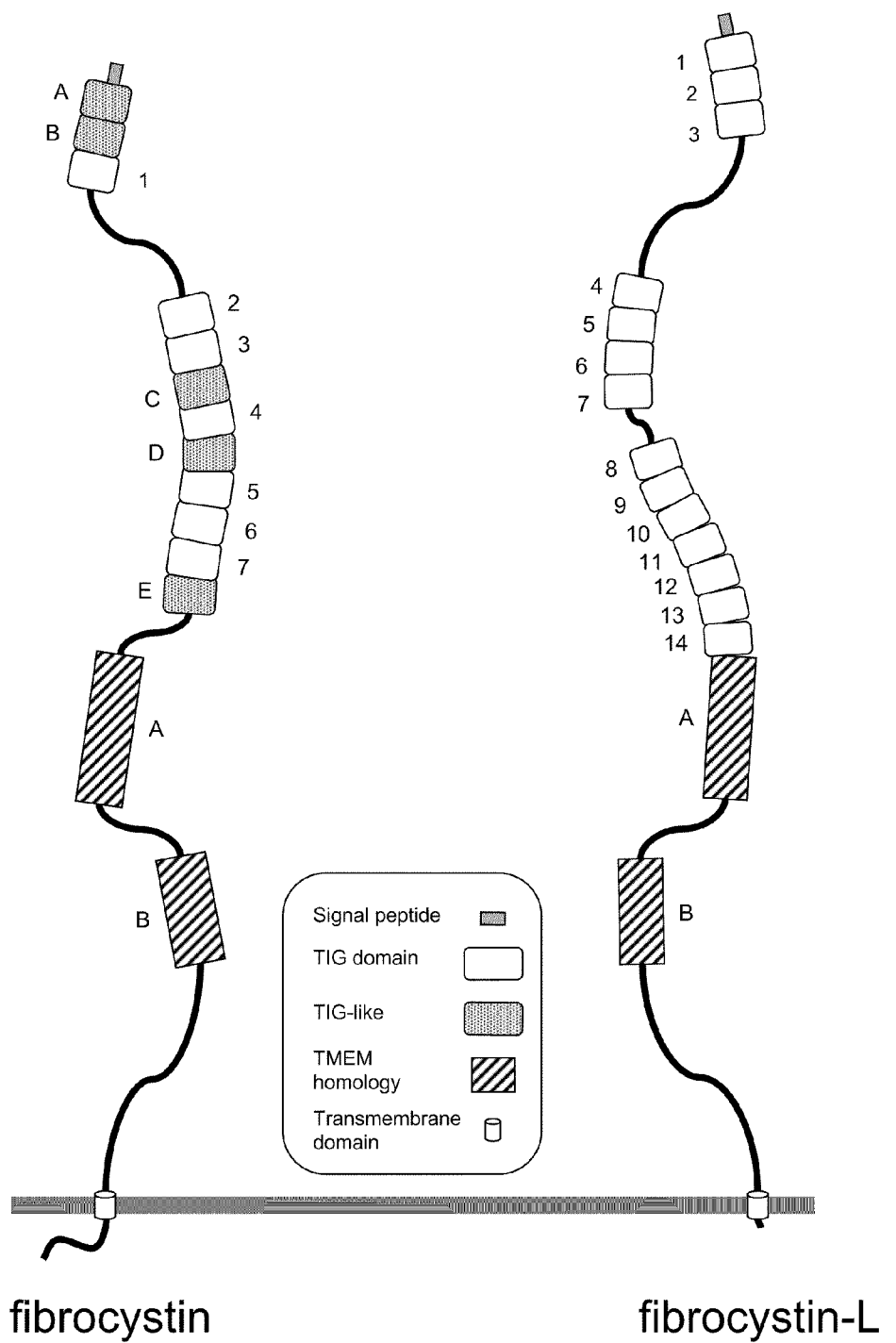
FIG. 3 is a diagram comparing the proposed structures of fibrocystin and fibrocystin-L.

Analysis of the longest ORF of the PKHDL1 sequence allowed the structure of the corresponding protein, termed fibrocystin-like (fibrocystin-L) to be determined. Fibrocystin-L was predicted to be larger than fibrocystin, with 4243 aa and a calculated unglycosylated molecular mass of 466 kDa. A signal peptide was predicted at the N-terminal end with cleavage after the sequence CAA (see FIGS. 2A-2D). Analysis of likely transmembrane regions in fibrocystin-L gave conflicting results but the most likely structure (predicted by SOSUI) is of a single transmembrane domain, from 4213-4235 aa, leaving a short, 8 aa, cytoplasmic tail. The predicted topology was therefore similar to fibrocystin with a large, 4212 aa, extracellular region and single transmembrane pass (FIG. 3). The extracellular region contains 56 putative N-linked glycosylation sites indicating that this region may be highly glycosylated. A single potential protein kinase C phosphorylation site is found in the C-terminal tail at position 4239 aa.

Figure 2A:
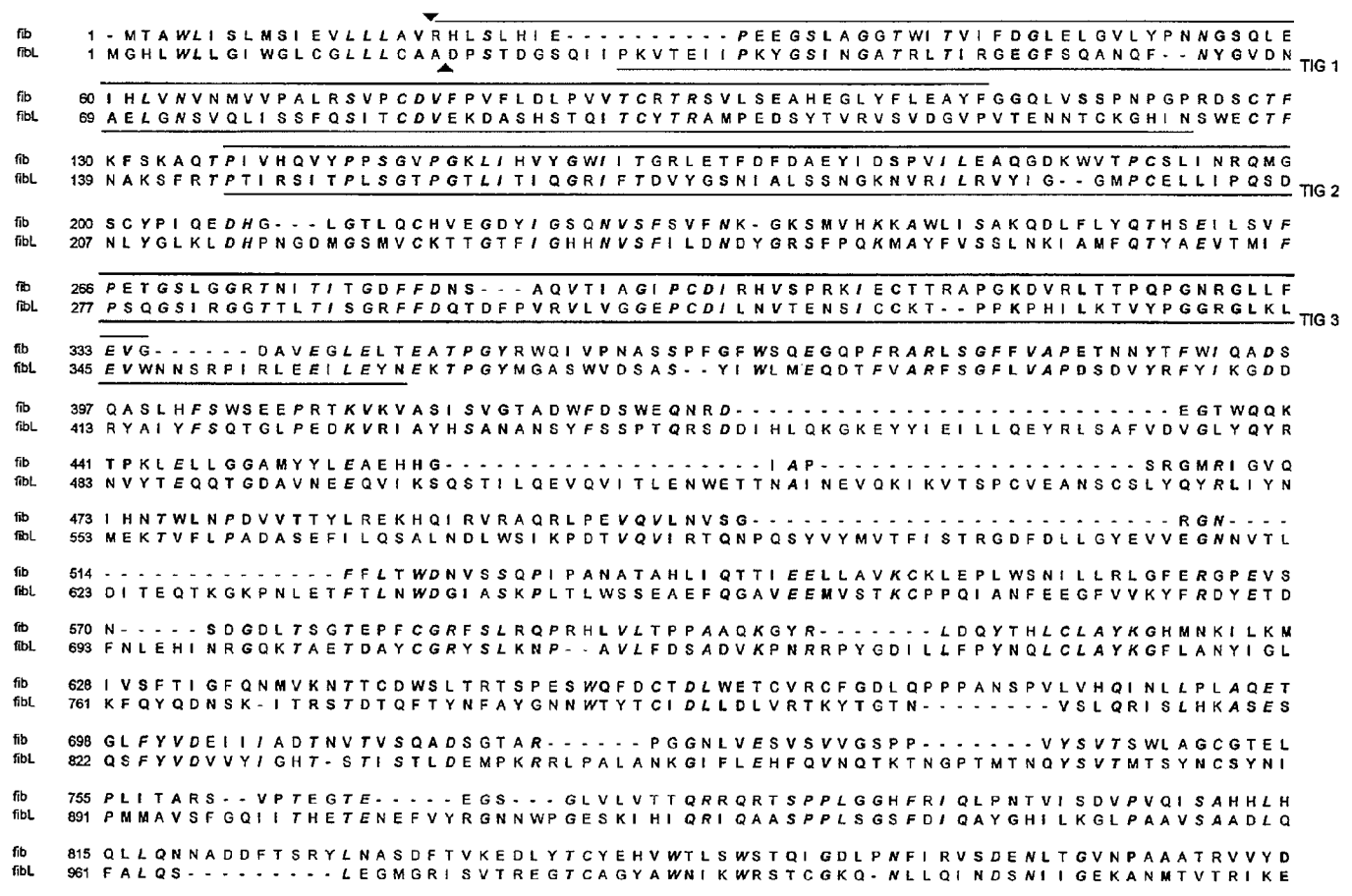
Figure 2C:
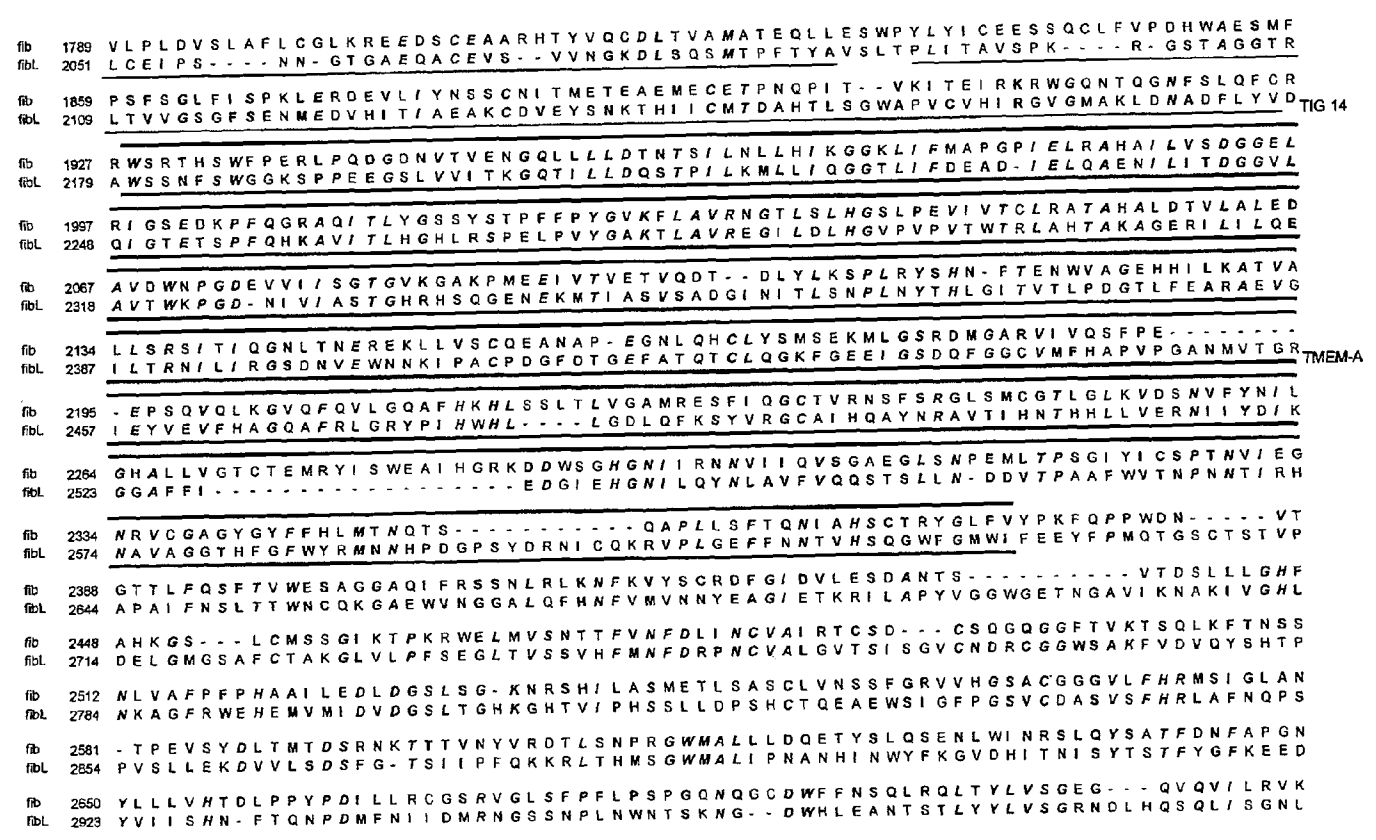
Figure 2D:
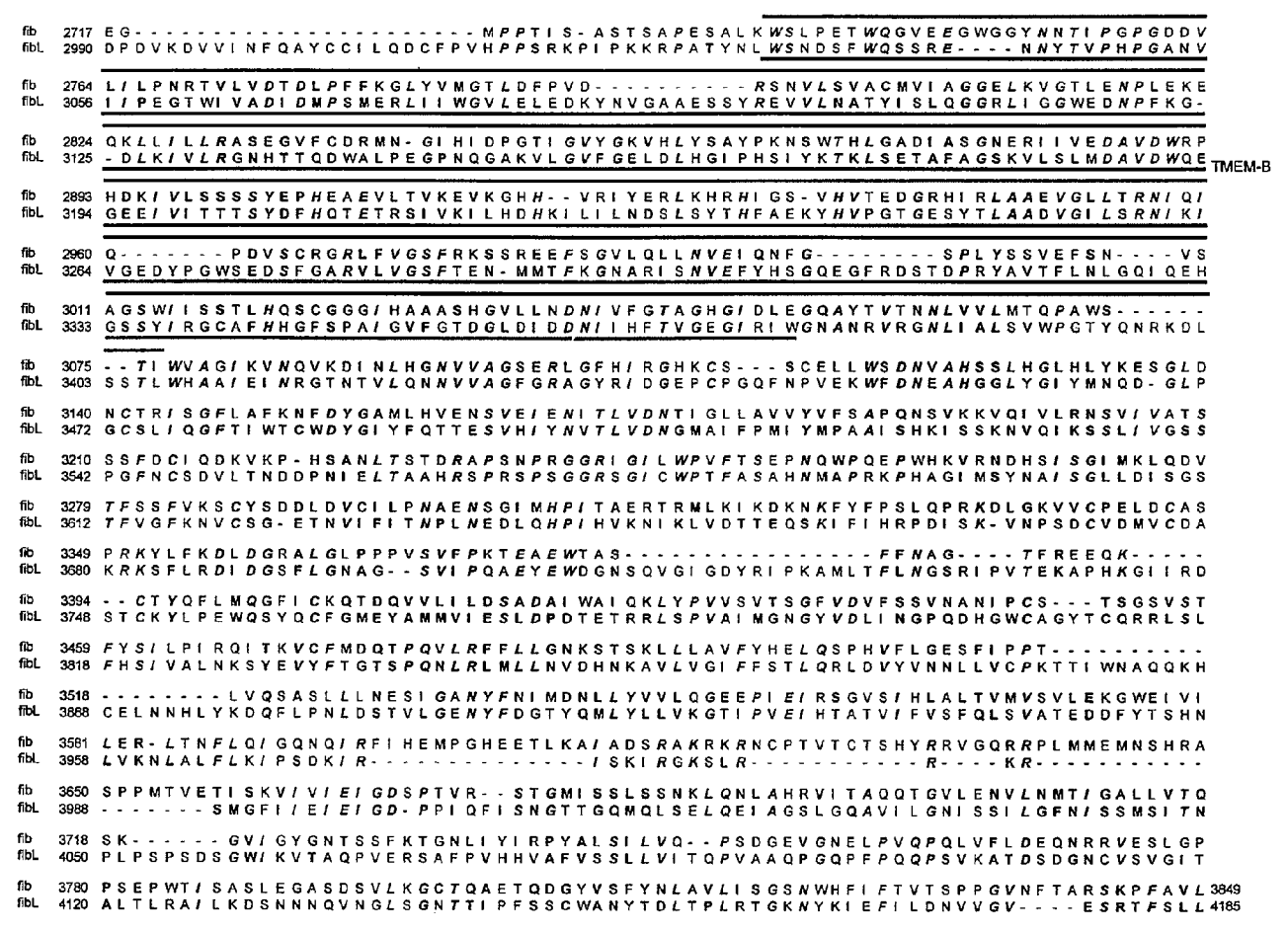

The protein most similar to fibrocystin-L is fibrocystin, which is homologous from the N-terminal end to 4185 aa (see FIGS. 2A-2D). In this region, the two proteins show homology of 25.0% and similarity of 41.5%. There is no significant homology between the two proteins in the transmembrane or short cytoplasmic regions. As with fibrocystin, the most clearly recognized protein domain in fibrocystin-L is the TIG/IPT domain. Analysis by Pfam indicated that fibrocystin-L contains 14 copies of this immunoglobulin-like fold, with three immediately after the signal peptide and the remaining 11 in tandem from 1067 aa to 2177 aa, with a gap between 1470 aa-1566 aa; almost one-third of the protein is in TIG domains (FIGS. 2A and 3). FIG. 2B shows that all the TIG domains closely match the TIG consensus and are similar to the corresponding domains of fibrocystin, the HGFR and members of the plexin family. In all the fibrocystin-L TIG domains, apart from TIG10, the cysteine residues, which are important to stabilize the domain through the formation of a disulfide bond, are present.

A second region of significant homology is to a protein of unknown function, TMEM2, and two related proteins. This region of homology also was noted with fibrocystin. Two TMEM regions of homology with the fibrocystins have been defined: TMEM domain-A (2180 aa-2375 aa) and -B (3032 aa-3376 aa; FIGS. 2A-2D and 2F). The size of TMEM-B has been extended further N-terminal compared to the area of homology that was previously described with fibrocystin. Interestingly, this homology is not only with the previously described proteins, TMEM2 and XP051860, but also to a newly described hypothetical protein from the thermorphilic, filamentous, photosynthetic bacteria, *Chloroflexus aurantiacus*. Indeed, the bacterial protein is more clearly related to the TMEM domains of fibrocystin and fibrocystin-L than either of the other human proteins as it does not require to be gapped to match the sequence (FIG. 2F).

In summary, the description of a second member of the fibrocystin protein family has helped to refine the likely structure of these proteins. A notable difference between fibrocystin-L and fibrocystin is the length of the predicted cytoplasmic tail. In fibrocystin-L it is only 8 aa, while in fibrocystin it contains 192 aa and has several possible PKA, PKC and casein kinase phosphorylation sites. Although the short fibrocystin-L tail in humans has a single potential PKC site, this is not conserved in the mouse. Fibrocystin-L is predicted to have 14 TIG domains, far more than the seven predicted in fibrocystin by Pfam and other programs. Inspection of sequence alignments of the two proteins suggests that fibrocystin may have further TIG-like domains C-terminal to those defined previously (see FIGS. 2A-2D and 3). A second important region of homology that is present twice in the fibrocystins is with TMEM2 and related proteins. TMEM2, XP051860 and the newly described sequence in the filamentous bacteria *C. aurantiacus*, have a single copy of the TMEM repeat; in the first two proteins is it interrupted by addition sequence (see FIG. 2F). In the TMEM2, XP051860 and *C. aurantiacus* proteins, as in the fibrocystins, this region is predicted to be extracellular. As *C. aurantiacus* is the only sequenced prokaryote with this protein domain, it appears likely that this may be an example of horizontal gene transfer.

Example 6

Fibrocystin-L Orthologs and Homologs

Murine fibrocystin-L is predicted to have 4249 aa with an overall identity of 81.9% and similarity of 90.0% to the human protein. This is higher than the corresponding figures of 72.6% and 83.1% for human and murine fibrocystin. The murine fibrocystin-L is predicted to have a signal peptide with cleavage at the corresponding position to the human protein and a similarly located single transmembrane domain, leaving a 6 residue C-terminal tail. Murine fibrocystin-L is also predicted to have 14 TIG domains and similar TMEM homology. Fifty-six N-linked glycosylation sites are predicted in the extracellular region of the protein but the C-terminal tail does not contain a PKC site.

BLAST analysis for related proteins in other species where the complete genomic sequence is available showed a fibrocystin-L ortholog in the fish *Takifugu rubripes*. Strong similarity is seen with several predicted proteins and the corresponding genome sequence, Scaffold 2621. The Fugu PKHDL1 ortholog is encoded by a genomic region of ~30 kb. Interestingly, analysis of Fugu genomic sequence with fibrocystin only identified the PKHDL1 ortholog, but with a much lower score and E value than with fibrocystin-L. This indicates that Fugu has only PKHDL1 and no PKHD1 ortholog. Analysis of available genomic sequence from other eukaryotes and prokaryotes revealed no clear full-length orthologs of PKHD1 or PKHDL1. However, other significant regions of homology were detected in these species. The strongest homology was with the TMEM domain in *C. aurantiacus* as described above. The next most significant region was with a conserved hypothetical protein from the bacterium *Thermoanaerobacter tengeongensis* that has 11 TIG domains, two from 246 aa-332 aa and nine tandemly arranged from 580 aa. This protein also has a fibronectin type III domain, and a signal peptide indicating that it is a secreted protein. Other high scoring homologies were with other TIG domain proteins, most notably to plexin-like proteins, that typically have four such domains.

Example 7

EST Analysis

Expression data for fibrocystin-L was examined in human and mouse EST libraries (Table 6) using the NCBI database on the World Wide Web at ncbi.nlm.nih.gov/UniGene/. There was an overrepresentation of PKHDL1 expression (16/58 clones; 27.5%) in human ESTs originating from endometrial adenocarcinoma. Fifty percent (8/16) were from well-differentiated endometrial adenocarcinoma, 6/16 (37.5%) from moderately differentiated adenocarcinoma, and 2/16 (12.5%) originated from poorly differentiated tumors. A number of other epithelial cancers show upregulated expression of fibrocystin-L. The mouse ESTs occurred most commonly in thymus and pituitary gland (Rathke's pouch).

TABLE 6

Tissue distribution of ESTs for PKHDL1 in human and mouse in Unigene database.

| Human | Number | Mouse | Number |
|---|---|---|---|
| Uterus (adenocarcinoma) | 16 | Thymus | 5 |
| Other | 8 | Pituitary - Rathke's Pouch | 4 |
| Germinal B cell center; lymph node | 7 | Embryo | 3 |
| Liver | 4 | Lymph node | 2 |
| Brain | 3 | Mixed | 2 |
| Pancreas | 3 | Brain | 1 |
| Adrenal | 2 | Whole mouse | 1 |
| Muscle | 2 | One cell embryo | 1 |
| Mixed | 2 | Urinary bladder | 1 |
| Pooled glandular | 2 | Spleen | 1 |
| Head and neck | 1 | Colon tumor | 1 |
| Fetal | 1 | | |
| Pooled organ | 1 | | |
| Mixed embryo | 1 | | |
| Vascular | 1 | | |
| Adipose | 1 | | |
| Larynx | 1 | | |
| Lung | 1 | | |
| Pituitary | 1 | | |
| Total Human ESTs | 58 | Total Mouse ESTs | 21 |

RT-PCR in human and mouse tissue and cell lines demonstrated PKHDL1 expression was seen in kidney, adrenal, brain, liver, lung, placenta, ovary, and tonsil. A limited number of human cancer tissues were also examined. Upregulation of PKHDL1 was observed to be 1.7× in endometrial cancer compared with the levels seen in normal endometrium by semi-quantitative RT-PCR using GAPDH as a control.

Example 8

Manufacture and Characterization of Fibrocystin-L Antibodies

Figure 8A:
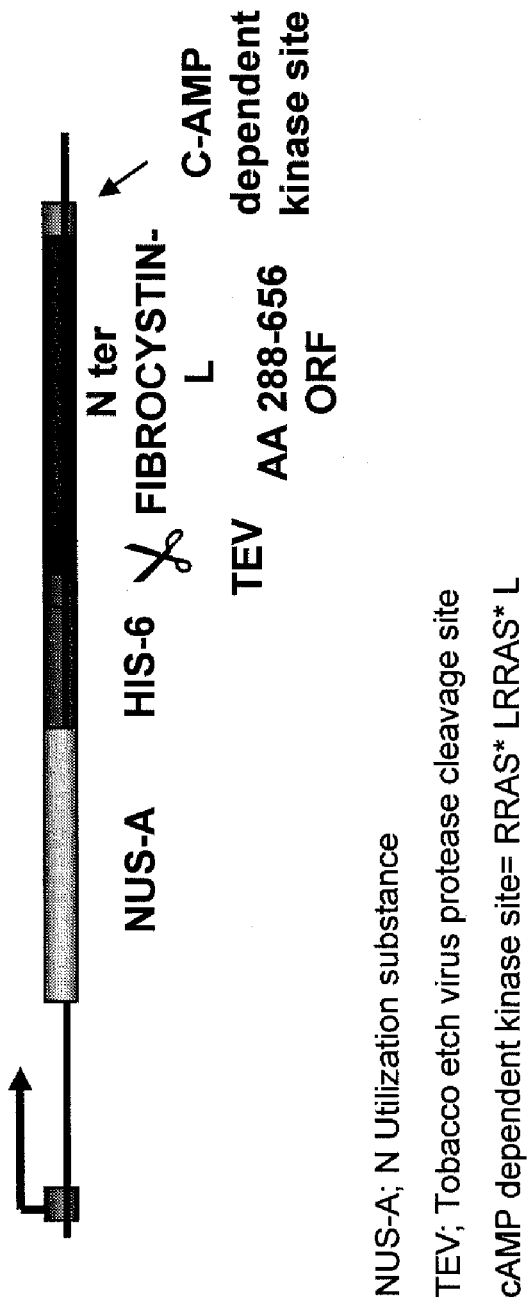
FIG. 8A is a schematic of the N terminal fusion expression construct of fibrocystin-L (371 amino acids of fibrocystin-L).
Figure 8B:
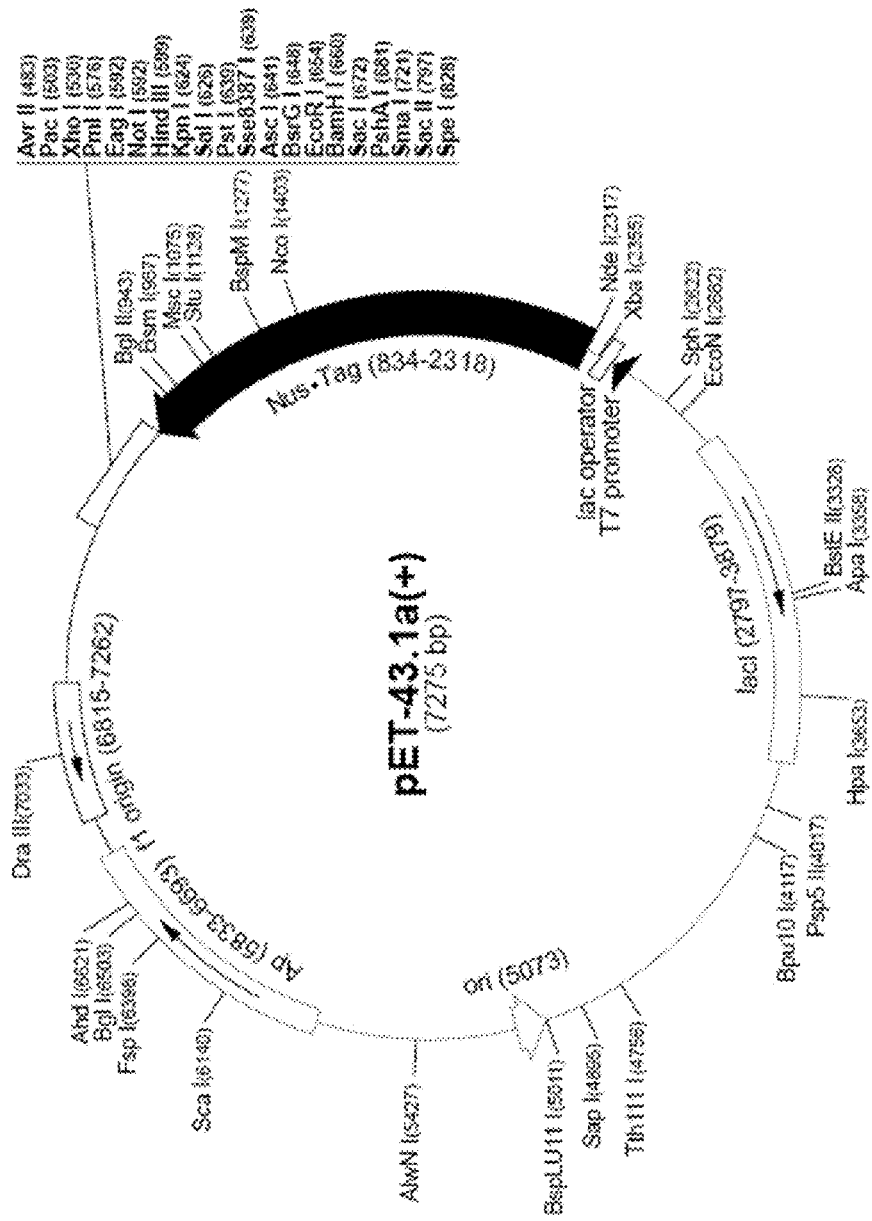
FIG. 8B is a schematic of the PET43 vector.

A NusA $(His)_6$-tagged N-terminal human fibrocystin-L expressed protein was produced as follows and used to immunize mice. A fragment of PKHDL1 was amplified and cloned from EST clone ADBBEB10 (human adrenal tissue) containing the 5' sequence of PKHDL1 (containing the sequence for the third TIG domain of fibrocystin-L (amino acids 288-656)) into pZERO, then subcloned into a modified pET-43a$^+$ (Novagen) vector with a tobacco etch virus (TEV) protease site between the NusA/His$_6$ ORF and the PKHDL1 region. See FIGS. 8A and 8B. The $(His)_6$ NusA fibrocystin-L fusion protein was produced in *E. coli* AD494 and DE3 strains; soluble protein fractions were purified by metal affinity chromatography on an imidazole gradient followed by a round of size exclusion chromatography using a Superdex 200 column. The calculated weight of 102.86 kDa including the NusA construct of the fusion protein was confirmed by running IPTG induced bacterial cell lysates on an SDS-PAGE gel.

The PKHDL1 cDNA described above also was used to transfect PEAK cells (Edge Biosystems). Cells were transfected with the plasmid construct using Lipofectamine® (Invitrogen) and stable transfectants were selected using puromycin selection (2 µg/mL). This construct contains a C-terminal Pk tag (a 14 amino acid sequence derived from the P and V proteins of the paramyxovirus), Simian Virus 5 SV5, and an N-terminal FLAG tag after the signal peptide. The cDNA was prepared by utilizing an adaptor primer to obliterate a BamH1 site and generate a SAP1 site for subcloning of the coding sequence of PKHDL1 with SAP1/Not1 ends into a PEAK plasmid (a modified pIRES PURO/PEAK 10 plasmid).

Figure 8C:
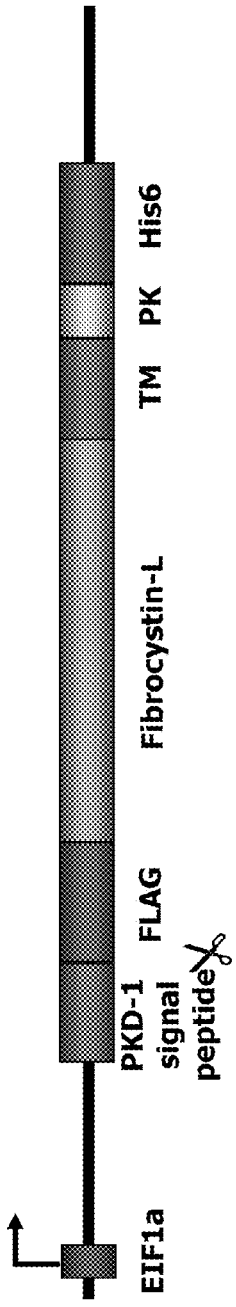
FIG. 8C is a schematic of the PK-FLAG tagged fibrocystin-L expressed in PEAK cells.

BALB/c ByJ mice were immunized with a subcutaneous injection of the purified recombinant $(His)_6$ NusA-tagged fibrocystin-L (uncleaved) protein (see FIG. 8C) emulsified in complete Freund's adjuvant (Difco) after a protein concentration step by centrifugation and buffer exchange to PBS (Millipore; Amicon Ultra centrifugal filter). Twenty-eight days after immunization, mice were screened for their immune responsiveness to the antigen.

Anti-sera from one mouse gave a strong positive band of the protein as confirmed by western blot and by overlay of tagged protein constructs. Confirmation of the identity of the prokaryotically expressed protein was confirmed by mass spectroscopy analysis of the expressed purified protein, which was excised from an acrylamide gel. Spleens were removed from immune-responsive mice three days after an intravenous boosting with antigen.

Single cell suspensions were prepared and red blood cells were removed by lysis with ammonium chloride potassium buffer (ACK). Lymphocytes and F/O myeloma cells (nonsecreting myeloma derived from SP2/0 BALB/c myeloma cells) were mixed in a ratio of 2:1 and centrifuged to form a cell pellet. The cell pellet was resuspended in 1 mL of a 50% solution of polyethylene glycol 1540 (Baker) and RPMI, then incubated at 37° C. for 90 seconds, washed and resuspended in fresh Iscove's Modified Dulbecco's Medium (IMDM) with 10% fetal bovine serum (Hyclone). Aliquots of 100 µl then were added to each well of five microtiter plates (Costar 3595). Twenty four hours later, 100 µl IMDM culture medium was replaced with fresh medium supplemented with 1M Hypoxanthine, 4 mM Aminopterin and 0.16M Thymidine (HAT), which was added to each microtiter well. Every 3-4 days thereafter, 100 µl IMDM culture medium was replaced with fresh medium containing HAT, HT and complete medium without HAT successively over a period of approximately 14 days. Upon reaching 75% confluence, the culture supernatants were tested for the presence of fibrocystin-L antibody. The hybridomas of interest were cloned in limiting dilution cultures at 1 cell per microtiter well and later subcloned at 0.3 cells per microtiter well. Balb/c spleen cells serve as feeder layer for fusions ($5 \times 10^4$ per well), cloning, and subcloning ($3 \times 10^6$ per well). Positive subclones were isotyped and cryopreserved.

Figure 8D:
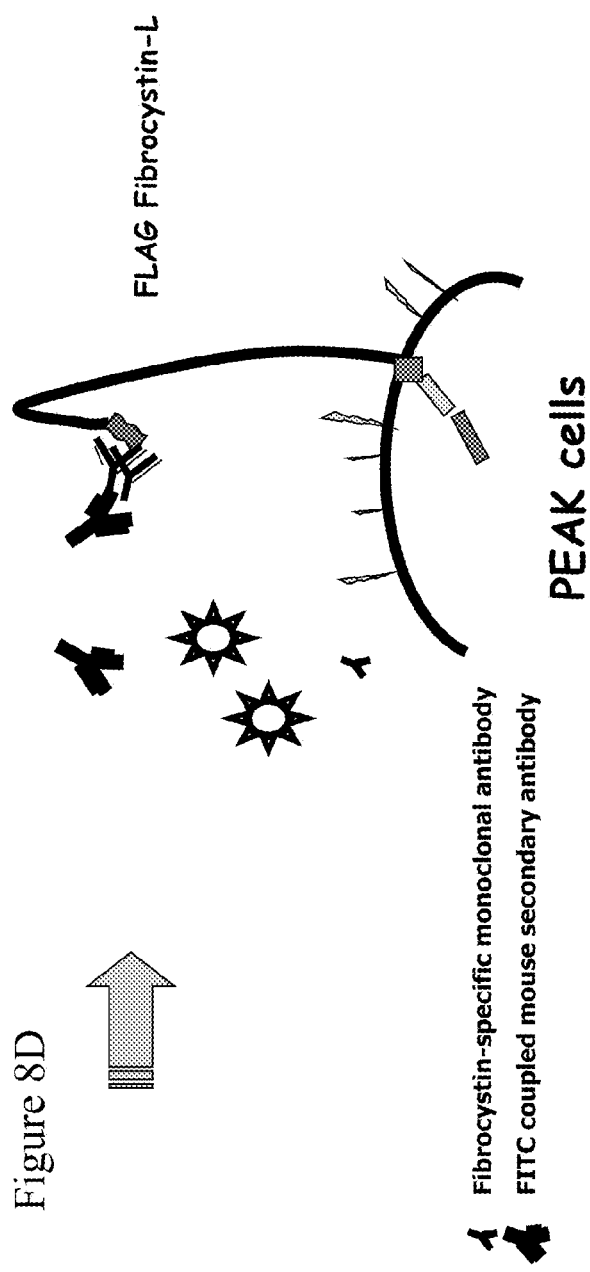
FIG. 8D is a schematic of the antibody-screening strategy using PEAK cell membranes by western blot.

Twenty-three reactive clones from 960 supernatants tested were detected in an initial screen using an Immunetics Miniblotter 28® system for western blotting and membrane preparations from transfected PEAK cells stably expressing the fibrocystin-L partial construct (confirmed by the detection of a GFP tag by immunofluoresence microscopy). See FIGS. 8C and 8D. Simultaneous western lanes were run using primary antibodies to FLAG and PK tags as positive controls. The reaction was detected with goat anti-mouse IgG secondary antibodies conjugated to horseradish peroxidase (Dako), and developed using a chemiluminescent substrate with the results being recorded on film.

Initial positivity was obtained by western blot from 14/960 hybridoma supernatants. Seven cloning plates subsequently had band reactivity (from 192 wells) and monoclonal antibodies generated. De StGrowth (1980) *J. Immunol. Methods* 35:1-21. Positive reactors underwent additional rounds of re-screening using the same system. All positive supernatants detected a single prominent reactive band migrating at ~75 kDa consistent with the size of the expressed tagged protein construct. No other reactive bands were detected from these lysates. Positive reactors underwent additional rounds of re-screening by western. Final repeated screenings of the chosen sub-cloned antibody supernatants from selected cells yielded 10 monoclonal antibodies (Table 7).

TABLE 7

Monoclonal antibodies generated to fibrocystin-L and isotype details

| Name | Isotype |
| --- | --- |
| FibLA-2 | IgG3 κ |
| FibLA-10.1 | IgG1 κ |
| FibLA-10.2 | IgG1 κ |
| FibLA-4.1 | IgG1 λ |
| FibLA-4.2 | IgG1 λ |
| FibLA-11.1 | IgG1 λ |
| FibLA-11.2 | IgG1 λ |
| FibLA-11.3 | IgG1 λ |
| FibLA-13.1 | IgG1 λ |
| FibLA-13.2 | IgG1 λ |

To confirm that these antibodies were sensitive and specific, each antibody was used to detect endogenous human fibrocystin-L in various tissues by Western blotting. Peroxidase conjugated secondary antibody (goat anti-mouse IgG) was used to detect the primary antibodies. Each antibody was able to detect endogenous fibrocystin-L.

Endometrial carcinoma tissue showed the highest level of expression of fibrocystin-L protein, followed by moderate expression in activated T human lymphocytes, kidney, spleen and the erythroleukemia K562 cell line. A high molecular weight protein was detected at ~500 kDa, with a second smaller protein detected in some tissues. This smaller product was clearly present in kidney, endometrium, and tonsillar tissue. Endogenous fibrocystin-L also was detected by Western blotting with mouse tissue membrane preparations; strongest levels were detected in kidney, followed by lung, thymus, liver, lymph node, spleen, and endometrium tissues using the FibLA4.1 and FibLA4.2 antibodies.

Example 8

Tissue Microarray Studies

Tissue microarray blocks were made from formalin-fixed paraffin embedded archival tissue, including 60 normal human tissue sections. The expression of fibrocystin-L was studied in the tissue microarray blocks using the FibLA-4.1 and FibLA-11.3 antibodies and compared with the staining using an isotype control antibody. The intensity of staining was graded on a scale of 0-4. Expression levels of fibrocystin-L were demonstrated to be at a low level across many tissues (Table 8). Staining was most intense in fallopian tube epithelium in the normal tissue dataset. Control slides stained with IgG1 isotype control antibody were negative. Staining intensity also was very prominent in thyroid epithelium (apical). Other sites with prominent staining were liver parencyhmal cells, particularly around the central veins (control liver sections were negative); adrenal cortex, in all three layers (zona fascicularis, reticulata and glomerulosa), gallbladder endothelium (apical and cytoplasmic), testis Leydig cells, and the breast duct epithelium and spleen red pulp. Follicles, the sites of B cells, were negative.

Cilia are reported to occur in several of these unusual sites of staining; testicular interstitium in fertile men (containing myoid cells, fibroblast-like cells and Leydig cells) have one cilium per cell in the 9+0 microtubule configuration (Takayama (1981) *Int. J. Androl.* 4:246-256). In thyroid follicular cells, cilia are thought to be in the 9+2 microtubule configuration. Although the number of cilia per cell seen in scanning electron microscopy studies has been debated, the most recent studies have determined one 9+2 cilium is present on each follicular thyroid cell with cilia extending into the follicular lumen and abnormal secondary cilia observed in studies of follicular carcinoma (Martin (1988) *Virchows Arch. B Cell Pathol. Incl. Mol. Pathol.* 55:159-166). Single cilia are reported in the cells of rat cortex and medulla (Wheatley (1967) *J. Anat.* 101:223-237). Ward et al. also have previously detected polycystin-1 in Leydig cells of the testis and the adrenal cortex (Ward et al. (1996) *Proc. Natl. Acad. Sci. USA* 93:1524-1528).

TABLE 8

Fibrocystin-L expression in normal human tissues

| Tissue | 11.3 Intensity | Extent | 4.1 Intensity | Extent |
| --- | --- | --- | --- | --- |
| Thyroid | 1 | 2 | 3 | 1 | 1 | 2 |
| Esophagus LS | 1 | 1 | 3 | 0 | 0 | 0 |
| Esophagus XS | 1 | 0 | 0 | 1 | 0 | 0 |
| Stomach Mucosa LS | 1 | 1 | 2 | 1 | 0 | 0 |
| Stomach Muscularis | 1 | 0 | 0 | 1 | 1 | 3 |
| Small Bowel | 1 | 0 | 0 | 1 | 0 | 0 |
| Sigmoid Colon Mucosa | 1 | 0 | 0 | 1 | 0 | 0 |
| Sigmoid Colon Muscularis | 1 | 0 | 0 | 0 | 0 | 0 |
| Colon Submucosa | 0 | 0 | 0 | 1 | 1 | 1 |
| Tonsil | 1 | 1 | 3 | 1 | 2 | 3 |
| Adrenal | 1 | 2 | 3 | 1 | 1 | 3 |
| Pancreas | 1 | 1 | 1 | 1 | 1 | 2 |
| Ureter | 1 | 1 | 3 | 1 | 1 | 4 |
| Bladder Wall | 1 | 0 | 0 | 1 | 0 | 0 |
| Bladder Mucosa | 1 | 0 | 0 | 0 | 0 | 0 |
| Kidney | 1 | 2 | 3 | 1 | 2 | 3 |
| Lymph Node (colon/rectum) | 1 | 1 | 1 | 1 | 0 | 0 |
| Spleen | 1 | 2 | 3 | 1 | 2 | 2 |
| Thymus, preinvoluted | 1 | 0 | 0 | 1 | 0 | 0 |
| Thymus, involuted | 1 | 0 | 0 | 1 | 0 | 0 |
| Liver | 1 | 2 | 4 | 1 | 2 | 4 |
| Skeletal Muscle | 1 | 1 | 1 | 1 | 1 | 1 |
| Lung (bronchioles) | 1 | 1 | 1 | 1 | 0 | 0 |
| Heart (epicardium) | 1 | 0 | 0 | 0 | 0 | 0 |
| Heart (myocardium) | 1 | 1 | 1 | 1 | 0 | 0 |
| Fallopian tube | 1 | 3 | 4 | 1 | 3 | 4 |
| Endometrium | 1 | 1 | 2 | 1 | 0 | 0 |
| Breast Stroma | 1 | 0 | 0 | 1 | 0 | 0 |
| Breast Ducts | 1 | 1 | 4 | 1 | 0 | 0 |
| Hypodermis | 1 | 0 | 0 | 0 | 0 | 0 |
| Skin (thin) | 1 | 0 | 0 | 1 | 0 | 0 |
| Hippocampus | 1 | 1 | 4 | 1 | 0 | 0 |
| Cervix | 1 | 1 | 3 | 1 | 0 | 0 |
| Placenta | 1 | 1 | 4 | 1 | 1 | 3 |
| Testis | 1 | 2 | 1 | 1 | 2 | 1 |
| Gall Bladder | 1 | 2 | 4 | 1 | 1 | 4 |
| Spleen | 1 | 2 | 2 | 1 | 2 | 2 |
| Prostate | 1 | 2 | 3 | 1 | 1 | 2 |

Example 9

Fibrocystin-L Expression in Kidney

Kidney tissue was examined by western blot and immunohistochemistry. There appeared to be predominantly proximal but also some distal tubule staining (both cytoplasmic in distribution). A granular pattern of cytoplasmic distal tubule type of staining also was detected, but it is possible this was artefactual. No staining was detected using an isotype control IgG1 primary antibody simultaneously tested. Positively staining proteinaceous casts also were found in medullary collecting ducts from normal kidney. Expression levels of fibrocystin-L were much lower when compared with fibrocystin levels detected using immunohistochemistry.

Example 10

Studies of Fibrocystin-L in Endometrium

As there was an overrepresentation of PKHDL1 cDNAs in endometrial carcinoma tissue, and since female reproductive tract epithelium (normal fallopian tube) appeared to have highest expression levels of the protein, human endometrial carcinoma sections were examined in greater detail using additional tissue microarrays. Custom-made high quality microarrays were obtained through the Mayo Clinic tissue array core facility and Mayo Clinic Endometrial Cancer Working group as follows.

Five micron sections were made from formalin-fixed, paraffin-embedded archival tissue using 1-mm punches mounted on glass slides, and dewaxed. Endogenous peroxidase activity was blocked with 0.03% hydrogen peroxide, all sections were subjected to heat-induced epitope retrieval by steaming in EDTA×40 minutes, and nonspecific binding sites were blocked in 5% Bovine Serum Albumin (Sigma) in PBS (pH 7.5). Immunohistochemical staining was performed on a Dako Autostainer (DakoCytomation, Carpenteria, Calif.). Staining was performed using the Dako Envision+system HRP using 3,3-diaminobenzidine (DAB) (Dako; Code K4006) with primary monoclonal antibody against fibrocystin-L (4.1 and 11.3 were found to be consistent for immunochemistry and western blotting). This system uses a two-step staining procedure that employs HRP-labeled polymer conjugated with secondary antibodies. The labeled polymer does not contain avidin or biotin and as such, nonspecific staining was avoided from endogenous avidin-biotin activity, which is often problematic in kidney and liver tissue. The tissue was immunostained with immunohistochemical staining optimized for human endometrium tissue. After deparaffinization in xylene, slides were rehydrated through a graded series of alcohol and placed in TBS-Tween 0.1% followed by a 5-minute block of the endogenous peroxidase from the Dako Envision+horseradish peroxidase kit. Antigen retrieval was then performed using steamer boiling in 1 mM EDTA pH 8.0 for 40 minutes and then rinsed and washed in TBS-Tween 0.1%. The primary antibody (4.1:1 in 50 dilution in fish blocking buffer; or mouse IgG1 isotype control (1:500 dilution; R& D Systems; Catalog MAB002)) was incubated on the tissue in a humidified container for 30 minutes, then washed in TBS-Tween 0.1% for 5 minutes on a horizontal shaker. The secondary antibody was added and incubated again for 30 minutes. After a further 5 minute wash step in TBS-Tween 0.1%, the peroxidase activity was visualized by incubating with DAB a at room temperature for 10 minutes then rinsing in $H_2O$. The slides then were counterstained in 1:20 hematoxylin for two minutes at room temperature.

Stained slides were scanned and the digitized images were available for viewing along with the grid overlay (linked to an excel database containing the specimen information and pathologists annotations) on the Bacus Webslide® Browser software system (World wide web at bacuslabs.com) from a desktop PC. Grading of the normal human tissue slides for fibrocystin-L was evaluated relative to epithelial staining intensity in the corresponding negative control slide and performed by an experienced pathologist. The reviewer assigned a score of 0 for no staining, 1+ for weak staining, 2+ for moderate staining, and 3+ for strong staining Eight slides containing human endometrial tissue, carcinoma of the endometrium in the same patients and other miscellaneous cancer tissues from the same index cases were also evaluated on the same slides. Endometrial cancer slides are currently being graded by an experienced pathologist with specific expertise in endometrial pathology. A preliminary analysis of the staining in these tissues was performed using a scale of 0-3 grading for immunoreactivity. Fifty-eight patient samples from a total of 191 cases of endometrial carcinoma were excluded from the paired analysis due to the absence of either the index normal or endometrial carcinoma tissue punch or an insufficient tissue section available for quantitation.

The microarrays from this cohort of cancer patients incorporated normal and endometrial cancer tissues but also additional sections of synchronous cancers occurring in 521 patients. There was widespread low intensity epithelial expression in the normal tissues but marked upregulation of the protein in the endometrial cancer tissue. Staining also was localized in the ciliated epithelium of endometrial epithelium and in several ovarian cancers. Fibrocystin-L immunoreactivity was variable within normal endometrium, with the majority of cases showing weak fibrocystin-L epithelial expression. A low level of stromal immunoreactivity also was seen in the majority of normal and endometrial cancer specimens. The staining was cytoplasmic in normal endometrial endothelium. High levels of fibrocystin-L expression seemed to be localized in the apical membranes of endometrial cancer tissue in many of the cases where upregulated expression was seen. Staining in fallopian tube carcinomas also was examined (n=2), but the intensity seemed less than the levels detected in normal fallopian tube endothelium.

Example 11

Analysis of Fibrocystin-L in Endometrial Cancer Microarray Cohort

Of 521 patient samples in the dataset, 135 patients had staining data from both normal and cancer tissues. Eighty-six of 133 (65%) patient sections showed upregulation of the protein (median staining intensity) and the minority of cases showed either unchanged (43/133; 32%) or down-regulation (4/133; 3%) of the protein compared with normal endometrium from these same patients. Paired analysis (using median intensity of staining of normal and tumor tissues) demonstrated there was a statistically significant upregulation of fibrocystin-L in the cancers ($p<0.0001$; Wilcoxon signed rank test (n=135)). Similar analysis using maximal staining intensity demonstrated a statistically significant difference in the staining intensity ($P<0.0001$; t test) in these two groups and contingency table analysis using maximal grade intensity also demonstrated a statistically significant difference in the staining intensity ($P<0.0027$; Pearson test; see Table 9).

There was no correlation between survival ($P=0.67$; log rank test) or recurrence rates (0.96 NS: log rank test) and patients with high, medium or low expression of this protein.

No correlation was observed between staining intensity of fibrocystin-L and histologic grade (n=178; P=0.10; Pearson), cancer stage, body mass index, age, depth of myometrial invasion or vaginal recurrence or hematologic spread. There did seem to be a trend toward significance between fibrocystin-L staining intensity and nodal invasion (P=0.19; NS).

TABLE 9

Contingency table analysis of maximum grade of staining intensity in cancer of endometrium (Y axis) by maximum grade observed in normal tissue sections (X axis)

| Count (%) Column % Row % | 0 | 1 | 2 | 3 | Total (%) |
|---|---|---|---|---|---|
| 0 | 20 | 3 | 0 | 0 | 23 |
|  | 14.81 | 2.22 | 0 | 0 | 17.04 |
|  | 27.78 | 6.25 | 0 | 0 |  |
|  | 86.96 | 13.04 | 0 | 0 |  |
| 1 | 16 | 21 | 1 | 1 | 39 |
|  | 11.85 | 15.56 | 0.74 | 0.74 | 28.89 |
|  | 22.22 | 43.75 | 7.69 | 50.00 |  |
|  | 41.03 | 53.85 | 2.56 | 2.56 |  |
| 2 | 16 | 16 | 6 | 1 | 39 |
|  | 11.85 | 11.85 | 4.44 | 0.74 | 28.89 |
|  | 22.22 | 33.33 | 46.15 | 50.00 |  |
|  | 41.03 | 41.03 | 15.38 | 2.56 |  |
| 3 | 20 | 8 | 6 | 0 | 34 |
|  | 14.81 | 5.93 | 4.44 | 0 | 25.19 |
|  | 27.78 | 16.67 | 46.15 | 0 |  |
|  | 58.82 | 23.53 | 17.65 | 0 |  |
|  | 72 | 48 | 13 | 2 |  |
|  | 53.33 | 35.56 | 9.63 | 1.48 | Total = 135 |

Example 12

Expression of Fibrocystin-L in Other Human Cancers

Immunohistochemistry also was used to examine the extent of fibrocystin-L staining in the 109 cases of synchronous cancers from this patient cohort (Table 10). A subset of the breast, ovarian and colon cancers seemed to have significant staining of fibrocystin-L. Eleven out of twenty two (50%) ovarian cancers and five out of thirty (20%) breast cancers had grade 2 or 3 staining intensity.

Expression of fibrocystin-L also was assessed in K562 erythroleukemia cells using the FibLA-4.1 monoclonal antibody. Fibrocystin-L was present in abundant amounts in the cytoplasm of K562 cells (confocal and immunoflouoresence microscopy data) as indicated in images of fixed permeabilized K562 cells grown in culture and also was detectable in membrane preparations from this cell line by western blot.

TABLE 10

Analysis of fibrocystin-L immunostaining in synchronous/metachronous cancers studied in patients with endometrial carcinoma

| Tissue | Number | No. (%) with grade 2 or 3 intensity staining |
|---|---|---|
| Breast | 30 | 5/30 (20%) |
| Ovary | 22 | 11/22 (50%) |
| Colon | 20 | 3/20 (15%) |
| Lymphoma | 6 | 0/6 (0%) |
| Lung | 5 | 2/5 (40%) |
| Thyroid | 5 | 2/5 (40%) |
| Melanoma | 2 | 1/2 (50%) |
| Omentum | 4 | 1/4 (25%) |
| Bladder | 2 | 0/2 (0%) |
| Skin/Vulva | 2 | 0/2 (0%) |
| Skin (scalp) | 1 | 0/0 (0%) |
| Mouth/Tongue | 2 | 1/2 (50%) |
| Myeloma | 1 | 1/1 (100%) |
| Renal clear cell | 1 | 1/1 (100%) |
| Stomach | 2 | 0 (0%) |
| GIST | 1 | 0 (0%) |
| Perineal | 1 | 0 (0%) |
| Appendix | 1 | 2 (100%) |
| Cecum | 1 | 0 (0%) |

GIST; gastrointestinal stromal tumor

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining whether a subject has endometrial cancer, comprising:
   (a) using an antibody having specific binding affinity for a fibrocystin-L polypeptide comprising the amino acid sequence of SEQ ID NO:3 to measure the level of fibrocystin-L polypeptide in an endometrial sample from the subject, and
   (b) determining that the subject has endometrial cancer if the level of fibrocystin-L polypeptide in the endometrial sample is increased relative to the level in a corresponding control sample, or determining that the subject does not have endometrial cancer if the level of fibrocystin-L polypeptide in the endometrial sample is not increased relative to the level in the corresponding control sample.

2. The method of claim 1, wherein step (a) comprises using immunohistochemistry, western blotting, or ELISA.

3. A method for determining whether an endometrial tissue sample from a subject contains cancer cells, comprising:
   (a) measuring the level of fibrocystin-L in the endometrial tissue sample by contacting the sample with an antibody having specific binding affinity for a fibrocystin-L polypeptide comprising the amino acid sequence of SEQ ID NO:3, and
   (b) determining that the sample contains cancer cells if the level of fibrocystin-L in the sample is increased relative to a control level, or determining that the sample does not contain cancer cells if the level of fibrocystin-L in the sample is not increased relative to the control level.

* * * * *